US011965170B2

(12) United States Patent
Wilding Crawford

(10) Patent No.: US 11,965,170 B2
(45) Date of Patent: Apr. 23, 2024

(54) MUTATION OF GROWTH REGULATING FACTOR FAMILY TRANSCRIPTION FACTORS FOR ENHANCED PLANT GROWTH

(71) Applicant: Pairwise Plants Services, Inc., Durham, NC (US)

(72) Inventor: Brian Charles Wilding Crawford, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 199 days.

(21) Appl. No.: 17/126,469

(22) Filed: Dec. 18, 2020

(65) Prior Publication Data

US 2021/0189414 A1 Jun. 24, 2021

Related U.S. Application Data

(60) Provisional application No. 62/951,593, filed on Dec. 20, 2019.

(51) Int. Cl.
*C12N 15/82* (2006.01)

(52) U.S. Cl.
CPC ..... *C12N 15/8262* (2013.01); *C12N 15/8213* (2013.01)

(58) Field of Classification Search
CPC ........................ C12N 15/8262; C12N 15/8213
See application file for complete search history.

(56) References Cited

U.S. PATENT DOCUMENTS

| | | | |
|---|---|---|---|
| 2006/0174380 A1 | 8/2006 | Carrington et al. | |
| 2015/0315605 A1 | 11/2015 | Li et al. | |

FOREIGN PATENT DOCUMENTS

| | | | |
|---|---|---|---|
| CN | 110157730 A | 8/2019 | |
| WO | 2013102762 A1 | 7/2013 | |
| WO | 2019158911 A1 | 8/2019 | |
| WO | WO-2019158911 A1 * | 8/2019 | ............... A01H 5/10 |

OTHER PUBLICATIONS

Nelissen et al. "Dynamic Changes in ANGUSTIFOLIA3 Complex Composition Reveal a Growth Regulatory Mechanism in the Maize Leaf" 2015 Plant Cell 27: 1605-1619. (Year: 2015).*
International Search Report and Written Opinion corresponding to PCT/US2020/065858; dated May 7, 2021 (20 pages).
Chandran, Viswanathan , et al., "miR396-OsGRFs Module Balances Growth and Rice Blast Disease- Resistance", Front. Plant Sci. 9, Article No. 1999, 2019, 1-16.
Hu, Jiang , et al., "A Rare Allele of GS2 Enhances Grain Size and Grain Yield in Rice", Molecular Plant 8(10), 2015, 1455-1465.

(Continued)

*Primary Examiner* — Matthew R Keogh
*Assistant Examiner* — Rebecca Stephens
(74) *Attorney, Agent, or Firm* — Myers Bigel, P.A.

(57) ABSTRACT

This invention relates to compositions and methods for modifying Growth Regulating Factor (GRF) family transcription factors in plants to produce plants having improved phenotypic characteristics including increased growth. The invention further relates to plants produced using the methods and compositions of the invention.

4 Claims, 9 Drawing Sheets

Specification includes a Sequence Listing.

(56) References Cited

OTHER PUBLICATIONS

Li, Shan , et al., "Modulating plant growth-metabolism coordination for sustainable agriculture", Nature, 560, 2018, 595-600.
Liebsch, Daniela , et al., "MicroRNA miR396, GRF transcription factors and GIF co-regulators: a conserved plant growth regulatory module with potential for breeding and biotechnology", Current Opinion in Plant Biology, 53, 2020, 31-42.
Liu, Jing , et al., "The BnGRF2 gene (GRF2-like gene from *Brassica napus*) enhances seed oil production through regulating cell number and plant photosynthesis", Journal of Experimental Botany 63(1), 2012, 3727-3740.
Noon, Jason B., et al., "Homeostasis in the soybean miRNA396-GRF network is essential for productive soybean cyst nematode infections", Journal of Experimental Botany 70(5), 2019, 1653-1668.
Soto-Suárez, Mauricio , et al., "The *Arabidopsis* miR396 mediates pathogen-associated molecular pattern-triggered immune responses against fungal pathogens", Scientific Reports 9, Article No. 44898, 2017, 1-14.
Van Daele, Inge , et al., "A comparative study of seed yield parameters in *Arabidopsis thaliana* mutants and transgenics", Plant Biotechnology Journal 10(4), 2012, 488-500.
International Search Report and the Written Opinion of the International Searching Authority corresponding to International Patent Application No. PCT/US2022/033701 dated Nov. 25, 2022 (21 pages).
Chen, Feng, et al., "Genome-wide identification of GRF transcription factors in soybean and expression analysis of GmGRF family under shade stress", BMC Plant Biology. 19:269 (2019).
Liu, Weican, et al., "Tissue-Specific Regulation of Gma-miR396 Family on Coordinating Development and Low Water Availability Responses", Frontiers in Plant Science. 8:1112 (2017).

* cited by examiner

```
  1                    10                         20        26
  |                    |                          |         |
  A A C C G T T C A A G A A A G C C T G T G G A A C G
    N     R     S     R     K     P     V     E
        ├──────────────miRNA396 BINDING SITE──────────────▶
                  ┌──┐
                  └─┬┘
          TC>AA S>K MUTATION
```

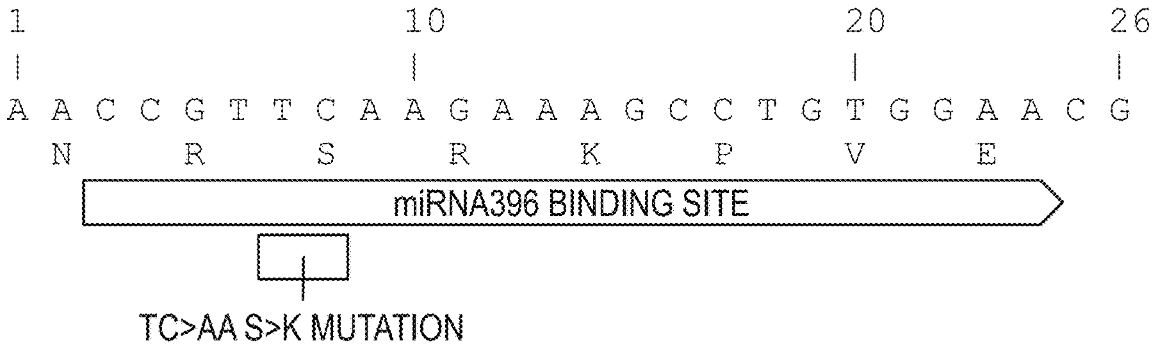

*FIG. 1*

| | | |
|---|---|---|
| Zm GRF6 TGTGG (WILDTYPE) FRAME 1 | AACCGTTCAAGAAAGCCTGTGGAAACG<br>  N   R   S   R   K   P   V   E   T | |
| Zm GRF6 TGTAA FRAME 1 | AACCGTTCAAGAAAGCCTGTAAAACG<br>  N   R   S   R   K   P   V   K   T<br>                                  GG>AA | |
| Zm GRF6 TATAA FRAME 1 | AACCGTTCAAGAAAGCCTATAAAACG<br>  N   R   S   R   K   P   I   K   T<br>                                  GG>AA | |
| Zm GRF6 TGTCA FRAME 1 | AACCGTTCAAGAAAGCCTGTCAAACG<br>  N   R   S   R   K   P   V   K   T<br>                                  GG>CA | |
| Zm GRF6 A AND TATAA FRAME 1 | AACCGTTCAAAAAGCCTATAAAACG<br>  N   R   S   K   K   P   I   K   T<br>              G>A              GG>AA | |
| Zm GRF6 TCTCA FRAME 1 | AACCGTTCAAGAAAGCCTCTCAAAACG<br>  N   R   S   R   K   P   L   K   T<br>                                  GG>CA | |
| Zm GRF6 TGTAC FRAME 1 | AACCGTTCAAGAAAGCCTGTACAAACG<br>  N   R   S   R   K   P   V   Q   T<br>                                  GG>AC | |
| Zm GRF6 A AND TGTGG FRAME 1 | AACCGTTCAAAAAGCCTGTGGAAACG<br>  N   R   S   K   K   P   V   E   T<br>              G>A | |
| Zm GRF6 A AND TGTAA FRAME 1 | AACCGTTCAAAAAGCCTGTAAAACG<br>  N   R   S   K   K   P   V   K   T<br>              G>A              GG>AA | |

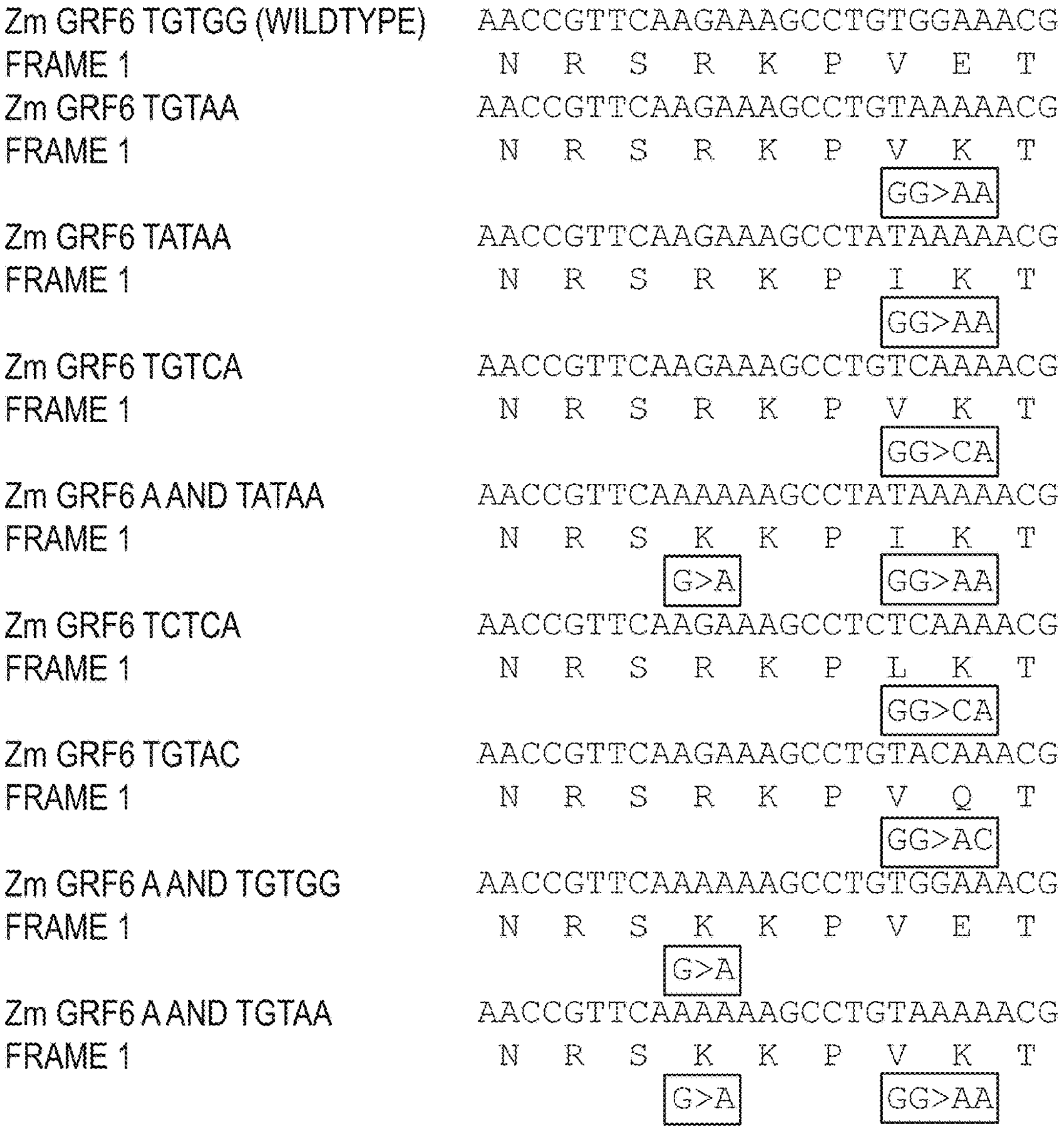

*FIG. 2*

```
                                TTTVNNNNNNNNNNNNNNNNNNNN     15 nt
                                   NNNNNNNNNNNNNNNNNNNNNGG   19 nt
                                TTTVNNNNNNNNNNNNNNNNNNNN     17 nt
              ┌─miRNA396 BINDING SITE─▷
              AACCGTTCAAGAAAGCCTGTGGAAACG
                N   R   S   R   K   P   V   E   T
17 nt TTTVNNNNNNNNNNNNNNNNNNNN
 7 nt           NNNNNNNNNNNNNNNNNNNNNGG
15 nt   TTTVNNNNNNNNNNNNNNNNNNNN
```

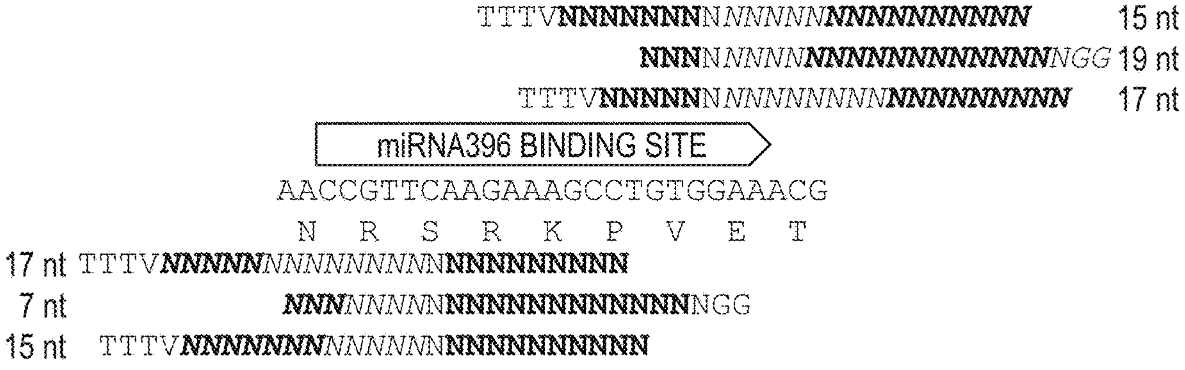

*FIG. 3*

```
1        10        20        30        40        50      6062
|         |         |         |         |         |       | |
                        ◁──GUIDE SPACER──┐
                       ┌─miRNA396 BINDING SITE─▷
CACATGCACCGCGGCCGCAACCGTTCAAGAAAGCCTGTGGAAACGCAGCTCGCGCCCCAGTC
  H   M   H   R   G   R   N   R   S   R   K   P   V   E   T   Q   L   A   P   Q
                                    [R>K]              ┌┤─BASE EDIT B (GG>CA)
                          BASE EDIT A ─┤├              ┌┤─BASE EDIT C (GG>AA)
                                                       [E>K]
```

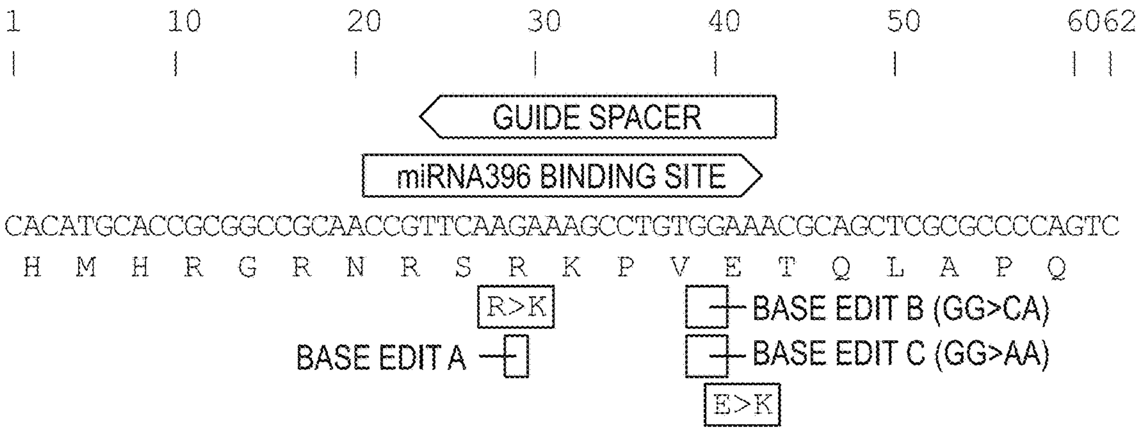

*FIG. 4A*

```
1        10        20        30        40        50      6062
|         |         |         |         |         |       | |
                             ◁──GUIDE SPACER──┐
                            ┌─miRNA396 BINDING SITE─▷
CACATGCACCGCGGCCGCAACCGTTCAAGAAAGCCTGTGGAAACGCAGCTCGCGCCCCAGTC
  H   M   H   R   G   R   N   R   S   R   K   P   V   E   T   Q   L   A   P   Q
                       ┌──────DELETION A──────┐
              DELETION B ─┤────────┐
              DELETION C ─┤────┐              ┤├─BASE EDIT A
```

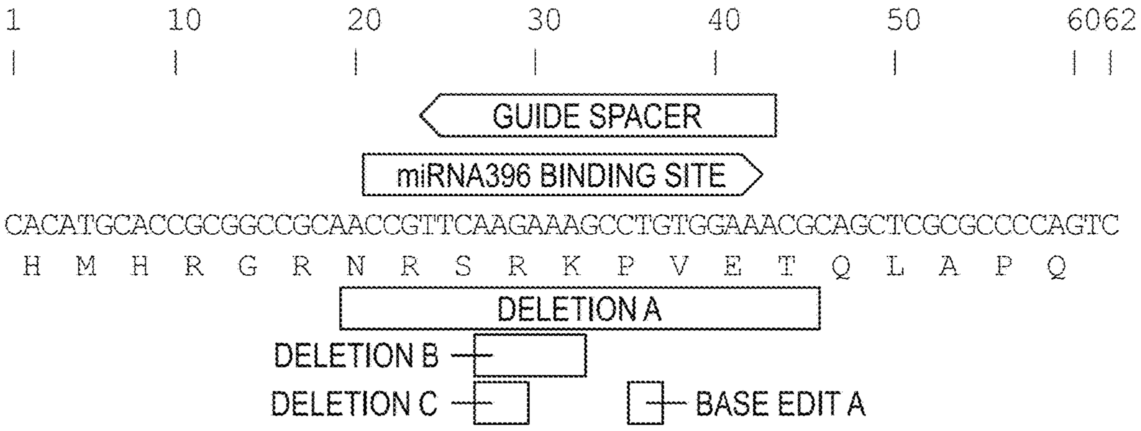

*FIG. 4B*

| SEQUENCE | PAM | SCORE | GENE |
|---|---|---|---|
| TTTCCACAGGCTTTCTTGAA | CGG | 100.0 | GRMZM5G893117 |
| TTTCCACAGGCTTTCTTGAA | CGG | 100.0 | GRMZM2G034876 |
| CTTCCACAGGCTTTCTTGAA | CGG | 100.0 | GRMZM2G045977 |
| TTTCCACAGGCTTTCTTGAA | CGG | 100.0 | GRMZM2G033612 |
| CTTCCACAGGCTTTCTTGAA | CGG | 100.0 | GRMZM2G129147 |
| TTTCCACAGGCTTTCTTGAA | CGG | 100.0 | GRMZM2G105335 |
| CTTCCACAGGCTTTCTTGAA | CGG | 100.0 | GRMZM2G124566 |
| TTTCCACAGGCTTTCTTGAA | CGG | 100.0 | GRMZM2G018414 |
| CTTCCACAGGCTTTCTTGAA | CGG | 100.0 | GRMZM2G041223 |
| ATTCCACAGGCTTTCTTGAA | CGG | 100.0 | GRMZM2G119359 |
| CTTCCACAGGCTTTCTTGAA | CGG | 100.0 | GRMZM2G067743 |
| CTTCCACAGGCTTTCTTGAA | CGG | 100.0 | GRMZM5G850129 |
| ATTCCACAGGCTTTCTTGAA | CGG | 100.0 | GRMZM2G098594 |

FIG. 7

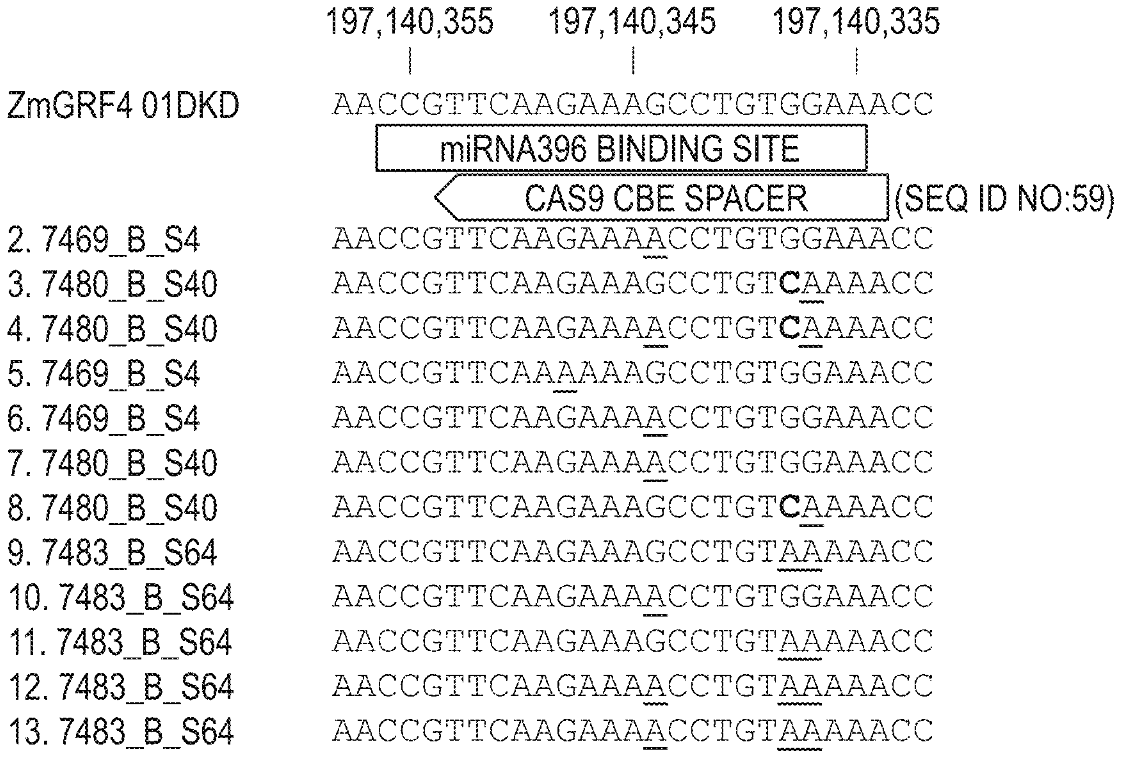

FIG. 8

| SEQUENCE | PAM | SCORE | GENE |
|---|---|---|---|
| CACAGGCTTTCTTGAACGGTTCT | TTTC | 100.0 | GRMZM5G893117 |
| CACAGGCTTTCTTGAACGGTTGC | TTTC | 100.0 | GRMZM2G034876 |
| CACAGGCTTTCTTGAACGGTGAC | TTTC | 100.0 | GRMZM2G033612 |
| CACAGGCTTTCTTGAACGGTTCT | TTTC | 100.0 | GRMZM2G105335 |
| CACAGGCTTTCTTGAACGGTGGC | TTTC | 100.0 | GRMZM2G018414 |
| CACAGGCTTTCTTGAACTGTGAA | TTTC | 50.0 | GRMZM2G092607 |

*FIG. 11*

SEQUENCE LISTING

```
<160> NUMBER OF SEQ ID NOS: 304

<210> SEQ ID NO 1
<211> LENGTH: 22
<212> TYPE: DNA
<213> ORGANISM: Zea mays

<400> SEQUENCE: 1

ccgttcaaga aagcctgtgg aa                                              22


<210> SEQ ID NO 2
<211> LENGTH: 22
<212> TYPE: DNA
<213> ORGANISM: Zea mays

<400> SEQUENCE: 2

tcgttcaaga aagcatgtgg aa                                              22


<210> SEQ ID NO 3
<211> LENGTH: 22
<212> TYPE: DNA
<213> ORGANISM: Zea mays

<400> SEQUENCE: 3

ccgttcaaga aagcatgtgg aa                                              22


<210> SEQ ID NO 4
<211> LENGTH: 62
<212> TYPE: DNA
<213> ORGANISM: Zea mays

<400> SEQUENCE: 4

cacatgcacc gcggccgcaa ccgttcaaga aagcctgtgg aaacgcagct cgcgccccag     60

tc                                                                    62


<210> SEQ ID NO 5
<211> LENGTH: 62
<212> TYPE: DNA
<213> ORGANISM: Zea mays

<400> SEQUENCE: 5

cacatgcacc gtggccgcaa ccgttcaaga aagcctgtgg aatccaagac cgcctcctcg     60

cc                                                                    62


<210> SEQ ID NO 6
<211> LENGTH: 62
<212> TYPE: DNA
```

-continued

<213> ORGANISM: Zea mays

<400> SEQUENCE: 6
cacatgaacc ggggacgcca tcgttcaaga aagcatgtgg aaggccagcc tggccatgcc 60
gc 62

<210> SEQ ID NO 7
<211> LENGTH: 62
<212> TYPE: DNA
<213> ORGANISM: Zea mays

<400> SEQUENCE: 7
cacatgaacc ggggacgcca tcgttcaaga aagcatgtgg aagaccagcc tggccatgcc 60
gc 62

<210> SEQ ID NO 8
<211> LENGTH: 62
<212> TYPE: DNA
<213> ORGANISM: Zea mays

<400> SEQUENCE: 8
cacataaaac gtggttgcca ccgttcaaga aagcatgtgg aaggccgaaa ggcaacaccg 60
ac 62

<210> SEQ ID NO 9
<211> LENGTH: 62
<212> TYPE: DNA
<213> ORGANISM: Zea mays

<400> SEQUENCE: 9
cacatgcacc gcggccgcaa ccgttcaaga aagcctgtgg aagcgcagct cgtgcccccg 60
cc 62

<210> SEQ ID NO 10
<211> LENGTH: 62
<212> TYPE: DNA
<213> ORGANISM: Zea mays

<400> SEQUENCE: 10
cacatcaata ggaaccgcca ccgttcaaga aagcctgtgg aaaaccaacc tagaaaggcc 60
ac 62

<210> SEQ ID NO 11
<211> LENGTH: 62
<212> TYPE: DNA
<213> ORGANISM: Zea mays

<400> SEQUENCE: 11
cacatccacc gcgggaagag ccgttcaaga aagcctgtgg aagtgacctc ccccgccgcc 60
ta 62

<210> SEQ ID NO 12
<211> LENGTH: 62
<212> TYPE: DNA
<213> ORGANISM: Zea mays

<400> SEQUENCE: 12
cacatgcacc ggggcaagaa ccgttcaaga aagcctgtgg aaatgtcctt ggccacgccg 60
gc 62

<210> SEQ ID NO 13
<211> LENGTH: 62
<212> TYPE: DNA
<213> ORGANISM: Zea mays

<400> SEQUENCE: 13
cacattcacc gcgggaagag ccgttcaaga aagcctgtgg aagtgacctc ctcccccgcc 60
gc 62

<210> SEQ ID NO 14
<211> LENGTH: 62
<212> TYPE: DNA
<213> ORGANISM: Zea mays

<400> SEQUENCE: 14
cacatgcacc gcggccgcaa ccgttcaaga aagcctgtgg aagcgcagct cgcgcccccg 60
cc 62

<210> SEQ ID NO 15
<211> LENGTH: 62
<212> TYPE: DNA
<213> ORGANISM: Zea mays

<400> SEQUENCE: 15
cacatgcacc ggggcaagaa ccgttcaaga aagcctgtgg aaatgtcctt ggccacgccg 60
gc 62

<210> SEQ ID NO 16
<211> LENGTH: 62
<212> TYPE: DNA
<213> ORGANISM: Zea mays

<400> SEQUENCE: 16
cacgtccacc gcggccgcgg ccgttcaaga aagcctgtgg aagccgccgc ggcaccggcg 60
gc 62

<210> SEQ ID NO 17
<211> LENGTH: 62
<212> TYPE: DNA
<213> ORGANISM: Zea mays

<400> SEQUENCE: 17
cacatcaaca gaaaccgtca ccgttcaaga aagcctgtgg aaaatcaacc taagaagacc 60
ac 62

<210> SEQ ID NO 18
<211> LENGTH: 62
<212> TYPE: DNA
<213> ORGANISM: Zea mays

<400> SEQUENCE: 18
cacatgcacc gtggccgcaa ccgttcaaga aagcctgtgg aatccaagac cgcctcgtcg 60
tc 62

<210> SEQ ID NO 19
<211> LENGTH: 1646
<212> TYPE: DNA
<213> ORGANISM: Zea mays

<400> SEQUENCE: 19

```
gagcgaagca aagcacatca cgagcccagc ctgcgcctgc ggagggaggg ggctcattaa     60
agagggggcg cgagcgcgac cggccgcggg gagcaagcag cgcgcgagag agacaggttg    120
agatggcgat gccgtatgcc tctctttccc cggcaggcgc cgccgaccac cgctcctcca    180
cagccacggc gtccctcgtc cccttctgcc gctccactcc gctctccgcg ggcggcgggc    240
tgggcgagga ggacgcccag gcgagcgcga ggtggccggc cgcgaggccg gtggtgccgt    300
tcacgccggc gcagtaccag gagctggagc agcaggcgct catatacaag tacctggtgg    360
cgggcgtgcc cgttccgccg gatctcgtgg ttccaatccg ccgcggcctc gactccctcg    420
caacccgctt ctacggccaa cccacactcg ggtacggacc gtacctgggg aggaaactgg    480
atccggagcc cggccggtgc cggcgaacgg acggcaagaa gtggcggtgc tccaaggagg    540
ccgccccgga ctccaagtac tgcgagcgcc acatgcaccg cggccgcaac cgttcaagaa    600
agcctgtgga aacgcagctc gcgccccagt cccaaccgcc cgccgccgca gccgtctccg    660
ccgctccgcc cctggcagcc gccgccgccg ccaccaccaa cggcagcggc ttccagaacc    720
actctctcta cccggccatc gccggcagca ctggtggtgg aggaggagtt ggcgggtccg    780
gcaatatctc ctccccgttc tcctcgtcga tggggggatc gtctcagctg cacatggaca    840
gtgctgccag ctactcctac gcagctcttg gtggtggaac tgcaaaggat ctcaggtaca    900
acgcttacgg aataagatct ctggcggacg agcacaacca gctgatcgca gaagccatcg    960
actcgtcgat agagagccag tggcgcctcc ccagctcgtc gttcccgctc tcgagctacc   1020
cacatctcgg ggcgctgggc gacctgggcg gccagaacag cacggtgagc tcgctgccga   1080
agatggagaa gcagcagccg ccctcgtcct tcctagggaa cgacaccggg gccggcatgg   1140
ccatgggctc cgcctccgcg aagcaggagg gccagacgct gcggcacttc ttcgacgagt   1200
ggcccaaggc gcgggactcc tggccgggcc tctccgacga gaccgccagc ctcgcctcgt   1260
tccccccggc gacccagctg tcgatgtcca tacccatggc gtcctccgac ttctccgtgg   1320
ccagctccca gtcgcccaac gatgactaat ggtgcgtgga tcgtcgcgtt ctggcccttt   1380
gtctgtcttc cctccagtcc tccacccacc gcgcagtagt agctgcggaa acagcccatg   1440
ctcctgtata tttgtcggtc attttccgtg tcagatctgt gtaccaaacc aagcggcggc   1500
ggccgtcgtc tctccccgcc tccgcctcgc ctcatgtggg tgggtgaaca tgagaccgtt   1560
ttgcttaggc tcaaagcttt gtgtgacccc actgatcggt tgtctgcgta ctacctgaaa   1620
gcctgctgct tttgtagcat tactgt                                        1646
```

<210> SEQ ID NO 20
<211> LENGTH: 1718
<212> TYPE: DNA
<213> ORGANISM: Zea mays

<400> SEQUENCE: 20

```
aacccccacc tgaccttctc ttcctccctc ccccgaccgc ctgtctgtcc tccgcgcatc     60
cgttctctat cgaaagggag gaggaggagc gcgcgggagt gggctggggg cccaccgatg    120
ctgagctcgg cgtcctcggc cggggcggcc atggggatgg gcggcgggta ccaacaccag    180
ccgctgccac tgccgcagcg cggggcggcg gccgcggtct tcaccgccgc gcagtgggcg    240
gagctggagc agcaggcgct catctacaag tacctcatgg ccggcgtccc cgtcccgccc    300
gatctcctcc gccccgcccc ccacgccgcc gccttctcct tcgccagccc cgccgcgtcg    360
cccttctacc atcaccacca ccaccacccg tccctgagtt actacgccta ctacgggaag    420
```

aagctggacc cggagccgtg gcggtgccgc cgcaccgacg gcaagaagtg gcggtgctcc 480
aaggaggcgc accccgactc caagtactgc gagcgccaca tgcaccgtgg ccgcaaccgt 540
tcaagaaagc ctgtggaatc caagaccgcc tcctcgccgc cccagctgtc caccgtcgtc 600
accaccacca ccacccggga ggccgccgcc gcgacgcccc ttgagtccct cgcgggggcg 660
gggggtaagg ctcacggcct gtccctcggc ggcggggctg gctcgtcgca cctcagcgtc 720
gacgcttcga acgctcactt tcgctatggc agcaagtacc ctcttggagc taaatccgat 780
gctggcgagc tgagcttctt ctcaggagca ccagggaact ccaggggctt caccattgat 840
tctccagcag ataactcttg gcactccctg ccatccaacg tgccccgtt tacactgtcc 900 aagggcagag actctggcct cctgcccggt gcctactcct actcccacat tgaaccaccg 960
caggtgctcg gccaggtcac catcgcctcg ctgtcacagg accaggagcg ccaccagtcg 1020
tcgttcagca gcggcggggc cggcgctggt ggattgctgg ggagcgtgaa gcaggagaac 1080
cagccgctga ggcccttctt cgacgagtgg cctgggacgc gggactcgtg gtcggagatg 1140
gacgacgcga ggtccagtag gacctccttc tcgacgaccc agctctccat ctccattccg 1200
atgcccagat gtgattgaga acgaagctcg tgcgcggcca gtaggtggcg ttgtcgcatg 1260
acgcgcaccc agcatcgcgc tcgctgctag cgagccaccg tcacccggtg attgatgccc 1320
tcatcctagc tatttgtttc gctgaatcgc attaagaaca gaactctatg taagagcagg 1380
atccttcctc atgtatcaat gggggcaatg aactccattc tgtttctatg gttgtagtac 1440
cgaccatgct ttgtatttgt tgtacccaga ccgagaatga aaaccgccca gtcgtcaggc 1500
gttgtcgtcg ctgcatcaga tgatccaagt gtattgtgtg ctttccaggc tgtgtaagat 1560
ctgatggcga atctgttact gcagtgtagg tgtgtagcat ctgtggtatg gtaccttttg 1620
ttgtgctact ggatctggat tgatgcaaaa tctggtgctg ccgtaggccc ctcttccttt 1680
tctctactgc tataataata atacatcttt tttttatg 1718

<210> SEQ ID NO 21
<211> LENGTH: 3536
<212> TYPE: DNA
<213> ORGANISM: Zea mays

<400> SEQUENCE: 21
accgagcaca catacacact caccagcagg cagcagcagc tagccaagct ataccactag 60
aaccagagca caactcaaag caatgccgcc gcctcctcct cctccgcccc actcccacgc 120
ttcccatccc gcgccgcatg gacgcgagca gcactagcgc gggggcacac agcacggcga 180
gcgggcgggg gcgcgacgat ggacctgggc gggtcggtgg tgatggacgc gggcgcctcg 240
gagctgggcc tgctcggcgg cggatctagc aggctgctca agcacgggcg ggggcccaat 300
gcggcggggg gagacgacga cgtgtggggc ggcggcaggg ccaagcagcc caggacaggg 360
acagcgcccg tcgtcgccgg ggacgtggcg gctgccacca aggcggcggc ggcgccgttc 420
ctgctgggct cgtgcagtcc cggccacggc ggggagcaga tgctcagctt ctcgtccgcc 480
gccgccgccg ccgcggcctc gtgcgcctcc tccaccgctg cggctgatgg cggcggggcc 540
atgccgctgt actacgggac cccggcctct tgctcaggtg agcgcgagca cggcgacggc 600
gtacccgtgc tactgcttgt tgtggcggtg ccgcttgctg ctgcaaagct tacttctttt 660
tttcccgttg cttgttgatt ggattttggt gattgaaaag cttgctatcc acttcttctc 720
cagtattatt gcttttcggt tcgattcgat tcaccctgct ttctctcttt gctcttggtc 780

-continued

```
tcgtagctac agatttattt atttttactt ggttatgtct actgactgac tactgcttat    840
ccttaagctg atctgtgccc tcttccgttt cttctcctct tcttctttct tctagcttca    900
gttatttagt gcatctactc tagattcatg ggttttcat gaccagtgtt gactctttta     960
acctgccaat gatctttgta tggggttttc ctctctcttt tcgtcttctg gagatttaga   1020
ttagtgacga ctgtaaaagt tcttccacct ctggaaaaaa gaaatggttt taaatagtat   1080
tttaaaaaaa gctttattga atcatccgtg atatgtatcg acataagttt gcacttcttt   1140
ttgctgacat ccgccaacgc ttttcttgtc ctcaacggcg ccgcgatcgt gtggattcct   1200
ttttgtcacg ccgcctgctg ataatacgac tactagttct tattagagga agaatgaaaa   1260
agaatggcgt gatctacctc ggacctatac cttcacccct ttctcactca gaaacctaaa   1320
aaccaagaaa cagctaaaag agcatgaatg cacgcaagaa agtctcaaga atacaatgga   1380
gcctcgcgat tcaagttcac tgtcgggacc caacagtgtg gtccttggtc ggcttgctat   1440
ggacatcacc tataaatctg tgctgcttat caggtttctg atccttgcat gcaggcgctc   1500
cgttccaggt ttttgtgtct ttttttgctt gccttttatc ctgccctagg atcgtgttta   1560
ggaaacgctt gcatctcggc ggtcatctct atgaagcagt acacatgttt ttggctgcgc   1620
cttgttggct tccaccgttt tgctgctcat ctctcctaac tatgcctgcc tgtttgctcc   1680
ccgcaggatt gagctcggtg agcttgagca ccagcatgca gggggcaatg gccagggtga   1740
gggccccatt cacgccgtcc cagtggatcg agctcgaaca ccaggccctg atctacaagt   1800
acctggccgc gaacagcccc atacctcaca gcctcctcat ccccatcagg aggagcctcg   1860
cagcgtctcc ctacccgcct tcatacttcg gcacgagcac attggggtgg ggctctttcc   1920
agctgggcta ctccggcaat gcggatctgg agcctgggcg gtgccgccgg acggacggca   1980
agaaatggcg gtgctccagg gacgcggtcg ccgaccagaa gtactgcgag cgacacatga   2040
accggggacg ccatcgttca agaaagcatg tggaaggcca gcctggccat gccgcgaaag   2100
ccatgtccgc ggtggcggcg gcggctgctg ctgctgccca gcctgctgct ctggccggcg   2160
ccggagctcc tgctgctggc ctcactgtca atcagcacca gctgccggcg aagagctacg   2220
ccacgggtgc gactgaccct tgctctctgc aatataacag ggaactggtg aacaaacaga   2280
atgagagcga aaacatgcag gactccgaca acctctcgat gctgacttcc atgaacacag   2340
gaaacacagg cagcgtgttc ccattctcga aacaaaacac caatcctttt gaagtgacca   2400
gctcaaggct agagttcggc ctcgtttcat cggattcact gatgagttcc cctcacagtt   2460
ccttggagaa cgtcaacctg ctcggctcac agagtatgaa cgaacaccag aacccagcct   2520
ccctgcaaca cttcgtggac tggcccagga cgcctgccca gggaggcctt tcatggcccg   2580
aagctgaaga catgcaggct cagaggtcac agctctccat atctgctccc atggcatcct   2640
ccgagctatc gtcggcctcc acatccccca tccacgagaa gctgatgctg tcgcctctga   2700
agctgagccg cgagtacagc ccgactggtc tcggcattgc ggcgaacaga gacgaggcta   2760
gccagctaga agcaacctgg gcgacgatgt tccgtgactc ttcgatgggc ggtccgttgg   2820
gggaggttct ggccaagaac ggcaacgtgg aagcgagaaa ttacctgtcg gcgcctctga   2880
accttctcac cgactactgg gattcaagcc acgggatgga gtcctcccct gtgggcgttc   2940
tgcagaagac gaccgccttc ggatcggtct ccagcagtac agggagcagc cctagggttg   3000
agaaccacgg cgcctacgac ggtttcggca acctgcggga tgatctcggc tcaattgtag   3060
tgcgccatcc aagcatccgc cttgtgtgag ctttctgagt tctgaccatg gaaaactgca   3120
acaagacggc ggcccgcagc catagaagtg ggcatatggg ctactatgct aatcctcaaa   3180
```

gcgtgagggg ggggcattta cctcgtagtt tgtcatttga gactgatctc ctgtttttttg 3240 tcacttcagt tcttcttttg cttccctttt taacttggct ttgtaacttt caccttcctt 3300
ggatcgtgaa aagcgctgtg gtgtgtggtg tggatggatt tggtgcgccg ctgatgcata 3360
tcatcatgtg atagaagaag ccagtatccg tcgaggatta ctgcgagtat cgcctgtttg 3420
ttgttcatac gtcatactgc tgcactgcac ttcactgttt gtgtgcccgt tgttgcattg 3480
tatggttcgg ttatattaat ttacaaacag gtcgtgaggc tgcacattta gattcg 3536

<210> SEQ ID NO 22
<211> LENGTH: 2086
<212> TYPE: DNA
<213> ORGANISM: Zea mays

<400> SEQUENCE: 22
cgagcaccgc gcgcgcacag acacacactc accagcaggc agcagctagc tagctctcta 60
gcaacgagca caaaacgagc aatgccgcta gttccgtccc actccctcgc ttcccatccc 120
gcaccccatg gaagggagca gcactagcta gcgtgggaca gggcggggtg gtgtcgtggt 180
gatggaagcg ggcggcggcg cctcggaact cggcctgctc ggcgccggat ctggcaggct 240
gctcaagcac gggcggggcg acgcggcggg gggagaggac cacgggtggg tcgtcgtcgt 300
cggcggcggc ggcagggcca agcaggccag gaccgcgtcc gtcggcaccg gggacgcggc 360
ggccacggcg gccgtgccgt tcctgctggg ctcctgcggc ggccccggcc acggcgggga 420
acggatgctc agcttctcgt ccgccgccgc cgccgccccg gatgatggcg gtgccatgcc 480
gccgctgtac tacgggaccc cggcctcttg ctcaggattg atgagctcgg cgagggtgag 540
aggccccttc acgccgccgc agtggatcga gctggagcac caggccctga tctacaagta 600
cctgtccgcg aacagccccg tacctcacag cctcctcgtc cccatcagga ggagcgggag 660
cctcgcatcg tctccctacc cgcctcccta cttcggcacg agcacattcg ggtggggctc 720
cttccagctg ggctactccg gcaatgcgga tctggagcct gggcggtgcc gccggacgga 780
cggcaagaag tggcggtgct ccagggacgc ggtcgccgac cagaagtact gcgagcgaca 840
catgaaccgg ggacgccatc gttcaagaaa gcatgtggaa gaccagcctg gccatgccgc 900
gaaagccatg tccgcggtgg ccgtggcggc tgctgctgct gctgctaccc agcatgctgc 960
tgctctggcc ggcgccggag ctactgctgc tgctggcctc gctgtcaatc ggcaccggca 1020
gccggggaag agctatgcca cgggtgcgac tgatccatgc tctctgcaat atagcaggga 1080
actggcgaac aaactgtcga acgagagcga aaacatgcag gactctgaca atgtctcgat 1140
gctgacttcc atgaacacag gaaacactgc aggcagcgtg tttccgttct cgaaacagaa 1200
cactgctctt ttcgaagtga gcagctcaag gccagagttt ggccttgttc catcggattc 1260
actgacgagt tcacctcata gttccttgaa gagtgtcaaa aatctgctca gctcacggag 1320
tctgagtgag caccagagct ccgcctccct gcaacacttt gtggactggc ccaggacgcc 1380
acctgcccag ggaggtcttt catggcccga ggcagaggac atgcccagag ctcagaggtc 1440
ccagctctca gtatccgctc caatggcatc ctccgagcta tcatcggcct ccacatctcc 1500
catccacgac cacgagaagc tgattctgtc acctctcaag ctgggccgcg agtataccccc 1560 atctggcgtc gtcagcgctg cagcgaacag atacgaggtt agccagctag aagcgacctg 1620
ggcgacgatg ttccgcgact cttcgacggg cggcccgttg ggggaggttc tggccaagaa 1680
caacagcaac gcggaagcaa gaggttgccc gtcggcggcg ccacctctaa ccgactacta 1740

-continued

```
ctgctgggat tcaggccacg gcatgcagtc gtcccccgtg ggagttctgc agaggacgac   1800

cgccttcgga tcggtctcca gcagcacggg cagcagccct agggtcgaga accacggcgc   1860

ctgctgcgat ggtaccagca acctgatgga tgatctcggt tcagttgtag tgagacatcc   1920

cagcatccgc ctcttgtgag cccgctgggt tctggccatg gaaaaagcgt gagggggagc   1980

atttaccacg tagtttgtca tttgagactg atctcctgtt tctgtcacct gagttcttct   2040

tttgttgccc ttatacctgg ctttgtaact ctcaccttcg ttggat                  2086


<210> SEQ ID NO 23
<211> LENGTH: 2328
<212> TYPE: DNA
<213> ORGANISM: Zea mays

<400> SEQUENCE: 23

aggggcaagc tataatttg ttctgttgtc cagaacagcc aacaggtgtg gggctgtggg      60

cattcaattg cttttgcttc ctccgttccc ccatctggcc atctcccctt cccctgctcc    120

cccgaagcag caagccagcc tgcccacccg cagccatcac ctccgccgct ctccaccatg    180

aatcccatcc accagcacgg catcgtaccc aatccttcgt gactgttgcc tccgcgcatc    240

tccgggagca atggaaggag gccgagatgt gttcttaggt gcggcggcaa gggcgccgcc    300

gccgccgccg tcttgcccgt ttcacggatc cgctaccgcc acccgctccg gtggagcgca    360

gatgctcagc ttctcctcca atggcgtagc agggttgggt ctgtgctcag gtgccagcaa    420

gatgcagggt gtgttgtcga gggtgaggag gcccttcact ccgacgcagt ggatggagct    480

ggagcaccag gccctgatct acaagcactt cgctgtgaat gcccctgtgc cgtccagctt    540

gctcctccct atcaaaagaa gcctcaatcc atggagcagc cttggctcca gctcattggg    600

atgggcacca tttcgttccg gctctgctga tgcagaacca ggaagatgcc gccgcacaga    660

tggcaagaag tggcggtgct ctagagatgc tgtcggggac caaaaatact gtgagcgaca    720

cataaaacgt ggttgccacc gttcaagaaa gcatgtggaa ggccgaaagg caacaccgac    780

cactgcagat ccaaccatgg ctgtttctgg tggttcattg ttgcacagcc atgctgttgc    840

ttggcagcag cagggcaaaa gctcagctgc taatgtgact gatccattct cactagggtc    900

caacaggtga agtcacctga tcgtctgatc ctgcattgtt atactcattt ctgccactta    960

agtttgtgaa tttttatttt ctcaacattt ttttctcgaa cacgcaggag aactgtgcat   1020

catatattaa aagaagtaaa aaagtctaaa gaagaccaaa atctgccata agaggcagaa   1080

agagatagga agtgggaggg gcaccagcac actatatttt ctcaacataa atgacaatct   1140

atggttgata catgtgccag tctagcagtc agggttcagg acgtaccaaa acattgaaaa   1200

tgttatatcc tttagacatt gaaattttgt ccatagccat tcatagttga aaattttgtt   1260

cttgatttct ttcaactggt cagtgatttc ttcatgtaac ctgtcattga tgcattccat   1320

cttttgcccc gtgcccattc ctatatataa gattttatta ttatgtttgt ttgttcaaac   1380

aattatggta agcatgtgca aagaaaggca gtaggaagca ctataaataa ctgaaatgat   1440

atggtactta tgtcagtaca aactttagag ataggtgaat tctgttcatg atgacccttt   1500

caaattttga cgacttacta tagtcagcag tgaaagaaaa acaggacagt gtttcctttt   1560

ccttccatga acttgaaatg ttgactctgg tttgcaggaa tttgctggat aagcagaatc   1620

taggtgacca gttctctgta tccacttcca tggactcctt tgacttctca tcatcacatt   1680

cttccccaaa ccaagccaaa gttgcatttt caccggtggc catgcagcac gaacatgatc   1740

agctgtatct tgtgcatgga gccggcagct cagcagaaaa cgttaacaag tctcaggatg   1800
```

gtcagctgct agtctcgagg gaaacaattg acgacggacc tctgggcgag gtgttcaagg 1860
gcaagagttg ccagtcagca tccgcagaca tcttaactga ccattggact tcgactcgtg 1920
acttgcgtcc tccaaccgga gtcctacaaa tgtctagcag caacacagtg ccagcagaga 1980
atcacacgag taacagtagc tatctcatgg cgaggatggc gaattctcag accgtcccaa 2040
cactccactg agtgttcatc aggctggtct ttgttgggac cacaaaataa ctgaagccat 2100
gttgatgtcc tgagtttgct gatactaggt tttcagtcga gtcttgtaac tcctgtttta 2160
gagctgttat atgttcacgt catgtcgcct ttcattttcg gttcattcag atgggtgttc 2220
taataatttc tttccttctt acctgtgaag gatttgagtt ccaatctgag acgtgggttt 2280
gttctaactt ggaggtattt atgaatatta ggcacttctg atttccat 2328

<210> SEQ ID NO 24
<211> LENGTH: 2279
<212> TYPE: DNA
<213> ORGANISM: Zea mays

<400> SEQUENCE: 24
gagagagaga gaactagaag catatatggc gatgcccttt gcctccctgt ctccggcagc 60
cgaccaccgc ccctcctccc tcctccccta ctgccgcgcc gcccctctct ccgcggtggg 120
agaggacgcc gccgcgcagg cgcaacagca gcagcagcac gctatgagcg gcaggtgggc 180
agcgaggccg ccggcgctct tcaccgcggc gcagtacgag gagctggagc accaggcgct 240
tatatacaag tacctcgtcg ccggcgtgcc cgtcccgccg gacctcctcc tcccccctacg 300 ccgaggcttc gtctaccacc aacccgcccg taagcaagca cggcccccgc gccgcctccg 360 cacccccttca cactcacacg cacgtttaac cgcttttgca ctgcacaacc ccggccgccc 420
ggcggcggcg tccgtgcctt gatctggttg tttactcgga tcgagggatt cagatgtcct 480
ctccgtccgt ttgttaatcg gctccggtca tttcttaatc tcgtcctgga ttcggtcacg 540
aaaagctaga ggtcaagatt ttgctctcga ttactatatc cttgcctcat gttctaatgg 600
agtttatttt attggtctga tgtgattaga taggatgcta gccaggcttg tctccggcca 660
aaagcggcgg tttagtttat tgatgattgc ttctttcctt gggggattta ttcctgtctg 720
gttgttggga gcctaaccac gctcctattg ctgctgcggt ttactaacca tctgcgccag 780
tacacctact ccatggaccc caaaatacag ttcttccaac cattcccccc ctccatctgc 840
tttctcgcgg gcaaataaaa acgtgtagaa cgacggtgta gtaggcagat ctactccttg 900
tgccgctacg ctagcccgct accgaagatc gggcccgttt caaccggttc gttggtctga 960
gcggagctaa gatggggcgc atttcatttt ttggtccttt cgtctgattg gagaagtgcc 1020
cattccggta tcgctccccg gcctccaaat acgcaccgac acagaacgtg ttcgtacgca 1080
cgtacacatg gtatgcgcac cgtgctgctg gccatagccg ttgactcacc gggattcact 1140
cctctctcgc gtgtgtgtgt gtggcttcct tgcagttggg tacgggccct acttcggcaa 1200
gaaggtggac ccggagcccg ggcggtgccg gcgtacggac ggcaagaagt ggcggtgctc 1260
caaggaggcc gccccggact ccaagtactg cgagcgccac atgcaccgcg gccgcaaccg 1320
ttcaagaaag cctgtggaag cgcagctcgt gcccccgccg cacgcccagc agcagcagca 1380
gcagcaggcc cccgcgccca ccgctggctt ccagagccac cccatgtacc catccatcct 1440
cgccggcaac ggcggcggcg gcggcggggt aggtggtggt gctggtggcg gtggcacgtt 1500
cggcctgggg cccacctctc agctgcacat ggacagtgcc gctgcttacg cgactgctgc 1560

-continued

```
tggtggaggg agcaaagatc tcaggtactc tgcctacggg gtgaagtctc tgtcggacga   1620

gcacagccag ctcttgtccg gcggcggcgg catggacgcg tcaatggaca actcgtggcg   1680

cctgttgccg tcccaaaccg ccgccacgtt ccaggccaca agctaccctc tgttcggcgc   1740

gctgagcggt ctggacgaga gcaccatcgc ctcgctgccc aagacgcaga gggagcccct   1800

ctccttcttc gggagcgact tcgtgacccc gaagcaggag aaccagacgc tgcgcccctt   1860

cttcgacgag tggcccaagt cgagggactc gtggccggag ctgaacgagg acaacagcct   1920

cggctcctcg gccacccagc tctccatctc catccccatg gcgccctccg acttcaacac   1980

cagctccaga tcgccgaatg gaataccgtc aagatgaacc tgagtaacca tgcggacccc   2040

aacatctcag agctgacgac tctttgctgc tggcctggcc tcatcgtacc ttgaggcgtc   2100

aaggaatact tcattaccac tagtatcatg ctcctggatt ttcgaacaat atatatatgc   2160

ttatgtaccg ctatttctct catcttttac acttctttac ccgtttggaa ttgtatgttc   2220

tgcgtggcac ggttgttcat ttgacctttt tggatttgat tgaaagctcc gtttcttgc    2279
```

<210> SEQ ID NO 25
<211> LENGTH: 1790
<212> TYPE: DNA
<213> ORGANISM: Zea mays

<400> SEQUENCE: 25

```
ccaccacaca aacggacaaa cccctgcctc ccaccagaaa agcaagcaga ccacacccac     60

ccgcctctaa accaaccagc ctgtccccat tccccgtccc cggcgatgca cgccagcatc    120

cactccctcc cgtcagcctc ttcttctccc cctgatgagc gctgagttct gtgctgccgc    180

tgctggtgct gtggccatgg agctcggagt cggggatgtg atggggctgc agcaaggcat    240

cgccgccgcc accgggccat cgtccggaga cagcgacctg ggtcttctca agcgagcagg    300

cctcgcccag gcagccacct cctacccctc ccctttcctc gaccaacaga agatgctcag    360

gttctccaag gcggcggcgg ctcacacgtc gccctcaggc ctagacttcg gaggaggccc    420

gagcgagcag gctttcctgc tgtccaggac caagcggccg ttcactccgt cgcagtggat    480

ggagctggag caccaggctc tcatatacaa gtatctcaat gccaaggccc ccataccttc    540

cagcctgctc gtttccatca gcaagagctt caggtcatcc aacagagagc ttgacagact    600

ctctaacgca gtgagctgga ggcctcttta ccaaggctac gcaaacgcag actccgaccc    660

agaacctggg aggtgccggc ggacagacgg aaagaagtgg cggtgctcca aggaggcgat    720

gcctgatcac aagtactgcg agcgccacat caataggaac cgccaccgtt caagaaagcc    780

tgtggaaaac caacctagaa aggccaccaa ggaggtgact accgctgctg ctggctcgtt    840

gccgtgtgcc gggccacaag gtagcttgaa gaaggcaaaa gttaatgact ccaagccagg    900

cactggcagc tattggacag atagcttaaa caggacaatg ctgagcagag agaaggcaaa    960

caaaccgacg gacgacgagt ctttgctgct tagttcgacg aagaacagtc agcccacctt   1020

gtccctgctc actcaactga agcagcagaa caaaccagat aagttaggtc ccacaccgga   1080

aaatgagccg aactcggaca cgatgttgaa agcctggggt ggcagccacc acaagagcat   1140

ttcctccaca cagcgccatg acgctgaatc cctccaatca gtcctccaaa atttcagcct   1200

agcccagaat gacaggttgg agtcagaaaa gaacagatat tctgattccg tgctagtctc   1260

atcggctttc tattctgcag acggtccaca aactacctgc cttacaccta acatgacaca   1320

agtgcagcag gactgcatat caagctcctg ggagatgcct caaggtggac ctctaggcga   1380

gatcttaacg aactccaaga ttagtgagga cttaagcaag tgtggatcta ggtcatatgg   1440
```

ttggctattg aatcttgacc atgcaccatg attcctcaat ccatggagag cttgacatag 1500
atatctcacc acggatgcaa acaatgagtc aggaaaaaag aaggtccaaa tgaccgtact 1560
gtttacccca tgcatgctcg ttatctacat ttgtacttct atttttgtag tattcagctg 1620
ttgaattatc agttcttctg aatctggctg tatcttaaac aaattctagt ttccgtcaaa 1680
tgatatcttg cttgctagat gcttaatgtt tccttttcag cagaaacttc agtggtccat 1740
tttaatcaaa agaaaactgt ttcaagatca agctctagta agcaaagttc 1790

<210> SEQ ID NO 26
<211> LENGTH: 1725
<212> TYPE: DNA
<213> ORGANISM: Zea mays

<400> SEQUENCE: 26
gccgactgca ccccacacca cccccccacc tcagctcacc ttgcgctgcc cctgtgcctg 60
ctgcatgcct gacaccggcg ccatatgcat gatagcggat gatgatacta gcacgtcttc 120
ccgttcccga gctgcctctg acaccagcac aaacctggag actactacta gtattggagt 180
cccctccatt tccacctccc ttgccactga agcgagagct ctcggagccg tcgtcctctg 240
tctctcatcc ttcttcgttg ttgagcaaag cgggctcgag gaggagatga tgctgagcgg 300
gcacggcggc gggaggcgcc tgttcacggc gtcgcagtgg caggagctgg agcaccaggc 360
gctcatcttc aaatacatgg cctccggcgc gcccgtgccg cacgacctcg tcctgccgct 420
ccgcctcgcc accggcgtcg acaccgcgcc ctccctcgcc ttcccgcccc agccttcgcc 480
gtcgctggcg tactggggct gctatggcgc gggggcgccg ttcggccgca aggcggagga 540
cccggagccc gggcggtgcc ggcggacgga cggcaagaag tggcgatgct ccagggaggc 600
ccacggagac tccaagtact gcgagaagca catccaccgc gggaagagcc gttcaagaaa 660
gcctgtggaa gtgacctccc ccgccgccta ccgcccgtcc gcgttctcca tctcgccgcc 720
tcgcgcggcc gacgcgccgc cgccgccgcc gggcctcggc cacccgcagc agcagcatct 780
ccgccacggc gctctctctc cagcaggccg cgcccacgcc gctggcgctc tccagctcca 840
cctcgactcg agcctgcacg cggcgtcgcc gccgccgtcc taccacaggt acgcccactc 900
ccacgctcac tacacgccgc cgccgccgcc gtcgctctac gactacgggc agtccaagga 960
gcttcgggag gcggcggagc tcaggcggcg gcacttccac gcgctcgggg ccgacctgag 1020
cctcgacaag ccgctggccg acgccggggc cgcggagaag cccctgcggc gtttcttcga 1080
cgagtggccg cgggagagag gcgacacgag gccgtcgtgg gcgggggcgg aggacgcgac 1140
gcagctctcc atctccatcc ccgcggcttc gccctcctct gaccacgctg cctctgccgc 1200
cgcgcgatgc cacaacgatg ggagtgatcg gtgcatctcc tagctgcaac tgcaatgcaa 1260
gcctgcaacc gcgtggattg ttgttgattg gtgtagtttc ctagctgcaa ttcaagcctg 1320
caacagcgag cagtgagcag caaatgcgtg gggagggcac gcagctcagg ctgatgcgca 1380
aaatccgaag cgagtcaagc agcaatagga ctctaggtct atgatttgat cttcctttgt 1440
agcagtacgt taccaaaatg ttagctcgtt gttgttcggt gtgacatttt cgttcaggtt 1500
gctcctattg gctgctgcaa ctgcaacgct agctctgtgg cttttgtgtg ctttcagtct 1560
gcggtgcgag ccttgtcagc tcttttccgg tgacccacgc ctttgattcc tttctctgat 1620
tcctctgcgg gctctgtcat tttgatcgtt tgtcacatcc gtggattctt cctcgcggga 1680
ctactcccgt cacgaaatat aaacaaacgc acatggcttt ctttc 1725

<210> SEQ ID NO 27
<211> LENGTH: 2475
<212> TYPE: DNA
<213> ORGANISM: Zea mays

<400> SEQUENCE: 27

```
cacaatcaca cgcgacgcgg caggcgtacg ccgtcgccgc gtctccgtcc gtacccgccg     60
ctggtctcgt ggaccgtgcg gtgggcgggt gcgacgcgac tgtgagagca gcgggggccc    120
ggtcggctct cgtcgcgcgg ctgcagccag cactgcatgc aggcacagca gcagccgcgg    180
acacggcaga ttctgcagcg cgcaccctgc atgctgtcac ggctgtgaat ggcctgcgca    240
gcgctggcag cctgtgccgc cggagaactg tcccagacac tgaccggtac atgtggagaa    300
tcacgtccaa ggcactgacc ggtcgcgctg ccgcgcgtgc cctccttgct tcgctcacct    360
cacacacgtc gtacgcccca cccgcatgct gcacggcacg tcccgtctgc tcctgccagg    420
ctcccatgat gacaccgagc gagcggtacg gaacacagcc tactacagtg tctgacgcct    480
gacggacggg ttagcgtaag cagccagatt cgcgtcccgg agctctcgcc tttgttgacg    540
aggtgagggg ggactgggca cggctgctgc tcggtcgtgc tgcccgttac agtagttgga    600
ggaacgcagc agggccgttg ggtcggagca ccggtgcccg tcgttcgtgt ggtcgatcca    660
atggcccaaa tctcttccgc ggcccaacaa acccacacac gcaggcgcct gcgaggcttg    720
ctcgtgcgac ccacagcagc ctgctgccgg gcgccgccca ctacaaataa aaccccttcc    780
ccatggacgt cgcccaagag actcactgct actcgcgctc ttgccaccgt ctactctcca    840
acccttctgc catccctcgg caccagctcg ctgacgctac cgccacccct accgccaggc    900
cgcatagccg tgctccgctc accttctctc gcgctacagt ctcaagggta gctagccaag    960
ctaccaagct cgtcaggagc gagagaaaga ggccgccggc ggtgcgcggg gatgatgatg   1020
atgagcagcg gccgggcggg cggcggggcc accgcggggc ggtacccgtt cacggcgtcg   1080
cagtggcagg agctggagca ccaggcgctc atctacaagt gcctggcgtc cggcaagccc   1140
atcccttcct acctcatgcc gccgctccgc cgcatcctcg actccgccct cgccacgtcg   1200
ccgtccctcg cctacccgcc gcaaccctca ctgggctggg gctgcttcgg gatgggcttc   1260
acccggaagg ccgacgagga cccggagccc gggcggtgcc ggcgcacgga cggcaagaag   1320
tggcgctgct ccaaggaggc gtacccggac tccaagtact gcgagaagca catgcaccgg   1380
ggcaagaacc gttcaagaaa gcctgtggaa atgtccttgg ccacgccggc cccggcgccg   1440
gcccccgccg ccgccacaac cgccaccgcc acctcatccc cggcgccgtc ctaccaccgc   1500
ccggcccacg acgccacgcc gtctccgtac cacgcgctgt atggaggcgg cggcggcggc   1560
ggcggtagcc cttactcggc gtcggcacgc ccaggagcaa ccggaggcgg cggcgcgtac   1620
caccacgcgc agcatgtgag cccccttccac ctccacctcg agaccaccca cccgcacccg   1680
ccgccgccct acaactactc cgccgaccag agggactacg cgtacgggca cgcggccgcc   1740
aaggaggtcg gcgagcacgc cttcttctcg gacggcgcgg gcgagcgggt cgaccggcag   1800
gccgcggcgg ggcagtggca gttcaggcag ctcggggtgg agacgaagcc gggccccacg   1860
ccgctgttcc ccgtcgccgg gtacgggcac ggcgcggcgt cgccgtacgg cgtggagatg   1920
ggcaaggacg acgacgagca ggaggagagg cgccgccagc actgcttcgt tcttggagcc   1980
gacctgcggc tggagcggcc gtcgtcgggc catggccatg gccatgacca tgacgacgcc   2040
gccgccgcgc agaagccgct ccggcccttc ttcgacgagt ggccgcacca gaagggggac   2100
aaggccgggt cgtggatggg gctcgacggc gagacgcagc tctccatgtc catccccatg   2160
```

gccgccaccg acctccccgt cacctcccgc ttccgtaacg gtgggcacta cgagtgatgc 2220
cacatcaaac ctggcgctgg aaactcggaa cgtatggtgc tgatgctgac catgagatgt 2280
accgtttcgc tcaaggccgg ccgtcatcac cacggccaca tcaaaccggt ttgaagaact 2340
tgggaaggcc gaatgaaacc tccagaagaa tgatctgtcc tctttttctc cattttcttt 2400
tttcttttag tattactctg tattgcttcg cgtgtaatat gttttcctgt aatatcaagt 2460
gagggcgttt ctgaa 2475

<210> SEQ ID NO 28
<211> LENGTH: 1539
<212> TYPE: DNA
<213> ORGANISM: Zea mays

<400> SEQUENCE: 28
atgatgctga gcgggcacgg cggcgggagg cgcctgttca cggcgtcgca gtggcaggag 60
ctcgagcacc aggcgctcat cttcaagtac atggcctcgg gcgcgcccgt gccgcacgac 120
ctcgtcctac cgctccgcct cgccaccggc gtcgacaccg cgccctccct cgccttcccg 180
ccgcagcctt cgccgtcgcg tacgacctgc gcgcttctct cctcccgacc cgacctcccc 240
cgtcctcgcc tcatgtttca ctctgatcat cgacagccat cagcccatca catcatcgct 300
gatgactttg tacgtgtgac cgtgcatgca gtggcgtact ggggctgcta cggcgcgggg 360
gcgccgttcg gccgcaaggc ggcggaggac acggagccgg ggcggtgccg gcggacggac 420
ggcaagaagt ggcggtgctc cagggaggcc cacggcgact ccaagtactg cgagaagcac 480
attcaccgcg ggaagagccg ttcaagaaag cctgtggaag tgacctcctc ccccgccgcc 540
ggccccgctg cggcgtaccg accgtccgcg atctccacca tctcgccgcc ccgcgcggcc 600
gacgcgccgc cgccgagcct cgcctacccg cagcagcatc tcctccacgg cgcctcctcc 660
gcagcaggag cagcagcccg cgtccccgct ggcgctctcc agctccacct cgacgcgagc 720
ctgcacgcgg cggcggcggc ggcgtcgcca tcgccgccgc cgtcctacca caggtacgcc 780
cactacacac cgccagcgtc gtcgctcttc ccgggcggcg gctacggcta cgactacgac 840
tacgggcagt ccaaggagct caggcgacgg cacttccacg cgctcggggc cgacctgagc 900
ctcgacaagc cgctgcccga gcccgacacc ggctccgacg agaagcagcc cctgcggcgt 960
ttcttcgacg agtggccgcg ggagagcggc gacatggccg cggacgacgc gacgcagctt 1020
tccatctcca tccccgcggc ttcgccctcc gacctcgctg ctacctccgc ctccgccgcc 1080
gccgcgcgat tccacaacgg ggagtgatcg gtccatctcc tagctgcagc cctgcaacag 1140
cgtggattga ccgctgcatt tcctggctgc aatgcaagcc tgcaacagcg agcagtaagc 1200
cagtgacgtg gatgcatctc gtagcggcaa accctgcttc tgcctctgcg gtctgcgctg 1260
ctttgcgcgg gacggctcag ggctgaggc tcaaaaaagt ctgaaccgag tcaagcagta 1320
ctagggactc tatgacttgg tcttttgttc ttttgtagca gtacgttact cgtaccaaat 1380
gttgtttatt ttttgtgtga cattttcatt tcttccagtt ccagtctgtg atgcaagctt 1440
tgtcgctttt gtcagctctt tttcggtgac ccacgccggc cttcgtgatc gattccctta 1500
tacttatacc tgattcctct gccatattga tcgtttgtc 1539

<210> SEQ ID NO 29
<211> LENGTH: 1619
<212> TYPE: DNA
<213> ORGANISM: Zea mays

<400> SEQUENCE: 29
ggaaccctcc cgtgtcgacc tcaccccacc gcgcagccct gcacggccgc ggtcgcctat 60
aaggctagcc cagccagtgg tagcacgcac agcacagcag ccgccctgct cggcgtagga 120
gcagcccaga gcgagcgaga cagagggaaa gagacacggc cagccaggta aggcaaaaga 180
gagagggcgg aagcagcggc agagcggaga gggagagaga agagcatata tgggcatggc 240
gatgcccttt gcctccccgt ctccggcagc cgaccaccgc ccctcctccc tcctcccctt 300
ctgccgcgcc gcccctctct ccgcggcggg ggaggacgcc gcgcagcagc acgcgatgag 360
cggcaggtgg gccgcgaggc cggcgctctt caccgcggcg cagtacgagg agctggagca 420
ccaggcgctc atatacaagt acctcgtcgc cggcgtgccc gtcccgccgg acctcctcct 480
ccccctgcgc cgaggcttcg tcttccacca gccacccgcc cttgggtacg ggccctactt 540
cggcaagaag gtggacccgg agcccgggcg gtgccggcgt acggacggca agaagtggcg 600
gtgctccaag gaggccgccc cggactccaa gtactgcgag cgccacatgc accgcggccg 660
caaccgttca agaaagcctg tggaagcgca gctcgcgccc ccgccgcacg cccagccgca 720
gcagcagcag caggcccccg cgcccgctgc tggcttccag aaccactcgc tgtacccgtc 780
gatcctcacc ggcaacggcg gcggcggggt aggtgctggt gctggtggtg gcacgttcgg 840
cctggggccc acctctcagc tgcacatgga cagtgccgct gcctacgcga ctgctgccgg 900
tggagggagc aaatatctca ggtactctgc atacggggtg aaatctctgt cggacgagca 960
cagcacgctc ttgtcgggcg gcatggatcc gtcgatgatg gacaactcgt ggcgcctgct 1020
gccatcccaa accaacacat tccaagccac aagctaccct gtgttcggca cgctgagtgg 1080
gctagacgag agcaccatcg cgtcgctgcc gaagacccag agggagcccc tctctttctt 1140
cggcagcgac ttcgtaaccg ccgccaagca ggagaaccag acgctgcgcc ctttcttcga 1200
cgagtggccc aagtcgaggg actcgtggcc ggagctgggc gaggacagca gcctcggctt 1260
ctcggccacc cagctctcca tctccattcc catggcgacc tccgacttct ccaacaccag 1320
ctccagatcg ccgggtggaa taccgtcgag atgaacgagt accgtgcatg tggatcccag 1380
cgtcttaggg ttgacgactc ttcggtgctg gcctcgtcgt atcatgctcc taaattttcg 1440
aacgatatat gccttatgta acgctatttc tctcattgtt acaacaccct ttacccgttt 1500
ggaattgtgt tgaagtggat ggtctgcgtt gctcggttgt tcattcgacc ttttttcaat 1560
ttggaaactc cgtttctttg tactcagtga tctgtgcaag tgcaatgatt cggtccatg 1619

<210> SEQ ID NO 30
<211> LENGTH: 1750
<212> TYPE: DNA
<213> ORGANISM: Zea mays

<400> SEQUENCE: 30
cgcgatccaa gcctgccact acaaataaaa ctcccttccc catgaagctc acctaagtgc 60
ttcactcact cctgtcctct cctctcgacc agctgacctc gctgacggag cacacagcca 120
cgccgcagcg ccgcgtgggt gtctgtctat agccttgtag gtcgttcgca ggtaggtaac 180
cgtaacctag ctagctcgtc gggatgatga tgatgagcgg tcgagcggcc accgcggggc 240
ggtacccgtt cacggcgtcg cagtggcagg agctggagca ccaggcgctc atctacaagt 300
gcctggcgtc cggcaagccc atcccgtcct acctcatgcc accgctccgc cgcatcctcg 360
actccgccct cgccacgtcg ccgtcgctcg ccgccttccc gccgcaaccc tcgctggggt 420 ggggggctg cttcgggatg ggcttcagca ggaagcccgc cgacgaggac ccggagcccg 480

-continued ggcggtgccg gcgcacggac ggcaagaagt ggcgctgctc caaggaggcg tacccggact 540
ccaagtactg cgagaagcac atgcaccggg gcaagaaccg ttcaagaaag cctgtggaaa 600
tgtccttggc cacgccggcg ccggcctcct ccgccacaag cgccgccgcc gccgccacct 660
cctcgtccca ggcgccgtcc taccacagcc cggccccgc cgtgccgtac cacgcgccct 720
acggcgccgc gtaccatcac acgcagacgc aggtgacgat gagccccttc cacctcctcc 780
acctcgagac cacccacccg cacccgccgc cgccgccgcc gccgccctac tactacgcgg 840
accagaggga ctacgcctac ggcaaggagg tcggcgagcg cgccttcttc tccgacggcg 900
cgggcgagag ggaccggcag cagcaggccg cggggcagtg gcagttcaag cagctcggga 960
cgatggaggc gacgaagcag ccgtgcacca cgccgctgct cgtccccgcc gccgggtacg 1020
gccacggcgc ggcgtcgccg tacggcgtcg gtcaggccaa ggaagacgag gaggaggagg 1080
aaacgcggcg gcagcagcag cactgcttcg ttcttggcgc cgacctgcgg ctggcggagc 1140
ggccgtcggg ggcacatgac gccgccgcgc agaagccgct ccggcatttc atcgacgagt 1200
ggccgcacga gaaggggagc aataaggcgg ggtcgtggat ggggggctc gacggcgaga 1260
cgacgcagct ctccatgtct atcccgatgg cggccgctgc cgacctcccc gtcacctccc 1320
gctaccgtac gtgatggcgg cgcgcactat gagtgattgc cagcaagaaa tgttttgtgg 1380
ttgctgcgac ctcgaggtgg cgaggccaca tgaaaaaaa atactggagc tggaacacga 1440
gtggttcttt cctgtgccgt tttgctcagg gccggtcggc acggtttgaa gaagttggga 1500
agagaagtaa aataaacctc cttgggagtg ttacgtttcc tgtaattgct tgcttccttt 1560
gctgtacctg tgagacgacg cttagtgcta gaagtgaggg cctttcctga tctcagctct 1620
ggtctggatt tgccttttcc cgctgtcgga ttcctctgcc tgtctgtgat ggtttgtctg 1680
tgatggtttg tgctcagagc ctgcagcgaa tactaaaccg cagtaattaa tcaccatgct 1740
tcacccgaca 1750

<210> SEQ ID NO 31
<211> LENGTH: 852
<212> TYPE: DNA
<213> ORGANISM: Zea mays

<400> SEQUENCE: 31
cttcttccct cctctcgaga agctgcctgc tacccgcgcg ctgcctctcc cttccactcc 60
ataccatacc gccacgacaa cgtcgacaag cgcaataccg gagccctccg aaatggccga 120
ggacaaggag accgactcgc cgcagccgcc ggccaagctg ccccgcctct cccgcgccga 180
cacgagcgcc ggagaggtga ccatggcggc ctcgtcgccg ctggttcttg ggctggggct 240
gggcctcggc gggcgcggcg gcggcggcga gcgagacgcg gatgtgtccc ccgcgacggt 300
gactcccaag aggccgtcgg cgctgacgtt catgcagcag caggagctgg agcaccaggt 360
gctcatctac cgctacttcg ccgcgggcgc gccggtgccg gtgcacctgg tgctccccat 420
ctggaagagc gtcgccgcgt cctccttcgg cccgcagcgc tttccctcgc tgatgggcct 480
gggcagcctg tgcttcgact accgcagcag catggagccg gagcccgggc ggtgccggcg 540
cacggacggc aagaagtggc ggtgctcccg cgacgtggtg ccgggccaca agtactgcga 600
gcggcacgtc caccgcggcc gcggccgttc aagaaagcct gtggaagccg ccgcggcacc 660
ggcggcggcg gccggcggca gcagccccgt cctccgggtc gccgcgcccc agcacgtgct 720
cggcctctcc tcgcccacca gcgtcctcct cgcccacggc gccgcgcgtg ccacgtgagt 780
agcgcgccgc cgcgggccga ccgatggtgc cgtggtctac tggtcttggg cctcggaatc 840
acgaggggca aa 852

<210> SEQ ID NO 32
<211> LENGTH: 1725
<212> TYPE: DNA
<213> ORGANISM: Zea mays

<400> SEQUENCE: 32
gccgcccagc gcccacccac acccctgcct cccaggctcc cactacctgt ccccaacaat 60
gcacaccaac atccactctc tcgtcaggct cctctccccc aaaaatgagc gctgagttct 120
gcgctgctgc cggtgtcgtg gccatggagc tcggagtcgg agatgtgctg gggctgcagc 180
aaggcatcgc aatcaccgcg ccatcgccca gggacagcga cctgggtctt ctcaagcgag 240
caggcctcac ccaggctgcg gctgctgccc cctacccctc cccettcctt gacgaggaga 300 agatgctcag gttctccaag gcggctcaca cattgcactc aggcttggat tttggaggcc 360
caggtgagca ggctttcctg ctgtccagga ccaagatgcc atttactccc tcgcagtgga 420
tggagctgga gcaccaggct ctgatataca agtacctcaa tgcaaaggcc cccccatacc 480
ttccagcctg ctcatttcaa tcagcaagag cttcagatca tccaatagag agcttgacag 540
acttctctaa cgcagtgagc tggaggcctc tgtatcaagg ctacacaaat gcagactctg 600
acccagaacc tgggagatgc cgacgaacgg atggaaagaa gtggcggtgc tccaaggaag 660
caatggctga tcacaagtac tgtgagcggc acatcaacag aaaccgtcac cgttcaagaa 720
agcctgtgga aaatcaacct aagaagacca ccaaggaggt gcctgctgct gctggctcat 780
tgccatgtgc tgggccacaa ggtagcttga agaaggcaaa agttaatgac tccaagccag 840
gcactgtcag ctattgggca gatagtttaa acaggacaat gttgagcaga gagaaagcaa 900
acaaaccgac ggaagatagc tctttgctgc ttacttctac gaacagccaa cccaccttgt 960
ccctgctctc tcagctgaag cagcaaaaca aaccagataa gttaggcccc acactggaaa 1020
atgagtcaaa cccagacaca atattgaaag cctggggtgg caaccagcct agccacaaga 1080
gcatttcctc tacagagcgc catgatgctg aatccctcca atcagtcctt caaaatttca 1140
gcctagccca gaatgagaag atggagtcag aaaagaacaa atattctgat tccgtgctag 1200
tttcgtcgac tttctattct gcagacggtc caagagctac ctgccttaca cctaacatga 1260
cacaggtgaa gcaggattgc atatcaagct cttgggagat gcctcaaggt ggacctctag 1320
gcgaaatctt aacgaactcc aagaatagca aggacttaag caagtgtaaa ccaaggtcat 1380
atggttggtt gttgaatctt gaccatgcac catgattcct caatccatga agagcttgac 1440
atagatatcc catcatgtag gcaaacaatg gtcagaaaaa ggttatgacc acattgcttg 1500
ccccatgcat gcttgctatc tacatttgta tttctgttac gtagcattta gctagttgaa 1560
ttatcagttc ttctggatac ggctgtatct taaacaagtt ctagtttgtg tcagatgata 1620
tcttgcttgc tagatgtttc atgttccact ttcaacagga acttcagaca accactttga 1680
ttgacagaaa actgtttgaa gaaccagctc tagtaaacaa ggttc 1725

<210> SEQ ID NO 33
<211> LENGTH: 1668
<212> TYPE: DNA
<213> ORGANISM: Zea mays

<400> SEQUENCE: 33
aaatccaaag cgagcagatc ccccgcccct aaccgactcc cctcgcttcc attccattaa 60

```
tggccgccac caagagccct ccaacacaca cctgacctcc ccttcccccc tctctccgcc    120

gcccgttccc cgcgcctccg cccgtacgtc ccgttcccgg tcggccggcc ggtccaaagg    180

gaggggagga ggaggaacgc gggagtcggg gcccgcaccg atgctgagct cggcatcctc    240

ggccgcggga gcggccatgg ggatgggcgg cggcgggtac gcgcaccagc ccccgccaca    300

gcgcacggtc ttcaccgccg cgcagtgggc ggagctggag cagcaggcgc tcatctacaa    360

gtacctcatg gccggcgtcc ccgtcccgcc cgacctcctc ctccccgtcc gccccggccc    420

cgccgccgcc ttctccttcg ccggccccgc cgccgcgtcg cccttctacc accaacacca    480

cccgtccctg agctactacg cctactacgg caagaaactg gacccggagc cgtggcggtg    540

ccgccgcacc gacggcaaga agtggcggtg ctccaaggag gcgcaccccg actccaagta    600

ctgcgagcgc cacatgcacc gtggccgcaa ccgttcaaga aagcctgtgg aatccaagac    660

cgcctcgtcg tcgtcgcccg cgcacccgtc gccgccccag ctgtccaccg tcaccaccac    720

cgcgcctctc gagccccttg cagcggcggg gggcaaggtc cacggcctgt ccctcggcgg    780

cggcgctgct ggctcgtcgc acctcggcgt cgatgcttcg aatgctcact atcgttatgg    840

tagcaacagg taccctctcg gagctaaacc ggacggcggc gagttgagct tcttctcagg    900

agcgtcatcg gggaacaact cgaggggcgg cttcaccatc gactctccat cagataacaa    960

ctcgtggcac tccgccctgg cgtccagcgt gcccccgttc acgctgtcga cgaagagcgg   1020

ggactccggc ctcctgcccg gcgcctacgc ctcctactcc cagtcccact cccacatgga   1080

gccgccgcgg gagctcgggc aggtcaccat cgcctcgctg gcgcaggagc aggagcgcca   1140

gcagccgttc agtggtggga tgctcgggaa cgtgaagcag gagaaccaga accagccgct   1200

gcggcccttc ttcgacgagt ggcccgggac gcgggcggac tcgtggccgc cggagatgga   1260

cggcgcgccg cgggccggca ggacctcctt ctcctcctcc accacccagc tctccatctc   1320

catcccgatg cccagatgcg actgacgagg aaccgtcgat cgggcggcca ctagacggtg   1380

gacgctcacg ctcactagtg cgctgtcgcc tggagtggag atcgatcgtc acgccgccgc   1440

cgcctacgcc ctcgtcctac ctatttgttt tgccgtagtg tattgtaccg acctcattaa   1500

gaacagaaca gaacagaagt ctctgtgtaa gagccggctc cttcctgttc ctatggtttg   1560

tactagtagc gtgctttgta tttgttgtac ccctcaagac cgagaatgaa acccgcccgc   1620

cgtcagtctg tctttgcgtt ttagtagatg atgcgagtgt ttcgtgtg                1668
```

<210> SEQ ID NO 34
<211> LENGTH: 27
<212> TYPE: DNA
<213> ORGANISM: Artificial sequence
<220> FEATURE:
<223> OTHER INFORMATION: Synthetic binding site of GRF5

<400> SEQUENCE: 34

```
aaccgttcaa gaaagcctgt aaaaacg                                          27
```

<210> SEQ ID NO 35
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 35

```
aaccgttcaa gaaagcctat aaaaacg                                          27
```

-continued

<210> SEQ ID NO 36
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 36
aaccgttcaa gaaagcctgt caaaacg 27

<210> SEQ ID NO 37
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 37
aaccgttcaa aaaagcctat aaaaacg 27

<210> SEQ ID NO 38
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 38
aaccgttcaa gaaagcctct caaaacg 27

<210> SEQ ID NO 39
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 39
aaccgttcaa gaaagcctgt acaaacg 27

<210> SEQ ID NO 40
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 40
aaccgttcaa aaaagcctgt ggaaacg 27

<210> SEQ ID NO 41
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 41
aaccgttcaa aaaagcctgt aaaaacg 27

<210> SEQ ID NO 42
<211> LENGTH: 9
<212> TYPE: PRT
<213> ORGANISM: Zea mays

<400> SEQUENCE: 42

Asn Arg Ser Arg Lys Pro Val Glu Thr
1 5

<210> SEQ ID NO 43
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 43

Asn Arg Ser Arg Lys Pro Val Lys Thr
1 5

<210> SEQ ID NO 44
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 44

Asn Arg Ser Arg Lys Pro Ile Lys Thr
1 5

<210> SEQ ID NO 45
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 45

Asn Arg Ser Lys Lys Pro Ile Lys Thr
1 5

<210> SEQ ID NO 46
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 46

Asn Arg Ser Arg Lys Pro Val Gln Thr
1 5

<210> SEQ ID NO 47
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 47

Asn Arg Ser Lys Lys Pro Val Lys Thr
1 5

<210> SEQ ID NO 48
<211> LENGTH: 20
<212> TYPE: DNA
<213> ORGANISM: Artificial sequence
<220> FEATURE:
<223> OTHER INFORMATION: Synthetic spacer

<400> SEQUENCE: 48

-continued

```
caaccgttca agaaagcctg                                                   20


<210> SEQ ID NO 49
<211> LENGTH: 20
<212> TYPE: DNA
<213> ORGANISM: Artificial sequence
<220> FEATURE:
<223> OTHER INFORMATION: Synthetic spacer

<400> SEQUENCE: 49

aaccgttcaa gaaagcctgt                                                   20


<210> SEQ ID NO 50
<211> LENGTH: 20
<212> TYPE: DNA
<213> ORGANISM: Artificial sequence
<220> FEATURE:
<223> OTHER INFORMATION: Synthetic spacer

<400> SEQUENCE: 50

cgcaaccgtt caagaaagcc                                                   20


<210> SEQ ID NO 51
<211> LENGTH: 20
<212> TYPE: DNA
<213> ORGANISM: Artificial sequence
<220> FEATURE:
<223> OTHER INFORMATION: Synthetic spacer

<400> SEQUENCE: 51

ctttcttgaa cggttgcggc                                                   20


<210> SEQ ID NO 52
<211> LENGTH: 20
<212> TYPE: DNA
<213> ORGANISM: Artificial sequence
<220> FEATURE:
<223> OTHER INFORMATION: Synthetic spacer

<400> SEQUENCE: 52

ttcttgaacg gttgcggccg                                                   20


<210> SEQ ID NO 53
<211> LENGTH: 20
<212> TYPE: DNA
<213> ORGANISM: Artificial sequence
<220> FEATURE:
<223> OTHER INFORMATION: Synthetic spacer

<400> SEQUENCE: 53

tcttgaacgg ttgcggccgc                                                   20


<210> SEQ ID NO 54
<211> LENGTH: 20
<212> TYPE: DNA
<213> ORGANISM: Artificial sequence
<220> FEATURE:
<223> OTHER INFORMATION: Synthetic spacer

<400> SEQUENCE: 54

ttgaacggtt gcggccgcgg                                                   20


<210> SEQ ID NO 55
<211> LENGTH: 23
<212> TYPE: DNA
<213> ORGANISM: Artificial sequence
```

<220> FEATURE:
<223> OTHER INFORMATION: Synthetic spacer

<400> SEQUENCE: 55
cacaggcttt cttgaacggt tgc 23

<210> SEQ ID NO 56
<211> LENGTH: 20
<212> TYPE: DNA
<213> ORGANISM: Artificial sequence
<220> FEATURE:
<223> OTHER INFORMATION: Synthetic spacer

<400> SEQUENCE: 56
ttgaacggtt gcggccgcgg 20

<210> SEQ ID NO 57
<211> LENGTH: 20
<212> TYPE: DNA
<213> ORGANISM: Artificial sequence
<220> FEATURE:
<223> OTHER INFORMATION: Synthetic spacer

<400> SEQUENCE: 57
cacaggcttt cttgaacggt 20

<210> SEQ ID NO 58
<211> LENGTH: 20
<212> TYPE: DNA
<213> ORGANISM: Artificial sequence
<220> FEATURE:
<223> OTHER INFORMATION: Synthetic spacer

<400> SEQUENCE: 58
tttccacagg ctttcttgaa 20

<210> SEQ ID NO 59
<211> LENGTH: 20
<212> TYPE: DNA
<213> ORGANISM: Artificial sequence
<220> FEATURE:
<223> OTHER INFORMATION: Synthetic spacer

<400> SEQUENCE: 59
tgcgtttcca caggctttct 20

<210> SEQ ID NO 60
<211> LENGTH: 20
<212> TYPE: DNA
<213> ORGANISM: Artificial sequence
<220> FEATURE:
<223> OTHER INFORMATION: Synthetic spacer

<400> SEQUENCE: 60
ttcaagaaag cctgtggaaa 20

<210> SEQ ID NO 61
<211> LENGTH: 20
<212> TYPE: DNA
<213> ORGANISM: Artificial sequence
<220> FEATURE:
<223> OTHER INFORMATION: Synthetic spacer

<400> SEQUENCE: 61
aacggttgcg gccgcggtgc 20

<210> SEQ ID NO 62
<211> LENGTH: 20
<212> TYPE: DNA
<213> ORGANISM: Artificial sequence
<220> FEATURE:
<223> OTHER INFORMATION: Synthetic spacer

<400> SEQUENCE: 62
aagaaagcct gtggaaacgc 20

<210> SEQ ID NO 63
<211> LENGTH: 20
<212> TYPE: DNA
<213> ORGANISM: Artificial sequence
<220> FEATURE:
<223> OTHER INFORMATION: Synthetic spacer

<400> SEQUENCE: 63
tgaacggttg cggccgcggt 20

<210> SEQ ID NO 64
<211> LENGTH: 20
<212> TYPE: DNA
<213> ORGANISM: Artificial sequence
<220> FEATURE:
<223> OTHER INFORMATION: Synthetic spacer

<400> SEQUENCE: 64
ttgaacggtt gcggccgcgg 20

<210> SEQ ID NO 65
<211> LENGTH: 20
<212> TYPE: DNA
<213> ORGANISM: Artificial sequence
<220> FEATURE:
<223> OTHER INFORMATION: Synthetic spacer

<400> SEQUENCE: 65
acaggctttc ttgaacggtt 20

<210> SEQ ID NO 66
<211> LENGTH: 20
<212> TYPE: DNA
<213> ORGANISM: Artificial sequence
<220> FEATURE:
<223> OTHER INFORMATION: Synthetic spacer

<400> SEQUENCE: 66
cacaggcttt cttgaacggt 20

<210> SEQ ID NO 67
<211> LENGTH: 20
<212> TYPE: DNA
<213> ORGANISM: Artificial sequence
<220> FEATURE:
<223> OTHER INFORMATION: Synthetic spacer

<400> SEQUENCE: 67
agaaagcctg tggaaacgca 20

<210> SEQ ID NO 68
<211> LENGTH: 20
<212> TYPE: DNA
<213> ORGANISM: Artificial sequence
<220> FEATURE:
<223> OTHER INFORMATION: Synthetic spacer -continued

<400> SEQUENCE: 68
gaaacgcagc tcgcgcccca 20

<210> SEQ ID NO 69
<211> LENGTH: 20
<212> TYPE: DNA
<213> ORGANISM: Artificial sequence
<220> FEATURE:
<223> OTHER INFORMATION: Synthetic spacer

<400> SEQUENCE: 69
caggctttct tgaacggttg 20

<210> SEQ ID NO 70
<211> LENGTH: 20
<212> TYPE: DNA
<213> ORGANISM: Artificial sequence
<220> FEATURE:
<223> OTHER INFORMATION: Synthetic spacer

<400> SEQUENCE: 70
acaggctttc ttgaacggtt 20

<210> SEQ ID NO 71
<211> LENGTH: 20
<212> TYPE: DNA
<213> ORGANISM: Artificial sequence
<220> FEATURE:
<223> OTHER INFORMATION: Synthetic spacer

<400> SEQUENCE: 71
agaaagcctg tggaaacgca 20

<210> SEQ ID NO 72
<211> LENGTH: 166
<212> TYPE: PRT
<213> ORGANISM: Escherichia coli

<400> SEQUENCE: 72

```
Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160
```

Ala Gln Ser Ser Thr Asp
165

<210> SEQ ID NO 73
<211> LENGTH: 166
<212> TYPE: PRT
<213> ORGANISM: Artificial sequence
<220> FEATURE:
<223> OTHER INFORMATION: Synthetic tRNA-specific adenosine deaminase Tad

<400> SEQUENCE: 73

Ser Glu Val Glu Phe Ser His Glu Tyr Trp Met Arg His Ala Leu Thr
1 5 10 15

Leu Ala Lys Arg Ala Arg Asp Glu Arg Glu Val Pro Val Gly Ala Val
20 25 30

Leu Val Leu Asn Asn Arg Val Ile Gly Glu Gly Trp Asn Arg Ala Ile
35 40 45

Gly Leu His Asp Pro Thr Ala His Ala Glu Ile Met Ala Leu Arg Gln
50 55 60

Gly Gly Leu Val Met Gln Asn Tyr Arg Leu Ile Asp Ala Thr Leu Tyr
65 70 75 80

Val Thr Phe Glu Pro Cys Val Met Cys Ala Gly Ala Met Ile His Ser
85 90 95

Arg Ile Gly Arg Val Val Phe Gly Val Arg Asn Ala Lys Thr Gly Ala
100 105 110

Ala Gly Ser Leu Met Asp Val Leu His Tyr Pro Gly Met Asn His Arg
115 120 125

Val Glu Ile Thr Glu Gly Ile Leu Ala Asp Glu Cys Ala Ala Leu Leu
130 135 140

Cys Tyr Phe Phe Arg Met Pro Arg Gln Val Phe Asn Ala Gln Lys Lys
145 150 155 160

Ala Gln Ser Ser Thr Asp
165

<210> SEQ ID NO 74
<211> LENGTH: 166
<212> TYPE: PRT
<213> ORGANISM: Artificial sequence
<220> FEATURE:
<223> OTHER INFORMATION: Synthetic tRNA-specific adenosine deaminase Tad

<400> SEQUENCE: 74

Ser Glu Val Glu Phe Ser His Glu Tyr Trp Met Arg His Ala Leu Thr
1 5 10 15

Leu Ala Lys Arg Ala Trp Asp Glu Arg Glu Val Pro Val Gly Ala Val
20 25 30

Leu Val Leu Asn Asn Arg Val Ile Gly Glu Gly Trp Asn Arg Ser Ile
35 40 45

Gly Leu His Asp Pro Thr Ala His Ala Glu Ile Met Ala Leu Arg Gln
50 55 60

Gly Gly Leu Val Met Gln Asn Tyr Arg Leu Ile Asp Ala Thr Leu Tyr
65 70 75 80

Val Thr Phe Glu Pro Cys Val Met Cys Ala Gly Ala Met Ile His Ser
85 90 95

Arg Ile Gly Arg Val Val Phe Gly Val Arg Asn Ala Lys Thr Gly Ala
100 105 110

Ala Gly Ser Leu Met Asp Val Leu His Tyr Pro Gly Met Asn His Arg
115 120 125

```
Val Glu Ile Thr Glu Gly Ile Leu Ala Asp Glu Cys Ala Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165


<210> SEQ ID NO 75
<211> LENGTH: 166
<212> TYPE: PRT
<213> ORGANISM: Artificial sequence
<220> FEATURE:
<223> OTHER INFORMATION: Synthetic tRNA-specific adenosine deaminase Tad

<400> SEQUENCE: 75

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165


<210> SEQ ID NO 76
<211> LENGTH: 166
<212> TYPE: PRT
<213> ORGANISM: Artificial sequence
<220> FEATURE:
<223> OTHER INFORMATION: Synthetic tRNA-specific adenosine deaminase Tad

<400> SEQUENCE: 76

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
```

```
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165


<210> SEQ ID NO 77
<211> LENGTH: 228
<212> TYPE: PRT
<213> ORGANISM: Rattus norvegicus

<400> SEQUENCE: 77

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
            100                 105                 110

Ile Tyr Ile Ala Arg Leu Tyr His His Ala Asp Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225


<210> SEQ ID NO 78
<211> LENGTH: 199
<212> TYPE: PRT
<213> ORGANISM: Homo sapiens

<400> SEQUENCE: 78

Met Glu Ala Ser Pro Ala Ser Gly Pro Arg His Leu Met Asp Pro His
```

-continued

```
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195
```

<210> SEQ ID NO 79
<211> LENGTH: 621
<212> TYPE: DNA
<213> ORGANISM: Petromyzon marinus

<400> SEQUENCE: 79

```
acagatgcag agtatgtgag aattcacgaa aagctggaca tctatacctt caagaagcag     60

ttctttaaca ataagaagtc tgtgagccat aggtgctacg tgctgttcga gctgaagaga    120

aggggtgaaa gaagggcatg tttttggggg tatgctgtga acaagcccca gtctggaact    180

gagagaggca ttcacgccga aattttcagc atcagaaagg tggaggaata cctgagggat    240

aaccctggac agtttacaat taattggtat tctagctggt ctccatgcgc tgactgtgcc    300

gagaagatcc tggaatggta caaccaggag ctgagaggaa atggccatac cctgaagatt    360

tgggcctgca agctgtacta tgaaaagaac gcaagaaatc agatcggact gtggaacctg    420

agggataatg gtgtggggct gaacgtgatg gtgtccgagc actatcagtg ctgtagaaag    480

attttcattc agtcctcaca taatcagctg aacgagaata gatggctgga aaagactctg    540

aagagggctg agaagagaag gtccgaactg tcaattatga tccaggtgaa gatcctgcac    600

accactaagt cacctgccgt g                                              621
```

<210> SEQ ID NO 80
<211> LENGTH: 160
<212> TYPE: PRT
<213> ORGANISM: Artificial sequence
<220> FEATURE:
<223> OTHER INFORMATION: Synthetic polypeptide

<400> SEQUENCE: 80

```
Phe Glu Arg Asn Tyr Asp Pro Arg Glu Leu Arg Lys Glu Thr Tyr Leu
```

-continued

```
1               5                   10                  15

Leu Tyr Glu Ile Lys Trp Gly Lys Ser Gly Lys Leu Trp Arg His Trp
            20                  25                  30

Cys Gln Asn Asn Arg Thr Gln His Ala Glu Val Tyr Phe Leu Glu Asn
        35                  40                  45

Ile Phe Asn Ala Arg Arg Phe Asn Pro Ser Thr His Cys Ser Ile Thr
    50                  55                  60

Trp Tyr Leu Ser Trp Ser Pro Cys Ala Glu Cys Ser Gln Lys Ile Val
65                  70                  75                  80

Asp Phe Leu Lys Glu His Pro Asn Val Leu Glu Ile Tyr Val Ala Arg
                85                  90                  95

Leu Tyr Tyr His Glu Asp Glu Arg Asn Arg Gln Gly Leu Arg Asp Leu
            100                 105                 110

Val Asn Ser Gly Val Thr Ile Arg Ile Met Asp Leu Pro Asp Tyr Asn
        115                 120                 125

Tyr Cys Trp Lys Thr Phe Val Ser Asp Gln Gly Gly Asp Glu Asp Tyr
    130                 135                 140

Trp Pro Gly His Phe Ala Pro Trp Ile Lys Gln Tyr Ser Leu Lys Leu
145                 150                 155                 160


<210> SEQ ID NO 81
<211> LENGTH: 83
<212> TYPE: PRT
<213> ORGANISM: Bacillus phage AR9

<400> SEQUENCE: 81

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu


<210> SEQ ID NO 82
<211> LENGTH: 1592
<212> TYPE: DNA
<213> ORGANISM: Medicago truncatula

<400> SEQUENCE: 82

actgttaata atttttaaac gtcagcgcac taaaaaaacg aaaagacgga cacgtgaaaa      60

taaaaaacac acactagttt atgacgcaat actattttac ttatgatttg ggtacattag     120

acaaaaccgt gaaagagatg tatcagctat gaaacctgta tacttcaata cagagactta     180

ctcatatcgg atacgtacgc acgaagtatc atattaatta ttttaatttt taataaatat     240

tttatcggat acttatgtga tactctacat atacacaagg atatttctaa gatactttat     300

agatacgtat cctagaaaaa catgaagagt aaaaaagtga gacaatgttg taaaaattca     360

ttataaatgt atatgattca attttagata tgcatcagta taattgattc tcgatgaaac     420

acttaaaatt atatttcttg tggaagaacg tagcgagaga ggtgattcag ttagacaaca     480

ttaaataaaa ttaatgttaa gttcttttaa tgatgtttct ctcaatatca catcatatga     540
```

aaatgtaata tgatttataa gaaaattttt aaaaaattta ttttaataat cacatgtact 600 atttttttaaa aattgtatct tttataataa tacaataata aagagtaatc agtgttaatt 660
tttcttcaaa tataagtttt attataaatc attgttaacg tatcataagt cattaccgta 720
tcgtatctta attttttttt aaaaaccgct aattcacgta cccgtattgt attgtacccg 780
cacctgtatc acaatcgatc ttagttagaa gaattgtctc gaggcggtgc aagacagcat 840
ataatagacg tggactctct tataccaaac gttgtcgtat cacaaagggt taggtaacaa 900
gtcacagttt gtccacgtgt cacgttttaa ttggaagagg tgccgttggc gtaatataac 960
agccaatcga tttttgctat aaaagcaaat caggtaaact aaacttcttc attcttttct 1020
tccccatcgc tacaaaaccg gttcctttgg aaaagagatt cattcaaacc tagcacccaa 1080
ttccgtttca aggtataatc tactttctat tcttcgatta ttttattatt attagctact 1140
atcgtttaat cgatcttttc ttttgatccg tcaaatttaa attcaattag ggttttgttc 1200
ttttctttca tctgattgaa atccttctga attgaaccgt ttacttgatt ttactgttta 1260
ttgtatgatt taatcctttg tttttcaaag acagtcttta gattgtgatt aggggttcat 1320
ataaattttt agatttggat ttttgtattg tatgattcaa aaaatacgtc ctttaattag 1380
attagtacat ggatattttt tacccgattt attgattgtc agggagaatt tgatgagcaa 1440
gtttttttga tgtctgttgt aaattgaatt gattataatt gctgatctgc tgcttccagt 1500
tttcataacc catattcttt taaccttgtt gtacacacaa tgaaaaattg gtgattgatt 1560
catttgtttt tctttgtttt ggattataca gg 1592

<210> SEQ ID NO 83
<211> LENGTH: 2000
<212> TYPE: DNA
<213> ORGANISM: Zea mays

<400> SEQUENCE: 83
gtcgtgcccc tctctagaga taaagagcat tgcatgtcta aagtataaaa aattaccaca 60
tatttttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gtttttttttg caaatagctt gacctatata 300
atacttcatc cattttatta gtacatccat ttaggattta gggttgatgg tttctataga 360
ctaattttta gtacatccat tttattcttt ttagtctcta aattttttaa aactaaaact 420
ctattttagt tttttattta ataatttaga tataaaatga aataaaataa attgactaca 480
aataaaacaa ataccccttta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacacccccct ccacaccctc tttccccaac ctcgtgttcg ttcggagcgc 900
acacacacgc aaccagatct cccccaaatc cagccgtcgg cacctccgct tcaaggtacg 960
ccgctcatcc tccccccccc cctctctcta ccttctctag atcggcgatc cggtccatgg 1020

-continued

```
ttagggcccg gtagttctac ttctgttcat gtttgtgtta gagcaaacat gttcatgttc   1080

atgtttgtga tgatgtggtc tggttgggcg gtcgttctag atcggagtag gatactgttt   1140

caagctacct ggtggattta ttaattttgt atctgtatgt gtgtgccata catcttcata   1200

gttacgagtt taagatgatg gatggaaata tcgatctagg ataggtatac atgttgatgc   1260

gggttttact gatgcatata cagagatgct ttttttctcg cttggttgtg atgatatggt   1320

ctggttgggc ggtcgttcta gatcggagta gaatactgtt tcaaactacc tggtggattt   1380

attaaaggat aaagggtcgt tctagatcgg agtagaatac tgtttcaaac tacctggtgg   1440

atttattaaa ggatctgtat gtatgtgcct acatcttcat agttacgagt ttaagatgat   1500

ggatggaaat atcgatctag gataggtata catgttgatg cgggttttac tgatgcatat   1560

acagagatgc ttttttttcgc ttggttgtga tgatgtggtc tggttgggcg gtcgttctag   1620

atcggagtag aatactgttt caaactacct ggtggattta ttaattttgt atctttatgt   1680

gtgtgccata catcttcata gttacgagtt taagatgatg gatggaaata ttgatctagg   1740

ataggtatac atgttgatgt gggttttact gatgcatata catgatggca tatgcggcat   1800

ctattcatat gctctaacct tgagtaccta tctattataa taaacaagta tgttttataa   1860

ttattttgat cttgatatac ttggatgatg gcatatgcag cagctatatg tggatttttt   1920

agccctgcct tcatacgcta tttatttgct tggtactgtt tcttttgtcc gatgctcacc   1980

ctgttgtttg gtgatacttc                                                 2000


<210> SEQ ID NO 84
<211> LENGTH: 22
<212> TYPE: RNA
<213> ORGANISM: Zea mays

<400> SEQUENCE: 84

uuccacaggc uuucuugaac ug                                                22


<210> SEQ ID NO 85
<211> LENGTH: 21
<212> TYPE: RNA
<213> ORGANISM: Zea mays

<400> SEQUENCE: 85

uuccacagcu uucuugaacu u                                                 21


<210> SEQ ID NO 86
<211> LENGTH: 21
<212> TYPE: RNA
<213> ORGANISM: Zea mays

<400> SEQUENCE: 86

guucaagaaa gcuguggaag a                                                 21


<210> SEQ ID NO 87
<211> LENGTH: 21
<212> TYPE: RNA
<213> ORGANISM: Zea mays

<400> SEQUENCE: 87

guucaauaaa gcugugggaa a                                                 21


<210> SEQ ID NO 88
<211> LENGTH: 21
<212> TYPE: RNA
<213> ORGANISM: Zea mays
```

<400> SEQUENCE: 88
uuccacagcu uucuugaacu g 21

<210> SEQ ID NO 89
<211> LENGTH: 21
<212> TYPE: RNA
<213> ORGANISM: Zea mays

<400> SEQUENCE: 89
uuccacagcu uucuugaacu u 21

<210> SEQ ID NO 90
<211> LENGTH: 21
<212> TYPE: RNA
<213> ORGANISM: Zea mays

<400> SEQUENCE: 90
guucaauaaa gcugugggaa a 21

<210> SEQ ID NO 91
<211> LENGTH: 21
<212> TYPE: RNA
<213> ORGANISM: Zea mays

<400> SEQUENCE: 91
ucccacagcu uuauugaacu g 21

<210> SEQ ID NO 92
<211> LENGTH: 21
<212> TYPE: RNA
<213> ORGANISM: Zea mays

<400> SEQUENCE: 92
ggucaagaaa gcugugggaa g 21

<210> SEQ ID NO 93
<211> LENGTH: 21
<212> TYPE: RNA
<213> ORGANISM: Zea mays

<400> SEQUENCE: 93
ucccacagcu uuauugaacu g 21

<210> SEQ ID NO 94
<211> LENGTH: 21
<212> TYPE: RNA
<213> ORGANISM: Zea mays

<400> SEQUENCE: 94
ggucaagaaa gccgugggaa g 21

<210> SEQ ID NO 95
<211> LENGTH: 21
<212> TYPE: RNA
<213> ORGANISM: Zea mays

<400> SEQUENCE: 95
uuccacagcu uucuugaacu g 21

<210> SEQ ID NO 96
<211> LENGTH: 22
<212> TYPE: RNA

<213> ORGANISM: Zea mays

<400> SEQUENCE: 96
uuccacaggc uuucuugaac ug 22

<210> SEQ ID NO 97
<211> LENGTH: 957
<212> TYPE: DNA
<213> ORGANISM: Glycine max

<400> SEQUENCE: 97
atgaataaga gtgggggagg agagatgagt aagtggccgt tcacaatgtc tcagtggcag 60
gaactggaac atcaagcttt gatttacaaa tacatggtgg ctggtcttcc tgtccctcct 120
gatctagtcc ttcccattca gaacagcttc cactccattt cccaaacctt cttgcaccat 180
ccctctacca ccatgagtta ttgttccttc tatgggaaga aggtggaccc ggagccagga 240
cgatgcagga ggactgatgg gaaaaagtgg aggtgctcca aggaagccta cccagactcc 300
aagtactgtg agcgacacat gcaccgtggc cgcaaccgtt caagaaagcc tgtggaatca 360
caaactatga ctcagtcatc atctaatgtg tcatcattga ctgtaactgc tggcagcagc 420
agcagtgcaa ctggaaattt ccataacctt accaccacaa atgcatatgg taatccccaa 480
gggactggtt ctggatcaga ccaaacccac tatcacatgg attccattcc ctatgggatc 540
ccaagtaaag aatacaggta ttttcaagga cctaaatctg agggaggtga acatagtttc 600
ttgtccaaaa ctttaggaag caacaaggtt cttcacatgg agtcacagat ggataacact 660
ttgatgccaa ccagtggagt tgcctcattc tctacattga gatcaaataa taattccatg 720
ttgcagggtg attatctgca gccttctttc ttatctagtg agtatgcctc agcagaaact 780
gtgaagcaag agggtcagtt ccttcgacct ttctttgatg aatggcctaa aaggagggac 840
tcatggtctg gtctggaaga tgagggatcc aaccacactc aactctcaat atccattcct 900
atgtcagcat caaatttctc tacaactagc tctcattccc cacatggtga gatttaa 957

<210> SEQ ID NO 98
<211> LENGTH: 1377
<212> TYPE: DNA
<213> ORGANISM: Glycine max

<400> SEQUENCE: 98
atggaagcta agcctcttcg aactgttccc tcttcacaca acacttctgg aggtggaccc 60
cagaagaaga ttgacatggg acacaagatg gtaggtgatg ttggtgttgt tgttgttgat 120
gaaagaaaga gggttgttgt ggtcaaggaa gagaaagaga acacttcttc ctacagtgtt 180
gaacttcatc tcggggttga tgcttctcat tctgctccac aagaaataaa ccatgtgatc 240
actgaagctc agaggcgtga gcttcaccat caagttttca tcttcaacca tttggcatat 300
aatcttcctc ctccttatca ccttgtgcaa ttcccgagca acatgtcaga atacagtttc 360
ctgggttttg atcatgggag tatggtggat ccagagcctc ataggtgtag aagaactgat 420
ggaaagaaat ggaggtgtgg taagaatgtg gtgcctaacc agaagtactg tgaaagacac 480
atgcatagag gtcgaaatcg ttcaagaaag cctgtggaaa catctcaaat taactctcat 540
ctggcaacaa agccatctag caagtcacac aacaaacccg cctcaaggac acaatttgaa 600
atttcaaatc caaaccttat ggccattcga catagtgaca catcaagtac cccatcaagg 660
agtctcagtg ttgccaattg ctcttctgct aataataggt ggaaaaatag tgcaagttat 720
gctgactacc tcacatcgtt ttcttctgcg tctgcagtgt cccctggatc cactcttgcc 780

```
actccagttg ctcctaagat ggccaccttc agcagtgtga catccattgc ttcagataga    840

ggaagttgcc taaatatatg ccagaaagat aacaagtcca agagctgtat cagcaacaac    900

atcagtgtta aaagtggtgg gaaaggaaga attgttggtg acactaatgg catttctact    960

ggaataggct tctccccaac gagtgttctt caagtttctg gttgcaaccc ttcatacctg   1020

aatgacagaa ccaacataga atctgcatcc ggtaggtgcc ggagaacaga tggtaagaag   1080

tggcaatgca agagtgctgt tcttccgggt cagaagtact gtgccacaca catgcacaga   1140

ggtgctaaaa agcggctcac aagccatgaa ccggcagtta ccattgcgcg gttgcctaac   1200

tcttcagtca caaccaaaat gcagaaagcg cattgtgcaa ttccaaacac aaatctttcc   1260

atgtcagtcc cagcaagtga accattcata caatgtaatg agaaaagtca aagtaccagt   1320

gacactgata ccaccatcag tgacaccttg aatgagtgta gctatgcttc tttctga      1377
```

<210> SEQ ID NO 99
<211> LENGTH: 1008
<212> TYPE: DNA
<213> ORGANISM: Glycine max

<400> SEQUENCE: 99

```
atgagcgttc ctccgccgta tgcggcggcg atgtggacgc cgttcacggc ggcacagtgg     60

cacgagctgg agcaccaggc cctcatcttc aagtacctca aggcgggtct ctcggttccc    120

cctgacctcc ttctccccat tcgcaagagc ctccagttga tgtctcatcc atctctgggg    180

ttttatggga agaagataga ccctgaaccg ggtcggtgca ggagaaccga tgggaaaaag    240

tggaggtgtt cgagggatgc gcaccctgac tccaagtact gcgaccgcca tatgatacgg    300

cggcgttacc gttcaagaaa gcctgtggaa tcatctcaaa ctcactcttc ttcttcttct    360

tcttcttctt cttctgctac tgctgcttct tcaaattcaa atcctgttgc tggtggtggt    420

ggtggttctg ttgctaatgt ttctggaact gcaactgctg caaaaaccct tcacaccctt    480

cccttgcaca ccaatggtgc aagggaaggt ttcactttca cccttgggaa caacaccaac    540

accaccctcc cacaccttca catgaacccc ctcactcttt cagctgacaa taccaagaaa    600

acttacaggt ttggactgaa ctcagaagca gatgagcaca acgtcttaca gaaagatctg    660

ggaagtgtga ggtatcaagg ttatgacttt acctcagatg ccatgtggtc tcaaatgtct    720

cacattccat caaatactgt ttcggaatca agaagtggtt ctactatgct gggcaactgc    780

ttccaacatc aaacaatgcg agatgctgag ctgttgaacc tggaaacggc aaggaccaaa    840

gatcttgtct ttagtggcca gttaagttca gctgggggtt tgaaacagga atatcagtct    900

ccccagtctc tcttcagtga ctgggactgg aagaaggatt taagttcctc tgcccttgag    960

tataagccta acaaggattt taactgcaac ccagatgcca atgtttga                1008
```

<210> SEQ ID NO 100
<211> LENGTH: 1155
<212> TYPE: DNA
<213> ORGANISM: Glycine max

<400> SEQUENCE: 100

```
atgaatggaa ggaacgttaa cacaaacagg ttccctttca ctccttccca gtggcaagag     60

cttgaacacc aagctctcat ctacaaatac atggcttcag gtatctccat cccccctgac    120

cttctcttca ccatcaaaag aacaacccac ttggactcct caagactatt gcctcaccac    180

cctcaacact ttggatggaa ctatttgcca atggggttgg ggaggaaaat agacccggag    240
```

```
ccagggaggt gtagaagaac agatggaaag aaatggaggt gctcaaagga ggcgtatcca    300
gattcaaagt actgtgagag gcacatgcac agagggaaaa atcgttcaag aaagcctgtg    360
gaagttttga aaacaacacc aacgacagca gcagtggcaa caaacacaga tgcctcaacc    420
ccaacaacaa tcttatcaat caccaaaaac agtcctgcac atgcactctc cccaaccact    480
cattctctct ctcatgacac ttaccatcat catcatcatc accctcaccc tcagcaacat    540
tcctcccact ccttcctcta tcatcattct tcgaggccct cttccggtgc tgctttgtca    600
tttcaagaca acagtgcccc cttgtttctc gacactgctt cttgctctca gaataacaac    660
aacactgact gcaggaacag gtatgtgtat ggactgaagg aggaggtgga cgagcatgcc    720
ttcttcacag aaccttctgg aactatgaga agcttctctg cttcctcaat ggaagattca    780
tggcaactca caccactgac tataagctcc tcttcctctt cgaaacagag gaactgctct    840
ggtttatcca atgacaacaa cgagtactcc tacttgcaac ttcagagcct caatggcaac    900
aactcaaaac agccacaaca agatcaaggt tgctacatat caggcagtga tgtcaagtgc    960
gaaacattca tgaaacttgg gaaagaagaa cctcagaaaa ccgttcatcg cttcttcgat   1020
gaatggcccc ctaaaagcag aggatcgtgg cttgatttgg atgataaatc atccaccacc   1080
cagctttcaa tttccattcc aacttctact catgattttg caactttcaa ttcaacaacc   1140
caacgagatg gttga                                                    1155
```

<210> SEQ ID NO 101
<211> LENGTH: 1098
<212> TYPE: DNA
<213> ORGANISM: Glycine max

<400> SEQUENCE: 101

```
atgatgaatg gaagaaacag gtttcccttt accccatcac agtggcaaga gcttgaacac     60
caagctctca tctacaagta catggcttca ggcatttcca ttccccctga tcttctcttc    120
accataaaaa ggagctattt tgattcccct ctctcctcaa ggcttttgcc taaccagcca    180
caacactttg gatggaacta ccttcagatg ggtttgggaa gaaaaataga ccctgagcca    240
ggtaggtgta gaagaactga tggcaagaaa tggagatgct caaaagaagc atacccagat    300
tctaagtact gtgagaggca catgcacaga gggaagaatc gttcaagaaa gcctgtggaa    360
gttttgaaaa caacaacacc atcatcaaca atgacaacaa caaacacaaa ctcaaatgct    420
tcttcaacac aacaagcaat ctcatcaatc accaaaatta atactctttc acctcttgct    480
tcatctgaga ctcaccaaca ccaccctcaa cactatggct cctttctcta tcatcatcac    540
cctccttcaa ggtcctctgg cattggcttg tcctttgaag ataatagggc tcccttgttt    600
cttgacactg gctcttgctc tcagtccaac acagactgca ggagtaggta tgtttatgga    660
gagaaagagg aggtggatga gcatgctttc ttcacagaac cttgtggtgt tatgaaaagc    720
ttctctgctt cctctatgga tgactcatgg caactcacac cattgactat gagttcctca    780
tcttcttctt ccaaacagag gagttccttt ggcttgtcca gtgattactc ttgcttgcaa    840
cttcagagcc actcaaagca gcagcaacaa gagcatcatc aagatcaggg ttgctacatg    900
tttggtggtg gtcaagttgt gaaagaagaa cctcagaaaa cggttcatcg cttctttgat    960
gaatggcccc acaaaggaag agaagggtct tggcttgatt tggatgacaa atcttccaca   1020
acccaacttt caatttccat ccccacatgt tctcatgatt ttccaacttt cagttctaga   1080
aaccaccacg atggttga                                                 1098
```

-continued

<210> SEQ ID NO 102
<211> LENGTH: 1014
<212> TYPE: DNA
<213> ORGANISM: Glycine max

<400> SEQUENCE: 102
atgagcgttc ctccgccgtc tacggcggcg atgtggacgc cgttcacggc agcgcagtgg 60
cacgagctgg agcaccaggc cctcatcttc aagtacctca aggcgggtct ctcggttccc 120
cctgacctcc ttctccccat tcgcaagagc ctccaattga tatcgtctca cccatcgatg 180
gggtattatg ggaagaagat agaccctgaa ccgggtcggt gcaggagaac cgatgggaaa 240
aagtggaggt gttcgaggga tgcacaccct gactccaagt actgcgaccg ccatatgata 300
cgacgtcgtt accgttcaag aaagcctgtg gaatcatctc aaactcactc ttcttcttct 360
gcttctgctg cttcttcaaa ttcaaaccct gttgctgctg gtggtggtgg tggttctgtt 420
gctaatgttt ctgcaactgc tgcaaaaaac cttcacacac ttcccttgca catcaatggc 480
gcaagggaag gtttcacttt caccccttggg aacaacacca gcaccaacac caacaccaac 540
accaacaccc tccctcacct tcacatgaac cccctcactc tttcagctga caataccaag 600
aaaacttaca ggtttggact gaactcagaa gcagatgagc acaacgtctt acagaaagat 660
ctgggaagtg tgaggtatca aggttatgac tttacctcag atgccatgtg gtctcaaatg 720
tctcacattc catcaaatac tgtttcggaa tcgagaatcg gttctactat gctgggcaac 780
tgcttccagc atcaaacaat gcgagatgct gagctgttga atctggaaac ggcgaggacc 840
aaagaccttg tctttagtgg ccagctaagt tctgcagggg gtatgaaaca ggaatatcag 900
tctccccagt ctctcttcag tgactgggac tggaagaagg atttaagttc ctctgccctt 960
gagtataggc ccaacaagga ttttaactgc aacccagatg tcaatgttga ttaa 1014

<210> SEQ ID NO 103
<211> LENGTH: 1803
<212> TYPE: DNA
<213> ORGANISM: Glycine max

<400> SEQUENCE: 103
atggatcttg ggtggtgggg tttggagggg gtggtgggtt cagaaagtgg ttgtgtgttt 60
ggttcttctc ttgtttcaga tcctgagaca aagcacaagt ggtacggatc tggtttgctc 120
aagcaagaga gatctgccat agctactgaa gatgatgagt ggagaatttc caaagttgct 180
aaaactgatc atgacatgtc ttcagcctcc aaagcaatgc tctttcagca aagaaacaac 240
tctttgttga gatctaataa tgcaactctc ttctctgatg gtcatcacca atcacaaatg 300
ttgagcttct cttctccaaa gtcagattct ttgttgatag ataaggcttc ctcaaatgcc 360
acattgcctt tttcttccca ccaattgtct agctacacca gaaatacagg ttacaattca 420
ggaagcataa gcatgcatgg ggctttggct agtgtgagag ggccattcac tccatcacag 480
tggatggagc ttgaacacca agccttgatc tacaagtaca tcacagcaaa tgttcctgtg 540
ccaactcatc ttctcattcc catcagaaaa gcacttgatt ctgttggctt ctgcaacttc 600
tcagccggac tcctcagacc caactcattg ggatggggag gtttccatct aggattctcg 660
aacaatacag accctgagcc agggaggtgt aggagaacag atggaaagaa atggcgatgt 720
tcaagagatg ccgtagtaga tcagaagtat tgcgagcggc acatgaaccg aggacgccat 780
cgttcaagaa agcctgtgga aggccaatca ggccatgccc tcaccaccac caccagtaat 840
acacctaatg cttcctccaa ctctgtggtg cctggcaaca acaacaacac ctttgcacac 900

```
aacaatgtgc accaccctat tcctcctcat tcctctccgg tcaacaccat cactaggatg    960

tttacaagca acaaagagaa taataacagt accagtgaga ggatgcagga ccctgcactt   1020

cccatgcttc ctcccactct tgagctgaaa ccaaaggaga acaatccttt catgattcat   1080

aaacaccaaa tcccatctga tgaatactca agtaggaaca acaatgagtt tgggcttgtc   1140

acttctgatt ctttgcttaa cccctcagag aaaagaagct ttacttcttc acaaaagaat   1200

gattcttctg agtcccaaca acaacattcc ctcaggcact tcattgatga ctctcccaaa   1260

ccacagtcta atcatcatca tcgttcgtcg tctatatggc ctgaacttga caacatgcag   1320

tcagacagga ctcagttatc aatctccata ccaatatctt cctcagatca cttcatgtca   1380

ttcactactt ccttgccctc gaacgagaaa ctcacgttgt caccacttag gctttcaagg   1440

gagttagacc ccattcaaat ggggttggga gtgggaagtg cccccaatga agcaaacact   1500

aggcaagcca attggattcc aatcacttgg gagagttcaa tgggtggtcc tcttggagag   1560

gttttgaacc ttagtaacaa taacaacagc aatgctagtg atcaatgtgg caagaacaac   1620

aacaacactt cagctctcaa cctcatgaaa gatggatggg acaataatcc tccatcaggg   1680

tcatccccaa ctggggtgct tcaaaaatct gcatttggat cactttccaa tagcagtgct   1740

gggagcagtc caagggggc agagaacaac aaagaaggtg ccaccttgtg caatgccttg   1800

taa                                                                 1803
```

```
<210> SEQ ID NO 104
<211> LENGTH: 1134
<212> TYPE: DNA
<213> ORGANISM: Glycine max

<400> SEQUENCE: 104

atgatgaatg gaaggaacgt tgacacaaac aggttcccct tcactccttc ccagtggcaa     60

gagcttgaac accaagccct catctacaaa tacatggctt caggtatttc catccccccct   120

gaccttctct tcaccatcaa aagaacaacc cacttggact cctcaagact cttgcctcaa    180

cactttgggt ggaattattt gccaatggga ttggggagaa aaatagaccc agagccaggg    240

aggtgtagaa gaacagatgg gaaaaaatgg aggtgctcaa aggaggcgta tccagattca    300

aagtactgtg agaggcacat gcacagaggg aaaaaccgtt caagaaagcc tgtggaagtt    360

ttgaaaacaa caccaatgac agcagcaaca aacacagatg cctcaacccc aacaacaatc    420

ttatcaatca ccaaaaacag tcctgtactc ttcccaacca ctcattctct gtctcatgac    480

acttaccatc atcatcacca tcatcactct caccctcagc aacattcctc ccactccttc    540

ctctatcatt cttcgaggcc ctcttccggt ggtgtttctt tgtcatttca agacaacagt    600

gccccccttgt ttctcgacac tgcttcatgc tctcagaata acaacaacac tgactgcagg   660

tatgtgtatg gactaaaaga ggaggtggat gagcatgcct ttttcacaga accttctgga    720

actatgagaa gcttctctgc ttcctcaatg gaagattcat ggcaactcac accactgact    780

ataagctcct cttcctcttc aaaacagagg agttgctctg gtttatccaa tgacagcaat    840

gagtactcct acttgcaact tcagagcctc agtggcaaca actcaaagca tccacagcaa    900

gatcaaggtt gctacatatc aggcagtgat atcaagtgcg aaacattcat gaaacttggg    960

aaagaagaac ctcagaaaac cgttcatcgc ttcttcgatg aatggcctcc caaaagcaga   1020

ggatcatggc ttgatttgga tgataaatca tccacaaccc agctttcaat ttccattccc   1080

acttctactc atgattttgc aactttcagt tcaacaaccc aacgagatgg ttga         1134
```

<210> SEQ ID NO 105
<211> LENGTH: 1830
<212> TYPE: DNA
<213> ORGANISM: Glycine max

<400> SEQUENCE: 105
atggatcttg gggtggtggg tttggagggg gtggtgggtt cagaaagtgg ttgtgtgttt 60
ggttcttctc ttgcttcaga tcctgagaca aagcacaagt ggtacggatc tggtttgctc 120
aagcaagaga gatctgccat agctactgaa gatgatgagt ggagaatttc caaagttgct 180
aaaactgatc atgacatgtc ttcagcctcc aaagcaatgt tctttcagca aagaaacaac 240
tctttgttga gatctaataa tgcaactctt ttctctgatg gtcatcacca atcacaaatg 300
ttgaacttct cttctccaaa gtcagagact ttattggtag ataaggcttt ctcaaatgcc 360
acattgcctt tttcttatca tcaattgtct agttacagca gaaatacagg ttacaattcg 420
ggaagcataa gcatgcatgg ggctttggct agtgtgagag ggccattcac tccatcacag 480
tggatggagc ttgaacacca agccttgatc tacaagtaca tcacagcaaa tgttcctgtg 540
ccaactcatc ttctcattcc catcagaaaa gcacttgatt ccgttggctt ctgcaacttc 600
tcatctggac tcctcagatc caactcgttg ggatggggag gcttccattt gggattctcc 660
aacagcacag accctgagcc agggaggtgt aggagaacag atgggaaaaa atggcgatgc 720
tcaagagatg ctgtagtaga tcagaagtat tgcgaacggc acatgaaccg aggacgccat 780
cgttcaagaa agcctgtgga aggccaatca ggccatgccc tcaccaccac taacacacct 840
aatgcttcct caaactcaac cgtggtgccc ggcaaccaca acaacaacac ctttgcacac 900
atcaatgtgc accaccctct tcctcctcat tcctctccag ccaataccat caataggatg 960
tttatgagta ataataaaga gaacaacaac acgagtgaga ggatgaagga tggccttgcc 1020
cttcccatgc tacctcctac tcttgagctg aaaccaaagg acaacaacaa ctctttcatg 1080
gttcataaac accaagaacc atatgatgaa tcctcaagga acaagaatga gtttggactc 1140
gtcacttctg attccttgct taacccttca cagaaaagaa gctttgattc ttcttcttct 1200
tcttcacaaa aggatgattc ttctgagtcc caacaacaac attccctcag gcacttcatt 1260
gatgactctc ccaaaccaca gtctcatcat aatcataacc atcgttcgtc gtcatctatt 1320
tggcctgaac tcgacaacat gcagtcagac aggactcagt tatcaatctc cataccaata 1380
tcttcctcag atcacttcat gtcatttgca acttcctcgc cctcgaatga aaaactcaca 1440
ttgtcgccac taaggctttc gagggagttc gaccccattc aaatgggatt aggagtggga 1500
agtgcctcca atgaagcaaa cactaggcaa gccaattgga ttccaatcac ttgggagagt 1560
tcaatgggtg gtcctcttgg agaggttttg aaccttagta acaataataa taacagcaat 1620
gcaagtgatc aatgtggcaa gaacaacaac aacacttcag ctctcaacct catgaaagat 1680
gatgacgatg atgatgggtg ggacaatagt cctcctccaa tagggtcatc accaactggg 1740
gtgcttcaaa aaacagcatt tggatcactt tccaacagca gtgctgggag cagtccaaga 1800
ggggcaccag agaacaacaa caaagaatag 1830

<210> SEQ ID NO 106
<211> LENGTH: 1800
<212> TYPE: DNA
<213> ORGANISM: Glycine max

<400> SEQUENCE: 106
atggatcttg gggtggtggg tttggagggg gtggtgggtt cagaaagttg ttgtgtgttt 60

-continued

```
ggttcctctc ttgcttcaga tcctgagaca aagcacaaat ggtacggatc tggtgtgctc    120
aagcaagaga gatctgccat agcaagtgaa gatgatgagt ggagaacttc taaagtggcc    180
aaaactgatc atgacatgtc ttctgcctcc aaagcaatgc tctttcagca aagaaacaac    240
tctttgttga gatctaatgc taccctttc tctgatggcc atcatcacca atcacaaatg     300
ttgagcttct cttctccaaa gtcagagtct ttgttggtag ataaggcttc ctcaaatgcc    360
acattgcctt tttcttacca ccaattgtct agcaacacca gaaatgcagg ttacagttca    420
ggaagcataa gcatgcatgg ggctttggct ggtgtgagag ggccattcac tccgtcacag    480
tggatggagc ttgaacacca agccttgatc tacaaataca tcacttcaaa cgtgcctgtg    540
ccaacccatc tcatacccat tagaaaagca cttgattctt tgggcttctg caacttttca    600
actggactcc taaggcccaa cgcattggga tggggaggtt tccatctggg attctcgaac    660
aacacagacc ctgagccagg caggtgtagg agaacagatg gaaaaaaatg gcgatgctcg    720
agagatgccg tagtggatca aaagtattgc gagcggcaca tgaatagagg acgccatcgt    780
tcaagaaagc ctgtggaagg ccaattaggc catgccctca ccaccaccac caccaccaat    840
acacctaatg cttcctccaa ctctaccgtg gtgccccgca acaccaccac caccaccacc    900
tttgcacaca acaatgtgca ccaccctctt ccacctcatt cgtctcaggc caacaccatc    960
aataggatgt ttacaagcaa caaagagaat aacagtacca gtgagaggct gcaggaccct   1020
gctcttccca tgctgcctcc cactcttgag ctgaaaccaa aggagaacaa tcctttcatg   1080
attcataaac accacatccc agctgatgaa tactcaagga acagcaatga gtttggactc   1140
gtcacttctg attccttgct taaccctaca cagaaaagaa gctttacttc ttcacaaaag   1200
gatgattctg agtcccaaca acaacattcc ctcaggcact tcattgatga ctctcccaaa   1260
ccacagtctc ataatcatca ccaccatcat cattcgtcgt ctatttggcc cgaactggac   1320
agcatgcaat cagacaggac tcagttatca atctccatac cgatatcttc ctcagatttt   1380
atgtcattca ctacttcctc accctccaac gagaaactca cgttgtcacc attggggcat   1440
tcgagggagt tagaccccat tcaaatggag ttgggaatgg gaagtggtgc ctccaatgaa   1500
gcaaacacca ggcaagccaa ttggattcca atcacttggg agagttcaat gggtggtcct   1560
cttggagagg tattgaacct tagcaataac agcaatgcaa gtgatcaatg tggcaagaac   1620
aacaacactt cagctctcaa cctcatgaaa gatgggtggg acaataatcc tccactaggg   1680
tcatccccaa ctggggtgct tcaaaaatca gcatttggat cactttccaa tagcagtgct   1740
gggagcagtc caagggcaga aacaacaaa gaaggtgcca ccttgtgcaa tgccttgtaa    1800
```

<210> SEQ ID NO 107
<211> LENGTH: 1785
<212> TYPE: DNA
<213> ORGANISM: Glycine max

<400> SEQUENCE: 107

```
atggatcttg ggtagtgggg tttggagggg gtggtgggtt cagaaagtgg ttgcgtgttt     60
ggttcctctc ttgcttcaga tcctgagaca aagcacaagt ggtacggatc tggtgtgctc    120
aagcaagaga gatctgccat agcaagtgaa gatgatgagt ggggaactta taaagtggcc    180
aaaattgatc atgacatgtc ttctgcccct aaagcaatga tctttcagca aagaaacaac    240
tctttgttga gatctaataa tgctactctt ttttctgacg gccatcacca atctcaaatg    300
ttgagtttct cttctccaaa gtcagagact ttgttggtag atacagcttc ctcaaatgcc    360
acattgcctt tttcttacca tcaattgtct agttacagca gaaatacagg ttacagttca    420
```

ggaagcataa gcatgcatgg ggctttggct ggtgtgagag ggccattcac tccatcacag 480
tggatggagc ttgaacacca agccttgatc tacaaataca tcactgcaaa catgcctgtg 540
ccaactcatc ttctcatacc catcagaaaa gcacttgatt ctgttggctt ctgcaacttc 600
tcaactggac tcctcagatc caactcattg ggatggggag gtttccatct gggattctcg 660
aacagcacgg accctgagcc agggaggtgc aggagaacag atggaaagaa atggcgatgc 720
tcaagagatg ccgtagtaga tcagaagtat tgtgagcggc acatgaacag aggacgccat 780
cgttcaagaa agcctgtgga aggccaatca ggccatgccc tcaccaccac caccaccact 840
actaacacac ttaatgcttc ctcaaactca accgtggtgc ccggcaacaa cacctttgca 900
cacaacaaag tgcaccaccc tcttccacct aattcctctc cagccaatac catcaatagg 960
atgtttatga ataataaaga gaataacagc acgagtgaga ggatggagga ttgctctgcc 1020
cttcccatgc tacctcccac tcttgagctg aaaccgaagg agaaaaacaa tttcatgatt 1080
cataaacacc aagaccccta tgatgaatcc tcaaggaaca acaatgagtt tggactcgtc 1140
acttctgatt ccttgcttaa ccctacacag aaaagaagct ttgattcttc ttcttcacaa 1200
aaggatgatt ctgagtccca acaacaacat tccctcaggc acttcattga tgactctccc 1260
aaaccaccat ctcataatca tcatcgttcg tcgtccattt ggcccgaact cgacaacata 1320
cagtcagata ggactcagtt atcaatctcc ataccaatat cttcctcaga cttcatgtca 1380
ttcactactt cctcaccctc caacgagaaa ctcacgttgt cgccacttag gctttcgagg 1440
gcgttagacc ccattcaaat ggggttggga gtgggaagcg gtgcctccaa tgaagcaaat 1500
cctaggcaag ccaattggat tccaatcact tgggagagtt caatgggtgg ccctcttgga 1560
gaggttttga accttagcaa taacagcaat gcaagtgatc aatgtggcaa gaacaacact 1620
tcagctctca acctcatgaa agatgatgat gatgatgggt gggacaatag tcctccacta 1680
gggtcatcac caactggggt gttgcaaaaa acagcatttg gatcactctc caacagcagt 1740
gctgggagca gtccaagggg ggcaccagag aacaacaaag aatag 1785

<210> SEQ ID NO 108
<211> LENGTH: 1002
<212> TYPE: DNA
<213> ORGANISM: Glycine max

<400> SEQUENCE: 108
atgaacatca gtggcggagg aggaactgtg atgggtttca gtagtaatgg gaggtcccca 60
ttcacagtgt ctcagtggca ggaactggag caccaagctt tgattttcaa gtacatggtt 120
gcgggtcttc ctgtgcctcc cgatctcgtc ctccccattc agaagagctt cgactctact 180
ctctctcacg ctttctttca ccatcccaca ctgagttatt gttccttcta tgggaagaag 240
gtggaccctg agccaggacg atgcaggagg actgatggaa aaaagtggag gtgctccaag 300
gaagcatacc cagactccaa gtactgcgag cgccacatgc accgtggccg caaccgttca 360
agaaagcctg tggaatcaca aactatgact cactcgtctt caactgtcac atcactcact 420
gtgactggtg gtggtgacag taatggaact gtaaacttcc aaaaccttcc cacaaatgcc 480
tttggtaatc tccagggtac tgattctgga actgaccgca cgaattatca tctagattcc 540
attccctatg cgattccaag taaagaatac aggtgtcttc aaggacttaa atctgagggt 600
ggtgaacact gcttcttttc tgaagcttct ggaagcaaca aggttctcca aatggagtca 660
cagctggaaa acacatggcc ttcgatgtca accagagttg cctctttttc tacatcaaaa 720

-continued

```
tcaagtactg attccctgtt gcatagtgat tatccccaac attcgttttt atctggtgaa    780

tatgcatcgg gagaacacgt gaaggaggag ggccagcctc ttcgaccttt ttctaatgaa    840

tggcctaaaa gcagggagtc atggtctggt ctggaagatg atatatccaa ccaaacagcc    900

ttctccacaa ctcaactctc aatatccatt cctatgtctt ccgatttctc tgcaacgagc    960

tctcagtccc cacatggtga gaatgagatt caatttaggt aa                      1002


<210> SEQ ID NO 109
<211> LENGTH: 1737
<212> TYPE: DNA
<213> ORGANISM: Glycine max

<400> SEQUENCE: 109

atgggtgaat tatttggcgt tggaaaaaga aggaacatca gcagcagcaa caacaacaac     60

aacagttcta gtagtagcgt tcttgggttg gatgtgaagg tgcaacagag ccctgaagca    120

ttattccata ataggatgat gatgatggcg catcataatc atcaccaccg tccattgtca    180

tcaccctttg ataataatgg tgatggcgat ggtcccacga cttacatgtc ttttactaat    240

catataaacc ttgttagtgg tgcttcttct gttcttggtc ctgctattga tgctggctgt    300

ggtgctgctc ctcctgcacc tgtaagaact ttgcagcctt ttgacatttc ttcttatact    360

tcttctccca ccaccactac cacaaccttc aacttcaaac ccccttcagc aggtgtgatg    420

gcggcttcgt tggggtttcc tttcacaagt gcacaatgga gggagcttga aagacaagct    480

atgatataca agtacatgat ggcttctgtt cctgttccac atgatctcct cacaccctct    540

tctcgctctt cctgcatgga tggtggtttc aatctgaggt tggcaaatag cactgaccct    600

gagccaggta ggtgtagaag aacagatggt aaaaaatgga gatgttcaag agatgtggct    660

cctaaccaca agtactgtga gcgccatatg catagaggcc gtccccgttc aagaaagcct    720

gtggaagtta acaccaacag caccaccact cccactagcg tcaacaataa caaccatcaa    780

atcaaaaagg ctcgccatga gtgtaataat aatcctttttg ctacacctga cgttactgcg    840

gctatttcca accccacatc cagaaaaaat ggatcttctc cccattttct tgggtctact    900

accactcagc catacccttga ttcttccctc tcccttgata actttggtct aaaagctgct    960

agttttgact ccgtggcttc tgtttctgct aataaggaac ccaggggttt agagtggatg   1020

ctgaatggag atcctatttc cctgggtgct tctgactcac aatggcagtc tctgatgcac   1080

aataaagatg gaatgaccag tgttagttcc tgtaacacca ccgagtctca gtatctgaat   1140

tcattagcac tatataactc tggactagaa caacagaata gacgccatcc tttgttcctg   1200

aaccctcttg ttgttcccat ggaaaatctc caaccggaga aaccaagggg ttttattgat   1260

gcttggtcta acgctgaaag caatgccaac accaacacca ccaacaagaa ctctgctgca   1320

tcaattggta aattatccct ttcttctctt gatctatcaa tggggggtgc tgctgtgaat   1380

gaagatgtgg gtaatgttaa catgggtttg ggcctaatgg agcctaatgg aaaaacgcac   1440

actggtacta aaatttctct ctccaattgg caaaacccag caccttgggt ggcttcatca   1500

cttgggggtc cactagctga agttctaagg tcaagcacag tcactgccac caccaccacc   1560

aatgaagcaa cctccaacac accctcgcca gccaccacta cacatgctga atctccatct   1620

ggggtgttgc agaaaacgct tgtttcattg tctgatagca gtaacaatag cagcccaagg   1680

gttgcatcat caagggccaa ttctgagatg gccttgctaa ggtttcaatc aaattaa      1737


<210> SEQ ID NO 110
<211> LENGTH: 927
```

<212> TYPE: DNA
<213> ORGANISM: Glycine max

<400> SEQUENCE: 110
atgagtaagt ggcctttcac aatatctcag tggcaggaac tggaacatca agctttaatt 60
tacaaataca tggtggctgg tcttcctgtg cctcctgatc tagtcattcc cattcagaac 120
agcttccact ccatttccca aaccttcttg caccatccct ctaccaccat gagttattgt 180
tccttctatg ggaagaaggt ggacccggag ccaggacgat gcaggaggac tgatgggaaa 240
aagtggaggt gctccaagga agcctaccca gactccaagt actgtgagcg acacatgcac 300
cgtggccgca accgttcaag aaagcctgtg gaatcacaaa ctatgacaca gtcatcatcc 360
aatgtgtcat cattgactgt aactgctggc agcagcacca gtgcaactgg aaatttccag 420
aacctttcca ccacaaatgc atatggtaat ccccaaggga ctgcttctgg aacagaccaa 480
acccactatc acatggattc cattccctat gggatcccaa gtaaagaata caggtatttt 540
caaggatcta aatctgagga acatagtttc ttgtccaaaa ctttaggaag caacagggtt 600
ctacacatgg agccacagat ggacaacact ttgatgccaa ccggtggagt tgcctcattc 660
tctacattga gatcaaataa taattccatg ttgcagggtg attatctgca gccttctttc 720
ttatctagtg aatatgcctc ggcagaaact gtgaagcaag agggtcagtc ccttcgaccg 780
ttctttgatg aatggcctaa aagcagggac tcatggtctg gtctggaaga tgagagatcc 840
aatcacactc aactctcaat atccattcct atgtcatcgt caaatttctc tgcaactagc 900
tctcattccc cacatggtga gatttaa 927

<210> SEQ ID NO 111
<211> LENGTH: 1008
<212> TYPE: DNA
<213> ORGANISM: Glycine max

<400> SEQUENCE: 111
atggacttgc agttgaagca atggagtaac cggcatgagt cagaacaaga acattattcc 60
ccaaacatgc caaaatttct ccctcaacac cacccaccac catctccctc tgcactccct 120
ctctttgtac ctgaacaacc caacaccaaa gtctgcaccc tgtcagcatt ttctgattcc 180
acactacctt ctgctcccag attttccagg atggagagtt gcttcagctt tgcacagtgg 240
caagagcttg agttgcaggc tctgatattc aggtacatgc tggccggtgc tcctgttcct 300
cctgagctcc ttctaccaat caagaaaagc ttccttcaac tttataaccc tcctttgttg 360
gaatcagggt actactgggg aagagcagcg ctggatccgg agccggggcg gtgccggagg 420
accgacggca agaagtggcg gtgctcgaag gacgcggtgg cgggtcagaa gtactgcgac 480
cgccacatgc atcgtggccg aaaccgttca agaaagcctg tggaacaacg tgatggatct 540
ctttctgcta tagcctccgt ttcttcttca ccctcttctt catttaatct ccttcacctc 600
agtgaaagtt cctctggggc caagagtgac aacaagagct tctttgaaaa ccatgatcat 660
gtggatgggg atggaaattc agccaaatct gatggccatg tcttgaggca tttctttgat 720
gattggccaa ggacactgca agagcctgac aatggtgaaa gcaatggttg ccagaacaac 780
aactcaggaa catgtctttc tatgtcaaca ccaggaatca cttcctcgga tgtgtcgttg 840
aaattgtcca ctggccatgg agaggatgcg tgccacgcgg cctcaatggg aggaccactt 900
gcagaggcat taagatcatc caccaccagc tccacttctt caccaaccag tgttctgctt 960
cagttgcctc ctagttctgc ttctgaggct agtttcatta gcacctaa 1008

<210> SEQ ID NO 112
<211> LENGTH: 1026
<212> TYPE: DNA
<213> ORGANISM: Glycine max

<400> SEQUENCE: 112
atgaacaaca gcagtggcgg aggaggacga ggaactttga tgggtttgag taatgggtat 60
tgtgggaggt cgccattcac agtgtctcag tggcaggaac tggagcacca agctttgatc 120
ttcaagtaca tgcttgcggg tcttcctgtt cctctcgatc tcgtgttccc cattcagaac 180
agcttccact ctactatctc gctctcgcac gctttctttc accatcccac gttgagttac 240
tgttccttct atgggaagaa ggtggaccct gagccaggac gatgcaggag gactgatgga 300
aaaaagtgga ggtgctccaa ggaagcatac ccagactcca agtactgcga gcgccacatg 360
caccgtggcc gcaaccgttc aagaaagcct gtggaatcac aaactatgac tcactcatct 420
tcaactgtca catcactcac tgtcactggg ggtagtggtg ccagcaaagg aactgtaaat 480
ttccaaaacc tttctacaaa tacctttggt aatctccagg gtaccgattc tggaactgac 540
cacaccaatt atcatctaga ttccattccc tatgcgattc caagtaaaga atacaggtat 600
gttcaaggac ttaaatctga gggtggtgag cactgctttt tttctgaagc ttctggaagc 660
aacaaggttc tccaaatgga gtcacagctg gaaaacacat ggcctttgat gtcaaccaga 720
gttgcctctt tttctacgtc aaaatcaagt aatgattccc tgttgcatag tgattatccc 780
cggcattcgt tttatctggg tgaatatgtg tcgggagaac acgtaaagga ggagggccag 840
cctcttcgac ctttttttaa tgaatggcct aaaagcaggg agtcatggtc tggtctagaa 900
gatgagagat ccaaccaaac agccttctcc acaactcaac tctcaatatc cattcctatg 960
tcttccaatt tctctgcaac gagctctcag tccccacatg gtgaagatga gattcaattt 1020
aggtaa 1026

<210> SEQ ID NO 113
<211> LENGTH: 1155
<212> TYPE: DNA
<213> ORGANISM: Glycine max

<400> SEQUENCE: 113
atggacttcc atctgaagca atggagaaac cagcacgagt cagaggaaca acattctaca 60
aagatgccaa aacttctccc tgaatcccat caacaacaac agccatcagc ctctgcactc 120
cctttgtttg tacctgaacc caacagcagc aaagtcagca ccctgtcaga ttcaacatta 180
gcttctgcta caatgacttc taccaccact aacagattat ttcccaggat ggggagctac 240
ttcagcttgt ctcagtggca ggagcttgag ttgcaggctt tgatattcag gtacatgttg 300
gctggtgctg ctgttcctcc tgaactcctt caaccaatca agaaaagcct tcttcattct 360
ccacactatt acctccatca ccctctccaa cattaccaac cttctgcttt gttgcaatca 420
gggtattggg gtagaggagc gatggatccg gagccagggc ggtgccggag aaccgacggc 480
aagaagtggc gctgttcgag ggacgtggtg gctgggcaaa agtactgtga gcgccacatg 540
caccgtggaa gaaaccgttc aagaaagcct gtggaactac ccacaccaac tagtgctatt 600
aacaattgtg gtgtaactgg agttggatcc ctaggaccag gtgcttcatc atcttccatt 660
tgttcaccac ccttagcttc tgcttcattc aaatctcctt ttgatcttca tcttgatgaa 720
cgttcctctg ggaccaagaa tgaagacgaa gatcatgtgg gtggggatgg cagatcaggt 780
ggaggtggtg gccatatgct gaggcatttc ttcgatgatt ggccacgatc actccaagac 840

```
tctgacaacg ttgaaaacaa tgctgctgct ggccgtagcc tctctatttc aatgcccggt    900

gcttcctcgg atgtgtcatt gaaattgtcc acgggctatg gagaggactc gggcccagga    960

aatgagaatg taagcctcga gccagagcag ctgcagttga attgggccgg aggatgggcc   1020

tcgtctaatc aagtggcttc gatgggaggt ccacttgctg aggcactcag atcatctact   1080

tcaacctcat ctcccactag tgttttgcat cgtcacttgc ctcgtggatc tgagaccagc   1140

tttattagca cctga                                                    1155
```

<210> SEQ ID NO 114
<211> LENGTH: 1407
<212> TYPE: DNA
<213> ORGANISM: Glycine max

<400> SEQUENCE: 114

```
atggaagcta agcctcttcg aactgttccc tcttcacaca acacttctgg ggtaggaggt     60

ggaccccaga agaagattgg catggaacac aagatggaaa gtcgtgttgt tgatgagagg    120

aagagggttg ttatggtcaa ggaagagaac agcacttctt ctcccaacag tgttgaactt    180

catctcgggt ttgatgcttc tcattcgact ccacaagaaa taaaccatgt gatcactgaa    240

gctcagaggc gtgagcttca ccatcaagtt ttcatcttca accatttggc ttataatctt    300

cctcctcctt atcaccttgt gcaattccct agcaacatgt cagaatacag tttcctgggt    360

tttgatcatg ggattatggt ggatccagaa cctcataggt gtagaagaac tgatggaaag    420

aaatggaggt gtggtaagaa tgtggtgcct aaccagaagt actgtgaaag gcacatgcac    480

agaggtcgaa atcgttcaag aaagcctgtg gaaacatctc aagttaactc tcctttggca    540

acaaagcctt gtagcaagtc acacaccaaa ccatcctcaa agacacaatt tgaaatttca    600

agtccaaacc ttatcgccat tccacatatt gacacatcaa gtaccccatc aaggagcctc    660

agtgtcacca attgctcttc tgctaataat aggtcgaaaa atagggcagg ttatgctgac    720

tacctcatgt cgttttcttc cgcgtccaca gtgtcccctg gaaccactct tgccactcca    780

gttgccccta agatagctgc cttcagcagt gcgacatccg ttgttgcttc agatagcaaa    840

agttgcctaa agatatgcca gaaagataac cagtccaaga gctgtatcag caacaacatc    900

ggtgttaaaa gcggtgggaa aggaagcatt gttggtgata ctaatactaa tggcatctct    960

actggaataa gcttctcccc aacgagtgtt cttcaagttt cagtttctgg ttgcaaccct   1020

tcatacctga atgacggaac caacatagaa gctgcatccg gtaggtgccg gagaacagat   1080

ggtaagaagt ggcagtgcaa gagtgctgtt cttcctggtc agaaatactg tgccacacac   1140

atgcatagag gtgccaaaaa gcgtctcaca agccatgaac cagcagctac tgctaccagt   1200

tccgccgtta ccgttgcgcg gttgccttac tcttcagcca ctaccaacat acagaaagcg   1260

cattgtgcaa ttccaaacac aaatctttcc atgtcagtcc aagccaggga agcattcata   1320

caatgtaatg agaaaagtca aagtagcagt gacactgata ctactatcag tgacaccttg   1380

aatgagtata gctatgcttc tttctga                                       1407
```

<210> SEQ ID NO 115
<211> LENGTH: 1083
<212> TYPE: DNA
<213> ORGANISM: Glycine max

<400> SEQUENCE: 115

```
atgatgagtg caagtgcagg tgcaagaaat aggtctccgt tcacacaaat tcagtggcaa     60
```

-continued

```
gagcttgagc aacaagctct tgtttttaag tacatggtta caggaacacc tatcccacca    120

gatctcatct actctattaa aagaagtcta gacacttcaa tttcttcaag gctcttccca    180

catcatccaa ttgggtgggg atgttttgaa atgggatttg gcagaaaagt agacccagag    240

ccagggaggt gcagaagaac agatggcaag aaatggagat gttcaaagga ggcatatcca    300

gactcaaagt actgtgaaag acacatgcac agaggcagaa accgttcaag aaagcctgtg    360

gaagtttctt cagcaacaag caccgccaca aacacctccc aaacaatccc atcatcttat    420

accagaaacc tttccttgac caataacagt aaccccaaca taacaccacc accaccaccc    480

tcttctttcc ctttctctca tttgccctct tctatgccta ttgatcagtc ccaacccttt    540

tcccaatcct accaaaactc ttctctcaat cccttcttct actcccaatc aacctcctct    600

agacccccag atgctgattt tccaccccaa gatgccacca cccaccacct attcatggac    660

tctgctggct cttattctca tgatgaaaag aattatagca ggcatgttca tggaataagg    720

gaagatgtgg atgagagagc tttcttccca gaagcatcag gatcagctag gagctataca    780

gactcgtacc aacaactatc aatgagctcc tacaagtcct attcaaactc caactttcag    840

aacattaata atgatgccac caccaaccca agacagcaag agcagcaact acaacaacaa    900

caacactgtt ttgttttagg gacagacttc aaatcaacaa ggccaagcaa agagaaagaa    960

gctgagacaa caacaggtca gagacccctt caccgtttct ttggggagtg gccaccaaag   1020

aacacaacaa cagattcctg gctagatctt gcttccaact ccagaatcca aaccgatgaa   1080

tga                                                                 1083
```

<210> SEQ ID NO 116
<211> LENGTH: 1098
<212> TYPE: DNA
<213> ORGANISM: Glycine max

<400> SEQUENCE: 116

```
atgatgaatg gaaggaacag gttccccttt accccatcac agtggcaaga gcttgaacac     60

caagctctca tctacaagta catggcttca ggcatttcca ttccacctga tcttctcttc    120

accataaaaa ggagctattt tgattcccct ctgtcctcaa ggcttttgcc taaccagcca    180

cagcactttg gatggaacta ccttcagatg ggtttgggaa gaaaaataga ccctgagcca    240

ggtaggtgta gaagaactga tggcaagaaa tggagatgct ccaaagaagc atacccagat    300

tcaaagtact gtgagaggca catgcacaga gggaagaatc gttcaagaaa gcctgtggaa    360

gttttaaaat caacaacaac accatcatca tcaacaacaa actcaaatgc ttcttctaca    420

caacaagcaa tctcatcaat caccaaaatt aatagcactc tctcacctct tgcatcatct    480

gagactcacc aacaccacca ctatcctcaa cactatggct cctttctcta tcatcatcac    540

cctccttcaa ggtcctctgg cattggcttg tcttttgaag acaacagtgc tcccttgttt    600

cttgacactg gctcatgctc tcagtccaac acagactgca ggagtaggta tgtttatgga    660

gagaaagagg aggtggatga gcatgctttc ttcacagaac cttgtggtgt tatgaaaagc    720

ttctctgctt cctctatgga tgactcatgg caactcacac cattgactat gagctcctca    780

tcttcatctt ccaagcagag gagttccttt ggcttgtcca gtgattactc ttgcttgcaa    840

cttcagagcc actcaaagca gcagcagcaa gagcatcatc aagatcaggg ttgctacatg    900

tttggtgctg gtcaagttgt gaaagaagaa cctcagaaaa cggttcatcg cttctttgat    960

gaatggccac acaaaggaag agaaggctct tggcttgatt tggatgacaa atcttccaca   1020

acccaacttt caatttccat ccccacatct tctcatgatt tttcaacttt cagttccaga   1080
```

acccaccatg atggttga 1098

<210> SEQ ID NO 117
<211> LENGTH: 1038
<212> TYPE: DNA
<213> ORGANISM: Glycine max

<400> SEQUENCE: 117
atgatgagtg caagtgcaag aaataggtct cctttcacgc aaactcagtg gcaagagctt 60
gagcatcaag ctcttgtttt taagtacatg gttacaggaa cacccatccc accagatctc 120
atctactcta ttaaaagaag tctagacact tcaatttctt caaggctctt cccacatcat 180
ccaattgggt ggggatgttt tgaaatggga tttggcagaa aagtagaccc agagccaggg 240
aggtgcagaa gaacagatgg caagaaatgg agatgctcaa aggaggcata tccagactcc 300
aagtactgtg aaagacacat gcacagaggc agaaaccgtt caagaaagcc tgtggaagtt 360
tcttcagcaa taagcaccgc cacaaacacc tcccaaacaa tcccatcttc ttatacccga 420
aacctttcct tgaccaaccc caacatgaca ccaccctctt ccttcccttt ctctcctttg 480
ccctcttcta tgcctattga gtcccaaccc ttttcccaat cctaccaaaa ctcttctctc 540
aatcccttct tctactccca atcaacctcc tctagacccc cagatgctga ttttccaccc 600
caagatgcca ccacccacca gctattcatg gactctgggt cttattcgca tgatgaaaag 660
aattataggc atgttcatgg aataagagaa gatgtggatg agagagcttt cttcccagaa 720
gcatcaggat cagctaggag ctacactgaa tcataccagc aactatcaat gagctcctac 780
aagtcctatt caaactccaa ctttcagaac atcaatgatg ccaccaccaa cccaagacag 840
caagagcagc aacaacaaca acactgcttt gttttgggga cagacttcaa atcaacaaga 900
ccaactaaag agaaagaagc tgagacagct acgggtcaga gaccccttca ccgtttcttt 960
ggggagtggc caccaaagaa cacaacagat tcatggctag atcttgcttc caactccaga 1020
atccaaaccg atgaatga 1038

<210> SEQ ID NO 118
<211> LENGTH: 1167
<212> TYPE: DNA
<213> ORGANISM: Glycine max

<400> SEQUENCE: 118
atggacttcc atctgaagga atggagaaac cagcatgagt cagaggaaca acaacattct 60
acaaagatgc caaaacttct ccctgaatcc catcatcaac agccatctgc cactgcactc 120
cctttgtttg tacctgaacc caacagcagc agcaaagtca gcaccctgtc agattcaaca 180
ttagcagctg aaactgaaac aatgaccact acaaccacta acagattatt tcccaggatg 240
gggagctact tcagcttgtc tcagtggcag gagcttgagt tgcaggcttt gatattcagg 300
tacatgttgg ctggtgctgc tgttcctcct gaactccttc aaccaatcaa gaaaagcctt 360
cttcattccc ctcactattt cctccatcac cctctccaac attaccaacc tgctgctttg 420
ttgcaatcag ggtattgggg tagaggagcg atggatccgg agccagggcg gtgccggaga 480
accgacggca agaaatggcg gtgctcgagg gacgtggtgg ctgggcaaaa gtactgtgag 540
cgccacatgc atcgtggaag aaaccgttca agaaagcctg tggaactacc cacaccaact 600
agtgctaata attgtgatgg tggatctcta ggactaggtg cttcttcatc ttccatttct 660
tcaccacccc tagcttctgc ttcactcaaa tccccatttg atcttcttcg tcttaatgaa 720

```
cgttcctctg ggaccaagaa tgaagacgaa gaccatgtgg gtggggatgg cagatcaggt    780

ggagggggtg gccatatgct gaggcatttc ttcgatgatt ggccacgatc actgcaagac    840

tctgacaacg ttgaaaacaa tgctgctggc cctagcctct ctatttcaat gcccggaaat    900

gctgctgctg cttcctcgga tgtgtcattg aaattgtcca cgggctatgg agaggaccca    960

ggcccaagaa atgagaatgt gggcctcgtg gcagagcagc tgcagttgaa ttgggccgga   1020

ggatgggcct cgtctaatca agtggcttcc atgggaggac cactggccga ggcactcaga   1080

tcatctattt caacttcatc tcccactagt gttttgcatc acttgcctcg tggttctgga   1140

tctgagacca gcattattag cacctga                                       1167
```

<210> SEQ ID NO 119
<211> LENGTH: 1782
<212> TYPE: DNA
<213> ORGANISM: Glycine max

<400> SEQUENCE: 119

```
atgggtgaat tatttggcgt tgggaaaaga agggacatca tcagcaacaa caacagtgct     60

agtagtagcg ttcttgggtt ggatgtgaag gtgcagagcc ctgaagtatt attccataat    120

aggatgacca tgatggggca tcataatcat cacctccatc cattgtcatc cccctttgat    180

aataataacg atatttcctg tgctgctggt gatggcgatg gtgatggtcc cacgacttac    240

atgtctctca ctaatcatat aaaccttgtt agtggtgctt ctgttcttgg tcctgctatt    300

gatggtggct gtggtgctgc tcctgctgca cctgtaagaa ctttgcagcc ttttcaaatt    360

tcttcttata cttctcccac caccactacc acagccttcg aaccctttc aggtgtgatg    420

gcggcttcat tggggtttcc cttcacaagt gcacaatgga gggagcttga aaggcaggct    480

atgatataca agtacatgat ggcttcagtt cctgttccac ctgatctcct cattcctact    540

tcactcacat cctcttctcg ctcttcctgc atggatggtg gtttcaatct gaggttggca    600

aatagcactg accctgagcc aggtaggtgc agaagaacag atggaaaaaa atggagatgt    660

tcaagagacg tggctcctaa ccacaagtac tgcgagcgcc atatgcatag aggccgtccc    720

cgttcaagaa agcctgtgga agttaacacc aacaccactc ccactagcat caacaacaac    780

aataacaacc accaaatcaa aagggctcgc catgagtgta ataatccctt tgctacacct    840

gatgttgctg tggctatttc caatcccact tccagaaaag gtgaatcttc atcccatttt    900

cttgggtcta ctaccactca gccatacctt aaatctcccc tctgtcttgc taacttcggt    960

ctcaaagctg cgagttttga ctccgtggct tctgtttctg caaataagga acccaggggt   1020

ttggagtgga tgctgaatgg agatcctatt tccctggatg cttctaactc ccaatggcag   1080

tctctgatgc ataataaagt tggaatgagc agtgttagtt cctgtaatac caccgagtct   1140

cagtatctga attcatttgc actatatagc tctggactgg aacaacagaa cagacgccat   1200

cctttgttcc tgaatcctct tcttgttccc atgaaaaatc tccaaccaga gaaaccaagg   1260

ggtttcattg atgcttggtc taatgcagaa acagctcaaa gcaatgccaa caccaacaac   1320

aagaactctg ctgcatcaat tggtaaatta tccctctctt ctcttgatct atcaatgggg   1380

ggtggtgctg tgagtgaaga tgttgataat gttaacatgg gtttgggact aatggagact   1440

tatggaaaaa cacacactga tactaaaatc tctctctcaa attggcacaa cccggcacct   1500

tgggtggctt caagttcaac acttgggggt cctctagctg aagttctaag gtcaagcaca   1560

gtcactgcca cgaccaatga agcaacctcc aacgcaacct catcaccagc caccactaca   1620

catgctgaat ctaacagccc tctgggaaca atggtgtcat ctccatccgg ggtgttgcag   1680
```

aaaaccctta tttcattgtc tgatagcagt aacaatagca gccctacggt tgcatcatca 1740
agggccaatt ctgagatggc cttcctcagc tttaaattct ag 1782

<210> SEQ ID NO 120
<211> LENGTH: 1011
<212> TYPE: DNA
<213> ORGANISM: Glycine max

<400> SEQUENCE: 120
atggacttgc agttgaagca atggagaaac cagcatgagt cagagcaaga acaagaacat 60
tattccccaa acatggcaaa atttctatct caacaacaac acccaccacc atttccctct 120
gcactccctc tctttgtacc tgaacaaccc aacaccaaag tcagcacctt gtcagcattt 180
tctgattcca cattaccctc ttctcccaga tttcccagaa tggagagttg cttcagcttt 240
gcacaatggc aagagcttga gttgcaggct ctgatattca ggtacatgct ggccggtgct 300
cctgttcctc ctgagctcct tctaccaatc aagaaaagct tccttcaact ttatcaccct 360
cctaatttgt tggaatcagg gtactactgg cgaagagaag cactggatcc ggagccgggg 420
cggtgccgga ggaccgacgg caagaagtgg cggtgctcga aggacacggt ggcaggtcag 480
aagtactgcg accgccacat gcaccgtggc cggaaccgtt caagaaagcc tgtggaacaa 540
cgtgaaggat ctctttctgc tatagactct gtttcttctt cacactctgc ttcattcaat 600
ctccttcacc tcggtcaaag ttccgctgtg gccaagagtg acagcaagag cttgtctaga 660
aaccgtgatc atgtggatgg ggatggcaaa tcaaatggcc atgtcttgag gcatttcttt 720
gatgattggc caaggacact gcaagagcct gacaatggtg aaagcaatgg aagccagaac 780
aacaactcag gaaaatgtct ttctatgtca acaccaggaa tcgatccctc ggatgtgtcg 840
ttgaaattga ccactggcta tggagaggac gcgtgccagg cagcttcggt gggaggacca 900
cttgcagagg cattgagatc atccaccacc agctccactt cttcaccaac cagtgttctg 960
cttcagttgc ctcctagttc tgcttgtgag accagcttca ttagcaccta a 1011

<210> SEQ ID NO 121
<211> LENGTH: 62
<212> TYPE: DNA
<213> ORGANISM: Artificial sequence
<220> FEATURE:
<223> OTHER INFORMATION: Synthetic GRF

<400> SEQUENCE: 121
cacatgcacc gtggccgcaa ccgttcaaga aagcctgtgg aatcacaaac tatgactcag 60
tc 62

<210> SEQ ID NO 122
<211> LENGTH: 62
<212> TYPE: DNA
<213> ORGANISM: Artificial sequence
<220> FEATURE:
<223> OTHER INFORMATION: Synthetic GRF

<400> SEQUENCE: 122
catatgatac ggcggcgtta ccgttcaaga aagcctgtgg aatcatctca aactcactct 60
tc 62

<210> SEQ ID NO 123
<211> LENGTH: 62
<212> TYPE: DNA

<213> ORGANISM: Artificial sequence
<220> FEATURE:
<223> OTHER INFORMATION: Synthetic GRF

<400> SEQUENCE: 123
cacatgcaca gagggaaaaa tcgttcaaga aagcctgtgg aagttttgaa aacaacacca 60
ac 62

<210> SEQ ID NO 124
<211> LENGTH: 62
<212> TYPE: DNA
<213> ORGANISM: Artificial sequence
<220> FEATURE:
<223> OTHER INFORMATION: Synthetic GRF

<400> SEQUENCE: 124
cacatgcata gaggtcgaaa tcgttcaaga aagcctgtgg aaacatctca aattaactct 60
ca 62

<210> SEQ ID NO 125
<211> LENGTH: 62
<212> TYPE: DNA
<213> ORGANISM: Artificial sequence
<220> FEATURE:
<223> OTHER INFORMATION: Synthetic GRF

<400> SEQUENCE: 125
cacatgcaca gagggaagaa tcgttcaaga aagcctgtgg aagttttgaa aacaacaaca 60
cc 62

<210> SEQ ID NO 126
<211> LENGTH: 62
<212> TYPE: DNA
<213> ORGANISM: Artificial sequence
<220> FEATURE:
<223> OTHER INFORMATION: Synthetic GRF

<400> SEQUENCE: 126
catatgatac gacgtcgtta ccgttcaaga aagcctgtgg aatcatctca aactcactct 60
tc 62

<210> SEQ ID NO 127
<211> LENGTH: 62
<212> TYPE: DNA
<213> ORGANISM: Artificial sequence
<220> FEATURE:
<223> OTHER INFORMATION: Synthetic GRF

<400> SEQUENCE: 127
cacatgaacc gaggacgcca tcgttcaaga aagcctgtgg aaggccaatc aggccatgcc 60
ct 62

<210> SEQ ID NO 128
<211> LENGTH: 62
<212> TYPE: DNA
<213> ORGANISM: Artificial sequence
<220> FEATURE:
<223> OTHER INFORMATION: Synthetic GRF

<400> SEQUENCE: 128
cacatgcaca gagggaaaaa ccgttcaaga aagcctgtgg aagttttgaa aacaacacca 60
at 62

<210> SEQ ID NO 129
<211> LENGTH: 62
<212> TYPE: DNA
<213> ORGANISM: Artificial sequence
<220> FEATURE:
<223> OTHER INFORMATION: Synthetic GRF

<400> SEQUENCE: 129
cacatgaacc gaggacgcca tcgttcaaga aagcctgtgg aaggccaatc aggccatgcc 60
ct 62

<210> SEQ ID NO 130
<211> LENGTH: 62
<212> TYPE: DNA
<213> ORGANISM: Artificial sequence
<220> FEATURE:
<223> OTHER INFORMATION: Synthetic GRF

<400> SEQUENCE: 130
cacatgaata gaggacgcca tcgttcaaga aagcctgtgg aaggccaatt aggccatgcc 60
ct 62

<210> SEQ ID NO 131
<211> LENGTH: 62
<212> TYPE: DNA
<213> ORGANISM: Artificial sequence
<220> FEATURE:
<223> OTHER INFORMATION: Synthetic GRF

<400> SEQUENCE: 131
cacatgaaca gaggacgcca tcgttcaaga aagcctgtgg aaggccaatc aggccatgcc 60
ct 62

<210> SEQ ID NO 132
<211> LENGTH: 62
<212> TYPE: DNA
<213> ORGANISM: Artificial sequence
<220> FEATURE:
<223> OTHER INFORMATION: Synthetic GRF

<400> SEQUENCE: 132
cacatgcacc gtggccgcaa ccgttcaaga aagcctgtgg aatcacaaac tatgactcac 60
tc 62

<210> SEQ ID NO 133
<211> LENGTH: 62
<212> TYPE: DNA
<213> ORGANISM: Artificial sequence
<220> FEATURE:
<223> OTHER INFORMATION: Synthetic GRF

<400> SEQUENCE: 133
catatgcata gaggccgtcc ccgttcaaga aagcctgtgg aagttaacac caacagcacc 60
ac 62

<210> SEQ ID NO 134
<211> LENGTH: 62
<212> TYPE: DNA
<213> ORGANISM: Artificial sequence
<220> FEATURE:
<223> OTHER INFORMATION: Synthetic GRF

<400> SEQUENCE: 134
cacatgcacc gtggccgcaa ccgttcaaga aagcctgtgg aatcacaaac tatgacacag 60
tc 62

<210> SEQ ID NO 135
<211> LENGTH: 62
<212> TYPE: DNA
<213> ORGANISM: Artificial sequence
<220> FEATURE:
<223> OTHER INFORMATION: Synthetic GRF

<400> SEQUENCE: 135
cacatgcatc gtggccgaaa ccgttcaaga aagcctgtgg aacaacgtga tggatctctt 60
tc 62

<210> SEQ ID NO 136
<211> LENGTH: 62
<212> TYPE: DNA
<213> ORGANISM: Artificial sequence
<220> FEATURE:
<223> OTHER INFORMATION: Synthetic GRF

<400> SEQUENCE: 136
cacatgcacc gtggccgcaa ccgttcaaga aagcctgtgg aatcacaaac tatgactcac 60
tc 62

<210> SEQ ID NO 137
<211> LENGTH: 62
<212> TYPE: DNA
<213> ORGANISM: Artificial sequence
<220> FEATURE:
<223> OTHER INFORMATION: Synthetic GRF

<400> SEQUENCE: 137
cacatgcacc gtggaagaaa ccgttcaaga aagcctgtgg aactacccac accaactagt 60
gc 62

<210> SEQ ID NO 138
<211> LENGTH: 62
<212> TYPE: DNA
<213> ORGANISM: Artificial sequence
<220> FEATURE:
<223> OTHER INFORMATION: Synthetic GRF

<400> SEQUENCE: 138
cacatgcaca gaggtcgaaa tcgttcaaga aagcctgtgg aaacatctca agttaactct 60
cc 62

<210> SEQ ID NO 139
<211> LENGTH: 62
<212> TYPE: DNA
<213> ORGANISM: Artificial sequence
<220> FEATURE:
<223> OTHER INFORMATION: Synthetic GRF

<400> SEQUENCE: 139
cacatgcaca gaggcagaaa ccgttcaaga aagcctgtgg aagtttcttc agcaacaagc 60
ac 62

<210> SEQ ID NO 140
<211> LENGTH: 62

<212> TYPE: DNA
<213> ORGANISM: Artificial sequence
<220> FEATURE:
<223> OTHER INFORMATION: Synthetic GRF

<400> SEQUENCE: 140
cacatgcaca gagggaagaa tcgttcaaga aagcctgtgg aagttttaaa atcaacaaca 60
ac 62

<210> SEQ ID NO 141
<211> LENGTH: 62
<212> TYPE: DNA
<213> ORGANISM: Artificial sequence
<220> FEATURE:
<223> OTHER INFORMATION: Synthetic GRF

<400> SEQUENCE: 141
cacatgcaca gaggcagaaa ccgttcaaga aagcctgtgg aagtttcttc agcaataagc 60
ac 62

<210> SEQ ID NO 142
<211> LENGTH: 62
<212> TYPE: DNA
<213> ORGANISM: Artificial sequence
<220> FEATURE:
<223> OTHER INFORMATION: Synthetic GRF

<400> SEQUENCE: 142
cacatgcatc gtggaagaaa ccgttcaaga aagcctgtgg aactacccac accaactagt 60
gc 62

<210> SEQ ID NO 143
<211> LENGTH: 62
<212> TYPE: DNA
<213> ORGANISM: Artificial sequence
<220> FEATURE:
<223> OTHER INFORMATION: Synthetic GRF

<400> SEQUENCE: 143
catatgcata gaggccgtcc ccgttcaaga aagcctgtgg aagttaacac caacaccact 60
cc 62

<210> SEQ ID NO 144
<211> LENGTH: 62
<212> TYPE: DNA
<213> ORGANISM: Artificial sequence
<220> FEATURE:
<223> OTHER INFORMATION: Synthetic GRF

<400> SEQUENCE: 144
cacatgcacc gtggccggaa ccgttcaaga aagcctgtgg aacaacgtga aggatctctt 60
tc 62

<210> SEQ ID NO 145
<211> LENGTH: 22
<212> TYPE: DNA
<213> ORGANISM: Glycine max

<400> SEQUENCE: 145
ccgttcaaga aagcctgtgg aa 22

<210> SEQ ID NO 146

<211> LENGTH: 22
<212> TYPE: DNA
<213> ORGANISM: Glycine max

<400> SEQUENCE: 146
tcgttcaaga aagcctgtgg aa 22

<210> SEQ ID NO 147
<211> LENGTH: 1737
<212> TYPE: DNA
<213> ORGANISM: Triticum aestivum

<400> SEQUENCE: 147
atggacctgg gcggggtgct gatggcggcc gcggacgcgg gggtgggcgg cggggacctc 60
ggcatgctcg gatctaggct gctcaagcac gggaggggca atgaggccga cgagcacggc 120
tggggcggcg gcaggccggc gtccaagcag gcccgggtcg ccggggacag cgacgcggtg 180
tccgaggccg tcaaggcggc cgcgccctac ctgctcggca cctgcagccc cgggcacggc 240
cgggagaaga tgctcagctt ctcctcctcg cagccggcct cctgcccctc cgccgctcag 300
gccgcgctgc cgctctacta cggcacgccc gcttcttgct cagggttgag ctcagtgagg 360
gggcccttca cgccgtcgca gtggatggag ctggagcacc aggccctgat ctacaagtac 420
ctggcggcca acatcgccgt gcctcacaac ctcgtcgtcc ccatccgccg gagcgtcacc 480
tcgctctacc cgtccgccta ctttggctcc tccacattgg ggtgggggcc tttccagctg 540
ggctactccg ggagcgcgga cctggagccc gggcggtgcc gccggacgga cggcaagaag 600
tggcggtgct ccagggacgc cgtcgccgac cagaagtact gcgagcggca tatgaaccgg 660
ggacgccatc gttcaagaaa gcatgtggaa ggccagcctg gccatgccgc gaaagcgatg 720
cctgcgacgg ccgctgctgc cgcccagccc ggtgctctcg ccaccggggg cggcggcgga 780
gctcccgccg gcgccgccat ctgccacgag cagcaaccgt tgaagaacta cgccgccagc 840
accattgatc cttgttcact gcaatataac agggaaatgg tgagcaagca gcaacacgag 900
tgcgagcaag tgcaggactc cgacaccctc tcgatgctga cctccatgag cgcgaggaac 960
accaatgcag gcagcatgtt cccgttctca aaggaacatc ataaccacaa tcctttcgag 1020
gtgacgagct cgaggccgga ctacgggctg gtttcatccg actcgctgat gagctcccct 1080
cacagctccc tggagaacgt caacctgctc acctcgcagc gagctctctc gagcgagcag 1140
cagagctcgc tctccctgca gcacttcgcg gactggccga ggacgccctc gcagcagggg 1200
cagggaggag gtctctcatg gccggacgcc gaggacatgc aagctcatca gaggacccag 1260
ctctcggtgt ccgccgttcc aatggcgtcc tctgacctgt cgtcggcctc cacgtccccg 1320
atccacgaga agctcatgct gtcgcccctc aagctgagcc gcgagtacag ccccatcggc 1380
ctcagcgtcg cggccacggc ggcggtggcg aaggacgagg gggaggcgaa ctggatgccc 1440
atgttccgcg actcgtccat gggcgggccg ctgggggagg ctctgaacaa gaacaatggc 1500
ggcaacatgg aggccaagag ctacctgtcg gcgtcgctga acctgatgac ggacgcctgg 1560
gactcgagcc cgctggagtc gtcgccggtg gggtcctgc agaggaccgc cttcggatcg 1620
gtgtccagca gcaccggcag cagccccagg caggagtacc acggcgtgta tgatggtaac 1680
ccgcgggatg atctcggctc catcgtcgtg aatcacccca gcatccgcct gatgtga 1737

<210> SEQ ID NO 148
<211> LENGTH: 678
<212> TYPE: DNA
<213> ORGANISM: Triticum aestivum

<400> SEQUENCE: 148

```
atgaccgagc gaaggcagga gcactcgccg ccgtccaaga tcccccgcct ctccggcgcc     60
gacgacgatg acggcgcagg gacggtgacc atggcggcgc cgtcgccgct ggttcttggg    120
ctgggtctcg gcgtaggcgg cagcagcagt gacagcggac gcggcgacgc ggaggcctct    180
gcggcgacgc ggccgtcggc gctgacgttc atgcagcggc aggagctgga gcaccaggtg    240
ctcatctacc gctacttcgc cgccaacgct cccgtgcccg tgcacctcgt gctccccatc    300
tggaagagcg tcgccgcttc ctcctccgcc ccgcagaggt ttccatccct ggcggggctg    360
gggagcatgt gctacgacca caggagcagc atggagccgg agccggaccg gtgccggcgc    420
acggacggca agaagtggcg gtgctcgcgc ggcgtggtgc cggggcacaa gtactgcgag    480
cgccacgtcc accgcggccg cagccgtgca agaaagcctg tggaagccgc ggcggccaca    540
tcagccgtcc cgatccgcgc gatgcacgcc gccgacgcgc agggcgccac cagtgcgcac    600
gcggcgccac cgcagcgcct cggcttctcc tcccccgccg gcgtctacct ggcgcacggc    660
accgcccgtg ccacctga                                                   678
```

<210> SEQ ID NO 149
<211> LENGTH: 1176
<212> TYPE: DNA
<213> ORGANISM: Triticum aestivum

<400> SEQUENCE: 149

```
atggcgatgc cctttgcctc cctgtcgccg gcagccgacc accaccgctc ctcccccatc     60
ttccccttct gccgctcctc ccctctctac tcggcagggg aggaggcggc gcagcagcag    120
cagcagcacg cgatgagcgg cgcgaggtgg gcggcgatga ggccggcgac cttcacggcg    180
gcgcagtacc aggagctgga gcagcaggcg ctcatctaca agtacctcgt cgccggcgtg    240
cccgtcccgc cggatctcct cctccccatc cgccgcgact tcgactccct cgcctcgcgc    300
ttctaccacc accacgccct tgggtacggg tcctacttcg ggaagaagct ggatccggag    360
ccggggcggt gccggcggac ggacggcaag aagtggcggt gctccaagga ggccgcccag    420
gactccaagt actgcgagcg ccacatgcac cgcggccgca accgttcaag aaagcctgtg    480
gaaacgcagc tcgtcgccac gccccactcc cactcccact cccagcagct gcagcagcac    540
gcccccgccg ccaccgccgc cgcgttccac agccactcgc cgtacccggc gatcgccact    600
ggcggcggcg gcggcgcggc cggctccttc ggcctggggt ctgctcagct gcacatggac    660
aatgctgctg cgccttacgc gaccgctggt gcggccggaa acaaggattt caggtattct    720
gcctatgggt ttaggacttc ggcgctggag gagcacaacc agttcatcag cgcggccatg    780
gacaccgcca tggacaacta ctcatggcgc ctgatgccgg cccagaactc ggcgttctca    840
ctctcgagct accccatgct gggcaccctg ggcgacctgg accagagcgc gatctgctcg    900
ctggccaaga cggagaggga gccgctgtcc ttcggcggcg gcggcggctt cgaggacgac    960
gagtcggcgg tgaagcagga gaaccagacg ctgcggccct tcttcgacga gtggcccaag   1020
gacagggact cgtggccgga gctgcaggac catgactcca accacaacag caacgccttc   1080
tcggccacca agctgtccat ctccatcccg gtgaccagct ccgacttctc caccaccgcc   1140
ggctcccgct cgccccacgg tatatactcc cggtga                              1176
```

<210> SEQ ID NO 150
<211> LENGTH: 1824
<212> TYPE: DNA

<213> ORGANISM: Triticum aestivum

<400> SEQUENCE: 150
atggacctgg gcggggtgct gatggcggcc gcggacgcgg gggtgggcgg cggggagctc 60
ggcatgctcg gatctaggct gctcaagcac gggaggggca atgccgcggc ggcggaggcc 120
gacgagcgtc acgagcacgg gtggggcggc ggcaggccgg ccgccaagca ggcccgggtc 180
gccggggaca gcgacgccgt gtccgaggcc gtcaaggcgg ccgcgccata cctgctgggc 240
acctgcagcc ccgggcacgg ccgggagaag atgctcagct tctcctcctc gcagcagccg 300
ccctcctgcc cctccgccgc cgccgccgct caggccgcgc tgccgctcta ctacggcacg 360
cccgcttctt gcttagggtt gagctcggtg agcttgagcg ccagcatcca gggcgccatg 420
gccagggtga gggggccctt cacgccgtcg cagtggatgg agctggagca ccaggccctg 480
atctacaagt acctggcggc caacatcgcc gtgccgcaca gcctcctcgt ccccatccgc 540
cggagcgtca cctcgctcta cccgtccgcc tactttggct cctccacatt ggggtggggg 600
cctttccagc tgggctactc cgggagcgcg gacctggagc ccgggcggtg ccgccggacg 660
gacggcaaga agtggcggtg ctccagggac gccgtcgctg accagaagta ctgcgagcgg 720
catatgaacc ggggacgcca tcgttcaaga aagcatgtgg aaggccagcc tggccatgcc 780
gcgaaagcga tgcctgcgac ggtggcggct gctgccgccc agcccggtgc tctcgccacc 840
gggggcggcg gcggagccac cgccggcgcc gccatctgcc acgagcagca gccgttgaag 900
agctactccg ccagcaccat tgatccttgt tcactgcaat acaacaggga aatggcgagc 960
aagcagcaac acgagtgcga gcaagtgcag gactcggaca ccctctcgat gctgacctcc 1020
atgagcgcga ggaacaccaa cacgggcagc atgttcccgt tctcaaagga acatcataac 1080
cacaatcctt tcgaggtgac gagctcgagg ccggactacg ggctggtttc ctccgactcg 1140
ctgatgagct ccccccacag ctccctggag aacgtcaacc tgctcacctc gcagcgagcg 1200
ctctcgagcg agcagcagag ctcgctctcc ctgcagcact tcgcggactg gccgaggacg 1260
ccgtcgcagc aggggcaggg agggggaggc ctctcatggc cggacgccga gaacatgcag 1320
ctggctcatc agcggaccca gcagctctcg gtgtccgccg ctccgatggc gtcctccgac 1380
ctgtcgtcgg cctccacgtc cccatccac gagaagctca tgctgtcgcc cctcaagctg 1440
agccgcgagt acagccccat cggcctcagc gtcgcggcca cggcggcagc ggcggcgaag 1500
gacgaggggg aggcgaactg gatgcccatg ttccgcgact cgtccatggg cgggccactg 1560
ggggaggctc tgaacaagaa caatggcggc aacatggagg ccaagaacta cctgtcggcg 1620
tcgctgaacc tcatgacgga cgcctgggac tcgagcccgc tggagtcgtc gccggtgggg 1680
gtcctgcaga ggaccgcctt cgggtcggtg tccagcagca ccggcagcag ccccaggcag 1740
gagtaccacg gcgtgtatga tggtaatccg cgggatgatc tcggctccat cgtcgtgaat 1800
caccccagca tccgcctcat gtga 1824

<210> SEQ ID NO 151
<211> LENGTH: 690
<212> TYPE: DNA
<213> ORGANISM: Triticum aestivum

<400> SEQUENCE: 151
atgaccgagc gaaggcagga gcactcgccg ccgtccaagc tcccccgcct ctccggcccc 60
gacgccgacg ccgacgacaa tgatggcgca gggacggtga ccatggcggc gccgtcgccg 120
ctggttcttg ggctgggtct cggcgtaggc ggcagctgca gtgacagcgg acgcggcgac 180

```
gcggaggcct ctgcggcgac gcggccgtcg gcgctgacgt tcatgcagcg gcaggagctg    240

gagcaccagg tgctcatcta ccgctacttc gccgccaacg ctcccgtgcc ggtgcacctc    300

gtcctcccca tctggaagag cgtcgccgcc tcctcctccg ccccgcagag gttcccatcc    360

ctggcgggac tggggagcat gtgctacgac cacaggagca gcatggagcc ggagccggac    420

cggtgccggc gcacggacgg caagaagtgg cggtgctcgc gcggggtggt gccggggcac    480

aagtactgcg agcgccacgt ccaccgcggc cgcggccgtg caagaaagcc tgtggaagcc    540

gcggcggcca catcagccat cccgatccgc gcgatgcacg ccgccgacgc gcagggcgcc    600

accagcgcgc acgcggcgcc gccgcagcgc ctcggcttct cctcccccgc cggcgtgtac    660

ctggcccacg gcaccgcccg tgccacctga                                      690
```

<210> SEQ ID NO 152
<211> LENGTH: 1248
<212> TYPE: DNA
<213> ORGANISM: Triticum aestivum
<220> FEATURE:
<221> NAME/KEY: misc_feature
<222> LOCATION: (46)..(51)
<223> OTHER INFORMATION: n is a, c, g, or t

<400> SEQUENCE: 152

```
atgcttcctg agctcaccgc cgccgccatg gagctcgggc aggtgnnnnn ntacacgccg     60

ccggcgacca aggacgcgag atccggcggc ggcttcgccc aggccgccgc ttgcccctac    120

ccctacccct ccccccttcct cgacgagcag aagatgctca gcttctccaa ggccgccgcc    180

cctccatcgt caggtatgga ttttggcagg tccaatgagc agaggctgct gctggccagg    240

agcaagatgc ccttcactcc ttcacagtgg atggagctgg agcaccaggc cctcatatac    300

aagtatctca atgcaaaggc ccccatacct tccagcctgc tcatctccat cagcaaaagc    360

ttcagaccct cctccgatag aatgccctgg aggcctgtct accaagggtt caccaatgca    420

gattctgacc cggaacctgg aagatgccgt cgaacagacg gcaagaaatg gcggtgctca    480

aaggaggcga tggccgagca caagtactgt gagcggcaca tcaataggaa ccgccatcgt    540

tcaagaaagc ctgtggaaaa ccaaacaagg aagaacgcca aagagacgcc tgctgctggc    600

tcgttatcgg ccgctgtctc acagggtggc tgtaagaaag caaaagctgg tgatgaactg    660

aagccaggga gcgtcagcta ttggacagat aatttaaaca gggcaatggt gagcaaagcc    720

aggggaaaca accctgaaga aggcaacagt gctccactcc tgaattctac taatcaacaa    780

cacacattgt ccttgttctc tcaactgaag caacagagca aaccagataa gttcagcccg    840

gcagtcgata gtgaatcgat ctcctcaaat acagtattga agccctggga aagaagcaac    900

cagcagagca gcaaggacgt ttcttcgacg acgctccatg atcgcgggtg ccttcaatca    960

gtccttcaag atttcagcat gcataagaat gacaagatcg aggctcagaa aaacaatgct   1020

tcagtgccat caactttcta ttcacctaca gaaggtcaac acatcagctg ccttgcatct   1080

aacatgatgc aagtgcagga ggattgcatc tcaagctctt gggagatacc tcaaggtggg   1140

ccattaggtg aaatcctaac aaactccaag aacactgatg acttgaccaa taagtgtgaa   1200

tcaagatcat atggttggtt actgagtctt gatgaacatg aaatgtga                 1248
```

<210> SEQ ID NO 153
<211> LENGTH: 1164
<212> TYPE: DNA
<213> ORGANISM: Triticum aestivum

<400> SEQUENCE: 153
atggcgatgc cctttgcctc cctgtcgccg gcagccgacc accaccgctc ctcccccatc 60
ttccccttct gccgctcctc ccctctctac tcggtagggg aggagacggc gcatcagcag 120
cagcagcagc acacgatgag cggcgcgagg tgggcggcga ggccggcgac cttcacggcg 180
gcgcagtacg aggagctgga gcagcaggcg ctcatctaca agtacctcgt cgccggcgtc 240
cccgtcccgc cggatctcct cctccccatc cgccgcggct tcgactccct cgcctcgcgc 300
ttctaccacc accacgccct cgggtacggt tcctacttcg ggaagaagct ggatccggag 360
ccggggcggt gccggcggac ggacggcaag aagtggcggt gctccaagga ggccgcccag 420
gactccaagt actgcgagcg ccacatgcac cgcggccgca accgttcaag aaagcctgtg 480
gaaacgcagc tcgtcgccac gccccaccac tcccactccc agcagctgca gcagcacgcc 540
cccgccgcca gcgccgccgc gttccacagc cactcgccgt atccggcgat cgcctctggc 600
ggcggcggct ccttcgccgt gggatctgct cagctgcaca tggacaatgc tgcttcgcct 660
tacgcgaccg ctggtgccgc cggaaacaaa gatttcaggt attctgccta tgggtttagg 720
acttcggcga tggaggagca caaccagttc atctctgcgg ccatggagac cgccatggag 780
aactactcat gccgcctgat gccggcccag aactcatcct tctcactcgc cagctacccc 840
atgctgggca ccctgggcga ccttgaccag agcgcgatct gctcgctggc caagacggag 900
agggagcctc tgtccttctt cggcggcggc ggcggcttcg acgacgacga ctcggcggtg 960
aagcaggaga accagacgct gcggcccttc ttcgacgagt ggcccaagga cagggactcg 1020
tggccggagc tgcaggacca cgatgccaac aacagcagca acgccttctc ggccaccaag 1080
ctgtccatct ccatcccggt gaccagctcc gacttctcca ccaccgccgg ctcccgctcg 1140
cccaacggta tatactcccg gtga 1164

<210> SEQ ID NO 154
<211> LENGTH: 1107
<212> TYPE: DNA
<213> ORGANISM: Triticum aestivum

<400> SEQUENCE: 154
atgctgagct cgtcggcggc gatggggatg gggctgggcg ggtacggcca gcagcagcag 60
cagcagatgc agatgcagat gcagcggggg gcggagccgg tgttcacgcc ggcgcagtgg 120
gccgagctgg agcagcaggc gctgatttac aagtacctca tggcgggcgt gcccgtgccg 180
cccgatctcc tgctccccat ccgcccccac cccgccggcg ccgccggaac caccttctcc 240
ttcgccaacc ccgccgcctc gcccttctac caccaccacc acccctccat gagttactac 300
gcctactatg gcaagaagct cgacccggag ccgtggcggt gccgacgcac cgacggcaag 360
aagtggcggt gctccaagga ggcgcacccc gactccaagt actgcgagcg ccacatgcac 420
cgtggccgca accgttcaag aaagcctgtg gaatccaagt ctgcttcccc tgcgcaccag 480
tcgcagcagc cccagttgtc cgccgtcacg tccgcggccc gcgacgccga gcctctcccc 540
tccctcccgg cgggggctaa aacccatggc ctgtccctcg gcggggctgg ctcgtcgcag 600
atgcacgtcg acgcctcgtc atacggcggc aaatactccc ttggagctaa atctgatgtg 660
ggtgaactga gcttcttctc tggagcatca ggaaacaaca acaggggatt caccatcgat 720
tccccaacgg acagctcgtg gcactcaatg ggatccagcc tgaccccata ccaactgtcg 780
aaacctagag attccggcct catgcagggc ggcttctcgt attcccactt tgagccgtcg 840
caggagctcg ggcaggtaac catcgcctcg ctgtcccact cccaggagca ggaccgccgc 900

```
tctttcgggg gcggtggtgg aggtgggggt ggaggggcag ggctcatggg aaatgttaag    960

caggagaacc agccgctgag gcccttcttc gacgagtggc cggggaggcg ggactcgtgg   1020

tcggagatgg acgacgagcg ctccaacggc acctccttct cgacgaccca gctctcgatc   1080

tccatcccaa tgcctcgatg cgattga                                       1107
```

<210> SEQ ID NO 155
<211> LENGTH: 1227
<212> TYPE: DNA
<213> ORGANISM: Triticum aestivum

<400> SEQUENCE: 155

```
atggagctcg ggcaggtgct gggctacacg ccaccggcga ccaaggacgc gagatccggc     60

ggcggcttca cccaggctgc cgcttgcccc taccccctacc cctccccctt cctcgacgag   120

cagaagatgc tcagcttctc caaggccgcc gccgctcacc agccgccctc aggtatggat    180

tttgggaggt ccaatgagca gaggctgttg ctggccagga gcaagatgcc cttcacccct    240

tcacagtgga tggagctgga gcaccaggcc ctcatttaca agtatctcaa tgcaaaggcc    300

cccatacctt ccggcctgct catctccatc agcaagagct tcagaccctc ctccgataga    360

atgccctgga ggcctgtcta tcaagggttc accaatgcag attctgaccc ggaacctgga    420

agatgccgtc gaacagacgg caagaaatgg cggtgctcaa aggaggcgat ggccgagcac    480

aagtactgtg agcggcacat caataggaac cgccatcgtt caagaaagcc tgtggaaaac    540

caaacaagga agaacgccaa agagacacct gctgctggct cgatatcggc cgctgtctca    600

cagggtggct gtaagaaagc aaaagctggt gatgaactga agccagggag cgtcagttat    660

tggacagata atttaaacag ggcaatggtg agcaaagcca ggggaaacaa ccctgaagaa    720

ggcaacagtg ctccactcct gaattctact aatcaacaac acacattgtc cttgttctct    780

caactgaagc aacagagcaa accagataag ttcagcccgg cagtcgatag tgaatcgatc    840

tcctcaaata ctgtattgaa gccttgggaa agaagcaacc agcagagcag taaggacgtt    900

tcttccacga cgctccatga tcgcgggtgc cttcaatcag tccttcaaga tttcagcatg    960

cataagaatg acaagatcga gtctcagaaa aacaatgctt cagtgccatc tactttctat   1020

tcatctacag aaggtcgaca catcagctgc cttgcatcta acatgatgca agtgcaggag   1080

gattgcatct caagctcttg ggagatacct caaggtgggc ctttaggtga aatcctaaca   1140

aactccaaga atactgatga cttgaccaat aagtgtgaat caagatcata tggttggtta   1200

ctgagtcttg atgaacatga aatgtga                                       1227
```

<210> SEQ ID NO 156
<211> LENGTH: 1836
<212> TYPE: DNA
<213> ORGANISM: Triticum aestivum

<400> SEQUENCE: 156

```
atggacctgg gcggcgtgct gatggcggcc gcggacgcgg gggtgggcgg cggggacctg     60

ggcatgctcg gatctaggct gctcaagcac gggaggggca atgcggcggc ggcggaggcc    120

gacgagcacg gctggggcag cggcaggccg cccgccaagc aggcccgggt cgcggcctcg    180

gccgcgtccg gggacagcga cgccgtgtcc gaggccgtca aggcggcggc accctacctg    240

ctcggcacct gcagccccgg gcacggccgg gagaagatgc tcagcttctc ctcctcgcag    300

ccgccctcct gcccctcctc cgccgccgcc gccgccgctc aggccgcgct gccgctctac    360
```

-continued

```
tacggcacgc ccgcttcttg ctcagggttg agctcggtga gcttgagcgc cagcatccag    420
aacgccatgg ccagggtgag ggggcccttc acgccgtcgc agtggatgga gctggagcac    480
caggccctga tctacaagta cctggcggcc aacatcgccg tgcctcacaa cctgctcgtc    540
cccatccgcc ggagcgtcac ctcgctctac ccgtccgcct actttggctc ctccacattg    600
gggtgggggc ctttccagct gggctactcc gggagcgcgg acctggagcc cgggcggtgc    660
cgccggacgg acggcaagaa gtggcggtgc tccagggacg ccgtcgccga ccagaagtac    720
tgcgagcggc atatgaaccg gggacgccat cgttcaagaa agcatgtgga aggccagcct    780
ggccatgccg cgaaagcgat gcctgcgacg gtggcggcgg ctgctgccca gcccggtgct    840
ctcgccaccg gggcggcgg cggagctacc gccggcgccg ccgccatctg ccacgagcag    900
cagccgttga agaactacgc cgcgaacacc attgatcctt gttcactgca atataacagg    960
gaaatggtga gcaagcagca gcaacacgag tgcgagcaag tgcaggactc cgacaccctc   1020
tcgatgctga cctccatgag cgcgaggaac accaacacgg gcagcatgtt cccgttctca   1080
aaggagcatc acaatcacaa tcctttcgag gtgacgagct caaggccgga ctacgggctg   1140
gtttcatccg actcgctgat gagctcccct cacagctccc tggagaacgt caacctgctc   1200
acctcgcact cgcagcgagc gctctccaac gagcagcaga gctcgctctc cctgcagcac   1260
ttcgcggact ggccgaggac gccctcgcag caggggcaag gaggaggagg tctctcatgg   1320
ccggacgccg aggacatgca agcacatcag aggacccagc tctcggtgtc cgccgctcca   1380
atggcgtccc ccgacctgtc gtcggcctcc acgtccccga tccacgagaa gctcatgctg   1440
tcgcccctca agctgagccg cgagtacagc cccatcggcc tcagcatcgc ggcgacggcg   1500
gcggcggcga aggacgaggg ggaggcgaac tggatgccca tgttccgcga ctcgtccatg   1560
ggcgggccgc tgggggaggc cctgaacaag aacaatggcg gcaacatgga ggccaagaac   1620
tacctgtcgg cgtcgctgaa cctcatgacg gacgcctggg actcgagccc gctggagtcg   1680
tccccggtgg gggtcctgca gaggaccgcc ttcgggtcgg tgtcgagcag caccggcagc   1740
agccccaggc aggagtacca cggcgtgtat gatggtaacc cgcgggatga tctcggctcc   1800
atcgtcgtga atcaccccag catccgcctc atgtga                             1836
```

<210> SEQ ID NO 157
<211> LENGTH: 930
<212> TYPE: DNA
<213> ORGANISM: Triticum aestivum

<400> SEQUENCE: 157

```
atgatgctgg gagggcacgg cggcggcggc gggaggtgcc tgttcacggc gtcgcagtgg     60
cgggagctgg agcaccaggc gctcatctac aagtacatgg ccgccggctc gcaggtgccc    120
cacgagctgg tcctcccgct ccgccaccgc gacgccgccg ccttcgccgg catcgacacc    180
gccccctccg tcgcctgcta ccctcctccg cagccctccc tggggtgggg gctctacggg    240
gcgggggcgc agtacgcgcg gaagccggag gacccggagc ccgggcggtg ccggcggacg    300
gacggcaaga agtggcgctg ctccagggag gcgtacgggg agtccaagta ctgcgacagg    360
cacatgcacc gcggcaagaa ccgttcaaga aagcctgtgg aaccgatgag ctcctcctcc    420
gtctcctccc cggccgcctc ctaccgccag accaccctct ccatgtcgcc ccccacgccg    480
gccgacacgc ccagctacgg ccacggccac ctccgcgcag ctgcttctca gagccagata    540
aaccctctcc agctccacct cgacaccccg tcgcccccgc cgtcctacca caggtacgcg    600
ccggcgcagc agtacggggg ctccttcttc ccgagcaggc agcaggtgca ggaggaggcc    660
```

gaggcggagg cgaggcggcg gcagcacttc ctggctctcg gcgccgacct gagcctggac 720
aagccggacg ccaccaccgc ggcgtcctcg acaaccgagg agaagccgct gcggcgcttc 780
ttcgacgagt ggccgcgcga cgggaacgcc gtcgaggttc ggccctggaa tatgggccac 840
cgggacgaga cgctgctctc catgtccatc cccacgacga cggcctcgca ccccgacctc 900
gccgcctacc gccaccacaa cgatgaataa 930

<210> SEQ ID NO 158
<211> LENGTH: 1233
<212> TYPE: DNA
<213> ORGANISM: Triticum aestivum

<400> SEQUENCE: 158
atgatgatga tgggcggtcg cgcgggggcc ggcggcgtcg gggccggcgg gggccggtgc 60
ccgttcacgg cgacgcagtg gcaggagctg gagcaccagg cgctcatcta caagtacatg 120
gcctccggcg tgcccatccc ctccgacctc ctcctcccgc tccgccgcag cttcctcctc 180
gactccgccc tcgccacctc cccctccctc gccttccctc cccaggccgc actgggctgg 240
ggatgtttcg ggatggggtt cggccggaag gcggaggacc cggagccggg gcggtgccgg 300
cggactgacg gcaagaagtg gcgctgctcc aaggaggcgt acccggactc caagtactgc 360
gagaagcaca tgcaccgcgg caagaaccgt tcaagaaagc ctgtggaaat gtccttggcc 420
acgcccccgc cgccgccttc ctcctcggcc tcctcctcct cctccaacgt ccactccgcc 480
gtcaacgccg ccaccaccac cacctccccc gcgccgtcct accaccgcca cgccgccgcg 540
actcacgaca cgacgcccta ccacacgctc tacggcggcc cctactcctc cgccggccgc 600
cagcagcacg ccagcgccta ccaccacgcc gcgcaggtca gcccgttcca cctgcacctc 660
gacaccaccc acccgcaccc gccgccgtcc tactactcca ccatggacca cagcaaggac 720
agctacgcct acgggcacag cgtcaaggag gtgcacggcg gcggcgagca cgccttcttc 780
tcctccgacg tcaccactga cagggaccac caccaccacc aacaccacgc cggcgccggc 840
ggcaacgggc agtggcagtt caagcagctc ggcggcatgg agcccaagca gcacaacccc 900
acgtcgctct tccccggctg cggcgggtac ggcaacaacg cggcgtacgc catcgacctg 960
tccagcaaag aagaggacga ggagaaggag aggcggcagc agcagcagca ctgcttcctg 1020
ctgggcgccg acctgaggct cgacaagccg tcgtcggggc acggcgactc cgccgaccag 1080
aagcctctcc ggcccttctt cgacgagtgg ccgcacgaga agaccgggag caaggggtcg 1140
tggatggggc tcgagggggga gacgcagctc tccatctcca tcgccaacga actccccatc 1200
accaccacct cccgctacca ccatggtgaa tga 1233

<210> SEQ ID NO 159
<211> LENGTH: 1230
<212> TYPE: DNA
<213> ORGANISM: Triticum aestivum

<400> SEQUENCE: 159
atggcgatgc cgtatgcctc tctttccccg gcaggcgacc gccgctcctc cccggccgcc 60
accgcctccc tcctcccctt ctgccgctcc tccccctctct ccgccggcgg cggcaatggc 120
ggcatggggg aggaggcgcg gatggacggg aggtggatgg cgaggccggt gcccttcacg 180
gcggcgcagt acgaggagct ggagcaccag gcgctgatat acaagtacct ggtggccggc 240
gtgcccgtcc cgccggatct cgtgctcccc atccgccgcg gcatcgaatc cctcgccgcc 300

-continued

```
cgcttctacc acaaccccct cgccatcggg tacggatcgt acctaggcaa gaaggtggat    360

ccggagccgg gccggtgccg gcgcacggac ggcaagaagt ggcggtgcgc caaggaggcc    420

gcctccgatt ccaagtattg cgagcgccac atgcaccgcg gccgcaaccg ttcaagaaag    480

cctgtggaaa cgcagctcgt cccgcacacc cagccgccgg ccgcctccgc cgtgccgccc    540

ctcgccaccg gcttccacag ccactccctc taccccgcca tcggcggcag caccaacggt    600

ggtggaggcg gggggaacaa cggcatgtcc atgcccagca cgttctcctc cgcgctgggg    660

ccgcctcagc agcacatggg cagcaatgcc gcctctccct acgcggctct cggtggcgcc    720

ggaacatgca aagatttcag gtataccgca tatggaataa gatctttggc agacgagcac    780

agtcagctca tgacagaagc catgaatacc tccgtggaga acccatggcg cctgccgccg    840

tcgtctcaaa cgacctcatt cccgctttca agctacgctc ctcagcttgg agcaacgagt    900

gacctgggtc agaacaacaa ccacaacaac agcagcagca acagtgccgt caagtccgag    960

cggcagcagc cgctctcctt cccggggtgc ggcgactttg gcggcggcgg catggactcc   1020

gcgaagcagg agaaccagac gctgcggccg ttcttcgacg agtggccgaa gacgagggac   1080

tcgtggtcgg acctgacgga cgacaactcc agcctcgcct ccttctcggc cacccagctg   1140

tcgatctcga tacccatgac gtcctccgac ttctccgccg ccagctccca gtcgcccaac   1200

ggtatgctgt tcgccggcga gatgtactag                                     1230
```

<210> SEQ ID NO 160
<211> LENGTH: 1113
<212> TYPE: DNA
<213> ORGANISM: Triticum aestivum

<400> SEQUENCE: 160

```
atgctgagct cgtcggcggc gatggggatg gggctgggcg ggtacggcca gcagcagcag     60

cagcagcaga tgcagatgca gatgcagatg cagcgggggg cggggccggt gttcacgccg    120

gcgcagtggg ccgagctgga gcagcaggcg ctgatttaca agtacctcat ggcgggcgtg    180

cccgtgccgc ccgatctcct gctccccatc cgcccccacc ccgccggcgc cggagccacc    240

ttctccttcg ccaaccccgc cgcctcgccc ttctaccacc accaccaccc ctccatgagt    300

tactacgcct actatggcaa gaagctcgac ccggagccgt ggcggtgccg ccgcaccgac    360

ggcaagaagt ggaggtgctc caaggaggcg caccccgact ccaagtactg cgagcgccac    420

atgcaccgtg gccgcaaccg ttcaagaaag cctgtggaat ccaagtctgc ttcccctgcg    480

caccagtcgc agcagccccc gttgtccgcc gtcacgtccg ccacccgcga cgccgagcct    540

ctcccctccc tcccggcggg ggctaagacc catggcctgt ccctcggcgg ggctggctcg    600

tcgcagatgc acgtcgacgc ctcgtcatac ggcaacaaat actcccttgg agctaaatct    660

gacgtgggtg aactgagctt cttctctgga gcatcaggaa acaacaacag gggcttcacc    720

atcgattccc caacggacag ctcgtggcac tcaatgggat ccagcctgcc cccgtaccaa    780

ctgtcgaaac ctagagattc cggcctcatg caaggcggct tctcgtattc ccactttgag    840

ccgtcgcagg agcttgggca ggtaaccatc gcctcgctgt cccactccca ggagcaggac    900

cgccgctcct tcggtggcgg cggtggtggt ggaggtggag gggcagggct catgggaaat    960

gttaagcagg agaaccagcc gctgaggccc ttcttcgacg agtggccggg gaggcgggac   1020

tcgtggtcgg agatggacga cgagcgctcc aacggcacct ccttctcgac gacccagctc   1080

tcgatctcca tcccaatgcc tcgatgtgat tga                                1113
```

<210> SEQ ID NO 161
<211> LENGTH: 684
<212> TYPE: DNA
<213> ORGANISM: Triticum aestivum

<400> SEQUENCE: 161
atgaccgagc gaaggcagga acactcgccg ccgtccaagc tcccccgcct ctccggcccc 60
gacgccgacg acaacgacgg cgcagggacg gtgaccatgg cggcgccgtc gccgctggtt 120
cttgggctgg gtctcggcgt aggcggcagc agcagtgaca gtggacgtgg cgacgcggag 180
gcatctgcgg cgacgcggcc atcggcgctg acgttcatgc agcggcagga gctggagcac 240
caggtgctca tctaccgcta cttcgccgcc aacgctcccg tgcccgtgca cctcgtcctc 300
cccatctgga agagcgtcgc cgcctcctcc tccgccccgc agaggttccc atccctggcg 360
ggactgggga gcatgtgcta cgaccacagg agcagcatgg agccggagcc ggaccggtgc 420
cggcgcacgg acggcaaaaa gtggcggtgc tcgcgcggcg tgatgccggg gcacaagtac 480
tgcgagcgcc acgtccaccg cggccgcggc cgtgcaagaa agcctgtgga agccgcgccg 540
gccacatcag ccatcccgat ccgcgcaatg cacgccgccg acgcgcaggg cgccacaagc 600
gcgcacgcgg cgccaccgca gcgcctcggc ttctcctccc ccgccggcgt ctacctggcc 660
cacggcaccg cccgtgccac ctga 684

<210> SEQ ID NO 162
<211> LENGTH: 648
<212> TYPE: DNA
<213> ORGANISM: Triticum aestivum

<400> SEQUENCE: 162
atggccgacg agaaagaagc cgactcgctg cagccgccgt ccaagcagcc ccgcctctcc 60
tccgccgact cgaacgccgg tgcggtgacg atggcggtct cgtcgccgct gggtcttggc 120
ctcggcctgg gactcggcgg cgatagccgc ggcgagcagc aggccttcca agcacgggca 180
gccgcggcgg cggcgaaatc ggcgctgacg ttcatgcagc agcaggagct ggagcaccag 240
gtgctcatct accgctactt cgcggcgggg gcgcccgtgc cggtgaacct cgtgctgccc 300
atctggaaga gcatcgccgc ctcctccttc ggcccgcacc gcttcccctc cctgattggg 360
cttgggagcc tgtgcttcga ctaccggagc agcatggagc cggagcccgg gaggtgccgc 420
cgcacggacg gcaagaagtg gcggtgctcc cgcgacgtgc tgcaggggca caagtactgc 480
gagcggcacg tccaccgggg ccgcggccgt tcaagaaagc ctgtggaagg agcccccgca 540
gccccggcgc acagcggcag cagcaccacc gccccgcccc gcgccatcgg cttctccccc 600
gccggcatcc tccacgccac ccacagcgcc gccgcgcgcg ccacctga 648

<210> SEQ ID NO 163
<211> LENGTH: 963
<212> TYPE: DNA
<213> ORGANISM: Triticum aestivum

<400> SEQUENCE: 163
atgatgctgg gagggcacgg cggcggcggc ggcgggaggt gcctgttcac ggcgtcgcag 60
tggcgggagc tggagcacca ggcgctcatc tacaagtaca tggccgccgg ctcgcaggtg 120
ccccacgagc tggtcctccc gctccgccac cgcgacgctg ccgccttcgc cgccatcgac 180
accgtcccct ccctcgcctg ctaccctcct ccgcagccat ccctggggtg ggggctctac 240
ggggcggggg cgcagtacgc gcggaagccg gaggacccgg agccggggcg gtgccggcgg 300

-continued

```
acggacggca agaagtggcg ctgctccagg gaggcgtacg gggagtccaa gtactgcgac    360

aggcacatgc accgcggcaa gaaccgttca agaaagcctg tggaaccgat gtcctcctcc    420

tccgtctcct ccccggccgc ctcctaccgc cagaccgccc tctccatgtc gccccccacg    480

ccggccgaca cgcccaccta cggccacggc cacggccacg accacctccg cgcagctgct    540

ggtcagagtc agagccagat aaaccctctc cagctccacc tcgacacccc gtcgcccccg    600

ccgtcctacc acaggtacgc gccggcgcag cagtacgggg gctccttctt ccagaacagg    660

cagcaggtgc aggaggaggc ggaggcggag gcgaggcggc ggcagcactt cctggctctc    720

ggcgccgacc tgagcctgga caagcccgac gccaccaccg cggcgtcctc gacaaccgag    780

gagaagccgc tgcggcgctt cttcgacgag tggccgcgcg acgggaacgc cgtcgagggt    840

cggccctgga atatgggcca ccgggacgag acgctgctct ccatgtccat ccccacgacg    900

acggccacgc accccgacct cgccgccgcc tcgcgctacc accaccacca caacgatgaa    960

taa                                                                  963
```

<210> SEQ ID NO 164
<211> LENGTH: 1245
<212> TYPE: DNA
<213> ORGANISM: Triticum aestivum

<400> SEQUENCE: 164

```
atgatgatga tgggtggtcg cgcgggggcc ggcggcgtcg gggcaggcgg ggggcggtgc     60

ccgttcacgg cgacgcagtg gcaggagctt gagcaccagg cactcatcta caagtacatg    120

gcctccggcg tgcccatccc ctccgacctc ctcctcccgc tccgccgcag cttcctcctc    180

gactccgccc tcgccacctc cccctccctc gccttccctc cccaggccgc acttggctgg    240

ggttgctttg gcatggggtt cggccggaag gcggaggacc cggagccggg gcggtgccgg    300

cggacggacg gcaagaagtg gcgctgctcc aaggaggcgt acccggactc caagtactgc    360

gagaagcaca tgcaccgcgg caagaaccgt tcaagaaagc ctgtggaaat gtccttggcc    420

acgcccccgc cgccgccttc ctcctcggcc tcctcctcct cctccaacgt ccactccgcc    480

gtcaacgtcg ccaccaccac ctcctccccc gcgccgtcct accaccgcca cgccgccgcg    540

actcacgaca cgacgcccta ccacgcgctc tacggcggcc cctactcctc cgccggccgc    600

cagcagcacg ctagcgccta ccaccacgcc gcgcaggtca gcccgttcca cctgcacctc    660

gacaccaccc acccgcaccc gccgccgtcc tactactcca gcatggacca cagcaaggac    720

agctacgcct acgggcacag cgtcaaggag gtgcacggcg gcggcgagca cgccttcttc    780

tcctccgacg tcaccaccga cagggaccat caccaccacc accatcagca ccaacaccac    840

gctagcgccg gcggcaacgg ccagtggcag ttcaagcagc tcggcggcat ggagccgaag    900

cagcataacc caacgtcgct cttccccggc tgcggcggct acggcaacaa cgcggcctac    960

gccatcgacc tgtccagcaa agaagaggac gaggagaagg agaggcggca gcagcagcag   1020

cactgcttcc tgctgggcgc cgacctgagg ctcgacaagc cgtcgtcggg gcacggcgac   1080

tccgccgacc agaagcctct ccggcccttc ttcgacgagt ggccgcacga gaagaccggg   1140

agcaaggggt cgtggatggg gctcgagggg gagacgcagc tctccatctc catcgccaac   1200

gaactcccca tcaccaccac ctcccgctac caccatggtg aatga                  1245
```

<210> SEQ ID NO 165
<211> LENGTH: 1221
<212> TYPE: DNA
<213> ORGANISM: Triticum aestivum

<400> SEQUENCE: 165
atggcgatgc cgtatgcctc tctttccccg gcaggcgacc gccgctcctc cccggccgcc 60
accgcctccc tcctcccctt ctgccgctcc tccccgttct ccgccggcaa tggcggcatg 120
ggggaggagg cgcggatggc cggtaggtgg atggcgaggc cggcgccctt cacggcggcg 180
cagtacgagg agctggagca ccaggcgctg atatacaagt acctggtggc cggcgtgccc 240
gtcccgccgg atctcgtgct ccccatccgc cgcggcatcg agaccctcgc cgcccgcttc 300
taccacaacc ccctcgccat cgggtatgga tcgtacctgg gcaagaaggt ggatccggag 360
cccggccggt gccggcgcac ggacggcaag aagtggcggt gcgccaagga ggccgcctcc 420
gactccaagt attgcgagcg ccacatgcac cgcggccgca accgttcaag aaagcctgtg 480
gaaacgcagc tcgtctcgca ctcccagccg ccggccgcct ccgtcgtgcc gcccctcgcc 540
accggcttcc acaaccactc cctctacccc gccatcggcg gcaccaacgg tggtggaggc 600
ggggggaaca acggcatgcc caacacgttc tcctccgcgc tggggcctcc tcagcagcac 660
atgggcaaca atgcctcctc accctacgcg gctctcggtg gcgccggaac atgcaaagat 720
ttcaggtata ccgcatatgg aataagatct ttggcagacg agcacagtca gctcatgaca 780
gaagccatga atacctccgt ggagaaccca tggcgcctgc cgccatcgtc tcaaacgacc 840
acattcccgc tctcaagcta cgctcctcag cttggagcaa ctagtgacct gggtcagaac 900
aacaacagca gcagcagcaa cagtgccgtc aagtccgaac ggcagcagca gcagcagccc 960
ctctccttcc cggggtgcgg cgacttcggc ggcggcggcg ccatggactc cgcgaagcag 1020
gagaaccaga cgctgcggcc gttcttcgac gagtggccca agacgaggga ctcgtggtcg 1080
gacctgaccg acgacaactc cagcctcgcc tccttctcgg ccacccagct gtcgatctcg 1140
atacccatga cgtcctccga cttctcggcc gccagctccc agtcgcccaa cggtatgctg 1200
ttcgccggcg aaatgtacta g 1221

<210> SEQ ID NO 166
<211> LENGTH: 1116
<212> TYPE: DNA
<213> ORGANISM: Triticum aestivum

<400> SEQUENCE: 166
atgctgagct cgtcggcggc gatggggatg gggctggggg gctacggcca gcagcagcag 60
cagcagatgc agatgcagat gcagcggggc gcggggccgg tgttcacgcc ggcgcagtgg 120
gccgagctgg agcagcaggc gctgatttac aagtacctca tggcaggcgt gcccgtgccg 180
cccgatctcc tgctccccat ccgcccccac caccccgccg ccggcgccgc cggaaccacc 240
ttctccttcg ccagccccgc cgcctcgccc ttctaccacc accaccatcc ctccatgagt 300
tactacgcct actatggcaa gaagctcgac ccggagccgt ggcggtgccg gcgcaccgac 360
ggcaagaagt ggcggtgctc caaggaggcg caccccgact ccaagtactg cgagcgccac 420
atgcaccgtg gccgcaaccg ttcaagaaag cctgtggaat ccaagtctgc ttcccctgcg 480
caccagtcgc agcagccccc gctgtccgcc gtcacgtccg cggcccgcga cgccgagccg 540
ctcccctccc tcccggctgg ggctaaaacc catggcctgt ccctcggcgg ggctggctcg 600
tcgcagatgc acgtcgacgc ctcatcatac ggcggcaaat actcccttgg agctaaatct 660
gatgtgggtg aactgagctt cttctctgga gcatcaggaa acaacaacag gggcttcacc 720
atcgattccc caacggacag ctcgtggcac tcgatggggt ccagcctgcc cccgtaccaa 780

-continued ctgtcgaaac ctagagattc cggcctcatg caaggcggct tctcgtattc ccactatgag 840
ccgtcgcagg agcttgggca ggtaaccatc gcctcgctgt cccactccca ggagcaggac 900
tgccgctctt tgggtggtgg aggtggagga ggtggaggtg gaggtggagg gctcatggga 960
aatgtcaagc aggagaacca gccgctgagg cccttcttcg acgagtggcc ggggaggcgg 1020
gactcgtggt cggagatgga cgacgagcgc tccaacggca cctccttctc gacgacccag 1080
ctctcgatct ccatcccgat gcctcgatgc gattga 1116

<210> SEQ ID NO 167
<211> LENGTH: 1155
<212> TYPE: DNA
<213> ORGANISM: Triticum aestivum

<400> SEQUENCE: 167
atggcgatgc cctttgcctc cctgtcgccg gcagccgacc accaccgctc ctcccccatc 60
ttccccttct gccgctcctc ccctctctac tcggcagggg aggaggcggc gcagcagcag 120
cagcagcagc agcacgcgat gagcggcgcg aggtgggcgg cggcgaggcc ggcgaccttc 180
acggcggcgc agtacgagga gctggagcag caggcgctca tctacaagta cctcgtcgcc 240
ggcgtgcccg tcccgccgga tctcctcctc cccatccgcc ggggcttcga ctccctcgcc 300
tcgcgcttct accaccacca cgcccttggg tacgggtcct acttcgggaa gaagctggat 360
ccggagccgg ggcggtgccg gcggacggac ggcaagaagt ggcggtgctc caaggaggcc 420
gcccaggact ccaagtactg cgagcgccac atgcaccgcg gccgcaaccg ttcaagaaag 480
cctgtggaaa cgcagctcgt ctcccactcc cagcagctgc agcagcaggc ccccgccgcc 540
gcgttccacg gccactcgcc gtacccggcg atcgccactg gcgccggcgc gcccggctcc 600
ttcgccctgg ggtctactgc tcagctgcac atggataatg ctgctgcgcc ttacgcgacc 660
gctggcgccg ccgggaacaa agatttcagg tattctgcct atgggtttag gacttcggcg 720
atggaggacc acaaccagtt catcagtgcg gccatggaca ccgccatgga caactactca 780
tggcgcctgc tgccggccca gaactcgtcc ttctcactct cgagctaccc catgctgagc 840
accctgagcg acctggacca gagcgcgatc tgctcgctgg ccaagacgga gagggagccg 900
ctgtccttct tcggcgtggg cggcggcttc gacgacgacg agtcggcggt gaagcaggag 960
aaccagacgc tgcggccctt cttcgacgag tggcccaagg acagggactc gtggccggag 1020
ctgcaggacc atgactccaa ccacaacaat gaggccttct cggccaccaa gctgtccatc 1080
tccatcccgg tgaccagctc cgatttctcc accaccgccg gctcccgctc gccccacggt 1140
atatactccc ggtga 1155

<210> SEQ ID NO 168
<211> LENGTH: 639
<212> TYPE: DNA
<213> ORGANISM: Triticum aestivum

<400> SEQUENCE: 168
atggccgacg agaaagaagc cgactcgctg cagccgccgt ccaagcagcc ccgcctctcc 60
tccgccgact cgaacgccgg ggcggtgacg atggcggtct cgtcgccgct gggtcttggc 120
ctcggcctgg ggctcggtgg cgatagccgt ggcgagcagc aggccttcga agcacgggcg 180
gcggcgaagt cggcgctgac gttcatgcag cagcaggagc tggagcacca ggtgctcatc 240
taccgctact tcgcggcggg ggcgcccgtg ccggtgcacc tcgtgctgcc catctggaag 300
agcgtcgccg cctcctcctt cggcccgcac cgcttcccct ccctgattgg gctggggagc 360
ctgtgcttcg actaccggag cagcatggag ccggagcccg ggcggtgccg ccgcacggac 420
ggcaagaagt ggcggtgctc ccgcgacgtg gtgcaggggc acaagtactg cgagcggcac 480
gtccaccggg gccgcggccg ttcaagaaag cctgtggaag gagccccctc agcccgggcg 540
cacagcgaca gcaccgccac cgccccgccc tgcgccatcg gcttctcccc cgccggcatc 600
ctccacgcca cccacagcgc cgccgcgcgc gccacctga 639

<210> SEQ ID NO 169
<211> LENGTH: 951
<212> TYPE: DNA
<213> ORGANISM: Triticum aestivum

<400> SEQUENCE: 169
atgatgctgg gagggcacgg cggcggcggc ggcggcggga ggtgcctgtt cacggcgtcg 60
cagtggcggg agctggagca ccaggcgctc atctacaagt acatggccgc cggctcgcag 120
gtgccccacg agctggtcct cccgctccgc caccgcgacg cagccttcgc cgccatcgac 180
accgccccct ccctcgcctg ctaccctcct ccgcagccat ccctggggtg ggggctctac 240
ggggcgggat cgcagtacgc gcggaagccg gaggacccgg agcccgggcg gtgccggcgg 300
acggacggca agaaatggcg gtgctccagg gaggcgtatg ggagtccaa gtactgcgac 360 aggcacatgc accgcggcaa gaaccgttca agaaagcctg tggaaccaat gagctccgcc 420
tcctccgtct cctccccggc cgcctcgtac cgccacaccg ccctctccat gtcgcccccc 480
acgccggccg acacgcccag ctacggccac ggccacggcc acgaccacct ccgcgcagct 540
gctggtcaga gccagataaa ccctctccag ctccacctcg acaccccgtc gcccccgccg 600
tcctaccaca ggtacgcgcc ggcgcagcag tacgggggct ccttcttccc gagcaggcag 660
caggtgcagg aggaggaggc gaggcggcgg cagcacttcc tggctctcgg cgccgacctg 720
agcctggaca agccggacgc caccaccgcg gcgtcctcga caaccgagga gaagccgctg 780
cggcgcttct tcgacgagtg gccgcgcgac gggaacgccg tcgagggtag gccctggaat 840
atgggccacc gggacgagac gctgctctcc atgtccatcc ccacgacgac ggcctcgcac 900
cccgacctcg ccgccgcctc gcgctaccac caccaccaca acgatgaata a 951

<210> SEQ ID NO 170
<211> LENGTH: 1227
<212> TYPE: DNA
<213> ORGANISM: Triticum aestivum

<400> SEQUENCE: 170
atggcgatgc cgtatgcctc tctttccccg gcaggcgacc gccgctcctc cccggccgcc 60
accgccaccg cctccctcct cccettctgc cgctcctccc ccttctccgc cggcggcaat 120
ggcggcatgg gggaggaggc gccgatggac gggaggtgga tggcgaggcc ggtgcccttc 180
acggcggcgc agtacgagga gctggagcac caggcgctca tatacaagta cctggtggcc 240
ggcgtgcccg tcccgccgga tctcgtgctc cccatccgcc gcggcatcga gtccctcgcc 300
gcccgcttct accacaaccc cctcgccatc gggtacggat cgtacctggg caagaaggtg 360
gatccggagc cgggccggtg ccggcgcacg gacggcaaga agtggcggtg cgccaaggag 420
gccgcctccg actccaagta ctgcgagcgc cacatgcacc gcggccgcaa ccgttcaaga 480
aagcctgtgg aaacgcagct cgtgccccac tcccagccgc cggccgcctc cgccgtgccg 540
cccctcgcca ccggcttcca cggccactcc ctctaccccg ccgtcggcgg cggcaccaac 600

```
ggtggtggag gcggggggaa caacggcatg tccatgcccg gcacgttctc ctccgcgctg     660
gggccgcctc agcagcacat gggcaacaat gccgcctctc cctacgcggc tctcggcggc     720
gccggaacat gcaaagattt caggtatacc gcatatggaa taagatcttt ggcagatgag     780
cagagtcagc tcatgacaga agccatgaac acctccgtgg agaacccatg gcgcctgccg     840
ccatcttctc aaacgactac attcccgctc tcaagctact ctcctcagct tggagcaacg     900
agtgacctgg gtcagaacaa cagcagcaac aacaacagcg gcgtcaaggc cgagcgacag     960
cagcagcagc agccgctctc cttcccgggg tgcggcgact tcggcggcgg cgactccgcg    1020
aagcaggaga accagacgct gcggccgttc ttcgacgagt ggccgaagac gagggactcg    1080
tggtcggacc tgaccgacga caactcgaac gtcgcctcct tctcggccac ccagctgtcg    1140
atctcgatac ctatgacgtc ccccgacttc tccgccgcca gctcccagtc gcccaacggc    1200
atgctgttcg ccggcgagat gtactag                                        1227
```

<210> SEQ ID NO 171
<211> LENGTH: 1230
<212> TYPE: DNA
<213> ORGANISM: Triticum aestivum

<400> SEQUENCE: 171

```
atgatgatga tgggcggtcg cgcgggggcc ggcggcgtcg gggcaggcgg cggccggtgc      60
ccgttcacgg cgacgcagtg gcaggagctg gagcaccagg cgctcatcta caagtacatg     120
gcctccggcg tgcccatccc ctccgacctc ctcctcccgc tccgccgcag cttcctcctc     180
gactccgccc tcgccacctc cccctccctc gccttccctc cccaggccgc acttgggtgg     240
ggttgctttg gcatggggtt cggccggaag gcggaggacc cggagccggg gcggtgccgg     300
cggacggacg ggaagaagtg gcgctgctcc aaggaggcgt acccggactc caagtactgc     360
gagaagcaca tgcaccgggg caagaaccgt tcaagaaagc ctgtggaaat gtccttggcc     420
acgcccccgc cgccgccttc ctcctcggcc tcctcttcct cctccaacgt ccactccgcc     480
gtcaacgtcg ccaccaccac cacctcccca gcgccgtcct accaccgcca cgccgctgcg     540
actcacgaca cgacgcccta ccacgccctc tacggcggcc cctactcctc cgccggccgc     600
cagcagcacg ccagcgccta ccaccacgcg gcgcaggtca gcccgttcca cctgcacctc     660
gacaccaccc acccgcaccc gccgccgtcc tactactcca ccatggacca cagcaaggac     720
agctacgcct acgggcacag cgtcaaggag gtgcacggcg gcggcgagca cgccttcttc     780
tcctccgacg tcagcaccga cagggaccac caccaccatc agcaccaaca ccacgctagc     840
gccggcggca acggccagtg gcagttcaag cagctcggcg gcatggagcc caagcagcac     900
aaccccacgt cgctcttccc cggctacggc aacaacgcgg cgtacgccat cgacctgtcc     960
agcaaagaag aggacgagga gaaggagagg cggcaacagc agcagcactg cttcctgctg    1020
ggcgccgacc tgaggctcga caagccgtcg tcggggcacg gcgactccgc cgaccagaag    1080
cctctccggc cgttcttcga cgagtggccg cacgagaaga ctggcagcaa ggggtcgtgg    1140
atggggctcg agggggagac gcagctctcc atctccatcg ccaatgaact ccccatcacc    1200
accacctccc gctaccacca tggtgaatga                                     1230
```

<210> SEQ ID NO 172
<211> LENGTH: 636
<212> TYPE: DNA
<213> ORGANISM: Triticum aestivum

<400> SEQUENCE: 172
atggccgacg agaaagaagc cgactcgctg cagccgccgt ccaagcagcc ccgcctctcc 60
tccgccgact cgaacgccgg ggcggtgacg acggcggtct cgtcgccgct gggtcttggc 120
ctcggcctgg ggctcggcgg cgatagccgt ggcgagcagc aggccttcga agcacgggca 180
gccgcggcgg cggcgaaatc ggcgctgacg ttcatgcagc agcaggagct ggagcaccag 240
gtgctcatct accgctactt cgcggcgggt gcgcccgtgc cggtgcacct cgtgctcccc 300
atctggaaga gcgtcgccgc ctcctccttc ggcccgcacc gcttcccctc cctgattggg 360
ctggggagcc tgtgcttcga ctaccggagc agcatggagc cggagcccgg gcggtgccgc 420
cgcacggacg gcaagaagtg gcggtgctcc cgcgacgtgg tgcaggggca caagtactgc 480
gagcggcacg tccaccgggg ccgcggccgt tcaagaaagc ctgtggaagg agcctccgca 540
gccccggcgc acagcggcag ccccaccaca gccccgcccc gcgccatcgg cttctccccc 600
gccggcatcc tccacgccac ccacagcgcc acctga 636

<210> SEQ ID NO 173
<211> LENGTH: 62
<212> TYPE: DNA
<213> ORGANISM: Triticum aestivum

<400> SEQUENCE: 173
cacgtccacc ggggccgcgg ccgttcaaga aagcctgtgg aaggagcctc cgcagccccg 60
gc 62

<210> SEQ ID NO 174
<211> LENGTH: 62
<212> TYPE: DNA
<213> ORGANISM: Triticum aestivum

<400> SEQUENCE: 174
cacatgcacc ggggcaagaa ccgttcaaga aagcctgtgg aaatgtcctt ggccacgccc 60
cc 62

<210> SEQ ID NO 175
<211> LENGTH: 62
<212> TYPE: DNA
<213> ORGANISM: Triticum aestivum

<400> SEQUENCE: 175
cacatgcacc gcggccgcaa ccgttcaaga aagcctgtgg aaacgcagct cgtgccccac 60
tc 62

<210> SEQ ID NO 176
<211> LENGTH: 62
<212> TYPE: DNA
<213> ORGANISM: Triticum aestivum

<400> SEQUENCE: 176
cacatgcacc gcggcaagaa ccgttcaaga aagcctgtgg aaccaatgag ctccgcctcc 60
tc 62

<210> SEQ ID NO 177
<211> LENGTH: 62
<212> TYPE: DNA
<213> ORGANISM: Triticum aestivum

<400> SEQUENCE: 177

-continued cacgtccacc ggggccgcgg ccgttcaaga aagcctgtgg aaggagcccc ctcagcccgg 60
gc 62

<210> SEQ ID NO 178
<211> LENGTH: 62
<212> TYPE: DNA
<213> ORGANISM: Triticum aestivum

<400> SEQUENCE: 178
cacatgcacc gcggccgcaa ccgttcaaga aagcctgtgg aaacgcagct cgtctcccac 60
tc 62

<210> SEQ ID NO 179
<211> LENGTH: 62
<212> TYPE: DNA
<213> ORGANISM: Triticum aestivum

<400> SEQUENCE: 179
cacatgcacc gtggccgcaa ccgttcaaga aagcctgtgg aatccaagtc tgcttcccct 60
gc 62

<210> SEQ ID NO 180
<211> LENGTH: 62
<212> TYPE: DNA
<213> ORGANISM: Triticum aestivum

<400> SEQUENCE: 180
cacatgcacc gcggccgcaa ccgttcaaga aagcctgtgg aaacgcagct cgtctcgcac 60
tc 62

<210> SEQ ID NO 181
<211> LENGTH: 62
<212> TYPE: DNA
<213> ORGANISM: Triticum aestivum

<400> SEQUENCE: 181
cacatgcacc gcggcaagaa ccgttcaaga aagcctgtgg aaatgtcctt ggccacgccc 60
cc 62

<210> SEQ ID NO 182
<211> LENGTH: 62
<212> TYPE: DNA
<213> ORGANISM: Triticum aestivum

<400> SEQUENCE: 182
cacatgcacc gcggcaagaa ccgttcaaga aagcctgtgg aaccgatgtc ctcctcctcc 60
gt 62

<210> SEQ ID NO 183
<211> LENGTH: 62
<212> TYPE: DNA
<213> ORGANISM: Triticum aestivum

<400> SEQUENCE: 183
cacgtccacc ggggccgcgg ccgttcaaga aagcctgtgg aaggagcccc cgcagccccg 60
gc 62

<210> SEQ ID NO 184
<211> LENGTH: 62

<212> TYPE: DNA
<213> ORGANISM: Triticum aestivum

<400> SEQUENCE: 184
cacgtccacc gcggccgcgg ccgtgcaaga aagcctgtgg aagccgcgcc ggccacatca 60
gc 62

<210> SEQ ID NO 185
<211> LENGTH: 62
<212> TYPE: DNA
<213> ORGANISM: Triticum aestivum

<400> SEQUENCE: 185
cacatgcacc gcggccgcaa ccgttcaaga aagcctgtgg aaacgcagct cgtcccgcac 60
ac 62

<210> SEQ ID NO 186
<211> LENGTH: 62
<212> TYPE: DNA
<213> ORGANISM: Triticum aestivum

<400> SEQUENCE: 186
cacatgcacc gcggcaagaa ccgttcaaga aagcctgtgg aaatgtcctt ggccacgccc 60
cc 62

<210> SEQ ID NO 187
<211> LENGTH: 62
<212> TYPE: DNA
<213> ORGANISM: Triticum aestivum

<400> SEQUENCE: 187
cacatgcacc gcggcaagaa ccgttcaaga aagcctgtgg aaccgatgag ctcctcctcc 60
gt 62

<210> SEQ ID NO 188
<211> LENGTH: 62
<212> TYPE: DNA
<213> ORGANISM: Triticum aestivum

<400> SEQUENCE: 188
catatgaacc ggggacgcca tcgttcaaga aagcatgtgg aaggccagcc tggccatgcc 60
gc 62

<210> SEQ ID NO 189
<211> LENGTH: 62
<212> TYPE: DNA
<213> ORGANISM: Triticum aestivum

<400> SEQUENCE: 189
cacatcaata ggaaccgcca tcgttcaaga aagcctgtgg aaaaccaaac aaggaagaac 60
gc 62

<210> SEQ ID NO 190
<211> LENGTH: 62
<212> TYPE: DNA
<213> ORGANISM: Triticum aestivum

<400> SEQUENCE: 190
cacatgcacc gcggccgcaa ccgttcaaga aagcctgtgg aaacgcagct cgtcgccacg 60
cc 62

<210> SEQ ID NO 191
<211> LENGTH: 62
<212> TYPE: DNA
<213> ORGANISM: Triticum aestivum

<400> SEQUENCE: 191
cacatcaata ggaaccgcca tcgttcaaga aagcctgtgg aaaaccaaac aaggaagaac 60
gc 62

<210> SEQ ID NO 192
<211> LENGTH: 62
<212> TYPE: DNA
<213> ORGANISM: Triticum aestivum

<400> SEQUENCE: 192
cacgtccacc gcggccgcgg ccgtgcaaga aagcctgtgg aagccgcggc ggccacatca 60
gc 62

<210> SEQ ID NO 193
<211> LENGTH: 62
<212> TYPE: DNA
<213> ORGANISM: Triticum aestivum

<400> SEQUENCE: 193
catatgaacc ggggacgcca tcgttcaaga aagcatgtgg aaggccagcc tggccatgcc 60
gc 62

<210> SEQ ID NO 194
<211> LENGTH: 62
<212> TYPE: DNA
<213> ORGANISM: Triticum aestivum

<400> SEQUENCE: 194
cacatgcacc gcggccgcaa ccgttcaaga aagcctgtgg aaacgcagct cgtcgccacg 60
cc 62

<210> SEQ ID NO 195
<211> LENGTH: 62
<212> TYPE: DNA
<213> ORGANISM: Triticum aestivum

<400> SEQUENCE: 195
cacgtccacc gcggccgcag ccgtgcaaga aagcctgtgg aagccgcggc ggccacatca 60
gc 62

<210> SEQ ID NO 196
<211> LENGTH: 62
<212> TYPE: DNA
<213> ORGANISM: Triticum aestivum

<400> SEQUENCE: 196
catatgaacc ggggacgcca tcgttcaaga aagcatgtgg aaggccagcc tggccatgcc 60
gc 62

<210> SEQ ID NO 197
<211> LENGTH: 62
<212> TYPE: DNA
<213> ORGANISM: Triticum aestivum

<400> SEQUENCE: 197
cacatgcacc gtggccgcaa ccgttcaaga aagcctgtgg aatccaagtc tgcttcccct 60
gc 62

<210> SEQ ID NO 198
<211> LENGTH: 62
<212> TYPE: DNA
<213> ORGANISM: Triticum aestivum

<400> SEQUENCE: 198
cacatgcacc gtggccgcaa ccgttcaaga aagcctgtgg aatccaagtc tgcttcccct 60
gc 62

<210> SEQ ID NO 199
<211> LENGTH: 22
<212> TYPE: DNA
<213> ORGANISM: Triticum aestivum

<400> SEQUENCE: 199
ccgttcaaga aagcctgtgg aa 22

<210> SEQ ID NO 200
<211> LENGTH: 22
<212> TYPE: DNA
<213> ORGANISM: Triticum aestivum

<400> SEQUENCE: 200
ccgtgcaaga aagcctgtgg aa 22

<210> SEQ ID NO 201
<211> LENGTH: 22
<212> TYPE: DNA
<213> ORGANISM: Triticum aestivum

<400> SEQUENCE: 201
tcgttcaaga aagcatgtgg aa 22

<210> SEQ ID NO 202
<211> LENGTH: 22
<212> TYPE: DNA
<213> ORGANISM: Triticum aestivum

<400> SEQUENCE: 202
tcgttcaaga aagcctgtgg aa 22

<210> SEQ ID NO 203
<211> LENGTH: 19
<212> TYPE: RNA
<213> ORGANISM: Artificial sequence
<220> FEATURE:
<223> OTHER INFORMATION: Synthetic RNA Spacer
<220> FEATURE:
<221> NAME/KEY: misc_feature
<222> LOCATION: (1)..(19)
<223> OTHER INFORMATION: n is a, c, g, or u

<400> SEQUENCE: 203
nnnnnnnnnn nnnnnnnnn 19

<210> SEQ ID NO 204
<211> LENGTH: 22
<212> TYPE: DNA

<213> ORGANISM: Artificial sequence
<220> FEATURE:
<223> OTHER INFORMATION: Target strand
<220> FEATURE:
<221> NAME/KEY: misc_feature
<222> LOCATION: (4)..(22)
<223> OTHER INFORMATION: n is a, c, g, or t

<400> SEQUENCE: 204
aaannnnnnn nnnnnnnnnn nn 22

<210> SEQ ID NO 205
<211> LENGTH: 22
<212> TYPE: DNA
<213> ORGANISM: Artificial sequence
<220> FEATURE:
<223> OTHER INFORMATION: Non-target strand
<220> FEATURE:
<221> NAME/KEY: misc_feature
<222> LOCATION: (4)..(22)
<223> OTHER INFORMATION: n is a, c, g, or t

<400> SEQUENCE: 205
tttnnnnnnn nnnnnnnnnn nn 22

<210> SEQ ID NO 206
<211> LENGTH: 207
<212> TYPE: PRT
<213> ORGANISM: Artificial sequence
<220> FEATURE:
<223> OTHER INFORMATION: Synthetic cytosine deaminase

<400> SEQUENCE: 206

Thr Asp Ala Glu Tyr Val Arg Ile His Glu Lys Leu Asp Ile Tyr Thr
1 5 10 15

Phe Lys Lys Gln Phe Ser Asn Asn Lys Lys Ser Val Ser His Arg Cys
20 25 30

Tyr Val Leu Phe Glu Leu Lys Arg Arg Gly Glu Arg Arg Ala Cys Phe
35 40 45

Trp Gly Tyr Ala Val Asn Lys Pro Gln Ser Gly Thr Glu Arg Gly Ile
50 55 60

His Ala Glu Ile Phe Ser Ile Arg Lys Val Glu Glu Tyr Leu Arg Asp
65 70 75 80

Asn Pro Gly Gln Phe Thr Ile Asn Trp Tyr Ser Ser Trp Ser Pro Cys
85 90 95

Ala Asp Cys Ala Glu Lys Ile Leu Glu Trp Tyr Asn Gln Glu Leu Arg
100 105 110

Gly Asn Gly His Thr Leu Lys Ile Trp Val Cys Lys Leu Tyr Tyr Glu
115 120 125

Lys Asn Ala Arg Asn Gln Ile Gly Leu Trp Asn Leu Arg Asp Asn Gly
130 135 140

Val Gly Leu Asn Val Met Val Ser Glu His Tyr Gln Cys Cys Arg Lys
145 150 155 160

Ile Phe Ile Gln Ser Ser His Asn Gln Leu Asn Glu Asn Arg Trp Leu
165 170 175

Glu Lys Thr Leu Lys Arg Ala Glu Lys Arg Arg Ser Glu Leu Ser Ile
180 185 190

Met Phe Gln Val Lys Ile Leu His Thr Thr Lys Ser Pro Ala Val
195 200 205

<210> SEQ ID NO 207

<211> LENGTH: 228
<212> TYPE: PRT
<213> ORGANISM: Artificial sequence
<220> FEATURE:
<223> OTHER INFORMATION: Synthetic cytosine deaminase

<400> SEQUENCE: 207

Ser Ser Lys Thr Gly Pro Val Ala Val Asp Pro Thr Leu Arg Arg Arg
1 5 10 15

Ile Glu Pro His Glu Phe Glu Val Phe Phe Asp Pro Arg Glu Leu Arg
20 25 30

Lys Glu Thr Cys Leu Leu Tyr Glu Ile Asn Trp Gly Gly Arg His Ser
35 40 45

Ile Trp Arg His Thr Ser Gln Asn Thr Asn Lys His Val Glu Val Asn
50 55 60

Phe Ile Glu Lys Phe Thr Thr Glu Arg Tyr Phe Cys Pro Asn Thr Arg
65 70 75 80

Cys Ser Ile Thr Trp Phe Leu Ser Trp Ser Pro Cys Gly Glu Cys Ser
85 90 95

Arg Ala Ile Thr Glu Phe Leu Ser Arg Tyr Pro Asn Val Thr Leu Phe
100 105 110

Ile Tyr Ile Ala Arg Leu Tyr His Leu Ala Asn Pro Arg Asn Arg Gln
115 120 125

Gly Leu Arg Asp Leu Ile Ser Ser Gly Val Thr Ile Gln Ile Met Thr
130 135 140

Glu Gln Glu Ser Gly Tyr Cys Trp His Asn Phe Val Asn Tyr Ser Pro
145 150 155 160

Ser Asn Glu Ser His Trp Pro Arg Tyr Pro His Leu Trp Val Arg Leu
165 170 175

Tyr Val Leu Glu Leu Tyr Cys Ile Ile Leu Gly Leu Pro Pro Cys Leu
180 185 190

Asn Ile Leu Arg Arg Lys Gln Ser Gln Leu Thr Ser Phe Thr Ile Ala
195 200 205

Leu Gln Ser Cys His Tyr Gln Arg Leu Pro Pro His Ile Leu Trp Ala
210 215 220

Thr Gly Leu Lys
225

<210> SEQ ID NO 208
<211> LENGTH: 162
<212> TYPE: PRT
<213> ORGANISM: Artificial sequence
<220> FEATURE:
<223> OTHER INFORMATION: Synthetic cytosine deaminase

<400> SEQUENCE: 208

Ser Phe Glu Arg Asn Tyr Asp Pro Arg Glu Leu Arg Lys Glu Thr Tyr
1 5 10 15

Leu Leu Tyr Glu Ile Lys Trp Gly Lys Ser Gly Lys Leu Trp Arg His
20 25 30

Trp Cys Gln Asn Asn Arg Thr Gln His Ala Glu Val Tyr Phe Leu Glu
35 40 45

Asn Ile Phe Asn Ala Arg Arg Phe Asn Pro Ser Thr His Cys Ser Ile
50 55 60

Thr Trp Tyr Leu Ser Trp Ser Pro Cys Ala Glu Cys Ser Gln Lys Ile
65 70 75 80

Val Asp Phe Leu Lys Glu His Pro Asn Val Asn Leu Glu Ile Tyr Val

-continued

```
                85                  90                  95

Ala Arg Leu Tyr Tyr Pro Glu Asn Glu Arg Asn Arg Gln Gly Leu Arg
            100                 105                 110

Asp Leu Val Asn Ser Gly Val Thr Ile Arg Ile Met Asp Leu Pro Asp
        115                 120                 125

Tyr Asn Tyr Cys Trp Lys Thr Phe Val Ser Asp Gln Gly Gly Asp Glu
    130                 135                 140

Asp Tyr Trp Pro Gly His Phe Ala Pro Trp Ile Lys Gln Tyr Ser Leu
145                 150                 155                 160

Lys Leu


<210> SEQ ID NO 209
<211> LENGTH: 1763
<212> TYPE: PRT
<213> ORGANISM: Artificial sequence
<220> FEATURE:
<223> OTHER INFORMATION: Synthetic adenosine deaminase

<400> SEQUENCE: 209

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285
```

-continued

```
Gly Ala Met Ile His Ser Arg Ile Gly Arg Val Val Phe Gly Val Arg
    290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp Ser Gly Gly Ser
        355                 360                 365

Ser Gly Gly Ser Ser Gly Ser Glu Thr Pro Gly Thr Ser Glu Ser Ala
    370                 375                 380

Thr Pro Glu Ser Ser Gly Gly Ser Ser Gly Gly Ser Asp Lys Lys Tyr
385                 390                 395                 400

Ser Ile Gly Leu Ala Ile Gly Thr Asn Ser Val Gly Trp Ala Val Ile
                405                 410                 415

Thr Asp Glu Tyr Lys Val Pro Ser Lys Lys Phe Lys Val Leu Gly Asn
            420                 425                 430

Thr Asp Arg His Ser Ile Lys Lys Asn Leu Ile Gly Ala Leu Leu Phe
        435                 440                 445

Asp Ser Gly Glu Thr Ala Glu Ala Thr Arg Leu Lys Arg Thr Ala Arg
    450                 455                 460

Arg Arg Tyr Thr Arg Arg Lys Asn Arg Ile Cys Tyr Leu Gln Glu Ile
465                 470                 475                 480

Phe Ser Asn Glu Met Ala Lys Val Asp Asp Ser Phe Phe His Arg Leu
                485                 490                 495

Glu Glu Ser Phe Leu Val Glu Glu Asp Lys Lys His Glu Arg His Pro
            500                 505                 510

Ile Phe Gly Asn Ile Val Asp Glu Val Ala Tyr His Glu Lys Tyr Pro
        515                 520                 525

Thr Ile Tyr His Leu Arg Lys Lys Leu Val Asp Ser Thr Asp Lys Ala
    530                 535                 540

Asp Leu Arg Leu Ile Tyr Leu Ala Leu Ala His Met Ile Lys Phe Arg
545                 550                 555                 560

Gly His Phe Leu Ile Glu Gly Asp Leu Asn Pro Asp Asn Ser Asp Val
                565                 570                 575

Asp Lys Leu Phe Ile Gln Leu Val Gln Thr Tyr Asn Gln Leu Phe Glu
            580                 585                 590

Glu Asn Pro Ile Asn Ala Ser Gly Val Asp Ala Lys Ala Ile Leu Ser
        595                 600                 605

Ala Arg Leu Ser Lys Ser Arg Arg Leu Glu Asn Leu Ile Ala Gln Leu
    610                 615                 620

Pro Gly Glu Lys Lys Asn Gly Leu Phe Gly Asn Leu Ile Ala Leu Ser
625                 630                 635                 640

Leu Gly Leu Thr Pro Asn Phe Lys Ser Asn Phe Asp Leu Ala Glu Asp
                645                 650                 655

Ala Lys Leu Gln Leu Ser Lys Asp Thr Tyr Asp Asp Asp Leu Asp Asn
            660                 665                 670

Leu Leu Ala Gln Ile Gly Asp Gln Tyr Ala Asp Leu Phe Leu Ala Ala
        675                 680                 685

Lys Asn Leu Ser Asp Ala Ile Leu Leu Ser Asp Ile Leu Arg Val Asn
    690                 695                 700
```

-continued

```
Thr Glu Ile Thr Lys Ala Pro Leu Ser Ala Ser Met Ile Lys Arg Tyr
705                 710                 715                 720

Asp Glu His His Gln Asp Leu Thr Leu Leu Lys Ala Leu Val Arg Gln
                725                 730                 735

Gln Leu Pro Glu Lys Tyr Lys Glu Ile Phe Phe Asp Gln Ser Lys Asn
            740                 745                 750

Gly Tyr Ala Gly Tyr Ile Asp Gly Gly Ala Ser Gln Glu Glu Phe Tyr
        755                 760                 765

Lys Phe Ile Lys Pro Ile Leu Glu Lys Met Asp Gly Thr Glu Glu Leu
    770                 775                 780

Leu Val Lys Leu Asn Arg Glu Asp Leu Leu Arg Lys Gln Arg Thr Phe
785                 790                 795                 800

Asp Asn Gly Ser Ile Pro His Gln Ile His Leu Gly Glu Leu His Ala
                805                 810                 815

Ile Leu Arg Arg Gln Glu Asp Phe Tyr Pro Phe Leu Lys Asp Asn Arg
            820                 825                 830

Glu Lys Ile Glu Lys Ile Leu Thr Phe Arg Ile Pro Tyr Tyr Val Gly
        835                 840                 845

Pro Leu Ala Arg Gly Asn Ser Arg Phe Ala Trp Met Thr Arg Lys Ser
    850                 855                 860

Glu Glu Thr Ile Thr Pro Trp Asn Phe Glu Glu Val Val Asp Lys Gly
865                 870                 875                 880

Ala Ser Ala Gln Ser Phe Ile Glu Arg Met Thr Asn Phe Asp Lys Asn
                885                 890                 895

Leu Pro Asn Glu Lys Val Leu Pro Lys His Ser Leu Leu Tyr Glu Tyr
            900                 905                 910

Phe Thr Val Tyr Asn Glu Leu Thr Lys Val Lys Tyr Val Thr Glu Gly
        915                 920                 925

Met Arg Lys Pro Ala Phe Leu Ser Gly Glu Gln Lys Lys Ala Ile Val
    930                 935                 940

Asp Leu Leu Phe Lys Thr Asn Arg Lys Val Thr Val Lys Gln Leu Lys
945                 950                 955                 960

Glu Asp Tyr Phe Lys Lys Ile Glu Cys Phe Asp Ser Val Glu Ile Ser
                965                 970                 975

Gly Val Glu Asp Arg Phe Asn Ala Ser Leu Gly Thr Tyr His Asp Leu
            980                 985                 990

Leu Lys Ile Ile Lys Asp Lys Asp  Phe Leu Asp Asn Glu  Glu Asn Glu
        995                 1000                1005

Asp Ile  Leu Glu Asp Ile Val  Leu Thr Leu Thr Leu  Phe Glu Asp
    1010                1015                1020

Arg Glu  Met Ile Glu Glu Arg  Leu Lys Thr Tyr Ala  His Leu Phe
    1025                1030                1035

Asp Asp  Lys Val Met Lys Gln  Leu Lys Arg Arg Arg  Tyr Thr Gly
    1040                1045                1050

Trp Gly  Arg Leu Ser Arg Lys  Leu Ile Asn Gly Ile  Arg Asp Lys
    1055                1060                1065

Gln Ser  Gly Lys Thr Ile Leu  Asp Phe Leu Lys Ser  Asp Gly Phe
    1070                1075                1080

Ala Asn  Arg Asn Phe Met Gln  Leu Ile His Asp Asp  Ser Leu Thr
    1085                1090                1095

Phe Lys  Glu Asp Ile Gln Lys  Ala Gln Val Ser Gly  Gln Gly Asp
    1100                1105                1110

Ser Leu  His Glu His Ile Ala  Asn Leu Ala Gly Ser  Pro Ala Ile
```

-continued

```
    1115                1120                1125

Lys Lys  Gly Ile Leu Gln Thr  Val Lys Val Val Asp  Glu Leu Val
    1130                1135                1140

Lys Val  Met Gly Arg His Lys  Pro Glu Asn Ile Val  Ile Glu Met
    1145                1150                1155

Ala Arg  Glu Asn Gln Thr Thr  Gln Lys Gly Gln Lys  Asn Ser Arg
    1160                1165                1170

Glu Arg  Met Lys Arg Ile Glu  Glu Gly Ile Lys Glu  Leu Gly Ser
    1175                1180                1185

Gln Ile  Leu Lys Glu His Pro  Val Glu Asn Thr Gln  Leu Gln Asn
    1190                1195                1200

Glu Lys  Leu Tyr Leu Tyr Tyr  Leu Gln Asn Gly Arg  Asp Met Tyr
    1205                1210                1215

Val Asp  Gln Glu Leu Asp Ile  Asn Arg Leu Ser Asp  Tyr Asp Val
    1220                1225                1230

Asp His  Ile Val Pro Gln Ser  Phe Leu Lys Asp Asp  Ser Ile Asp
    1235                1240                1245

Asn Lys  Val Leu Thr Arg Ser  Asp Lys Asn Arg Gly  Lys Ser Asp
    1250                1255                1260

Asn Val  Pro Ser Glu Glu Val  Val Lys Lys Met Lys  Asn Tyr Trp
    1265                1270                1275

Arg Gln  Leu Leu Asn Ala Lys  Leu Ile Thr Gln Arg  Lys Phe Asp
    1280                1285                1290

Asn Leu  Thr Lys Ala Glu Arg  Gly Gly Leu Ser Glu  Leu Asp Lys
    1295                1300                1305

Ala Gly  Phe Ile Lys Arg Gln  Leu Val Glu Thr Arg  Gln Ile Thr
    1310                1315                1320

Lys His  Val Ala Gln Ile Leu  Asp Ser Arg Met Asn  Thr Lys Tyr
    1325                1330                1335

Asp Glu  Asn Asp Lys Leu Ile  Arg Glu Val Lys Val  Ile Thr Leu
    1340                1345                1350

Lys Ser  Lys Leu Val Ser Asp  Phe Arg Lys Asp Phe  Gln Phe Tyr
    1355                1360                1365

Lys Val  Arg Glu Ile Asn Asn  Tyr His His Ala His  Asp Ala Tyr
    1370                1375                1380

Leu Asn  Ala Val Val Gly Thr  Ala Leu Ile Lys Lys  Tyr Pro Lys
    1385                1390                1395

Leu Glu  Ser Glu Phe Val Tyr  Gly Asp Tyr Lys Val  Tyr Asp Val
    1400                1405                1410

Arg Lys  Met Ile Ala Lys Ser  Glu Gln Glu Ile Gly  Lys Ala Thr
    1415                1420                1425

Ala Lys  Tyr Phe Phe Tyr Ser  Asn Ile Met Asn Phe  Phe Lys Thr
    1430                1435                1440

Glu Ile  Thr Leu Ala Asn Gly  Glu Ile Arg Lys Arg  Pro Leu Ile
    1445                1450                1455

Glu Thr  Asn Gly Glu Thr Gly  Glu Ile Val Trp Asp  Lys Gly Arg
    1460                1465                1470

Asp Phe  Ala Thr Val Arg Lys  Val Leu Ser Met Pro  Gln Val Asn
    1475                1480                1485

Ile Val  Lys Lys Thr Glu Val  Gln Thr Gly Gly Phe  Ser Lys Glu
    1490                1495                1500

Ser Ile  Leu Pro Lys Arg Asn  Ser Asp Lys Leu Ile  Ala Arg Lys
    1505                1510                1515
```

Lys Asp Trp Asp Pro Lys Lys Tyr Gly Gly Phe Asp Ser Pro Thr
1520 1525 1530

Val Ala Tyr Ser Val Leu Val Val Ala Lys Val Glu Lys Gly Lys
1535 1540 1545

Ser Lys Lys Leu Lys Ser Val Lys Glu Leu Leu Gly Ile Thr Ile
1550 1555 1560

Met Glu Arg Ser Ser Phe Glu Lys Asn Pro Ile Asp Phe Leu Glu
1565 1570 1575

Ala Lys Gly Tyr Lys Glu Val Lys Lys Asp Leu Ile Ile Lys Leu
1580 1585 1590

Pro Lys Tyr Ser Leu Phe Glu Leu Glu Asn Gly Arg Lys Arg Met
1595 1600 1605

Leu Ala Ser Ala Gly Glu Leu Gln Lys Gly Asn Glu Leu Ala Leu
1610 1615 1620

Pro Ser Lys Tyr Val Asn Phe Leu Tyr Leu Ala Ser His Tyr Glu
1625 1630 1635

Lys Leu Lys Gly Ser Pro Glu Asp Asn Glu Gln Lys Gln Leu Phe
1640 1645 1650

Val Glu Gln His Lys His Tyr Leu Asp Glu Ile Ile Glu Gln Ile
1655 1660 1665

Ser Glu Phe Ser Lys Arg Val Ile Leu Ala Asp Ala Asn Leu Asp
1670 1675 1680

Lys Val Leu Ser Ala Tyr Asn Lys His Arg Asp Lys Pro Ile Arg
1685 1690 1695

Glu Gln Ala Glu Asn Ile Ile His Leu Phe Thr Leu Thr Asn Leu
1700 1705 1710

Gly Ala Pro Ala Ala Phe Lys Tyr Phe Asp Thr Thr Ile Asp Arg
1715 1720 1725

Lys Arg Tyr Thr Ser Thr Lys Glu Val Leu Asp Ala Thr Leu Ile
1730 1735 1740

His Gln Ser Ile Thr Gly Leu Tyr Glu Thr Arg Ile Asp Leu Ser
1745 1750 1755

Gln Leu Gly Gly Asp
1760

<210> SEQ ID NO 210
<211> LENGTH: 1565
<212> TYPE: PRT
<213> ORGANISM: Artificial sequence
<220> FEATURE:
<223> OTHER INFORMATION: Synthetic adenosine deaminase

<400> SEQUENCE: 210

Ser Glu Val Glu Phe Ser His Glu Tyr Trp Met Arg His Ala Leu Thr
1 5 10 15

Leu Ala Lys Arg Ala Arg Asp Glu Arg Glu Val Pro Val Gly Ala Val
20 25 30

Leu Val Leu Asn Asn Arg Val Ile Gly Glu Gly Trp Asn Arg Ala Ile
35 40 45

Gly Leu His Asp Pro Thr Ala His Ala Glu Ile Met Ala Leu Arg Gln
50 55 60

Gly Gly Leu Val Met Gln Asn Tyr Arg Leu Ile Asp Ala Thr Leu Tyr
65 70 75 80

Val Thr Phe Glu Pro Cys Val Met Cys Ala Gly Ala Met Ile His Ser
85 90 95

-continued

```
Arg Ile Gly Arg Val Val Phe Gly Val Arg Asn Ser Lys Arg Gly Ala
            100                 105                 110

Ala Gly Ser Leu Met Asn Val Leu Asn Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Asp Phe Tyr Arg Met Pro Arg Gln Val Phe Asn Ala Gln Lys Lys
145                 150                 155                 160

Ala Gln Ser Ser Ile Asn Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
    290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
    450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510
```

```
Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
    530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
    610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
        675                 680                 685

Ile Glu Arg Met Thr Asn Phe Asp Lys Asn Leu Pro Asn Glu Lys Val
    690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
```

-continued

```
    930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn  Thr Gln Leu Gln Asn  Glu Lys Leu
        995                 1000                1005

Tyr Leu  Tyr Tyr Leu Gln Asn  Gly Arg Asp Met Tyr  Val Asp Gln
    1010                1015                1020

Glu Leu  Asp Ile Asn Arg Leu  Ser Asp Tyr Asp Val  Asp His Ile
    1025                1030                1035

Val Pro  Gln Ser Phe Leu Lys  Asp Asp Ser Ile Asp  Asn Lys Val
    1040                1045                1050

Leu Thr  Arg Ser Asp Lys Asn  Arg Gly Lys Ser Asp  Asn Val Pro
    1055                1060                1065

Ser Glu  Glu Val Val Lys Lys  Met Lys Asn Tyr Trp  Arg Gln Leu
    1070                1075                1080

Leu Asn  Ala Lys Leu Ile Thr  Gln Arg Lys Phe Asp  Asn Leu Thr
    1085                1090                1095

Lys Ala  Glu Arg Gly Gly Leu  Ser Glu Leu Asp Lys  Ala Gly Phe
    1100                1105                1110

Ile Lys  Arg Gln Leu Val Glu  Thr Arg Gln Ile Thr  Lys His Val
    1115                1120                1125

Ala Gln  Ile Leu Asp Ser Arg  Met Asn Thr Lys Tyr  Asp Glu Asn
    1130                1135                1140

Asp Lys  Leu Ile Arg Glu Val  Lys Val Ile Thr Leu  Lys Ser Lys
    1145                1150                1155

Leu Val  Ser Asp Phe Arg Lys  Asp Phe Gln Phe Tyr  Lys Val Arg
    1160                1165                1170

Glu Ile  Asn Asn Tyr His His  Ala His Asp Ala Tyr  Leu Asn Ala
    1175                1180                1185

Val Val  Gly Thr Ala Leu Ile  Lys Lys Tyr Pro Lys  Leu Glu Ser
    1190                1195                1200

Glu Phe  Val Tyr Gly Asp Tyr  Lys Val Tyr Asp Val  Arg Lys Met
    1205                1210                1215

Ile Ala  Lys Ser Glu Gln Glu  Ile Gly Lys Ala Thr  Ala Lys Tyr
    1220                1225                1230

Phe Phe  Tyr Ser Asn Ile Met  Asn Phe Phe Lys Thr  Glu Ile Thr
    1235                1240                1245

Leu Ala  Asn Gly Glu Ile Arg  Lys Arg Pro Leu Ile  Glu Thr Asn
    1250                1255                1260

Gly Glu  Thr Gly Glu Ile Val  Trp Asp Lys Gly Arg  Asp Phe Ala
    1265                1270                1275

Thr Val  Arg Lys Val Leu Ser  Met Pro Gln Val Asn  Ile Val Lys
    1280                1285                1290

Lys Thr  Glu Val Gln Thr Gly  Gly Phe Ser Lys Glu  Ser Ile Leu
    1295                1300                1305

Pro Lys  Arg Asn Ser Asp Lys  Leu Ile Ala Arg Lys  Lys Asp Trp
    1310                1315                1320

Asp Pro  Lys Lys Tyr Gly Gly  Phe Asp Ser Pro Thr  Val Ala Tyr
    1325                1330                1335
```

Ser Val Leu Val Val Ala Lys Val Glu Lys Gly Lys Ser Lys Lys
1340 1345 1350

Leu Lys Ser Val Lys Glu Leu Leu Gly Ile Thr Ile Met Glu Arg
1355 1360 1365

Ser Ser Phe Glu Lys Asn Pro Ile Asp Phe Leu Glu Ala Lys Gly
1370 1375 1380

Tyr Lys Glu Val Lys Lys Asp Leu Ile Ile Lys Leu Pro Lys Tyr
1385 1390 1395

Ser Leu Phe Glu Leu Glu Asn Gly Arg Lys Arg Met Leu Ala Ser
1400 1405 1410

Ala Gly Glu Leu Gln Lys Gly Asn Glu Leu Ala Leu Pro Ser Lys
1415 1420 1425

Tyr Val Asn Phe Leu Tyr Leu Ala Ser His Tyr Glu Lys Leu Lys
1430 1435 1440

Gly Ser Pro Glu Asp Asn Glu Gln Lys Gln Leu Phe Val Glu Gln
1445 1450 1455

His Lys His Tyr Leu Asp Glu Ile Ile Glu Gln Ile Ser Glu Phe
1460 1465 1470

Ser Lys Arg Val Ile Leu Ala Asp Ala Asn Leu Asp Lys Val Leu
1475 1480 1485

Ser Ala Tyr Asn Lys His Arg Asp Lys Pro Ile Arg Glu Gln Ala
1490 1495 1500

Glu Asn Ile Ile His Leu Phe Thr Leu Thr Asn Leu Gly Ala Pro
1505 1510 1515

Ala Ala Phe Lys Tyr Phe Asp Thr Thr Ile Asp Arg Lys Arg Tyr
1520 1525 1530

Thr Ser Thr Lys Glu Val Leu Asp Ala Thr Leu Ile His Gln Ser
1535 1540 1545

Ile Thr Gly Leu Tyr Glu Thr Arg Ile Asp Leu Ser Gln Leu Gly
1550 1555 1560

Gly Asp
1565

<210> SEQ ID NO 211
<211> LENGTH: 1565
<212> TYPE: PRT
<213> ORGANISM: Artificial sequence
<220> FEATURE:
<223> OTHER INFORMATION: Synthetic adenosine deaminase

<400> SEQUENCE: 211

Ser Glu Val Glu Phe Ser His Glu Tyr Trp Met Arg His Ala Leu Thr
1 5 10 15

Leu Ala Lys Arg Ala Arg Asp Glu Arg Glu Val Pro Val Gly Ala Val
20 25 30

Leu Val Leu Asn Asn Arg Val Ile Gly Glu Gly Trp Asn Arg Ala Ile
35 40 45

Gly Leu His Asp Pro Thr Ala His Ala Glu Ile Met Ala Leu Arg Gln
50 55 60

Gly Gly Leu Val Met Gln Asn Tyr Arg Leu Tyr Asp Ala Thr Leu Tyr
65 70 75 80

Ser Thr Phe Glu Pro Cys Val Met Cys Ala Gly Ala Met Ile His Ser
85 90 95

Arg Ile Gly Arg Val Val Phe Gly Val Arg Asn Ala Lys Thr Gly Ala
100 105 110

```
Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Cys Arg Phe Phe Arg Met Pro Arg Arg Val Phe Asn Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
        275                 280                 285

Lys Val Asp Asp Ser Phe Phe His Arg Leu Glu Glu Ser Phe Leu Val
    290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
        435                 440                 445

Phe Lys Ser Asn Phe Asp Leu Ala Glu Asp Ala Lys Leu Gln Leu Ser
    450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525
```

```
Leu Thr Leu Leu Lys Ala Leu Val Arg Gln Gln Leu Pro Glu Lys Tyr
    530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
    610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
        675                 680                 685

Ile Glu Arg Met Thr Asn Phe Asp Lys Asn Leu Pro Asn Glu Lys Val
    690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
    930                 935                 940

Val Lys Val Met Gly Arg His Lys Pro Glu Asn Ile Val Ile Glu Met
```

-continued 945 950 955 960

Ala Arg Glu Asn Gln Thr Thr Gln Lys Gly Gln Lys Asn Ser Arg Glu
965 970 975

Arg Met Lys Arg Ile Glu Glu Gly Ile Lys Glu Leu Gly Ser Gln Ile
980 985 990

Leu Lys Glu His Pro Val Glu Asn Thr Gln Leu Gln Asn Glu Lys Leu
995 1000 1005

Tyr Leu Tyr Tyr Leu Gln Asn Gly Arg Asp Met Tyr Val Asp Gln
1010 1015 1020

Glu Leu Asp Ile Asn Arg Leu Ser Asp Tyr Asp Val Asp His Ile
1025 1030 1035

Val Pro Gln Ser Phe Leu Lys Asp Asp Ser Ile Asp Asn Lys Val
1040 1045 1050

Leu Thr Arg Ser Asp Lys Asn Arg Gly Lys Ser Asp Asn Val Pro
1055 1060 1065

Ser Glu Glu Val Val Lys Lys Met Lys Asn Tyr Trp Arg Gln Leu
1070 1075 1080

Leu Asn Ala Lys Leu Ile Thr Gln Arg Lys Phe Asp Asn Leu Thr
1085 1090 1095

Lys Ala Glu Arg Gly Gly Leu Ser Glu Leu Asp Lys Ala Gly Phe
1100 1105 1110

Ile Lys Arg Gln Leu Val Glu Thr Arg Gln Ile Thr Lys His Val
1115 1120 1125

Ala Gln Ile Leu Asp Ser Arg Met Asn Thr Lys Tyr Asp Glu Asn
1130 1135 1140

Asp Lys Leu Ile Arg Glu Val Lys Val Ile Thr Leu Lys Ser Lys
1145 1150 1155

Leu Val Ser Asp Phe Arg Lys Asp Phe Gln Phe Tyr Lys Val Arg
1160 1165 1170

Glu Ile Asn Asn Tyr His His Ala His Asp Ala Tyr Leu Asn Ala
1175 1180 1185

Val Val Gly Thr Ala Leu Ile Lys Lys Tyr Pro Lys Leu Glu Ser
1190 1195 1200

Glu Phe Val Tyr Gly Asp Tyr Lys Val Tyr Asp Val Arg Lys Met
1205 1210 1215

Ile Ala Lys Ser Glu Gln Glu Ile Gly Lys Ala Thr Ala Lys Tyr
1220 1225 1230

Phe Phe Tyr Ser Asn Ile Met Asn Phe Phe Lys Thr Glu Ile Thr
1235 1240 1245

Leu Ala Asn Gly Glu Ile Arg Lys Arg Pro Leu Ile Glu Thr Asn
1250 1255 1260

Gly Glu Thr Gly Glu Ile Val Trp Asp Lys Gly Arg Asp Phe Ala
1265 1270 1275

Thr Val Arg Lys Val Leu Ser Met Pro Gln Val Asn Ile Val Lys
1280 1285 1290

Lys Thr Glu Val Gln Thr Gly Gly Phe Ser Lys Glu Ser Ile Leu
1295 1300 1305

Pro Lys Arg Asn Ser Asp Lys Leu Ile Ala Arg Lys Lys Asp Trp
1310 1315 1320

Asp Pro Lys Lys Tyr Gly Gly Phe Asp Ser Pro Thr Val Ala Tyr
1325 1330 1335

Ser Val Leu Val Val Ala Lys Val Glu Lys Gly Lys Ser Lys Lys
1340 1345 1350

```
Leu Lys  Ser Val Lys Glu Leu  Leu Gly Ile Thr Ile  Met Glu Arg
    1355                 1360                 1365

Ser Ser  Phe Glu Lys Asn Pro  Ile Asp Phe Leu Glu  Ala Lys Gly
    1370                 1375                 1380

Tyr Lys  Glu Val Lys Lys Asp  Leu Ile Ile Lys Leu  Pro Lys Tyr
    1385                 1390                 1395

Ser Leu  Phe Glu Leu Glu Asn  Gly Arg Lys Arg Met  Leu Ala Ser
    1400                 1405                 1410

Ala Gly  Glu Leu Gln Lys Gly  Asn Glu Leu Ala Leu  Pro Ser Lys
    1415                 1420                 1425

Tyr Val  Asn Phe Leu Tyr Leu  Ala Ser His Tyr Glu  Lys Leu Lys
    1430                 1435                 1440

Gly Ser  Pro Glu Asp Asn Glu  Gln Lys Gln Leu Phe  Val Glu Gln
    1445                 1450                 1455

His Lys  His Tyr Leu Asp Glu  Ile Ile Glu Gln Ile  Ser Glu Phe
    1460                 1465                 1470

Ser Lys  Arg Val Ile Leu Ala  Asp Ala Asn Leu Asp  Lys Val Leu
    1475                 1480                 1485

Ser Ala  Tyr Asn Lys His Arg  Asp Lys Pro Ile Arg  Glu Gln Ala
    1490                 1495                 1500

Glu Asn  Ile Ile His Leu Phe  Thr Leu Thr Asn Leu  Gly Ala Pro
    1505                 1510                 1515

Ala Ala  Phe Lys Tyr Phe Asp  Thr Thr Ile Asp Arg  Lys Arg Tyr
    1520                 1525                 1530

Thr Ser  Thr Lys Glu Val Leu  Asp Ala Thr Leu Ile  His Gln Ser
    1535                 1540                 1545

Ile Thr  Gly Leu Tyr Glu Thr  Arg Ile Asp Leu Ser  Gln Leu Gly
    1550                 1555                 1560

Gly Asp
    1565
```

<210> SEQ ID NO 212
<211> LENGTH: 364
<212> TYPE: PRT
<213> ORGANISM: Artificial sequence
<220> FEATURE:
<223> OTHER INFORMATION: Synthetic adenosine deaminase

<400> SEQUENCE: 212

```
Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125
```

```
Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
            180                 185                 190

Gly Ser Ser Gly Gly Ser Ser Glu Val Glu Phe Ser His Glu Tyr Trp
        195                 200                 205

Met Arg His Ala Leu Thr Leu Ala Lys Arg Ala Arg Asp Glu Arg Glu
    210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
    290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp
        355                 360


<210> SEQ ID NO 213
<211> LENGTH: 167
<212> TYPE: PRT
<213> ORGANISM: Artificial sequence
<220> FEATURE:
<223> OTHER INFORMATION: Synthetic adenosine deaminase

<400> SEQUENCE: 213

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
    50                  55                  60

Gln Gly Gly Leu Val Met Gln Asn Tyr Arg Leu Tyr Asp Ala Thr Leu
65                  70                  75                  80

Tyr Ser Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
            100                 105                 110

Ala Ala Gly Ser Leu Met Asp Val Leu His His Pro Gly Met Asn His
        115                 120                 125
```

```
Arg Val Glu Ile Thr Glu Gly Ile Leu Ala Asp Glu Cys Ala Ala Leu
    130                 135                 140

Leu Cys Arg Phe Phe Arg Met Pro Arg Arg Val Phe Asn Ala Gln Lys
145                 150                 155                 160

Lys Ala Gln Ser Ser Thr Asp
                165


<210> SEQ ID NO 214
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 214

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320
```

```
Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735
```

```
Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
```

```
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His
    1220                1225


<210> SEQ ID NO 215
<211> LENGTH: 1307
<212> TYPE: PRT
<213> ORGANISM: Acidaminococcus sp.

<400> SEQUENCE: 215

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285
```

-continued

```
Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
```

-continued 705 710 715 720

Ile Ser Phe Gln Arg Ile Ala Glu Lys Glu Ile Met Asp Ala Val Glu
725 730 735

Thr Gly Lys Leu Tyr Leu Phe Gln Ile Tyr Asn Lys Asp Phe Ala Lys
740 745 750

Gly His His Gly Lys Pro Asn Leu His Thr Leu Tyr Trp Thr Gly Leu
755 760 765

Phe Ser Pro Glu Asn Leu Ala Lys Thr Ser Ile Lys Leu Asn Gly Gln
770 775 780

Ala Glu Leu Phe Tyr Arg Pro Lys Ser Arg Met Lys Arg Met Ala His
785 790 795 800

Arg Leu Gly Glu Lys Met Leu Asn Lys Lys Leu Lys Asp Gln Lys Thr
805 810 815

Pro Ile Pro Asp Thr Leu Tyr Gln Glu Leu Tyr Asp Tyr Val Asn His
820 825 830

Arg Leu Ser His Asp Leu Ser Asp Glu Ala Arg Ala Leu Leu Pro Asn
835 840 845

Val Ile Thr Lys Glu Val Ser His Glu Ile Ile Lys Asp Arg Arg Phe
850 855 860

Thr Ser Asp Lys Phe Phe Phe His Val Pro Ile Thr Leu Asn Tyr Gln
865 870 875 880

Ala Ala Asn Ser Pro Ser Lys Phe Asn Gln Arg Val Asn Ala Tyr Leu
885 890 895

Lys Glu His Pro Glu Thr Pro Ile Ile Gly Ile Asp Arg Gly Glu Arg
900 905 910

Asn Leu Ile Tyr Ile Thr Val Ile Asp Ser Thr Gly Lys Ile Leu Glu
915 920 925

Gln Arg Ser Leu Asn Thr Ile Gln Gln Phe Asp Tyr Gln Lys Lys Leu
930 935 940

Asp Asn Arg Glu Lys Glu Arg Val Ala Ala Arg Gln Ala Trp Ser Val
945 950 955 960

Val Gly Thr Ile Lys Asp Leu Lys Gln Gly Tyr Leu Ser Gln Val Ile
965 970 975

His Glu Ile Val Asp Leu Met Ile His Tyr Gln Ala Val Val Val Leu
980 985 990

Glu Asn Leu Asn Phe Gly Phe Lys Ser Lys Arg Thr Gly Ile Ala Glu
995 1000 1005

Lys Ala Val Tyr Gln Gln Phe Glu Lys Met Leu Ile Asp Lys Leu
1010 1015 1020

Asn Cys Leu Val Leu Lys Asp Tyr Pro Ala Glu Lys Val Gly Gly
1025 1030 1035

Val Leu Asn Pro Tyr Gln Leu Thr Asp Gln Phe Thr Ser Phe Ala
1040 1045 1050

Lys Met Gly Thr Gln Ser Gly Phe Leu Phe Tyr Val Pro Ala Pro
1055 1060 1065

Tyr Thr Ser Lys Ile Asp Pro Leu Thr Gly Phe Val Asp Pro Phe
1070 1075 1080

Val Trp Lys Thr Ile Lys Asn His Glu Ser Arg Lys His Phe Leu
1085 1090 1095

Glu Gly Phe Asp Phe Leu His Tyr Asp Val Lys Thr Gly Asp Phe
1100 1105 1110

Ile Leu His Phe Lys Met Asn Arg Asn Leu Ser Phe Gln Arg Gly
1115 1120 1125

Leu Pro Gly Phe Met Pro Ala Trp Asp Ile Val Phe Glu Lys Asn
1130 1135 1140

Glu Thr Gln Phe Asp Ala Lys Gly Thr Pro Phe Ile Ala Gly Lys
1145 1150 1155

Arg Ile Val Pro Val Ile Glu Asn His Arg Phe Thr Gly Arg Tyr
1160 1165 1170

Arg Asp Leu Tyr Pro Ala Asn Glu Leu Ile Ala Leu Leu Glu Glu
1175 1180 1185

Lys Gly Ile Val Phe Arg Asp Gly Ser Asn Ile Leu Pro Lys Leu
1190 1195 1200

Leu Glu Asn Asp Asp Ser His Ala Ile Asp Thr Met Val Ala Leu
1205 1210 1215

Ile Arg Ser Val Leu Gln Met Arg Asn Ser Asn Ala Ala Thr Gly
1220 1225 1230

Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp
1250 1255 1260

Ala Asn Gly Ala Tyr His Ile Ala Leu Lys Gly Gln Leu Leu Leu
1265 1270 1275

Asn His Leu Lys Glu Ser Lys Asp Leu Lys Leu Gln Asn Gly Ile
1280 1285 1290

Ser Asn Gln Asp Trp Leu Ala Tyr Ile Gln Glu Leu Arg Asn
1295 1300 1305

<210> SEQ ID NO 216
<211> LENGTH: 1241
<212> TYPE: PRT
<213> ORGANISM: Butyrivibrio proteoclasticus

<400> SEQUENCE: 216

Met Leu Leu Tyr Glu Asn Tyr Thr Lys Arg Asn Gln Ile Thr Lys Ser
1 5 10 15

Leu Arg Leu Glu Leu Arg Pro Gln Gly Lys Thr Leu Arg Asn Ile Lys
20 25 30

Glu Leu Asn Leu Leu Glu Gln Asp Lys Ala Ile Tyr Ala Leu Leu Glu
35 40 45

Arg Leu Lys Pro Val Ile Asp Glu Gly Ile Lys Asp Ile Ala Arg Asp
50 55 60

Thr Leu Lys Asn Cys Glu Leu Ser Phe Glu Lys Leu Tyr Glu His Phe
65 70 75 80

Leu Ser Gly Asp Lys Lys Ala Tyr Ala Lys Glu Ser Glu Arg Leu Lys
85 90 95

Lys Glu Ile Val Lys Thr Leu Ile Lys Asn Leu Pro Glu Gly Ile Gly
100 105 110

Lys Ile Ser Glu Ile Asn Ser Ala Lys Tyr Leu Asn Gly Val Leu Tyr
115 120 125

Asp Phe Ile Asp Lys Thr His Lys Asp Ser Glu Glu Lys Gln Asn Ile
130 135 140

Leu Ser Asp Ile Leu Glu Thr Lys Gly Tyr Leu Ala Leu Phe Ser Lys
145 150 155 160

Phe Leu Thr Ser Arg Ile Thr Thr Leu Glu Gln Ser Met Pro Lys Arg
165 170 175

Val Ile Glu Asn Phe Glu Ile Tyr Ala Ala Asn Ile Pro Lys Met Gln

-continued

```
            180                 185                 190

Asp Ala Leu Glu Arg Gly Ala Val Ser Phe Ala Ile Glu Tyr Glu Ser
        195                 200                 205

Ile Cys Ser Val Asp Tyr Tyr Asn Gln Ile Leu Ser Gln Glu Asp Ile
    210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
        275                 280                 285

Ile Asp Ser Asp Glu Glu Val Val Gln Val Thr Lys Glu Ala Phe Glu
    290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala
    370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
    450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525

His Trp Trp Asn Gly Glu Glu Asn Phe Ala Ile Asn Asp Val Ala Met
    530                 535                 540

Ile Arg Arg Gly Asp Glu Tyr Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575

Val Gln Arg Lys Gly Ala Lys Ser Phe Leu Gly Leu Pro Lys Ala Leu
            580                 585                 590

Phe Lys Cys Ile Leu Glu Pro Tyr Phe Glu Ser Pro Glu His Lys Asn
        595                 600                 605
```

```
Asp Lys Asn Cys Val Ile Glu Glu Tyr Val Ser Lys Pro Leu Thr Ile
    610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
            660                 665                 670

Tyr Ser Cys Phe Asn Met Ser Gly Leu Lys Arg Ala Asp Glu Tyr Asn
        675                 680                 685

Asp Ile Gly Glu Phe Phe Ser Asp Val Asp Thr Arg Leu Cys Thr Met
    690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
            740                 745                 750

Asn Met Glu His Thr Ser Met Leu Leu Asn Ser Arg Ala Met Ile Gln
        755                 760                 765

Tyr Arg Ala Ala Ser Leu Pro Arg Arg Val Thr His Lys Lys Gly Ser
    770                 775                 780

Ile Leu Val Ala Leu Arg Asp Ser Asn Gly Glu His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
            820                 825                 830

Ile Lys Lys Ala Asn Glu Asp Ile Ile Arg Asn Arg Arg Tyr Thr Glu
        835                 840                 845

Asp Lys Phe Phe Leu Ser Leu Ser Tyr Thr Lys Asn Ala Asp Ile Ser
    850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
            900                 905                 910

Leu Asn Glu Ile Asp Gly Val Asn Tyr Arg Glu Leu Leu Lys Glu Arg
        915                 920                 925

Thr Lys Ile Lys Tyr His Asp Lys Thr Arg Leu Trp Gln Tyr Asp Val
    930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Val Glu Ser
                965                 970                 975

Met Ser Ser Thr Phe Lys Asp Lys Phe Ser Phe Leu Asp Glu Gln Ile
            980                 985                 990

Phe Lys Ala Phe Glu Ala Arg Leu  Cys Ala Arg Met Ser  Asp Leu Ser
        995                 1000                1005

Phe Asn  Thr Ile Lys Glu Gly  Glu Ala Gly Ser Ile  Ser Asn Pro
    1010                1015                1020
```

Ile Gln Val Ser Asn Asn Asn Gly Asn Ser Tyr Gln Asp Gly Val
    1025                1030                1035

Ile Tyr Phe Leu Asn Asn Ala Tyr Thr Arg Thr Leu Cys Pro Asp
    1040                1045                1050

Thr Gly Phe Val Asp Val Phe Asp Lys Thr Arg Leu Ile Thr Met
    1055                1060                1065

Gln Ser Lys Arg Gln Phe Phe Ala Lys Met Lys Asp Ile Arg Ile
    1070                1075                1080

Asp Asp Gly Glu Met Leu Phe Thr Phe Asn Leu Glu Glu Tyr Pro
    1085                1090                1095

Thr Lys Arg Leu Leu Asp Arg Lys Glu Trp Thr Val Lys Ile Ala
    1100                1105                1110

Gly Asp Gly Ser Tyr Phe Asp Lys Asp Lys Gly Glu Tyr Val Tyr
    1115                1120                1125

Val Asn Asp Ile Val Arg Glu Gln Ile Ile Pro Ala Leu Leu Glu
    1130                1135                1140

Asp Lys Ala Val Phe Asp Gly Asn Met Ala Glu Lys Phe Leu Asp
    1145                1150                1155

Lys Thr Ala Ile Ser Gly Lys Ser Val Glu Leu Ile Tyr Lys Trp
    1160                1165                1170

Phe Ala Asn Ala Leu Tyr Gly Ile Ile Thr Lys Lys Asp Gly Glu
    1175                1180                1185

Lys Ile Tyr Arg Ser Pro Ile Thr Gly Thr Glu Ile Asp Val Ser
    1190                1195                1200

Lys Asn Thr Thr Tyr Asn Phe Gly Lys Lys Phe Met Phe Lys Gln
    1205                1210                1215

Glu Tyr Arg Gly Asp Gly Asp Phe Leu Asp Ala Phe Leu Asn Tyr
    1220                1225                1230

Met Gln Ala Gln Asp Ile Ala Val
    1235                1240

<210> SEQ ID NO 217
<211> LENGTH: 1238
<212> TYPE: PRT
<213> ORGANISM: Candidatus Methanoplasma termitum

<400> SEQUENCE: 217

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

```
Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Ile Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
    370                 375                 380

Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
        435                 440                 445

Ser Ile His Ile Ile Lys Thr Leu Leu Asp Ser Val Gln Gln Phe Leu
    450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
        515                 520                 525

Gly Trp Asp Gln Asn Lys Val Tyr Asp Tyr Ala Ser Leu Ile Phe Leu
    530                 535                 540

Arg Asp Gly Asn Tyr Tyr Leu Gly Ile Ile Asn Pro Lys Arg Lys Lys
545                 550                 555                 560
```

```
Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Arg Pro Val
            580                 585                 590

Phe Leu Thr Ser Thr Lys Gly Lys Lys Glu Tyr Lys Pro Ser Lys Glu
        595                 600                 605

Ile Ile Glu Gly Tyr Glu Ala Asp Lys His Ile Arg Gly Asp Lys Phe
    610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
        675                 680                 685

Tyr Val Glu Lys Gly Asp Leu Phe Leu Phe Gln Ile Tyr Asn Lys Asp
    690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
    770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
    850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
    930                 935                 940

Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
                965                 970                 975

Val Phe Lys Asp Ala Pro Asp Glu Ser Pro Gly Gly Val Leu Asn Ala
```

```
            980                   985                   990

Tyr Gln Leu Thr Asn Pro Leu Glu  Ser Phe Ala Lys Leu  Gly Lys Gln
        995                   1000                  1005

Thr Gly  Ile Leu Phe Tyr Val  Pro Ala Ala Tyr Thr  Ser Lys Ile
    1010                 1015                 1020

Asp Pro  Thr Thr Gly Phe Val  Asn Leu Phe Asn Thr  Ser Ser Lys
    1025                 1030                 1035

Thr Asn  Ala Gln Glu Arg Lys  Glu Phe Leu Gln Lys  Phe Glu Ser
    1040                 1045                 1050

Ile Ser  Tyr Ser Ala Lys Asp  Gly Gly Ile Phe Ala  Phe Ala Phe
    1055                 1060                 1065

Asp Tyr  Arg Lys Phe Gly Thr  Ser Lys Thr Asp His  Lys Asn Val
    1070                 1075                 1080

Trp Thr  Ala Tyr Thr Asn Gly  Glu Arg Met Arg Tyr  Ile Lys Glu
    1085                 1090                 1095

Lys Lys  Arg Asn Glu Leu Phe  Asp Pro Ser Lys Glu  Ile Lys Glu
    1100                 1105                 1110

Ala Leu  Thr Ser Ser Gly Ile  Lys Tyr Asp Gly Gly  Gln Asn Ile
    1115                 1120                 1125

Leu Pro  Asp Ile Leu Arg Ser  Asn Asn Asn Gly Leu  Ile Tyr Thr
    1130                 1135                 1140

Met Tyr  Ser Ser Phe Ile Ala  Ala Ile Gln Met Arg  Val Tyr Asp
    1145                 1150                 1155

Gly Lys  Glu Asp Tyr Ile Ile  Ser Pro Ile Lys Asn  Ser Lys Gly
    1160                 1165                 1170

Glu Phe  Phe Arg Thr Asp Pro  Lys Arg Arg Glu Leu  Pro Ile Asp
    1175                 1180                 1185

Ala Asp  Ala Asn Gly Ala Tyr  Asn Ile Ala Leu Arg  Gly Glu Leu
    1190                 1195                 1200

Thr Met  Arg Ala Ile Ala Glu  Lys Phe Asp Pro Asp  Ser Glu Lys
    1205                 1210                 1215

Met Ala  Lys Leu Glu Leu Lys  His Lys Asp Trp Phe  Glu Phe Met
    1220                 1225                 1230

Gln Thr  Arg Gly Asp
    1235


<210> SEQ ID NO 218
<211> LENGTH: 1281
<212> TYPE: PRT
<213> ORGANISM: Eubacterium eligens

<400> SEQUENCE: 218

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95
```

-continued

```
Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
        115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
        195                 200                 205

Ile Ser Glu Lys Ala Leu Asp Glu Ile Glu Val Ile Glu Lys Asn Asn
    210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
        275                 280                 285

Leu Ala Tyr Thr Ser Thr Ser Phe Glu Val Pro Lys Met Phe Glu Asp
    290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
            340                 345                 350

Leu Ser Cys Phe Met Ser Gly Asn Trp Asn Leu Ile Thr Gly Cys Val
        355                 360                 365

Glu Asn Phe Tyr Asp Glu Asn Ile His Ala Lys Gly Lys Ser Lys Glu
    370                 375                 380

Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                405                 410                 415

Glu Phe Lys Asn Ser Asn Ala Lys Gln Tyr Ile Arg Glu Ile Ser Asn
            420                 425                 430

Ile Ile Thr Asp Thr Glu Thr Ala His Leu Glu Tyr Asp Asp His Ile
        435                 440                 445

Ser Leu Ile Glu Ser Glu Glu Lys Ala Asp Glu Met Lys Lys Arg Leu
    450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
```

```
        515                 520                 525

Gln Ser Pro Thr Leu Ala Asn Gly Trp Ser Gln Ser Lys Glu Phe Asp
    530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
            580                 585                 590

Pro Gly Ala Asn Lys Met Leu Pro Lys Val Phe Leu Ser Lys Lys Gly
        595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
            660                 665                 670

Ser Glu Phe Tyr Arg Glu Val Glu Met Gln Gly Tyr Arg Ile Asp Trp
        675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
            740                 745                 750

Tyr Arg Arg Ala Ser Val Lys Asn Pro Val Lys His Lys Lys Asp Ser
        755                 760                 765

Val Leu Val Asn Lys Thr Tyr Lys Asn Gln Leu Asp Asn Gly Asp Val
    770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
        835                 840                 845

Ile Asn Tyr Lys Val Thr Ala Arg Asn Asn Val Asn Asp Met Val Val
    850                 855                 860

Lys Tyr Ile Ala Gln Asn Asp Asp Ile His Val Ile Gly Ile Asp Arg
865                 870                 875                 880

Gly Glu Arg Asn Leu Ile Tyr Ile Ser Val Ile Asp Ser His Gly Asn
                885                 890                 895

Ile Val Lys Gln Lys Ser Tyr Asn Ile Leu Asn Asn Tyr Asp Tyr Lys
            900                 905                 910

Lys Lys Leu Val Glu Lys Glu Lys Thr Arg Glu Tyr Ala Arg Lys Asn
        915                 920                 925

Trp Lys Ser Ile Gly Asn Ile Lys Glu Leu Lys Glu Gly Tyr Ile Ser
    930                 935                 940
```

-continued

Gly Val Val His Glu Ile Ala Met Leu Ile Val Glu Tyr Asn Ala Ile
945 950 955 960

Ile Ala Met Glu Asp Leu Asn Tyr Gly Phe Lys Arg Gly Arg Phe Lys
965 970 975

Val Glu Arg Gln Val Tyr Gln Lys Phe Glu Ser Met Leu Ile Asn Lys
980 985 990

Leu Asn Tyr Phe Ala Ser Lys Glu Lys Ser Val Asp Glu Pro Gly Gly
995 1000 1005

Leu Leu Lys Gly Tyr Gln Leu Thr Tyr Val Pro Asp Asn Ile Lys
1010 1015 1020

Asn Leu Gly Lys Gln Cys Gly Val Ile Phe Tyr Val Pro Ala Ala
1025 1030 1035

Phe Thr Ser Lys Ile Asp Pro Ser Thr Gly Phe Ile Ser Ala Phe
1040 1045 1050

Asn Phe Lys Ser Ile Ser Thr Asn Ala Ser Arg Lys Gln Phe Phe
1055 1060 1065

Met Gln Phe Asp Glu Ile Arg Tyr Cys Ala Glu Lys Asp Met Phe
1070 1075 1080

Ser Phe Gly Phe Asp Tyr Asn Asn Phe Asp Thr Tyr Asn Ile Thr
1085 1090 1095

Met Gly Lys Thr Gln Trp Thr Val Tyr Thr Asn Gly Glu Arg Leu
1100 1105 1110

Gln Ser Glu Phe Asn Asn Ala Arg Arg Thr Gly Lys Thr Lys Ser
1115 1120 1125

Ile Asn Leu Thr Glu Thr Ile Lys Leu Leu Leu Glu Asp Asn Glu
1130 1135 1140

Ile Asn Tyr Ala Asp Gly His Asp Ile Arg Ile Asp Met Glu Lys
1145 1150 1155

Met Asp Glu Asp Lys Lys Ser Glu Phe Phe Ala Gln Leu Leu Ser
1160 1165 1170

Leu Tyr Lys Leu Thr Val Gln Met Arg Asn Ser Tyr Thr Glu Ala
1175 1180 1185

Glu Glu Gln Glu Asn Gly Ile Ser Tyr Asp Lys Ile Ile Ser Pro
1190 1195 1200

Val Ile Asn Asp Glu Gly Glu Phe Phe Asp Ser Asp Asn Tyr Lys
1205 1210 1215

Glu Ser Asp Asp Lys Glu Cys Lys Met Pro Lys Asp Ala Asp Ala
1220 1225 1230

Asn Gly Ala Tyr Cys Ile Ala Leu Lys Gly Leu Tyr Glu Val Leu
1235 1240 1245

Lys Ile Lys Ser Glu Trp Thr Glu Asp Gly Phe Asp Arg Asn Cys
1250 1255 1260

Leu Lys Leu Pro His Ala Glu Trp Leu Asp Phe Ile Gln Asn Lys
1265 1270 1275

Arg Tyr Glu
1280

<210> SEQ ID NO 219
<211> LENGTH: 1300
<212> TYPE: PRT
<213> ORGANISM: Francisella novicida U112

<400> SEQUENCE: 219

Met Ser Ile Tyr Gln Glu Phe Val Asn Lys Tyr Ser Leu Ser Lys Thr

-continued

```
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430
```

```
Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845
```

```
Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
```

```
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn
    1295                1300


<210> SEQ ID NO 220
<211> LENGTH: 1206
<212> TYPE: PRT
<213> ORGANISM: Unknown
<220> FEATURE:
<223> OTHER INFORMATION: Lachnospiraceae bacterium

<400> SEQUENCE: 220

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
    290                 295                 300

Ala Phe Phe Asp Ala Leu Arg Glu Ser Lys Gly Lys Asn Val Tyr Val
```

305 310 315 320

Lys Asn Asp Leu Ala Lys Thr Ala Met Ser Val Ile Val Phe Glu Asn
325 330 335

Trp Arg Thr Phe Asp Asp Leu Leu Asn Gln Glu Tyr Asp Leu Ala Asn
340 345 350

Glu Asn Lys Lys Lys Asp Asp Lys Tyr Phe Glu Lys Arg Gln Lys Glu
355 360 365

Leu Lys Lys Asn Lys Ser Tyr Ser Leu Glu His Leu Cys Asn Leu Ser
370 375 380

Glu Asp Ser Cys Asn Leu Ile Glu Asn Tyr Ile His Gln Ile Ser Asp
385 390 395 400

Asp Ile Glu Asn Ile Ile Ile Asn Asn Glu Thr Phe Leu Arg Ile Val
405 410 415

Ile Asn Glu His Asp Arg Ser Arg Lys Leu Ala Lys Asn Arg Lys Ala
420 425 430

Val Lys Ala Ile Lys Asp Phe Leu Asp Ser Ile Lys Val Leu Glu Arg
435 440 445

Glu Leu Lys Leu Ile Asn Ser Ser Gly Gln Glu Leu Glu Lys Asp Leu
450 455 460

Ile Val Tyr Ser Ala His Glu Glu Leu Leu Val Glu Leu Lys Gln Val
465 470 475 480

Asp Ser Leu Tyr Asn Met Thr Arg Asn Tyr Leu Thr Lys Lys Pro Phe
485 490 495

Ser Thr Glu Lys Val Lys Leu Asn Phe Asn Arg Ser Thr Leu Leu Asn
500 505 510

Gly Trp Asp Arg Asn Lys Glu Thr Asp Asn Leu Gly Val Leu Leu Leu
515 520 525

Lys Asp Gly Lys Tyr Tyr Leu Gly Ile Met Asn Thr Ser Ala Asn Lys
530 535 540

Ala Phe Val Asn Pro Pro Val Ala Lys Thr Glu Lys Val Phe Lys Lys
545 550 555 560

Val Asp Tyr Lys Leu Leu Pro Val Pro Asn Gln Met Leu Pro Lys Val
565 570 575

Phe Phe Ala Lys Ser Asn Ile Asp Phe Tyr Asn Pro Ser Ser Glu Ile
580 585 590

Tyr Ser Asn Tyr Lys Lys Gly Thr His Lys Lys Gly Asn Met Phe Ser
595 600 605

Leu Glu Asp Cys His Asn Leu Ile Asp Phe Phe Lys Glu Ser Ile Ser
610 615 620

Lys His Glu Asp Trp Ser Lys Phe Gly Phe Lys Phe Asp Thr Gln Ala
625 630 635 640

Ser Tyr Asn Asp Ile Ser Glu Phe Tyr Arg Glu Val Glu Lys Gln Gly
645 650 655

Tyr Lys Leu Thr Tyr Thr Asp Ile Asp Glu Thr Tyr Ile Asn Asp Leu
660 665 670

Ile Glu Arg Asn Glu Leu Tyr Leu Phe Gln Ile Tyr Asn Lys Asp Phe
675 680 685

Ser Met Tyr Ser Lys Gly Lys Leu Asn Leu His Thr Leu Tyr Phe Met
690 695 700

Met Leu Phe Asp Gln Arg Asn Ile Asp Asp Val Val Tyr Lys Leu Asn
705 710 715 720

Gly Glu Ala Glu Val Phe Tyr Arg Pro Ala Ser Ile Ser Glu Asp Glu
725 730 735

```
Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
    770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Val Ile Asp Ser Lys Gly Asn
            820                 825                 830

Ile Leu Glu Gln Ile Ser Leu Asn Ser Ile Ile Asn Lys Glu Tyr Asp
        835                 840                 845

Ile Glu Thr Asp Tyr His Ala Leu Leu Asp Glu Arg Glu Gly Gly Arg
    850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Asp Lys Leu Asn Tyr Leu Val Ile Asp Lys Ser Arg
    930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr  Met Lys Cys Glu Asn  Val Glu Lys
        995                 1000                1005

Ser Lys  Arg Phe Phe Asp Gly  Phe Asp Phe Ile Arg  Phe Asn Ala
    1010                1015                1020

Leu Glu  Asn Val Phe Glu Phe  Gly Phe Asp Tyr Arg  Ser Phe Thr
    1025                1030                1035

Gln Arg  Ala Cys Gly Ile Asn  Ser Lys Trp Thr Val  Cys Thr Asn
    1040                1045                1050

Gly Glu  Arg Ile Ile Lys Tyr  Arg Asn Pro Asp Lys  Asn Asn Met
    1055                1060                1065

Phe Asp  Glu Lys Val Val Val  Val Thr Asp Glu Met  Lys Asn Leu
    1070                1075                1080

Phe Glu  Gln Tyr Lys Ile Pro  Tyr Glu Asp Gly Arg  Asn Val Lys
    1085                1090                1095

Asp Met  Ile Ile Ser Asn Glu  Glu Ala Glu Phe Tyr  Arg Arg Leu
    1100                1105                1110

Tyr Arg  Leu Leu Gln Gln Thr  Leu Gln Met Arg Asn  Ser Thr Ser
    1115                1120                1125

Asp Gly  Thr Arg Asp Tyr Ile  Ile Ser Pro Val Lys  Asn Lys Arg
    1130                1135                1140
```

-continued

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu
    1205

<210> SEQ ID NO 221
<211> LENGTH: 1233
<212> TYPE: PRT
<213> ORGANISM: Unknown
<220> FEATURE:
<223> OTHER INFORMATION: Lachnospiraceae bacterium

<400> SEQUENCE: 221

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

```
Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
        355                 360                 365

Arg Lys Glu Ser Lys Lys Arg Leu Glu Gly Leu Glu Glu His Ile Arg
    370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
        435                 440                 445

Asn Ala Trp Thr Val Phe Arg Asn Leu Ile Arg Ile Leu Arg Arg Lys
    450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
        515                 520                 525

Lys Phe Asn Val Lys Phe His Thr Ile Val Arg Arg Asp Gly Arg Leu
    530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
        595                 600                 605

Ala Pro Val Thr Ile Thr Arg Glu Thr Tyr Glu Ala Tyr Arg Tyr Lys
    610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
        675                 680                 685

Asn Thr Phe Met Cys Trp Ala Lys Val Ser Ser Ser Gln Leu Asp Asp
    690                 695                 700

Leu Val Lys Ser Gly Asn Gly Leu Leu Phe Glu Ile Trp Ser Glu Arg
```

```
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
        755                 760                 765

Ser Ser Lys Pro Met Val Val His Arg Asp Gly Ser Arg Val Val Asp
    770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
    850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
    930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Lys Leu Ala Lys  Leu Ser Asp Leu His  Phe Arg Gly
        995                 1000                1005

Ile Lys  Asp Gly Glu Pro Cys  Ser Phe Thr Asn Pro  Leu Gln Leu
    1010                1015                1020

Cys Gln  Asn Asp Ser Asn Lys  Ile Leu Gln Asp Gly  Val Ile Phe
    1025                1030                1035

Met Val  Pro Asn Ser Met Thr  Arg Ser Leu Asp Pro  Asp Thr Gly
    1040                1045                1050

Phe Ile  Phe Ala Ile Asn Asp  His Asn Ile Arg Thr  Lys Lys Ala
    1055                1060                1065

Lys Leu  Asn Phe Leu Ser Lys  Phe Asp Gln Leu Lys  Val Ser Ser
    1070                1075                1080

Glu Gly  Cys Leu Ile Met Lys  Tyr Ser Gly Asp Ser  Leu Pro Thr
    1085                1090                1095

His Asn  Thr Asp Asn Arg Val  Trp Asn Cys Cys Cys  Asn His Pro
    1100                1105                1110

Ile Thr  Asn Tyr Asp Arg Glu  Thr Lys Lys Val Glu  Phe Ile Glu
    1115                1120                1125
```

Glu Pro Val Glu Glu Leu Ser Arg Val Leu Glu Glu Asn Gly Ile
    1130                1135                1140

Glu Thr Asp Thr Glu Leu Asn Lys Leu Asn Glu Arg Glu Asn Val
    1145                1150                1155

Pro Gly Lys Val Val Asp Ala Ile Tyr Ser Leu Val Leu Asn Tyr
    1160                1165                1170

Leu Arg Gly Thr Val Ser Gly Val Ala Gly Gln Arg Ala Val Tyr
    1175                1180                1185

Tyr Ser Pro Val Thr Gly Lys Lys Tyr Asp Ile Ser Phe Ile Gln
    1190                1195                1200

Ala Met Asn Leu Asn Arg Lys Cys Asp Tyr Tyr Arg Ile Gly Ser
    1205                1210                1215

Lys Glu Arg Gly Glu Trp Thr Asp Phe Val Ala Gln Leu Ile Asn
    1220                1225                1230

<210> SEQ ID NO 222
<211> LENGTH: 1227
<212> TYPE: PRT
<213> ORGANISM: Unknown
<220> FEATURE:
<223> OTHER INFORMATION: Lachnospiraceae bacterium

<400> SEQUENCE: 222

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

```
Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670
```

-continued

```
Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp  Leu Thr Ser Lys Ile  Asp Pro Ser
        995                 1000                1005

Thr Gly  Phe Val Asn Leu Leu  Lys Thr Lys Tyr Thr  Ser Ile Ala
    1010                1015                1020

Asp Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
```

-continued

```
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ser Asn Lys  Glu Trp Leu
    1205                1210                1215

Glu Tyr  Ala Gln Thr Ser Val  Lys His
    1220                1225


<210> SEQ ID NO 223
<211> LENGTH: 1264
<212> TYPE: PRT
<213> ORGANISM: Leptospira inadai

<400> SEQUENCE: 223

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125

Ser Glu Glu Val Ala Glu Lys Tyr Asn Lys Asn Leu Phe Ser Lys Glu
    130                 135                 140

Leu Ile Arg Asn Glu Ile Glu Lys Phe Cys Glu Thr Asp Glu Glu Arg
145                 150                 155                 160

Lys Gln Val Ser Asn Phe Lys Ser Phe Thr Thr Tyr Phe Thr Gly Phe
                165                 170                 175

His Ser Asn Arg Gln Asn Ile Tyr Ser Asp Glu Lys Lys Ser Thr Ala
            180                 185                 190

Ile Gly Tyr Arg Ile Ile His Gln Asn Leu Pro Lys Phe Leu Asp Asn
        195                 200                 205

Leu Lys Ile Ile Glu Ser Ile Gln Arg Arg Phe Lys Asp Phe Pro Trp
    210                 215                 220
```

-continued

```
Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
            260                 265                 270

Gly Glu Lys Ile Gln Gly Leu Asn Glu Tyr Ile Asn Leu Tyr Arg Gln
        275                 280                 285

Lys Asn Asn Ile Asp Arg Lys Asn Pro Leu Asn Val Lys Ile Leu Phe
    290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Lys Ser Ile Ile Ala Glu Leu Lys
            340                 345                 350

Lys Phe Leu Ser Ser Phe Asn Arg Tyr Glu Leu Asp Gly Ile Tyr Leu
        355                 360                 365

Ala Asn Asp Asn Ser Leu Ala Ser Ile Ser Thr Phe Leu Phe Asp Asp
    370                 375                 380

Trp Ser Phe Ile Lys Lys Ser Val Ser Phe Lys Tyr Asp Glu Ser Val
385                 390                 395                 400

Gly Asp Pro Lys Lys Lys Ile Lys Ser Pro Leu Lys Tyr Glu Lys Glu
                405                 410                 415

Lys Glu Lys Trp Leu Lys Gln Lys Tyr Tyr Thr Ile Ser Phe Leu Asn
            420                 425                 430

Asp Ala Ile Glu Ser Tyr Ser Lys Ser Gln Asp Glu Lys Arg Val Lys
        435                 440                 445

Ile Arg Leu Glu Ala Tyr Phe Ala Glu Phe Lys Ser Lys Asp Asp Ala
    450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
            500                 505                 510

Lys Ser Leu Gln Phe Phe Leu Lys Pro Leu Leu Ser Ala Glu Ile Phe
        515                 520                 525

Asp Glu Lys Asp Leu Gly Phe Tyr Asn Gln Leu Glu Gly Tyr Tyr Glu
    530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
                565                 570                 575

Ser Thr Leu Leu Lys Gly Trp Asp Glu Asn Arg Glu Val Ala Asn Leu
            580                 585                 590

Cys Val Ile Phe Arg Glu Asp Gln Lys Tyr Tyr Leu Gly Val Met Asp
        595                 600                 605

Lys Glu Asn Asn Thr Ile Leu Ser Asp Ile Pro Lys Val Lys Pro Asn
    610                 615                 620

Glu Leu Phe Tyr Glu Lys Met Val Tyr Lys Leu Ile Pro Thr Pro His
625                 630                 635                 640

Met Gln Leu Pro Arg Ile Ile Phe Ser Ser Asp Asn Leu Ser Ile Tyr
```

-continued

```
                645                 650                 655

Asn Pro Ser Lys Ser Ile Leu Lys Ile Arg Glu Ala Lys Ser Phe Lys
            660                 665                 670

Glu Gly Lys Asn Phe Lys Leu Lys Asp Cys His Lys Phe Ile Asp Phe
        675                 680                 685

Tyr Lys Glu Ser Ile Ser Lys Asn Glu Asp Trp Ser Arg Phe Asp Phe
    690                 695                 700

Lys Phe Ser Lys Thr Ser Ser Tyr Glu Asn Ile Ser Glu Phe Tyr Arg
705                 710                 715                 720

Glu Val Glu Arg Gln Gly Tyr Asn Leu Asp Phe Lys Lys Val Ser Lys
                725                 730                 735

Phe Tyr Ile Asp Ser Leu Val Glu Asp Gly Lys Leu Tyr Leu Phe Gln
            740                 745                 750

Ile Tyr Asn Lys Asp Phe Ser Ile Phe Ser Lys Gly Lys Pro Asn Leu
        755                 760                 765

His Thr Ile Tyr Phe Arg Ser Leu Phe Ser Lys Glu Asn Leu Lys Asp
    770                 775                 780

Val Cys Leu Lys Leu Asn Gly Glu Ala Glu Met Phe Phe Arg Lys Lys
785                 790                 795                 800

Ser Ile Asn Tyr Asp Glu Lys Lys Lys Arg Glu Gly His His Pro Glu
                805                 810                 815

Leu Phe Glu Lys Leu Lys Tyr Pro Ile Leu Lys Asp Lys Arg Tyr Ser
            820                 825                 830

Glu Asp Lys Phe Gln Phe His Leu Pro Ile Ser Leu Asn Phe Lys Ser
        835                 840                 845

Lys Glu Arg Leu Asn Phe Asn Leu Lys Val Asn Glu Phe Leu Lys Arg
    850                 855                 860

Asn Lys Asp Ile Asn Ile Ile Gly Ile Asp Arg Gly Glu Arg Asn Leu
865                 870                 875                 880

Leu Tyr Leu Val Met Ile Asn Gln Lys Gly Glu Ile Leu Lys Gln Thr
                885                 890                 895

Leu Leu Asp Ser Met Gln Ser Gly Lys Gly Arg Pro Glu Ile Asn Tyr
            900                 905                 910

Lys Glu Lys Leu Gln Glu Lys Glu Ile Glu Arg Asp Lys Ala Arg Lys
        915                 920                 925

Ser Trp Gly Thr Val Glu Asn Ile Lys Glu Leu Lys Glu Gly Tyr Leu
    930                 935                 940

Ser Ile Val Ile His Gln Ile Ser Lys Leu Met Val Glu Asn Asn Ala
945                 950                 955                 960

Ile Val Val Leu Glu Asp Leu Asn Ile Gly Phe Lys Arg Gly Arg Gln
                965                 970                 975

Lys Val Glu Arg Gln Val Tyr Gln Lys Phe Glu Lys Met Leu Ile Asp
            980                 985                 990

Lys Leu Asn Phe Leu Val Phe Lys  Glu Asn Lys Pro Thr  Glu Pro Gly
        995                 1000                1005

Gly Val  Leu Lys Ala Tyr Gln  Leu Thr Asp Glu Phe  Gln Ser Phe
    1010                1015                1020

Glu Lys  Leu Ser Lys Gln Thr  Gly Phe Leu Phe Tyr  Val Pro Ser
    1025                1030                1035

Trp Asn  Thr Ser Lys Ile Asp  Pro Arg Thr Gly Phe  Ile Asp Phe
    1040                1045                1050

Leu His  Pro Ala Tyr Glu Asn  Ile Glu Lys Ala Lys  Gln Trp Ile
    1055                1060                1065
```

Asn Lys Phe Asp Ser Ile Arg Phe Asn Ser Lys Met Asp Trp Phe
1070 1075 1080

Glu Phe Thr Ala Asp Thr Arg Lys Phe Ser Glu Asn Leu Met Leu
1085 1090 1095

Gly Lys Asn Arg Val Trp Val Ile Cys Thr Thr Asn Val Glu Arg
1100 1105 1110

Tyr Phe Thr Ser Lys Thr Ala Asn Ser Ser Ile Gln Tyr Asn Ser
1115 1120 1125

Ile Gln Ile Thr Glu Lys Leu Lys Glu Leu Phe Val Asp Ile Pro
1130 1135 1140

Phe Ser Asn Gly Gln Asp Leu Lys Pro Glu Ile Leu Arg Lys Asn
1145 1150 1155

Asp Ala Val Phe Phe Lys Ser Leu Leu Phe Tyr Ile Lys Thr Thr
1160 1165 1170

Leu Ser Leu Arg Gln Asn Asn Gly Lys Lys Gly Glu Glu Glu Lys
1175 1180 1185

Asp Phe Ile Leu Ser Pro Val Val Asp Ser Lys Gly Arg Phe Phe
1190 1195 1200

Asn Ser Leu Glu Ala Ser Asp Asp Glu Pro Lys Asp Ala Asp Ala
1205 1210 1215

Asn Gly Ala Tyr His Ile Ala Leu Lys Gly Leu Met Asn Leu Leu
1220 1225 1230

Val Leu Asn Glu Thr Lys Glu Glu Asn Leu Ser Arg Pro Lys Trp
1235 1240 1245

Lys Ile Lys Asn Lys Asp Trp Leu Glu Phe Val Trp Glu Arg Asn
1250 1255 1260

Arg

<210> SEQ ID NO 224
<211> LENGTH: 1373
<212> TYPE: PRT
<213> ORGANISM: Moraxella bovoculi 237

<400> SEQUENCE: 224

Met Leu Phe Gln Asp Phe Thr His Leu Tyr Pro Leu Ser Lys Thr Val
1 5 10 15

Arg Phe Glu Leu Phe Ile Asp Arg Thr Leu Glu His Ile His Ala Lys
20 25 30

Asn Phe Leu Ser Gln Asp Glu Thr Met Ala Asp Met His Gln Lys Val
35 40 45

Lys Val Ile Leu Asp Asp Tyr His Arg Asp Phe Ile Ala Asp Met Met
50 55 60

Gly Glu Val Lys Leu Thr Lys Leu Ala Glu Phe Tyr Asp Val Tyr Leu
65 70 75 80

Lys Phe Arg Lys Asn Pro Lys Asp Asp Glu Leu Gln Lys Ala Gln Leu
85 90 95

Lys Asp Leu Gln Ala Val Leu Arg Lys Glu Ile Val Lys Pro Ile Gly
100 105 110

Asn Gly Gly Lys Tyr Lys Ala Gly Tyr Asp Arg Leu Phe Gly Ala Lys
115 120 125

Leu Phe Lys Asp Gly Lys Glu Leu Gly Asp Leu Ala Lys Phe Val Ile
130 135 140

Ala Gln Glu Gly Glu Ser Ser Pro Lys Leu Ala His Leu Ala His Phe
145 150 155 160

```
Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
    370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
        435                 440                 445

His Gly Leu Ala Gly Val Asp Asn Pro Ile Gln Lys Ile His Asn Asn
    450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575
```

```
Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
    770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
        835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
        915                 920                 925

Arg Gln Phe Val Tyr Asp Ile Ile Lys Asp Lys Arg Tyr Thr Gln Lys
    930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
```

```
        995                 1000                1005

Ser Leu  Asn Asp Ile Thr Thr  Ala Ser Ala Asn Gly  Thr Gln Met
    1010                 1015                 1020

Thr Thr  Pro Tyr His Lys Ile  Leu Asp Lys Arg Glu  Ile Glu Arg
    1025                 1030                 1035

Leu Asn  Ala Arg Val Gly Trp  Gly Glu Ile Glu Thr  Ile Lys Glu
    1040                 1045                 1050

Leu Lys  Ser Gly Tyr Leu Ser  His Val Val His Gln  Ile Ser Gln
    1055                 1060                 1065

Leu Met  Leu Lys Tyr Asn Ala  Ile Val Val Leu Glu  Asp Leu Asn
    1070                 1075                 1080

Phe Gly  Phe Lys Arg Gly Arg  Phe Lys Val Glu Lys  Gln Ile Tyr
    1085                 1090                 1095

Gln Asn  Phe Glu Asn Ala Leu  Ile Lys Lys Leu Asn  His Leu Val
    1100                 1105                 1110

Leu Lys  Asp Lys Ala Asp Asp  Glu Ile Gly Ser Tyr  Lys Asn Ala
    1115                 1120                 1125

Leu Gln  Leu Thr Asn Asn Phe  Thr Asp Leu Lys Ser  Ile Gly Lys
    1130                 1135                 1140

Gln Thr  Gly Phe Leu Phe Tyr  Val Pro Ala Trp Asn  Thr Ser Lys
    1145                 1150                 1155

Ile Asp  Pro Glu Thr Gly Phe  Val Asp Leu Leu Lys  Pro Arg Tyr
    1160                 1165                 1170

Glu Asn  Ile Gln Ala Ser Gln  Ala Phe Phe Gly Lys  Phe Asp Lys
    1175                 1180                 1185

Ile Cys  Tyr Asn Ala Asp Lys  Asp Tyr Phe Glu Phe  His Ile Asp
    1190                 1195                 1200

Tyr Ala  Lys Phe Thr Asp Lys  Ala Lys Asn Ser Arg  Gln Ile Trp
    1205                 1210                 1215

Thr Ile  Cys Ser His Gly Asp  Lys Arg Tyr Val Tyr  Asp Lys Thr
    1220                 1225                 1230

Ala Asn  Gln Asn Lys Gly Ala  Ala Lys Gly Ile Asn  Val Asn Asp
    1235                 1240                 1245

Ile Leu  Lys Ser Leu Phe Ala  Arg His His Ile Asn  Glu Lys Gln
    1250                 1255                 1260

Pro Asn  Leu Val Met Asp Ile  Cys Gln Asn Asn Asp  Lys Glu Phe
    1265                 1270                 1275

His Lys  Ser Leu Met Tyr Leu  Leu Lys Thr Leu Leu  Ala Leu Arg
    1280                 1285                 1290

Tyr Ser  Asn Ala Ser Ser Asp  Glu Asp Phe Ile Leu  Ser Pro Val
    1295                 1300                 1305

Ala Asn  Asp Glu Gly Val Phe  Phe Asn Ser Ala Leu  Ala Asp Asp
    1310                 1315                 1320

Thr Gln  Pro Gln Asn Ala Asp  Ala Asn Gly Ala Tyr  His Ile Ala
    1325                 1330                 1335

Leu Lys  Gly Leu Trp Leu Leu  Asn Glu Leu Lys Asn  Ser Asp Asp
    1340                 1345                 1350

Leu Asn  Lys Val Lys Leu Ala  Ile Asp Asn Gln Thr  Trp Leu Asn
    1355                 1360                 1365

Phe Ala  Gln Asn Arg
    1370
```

<210> SEQ ID NO 225

```
<211> LENGTH: 1352
<212> TYPE: PRT
<213> ORGANISM: Parcubacteria bacterium

<400> SEQUENCE: 225

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
    50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
    130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
    290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
```

```
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Asp Val
        755                 760                 765

Gln Lys Tyr Gly Tyr Lys Ile Ser Phe Arg Asp Ile Asp Asp Glu Tyr
    770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815
```

Leu Tyr Phe Glu His Ile Leu Ser Ala Glu Asn Leu Asn Asp Pro Val
820 825 830

Phe Lys Leu Ser Gly Met Ala Glu Ile Phe Gln Arg Gln Pro Ser Val
835 840 845

Asn Glu Arg Glu Lys Ile Thr Thr Gln Lys Asn Gln Cys Ile Leu Asp
850 855 860

Lys Gly Asp Arg Ala Tyr Lys Tyr Arg Arg Tyr Thr Glu Lys Lys Ile
865 870 875 880

Met Phe His Met Ser Leu Val Leu Asn Thr Gly Lys Gly Glu Ile Lys
885 890 895

Gln Val Gln Phe Asn Lys Ile Ile Asn Gln Arg Ile Ser Ser Ser Asp
900 905 910

Asn Glu Met Arg Val Asn Val Ile Gly Ile Asp Arg Gly Glu Lys Asn
915 920 925

Leu Leu Tyr Tyr Ser Val Val Lys Gln Asn Gly Glu Ile Ile Glu Gln
930 935 940

Ala Ser Leu Asn Glu Ile Asn Gly Val Asn Tyr Arg Asp Lys Leu Ile
945 950 955 960

Glu Arg Glu Lys Glu Arg Leu Lys Asn Arg Gln Ser Trp Lys Pro Val
965 970 975

Val Lys Ile Lys Asp Leu Lys Lys Gly Tyr Ile Ser His Val Ile His
980 985 990

Lys Ile Cys Gln Leu Ile Glu Lys Tyr Ser Ala Ile Val Val Leu Glu
995 1000 1005

Asp Leu Asn Met Arg Phe Lys Gln Ile Arg Gly Gly Ile Glu Arg
1010 1015 1020

Ser Val Tyr Gln Gln Phe Glu Lys Ala Leu Ile Asp Lys Leu Gly
1025 1030 1035

Tyr Leu Val Phe Lys Asp Asn Arg Asp Leu Arg Ala Pro Gly Gly
1040 1045 1050

Val Leu Asn Gly Tyr Gln Leu Ser Ala Pro Phe Val Ser Phe Glu
1055 1060 1065

Lys Met Arg Lys Gln Thr Gly Ile Leu Phe Tyr Thr Gln Ala Glu
1070 1075 1080

Tyr Thr Ser Lys Thr Asp Pro Ile Thr Gly Phe Arg Lys Asn Val
1085 1090 1095

Tyr Ile Ser Asn Ser Ala Ser Leu Asp Lys Ile Lys Glu Ala Val
1100 1105 1110

Lys Lys Phe Asp Ala Ile Gly Trp Asp Gly Lys Glu Gln Ser Tyr
1115 1120 1125

Phe Phe Lys Tyr Asn Pro Tyr Asn Leu Ala Asp Glu Lys Tyr Lys
1130 1135 1140

Asn Ser Thr Val Ser Lys Glu Trp Ala Ile Phe Ala Ser Ala Pro
1145 1150 1155

Arg Ile Arg Arg Gln Lys Gly Glu Asp Gly Tyr Trp Lys Tyr Asp
1160 1165 1170

Arg Val Lys Val Asn Glu Glu Phe Glu Lys Leu Leu Lys Val Trp
1175 1180 1185

Asn Phe Val Asn Pro Lys Ala Thr Asp Ile Lys Gln Glu Ile Ile
1190 1195 1200

Lys Lys Ile Lys Ala Gly Asp Leu Gln Gly Glu Lys Glu Leu Asp
1205 1210 1215

```
Gly Arg  Leu Arg Asn Phe Trp  His Ser Phe Ile Tyr  Leu Phe Asn
    1220                 1225                 1230

Leu Val  Leu Glu Leu Arg Asn  Ser Phe Ser Leu Gln  Ile Lys Ile
    1235                 1240                 1245

Lys Ala  Gly Glu Val Ile Ala  Val Asp Glu Gly Val  Asp Phe Ile
    1250                 1255                 1260

Ala Ser  Pro Val Lys Pro Phe  Phe Thr Thr Pro Asn  Pro Tyr Ile
    1265                 1270                 1275

Pro Ser  Asn Leu Cys Trp Leu  Ala Val Glu Asn Ala  Asp Ala Asn
    1280                 1285                 1290

Gly Ala  Tyr Asn Ile Ala Arg  Lys Gly Val Met Ile  Leu Lys Lys
    1295                 1300                 1305

Ile Arg  Glu His Ala Lys Lys  Asp Pro Glu Phe Lys  Lys Leu Pro
    1310                 1315                 1320

Asn Leu  Phe Ile Ser Asn Ala  Glu Trp Asp Glu Ala  Ala Arg Asp
    1325                 1330                 1335

Trp Gly  Lys Tyr Ala Gly Thr  Thr Ala Leu Asn Leu  Asp His
    1340                 1345                 1350
```

<210> SEQ ID NO 226
<211> LENGTH: 1260
<212> TYPE: PRT
<213> ORGANISM: Porphyromonas crevioricanis

<400> SEQUENCE: 226

```
Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45

Arg Val Lys Lys Ile Ile Asp Thr Tyr His Lys Val Phe Ile Asp Ser
    50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240
```

```
Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
        355                 360                 365

Tyr Val Arg Asn Asp Ser Gln Leu Thr Asp Ile Ser Lys Lys Met Leu
    370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
            420                 425                 430

Cys Ile Ala Phe Leu Asp Asn Val Arg Asp Cys Arg Val Asp Thr Tyr
        435                 440                 445

Leu Ser Thr Leu Gly Gln Lys Glu Gly Pro His Gly Leu Ser Asn Leu
    450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
            500                 505                 510

Leu Lys Pro Leu Trp Gly Met Gly Asp Glu Pro Asp Lys Asp Glu Arg
        515                 520                 525

Phe Tyr Gly Glu Tyr Asn Tyr Ile Arg Gly Ala Leu Asp Gln Val Ile
    530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Met Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655
```

-continued

```
Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys  Arg Pro Glu Asp Ile  Gly Gly Leu
        995                 1000                 1005

Leu Arg  Ala Tyr Gln Phe Thr  Ala Pro Phe Lys Ser  Phe Lys Glu
    1010                 1015                 1020

Met Gly  Lys Gln Asn Gly Phe  Leu Phe Tyr Ile Pro  Ala Trp Asn
    1025                 1030                 1035

Thr Ser  Asn Ile Asp Pro Thr  Thr Gly Phe Val Asn  Leu Phe His
    1040                 1045                 1050

Val Gln  Tyr Glu Asn Val Asp  Lys Ala Lys Ser Phe  Phe Gln Lys
    1055                 1060                 1065

Phe Asp  Ser Ile Ser Tyr Asn  Pro Lys Lys Asp Trp  Phe Glu Phe
```

```
    1070                1075                1080

Ala Phe  Asp Tyr Lys Asn Phe  Thr Lys Lys Ala Glu  Gly Ser Arg
    1085                1090                1095

Ser Met  Trp Ile Leu Cys Thr  His Gly Ser Arg Ile  Lys Asn Phe
    1100                1105                1110

Arg Asn  Ser Gln Lys Asn Gly  Gln Trp Asp Ser Glu  Glu Phe Ala
    1115                1120                1125

Leu Thr  Glu Ala Phe Lys Ser  Leu Phe Val Arg Tyr  Glu Ile Asp
    1130                1135                1140

Tyr Thr  Ala Asp Leu Lys Thr  Ala Ile Val Asp Glu  Lys Gln Lys
    1145                1150                1155

Asp Phe  Phe Val Asp Leu Leu  Lys Leu Phe Lys Leu  Thr Val Gln
    1160                1165                1170

Met Arg  Asn Ser Trp Lys Glu  Lys Asp Leu Asp Tyr  Leu Ile Ser
    1175                1180                1185

Pro Val  Ala Gly Ala Asp Gly  Arg Phe Phe Asp Thr  Arg Glu Gly
    1190                1195                1200

Asn Lys  Ser Leu Pro Lys Asp  Ala Asp Ala Asn Gly  Ala Tyr Asn
    1205                1210                1215

Ile Ala  Leu Lys Gly Leu Trp  Ala Leu Arg Gln Ile  Arg Gln Thr
    1220                1225                1230

Ser Glu  Gly Gly Lys Leu Lys  Leu Ala Ile Ser Asn  Lys Glu Trp
    1235                1240                1245

Leu Gln  Phe Val Gln Glu Arg  Ser Tyr Glu Lys Asp
    1250                1255                1260


<210> SEQ ID NO 227
<211> LENGTH: 1324
<212> TYPE: PRT
<213> ORGANISM: Prevotella disiens

<400> SEQUENCE: 227

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175
```

-continued

```
Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Gln Asn Ala Glu
    370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
        435                 440                 445

Asn Ser Gly Asn Met Pro Arg Lys Val Glu Asp Tyr Phe Ser Leu Met
    450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
            500                 505                 510

Leu Leu Asp Ala Thr Lys Gln Phe Gln His Phe Ile Lys Pro Leu Leu
        515                 520                 525

Gly Thr Gly Glu Glu Ala Asp Arg Asp Leu Val Phe Tyr Gly Asp Phe
    530                 535                 540

Leu Pro Leu Tyr Glu Lys Phe Glu Glu Leu Thr Leu Leu Tyr Asn Lys
545                 550                 555                 560

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
            580                 585                 590

Thr Glu Lys Ser Asp Asn Gly Thr Gln Tyr Gly Gly Tyr Leu Phe Arg
```

-continued

```
        595                 600                 605

Lys Lys Asn Glu Ile Gly Glu Tyr Asp Tyr Phe Leu Gly Ile Ser Ser
    610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655

Tyr Glu Gly Glu Asn Ser Tyr Lys Glu Asp Lys Lys Arg Leu Asn Lys
            660                 665                 670

Val Ile Ile Ala Tyr Ile Glu Gln Ile Lys Gln Thr Asn Ile Lys Lys
        675                 680                 685

Ser Ile Ile Glu Ser Ile Ser Lys Tyr Pro Asn Ile Ser Asp Asp Asp
    690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
                725                 730                 735

Lys Glu Val Ile Asp Asn Leu Leu Lys Thr Ile Ser Pro Leu Lys Asn
            740                 745                 750

Lys Ala Glu Phe Leu Asp Leu Ile Asn Lys Asp Tyr Gln Ile Phe Thr
        755                 760                 765

Glu Val Gln Ala Val Ile Asp Glu Ile Cys Lys Gln Lys Thr Phe Ile
    770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
                805                 810                 815

Ala Lys Thr Phe Ser Ala Asn Leu Arg Lys Lys Arg Gly Ala Glu Asn
            820                 825                 830

Leu His Thr Met Leu Phe Lys Ala Leu Met Glu Gly Asn Gln Asp Asn
        835                 840                 845

Leu Asp Leu Gly Ser Gly Ala Ile Phe Tyr Arg Ala Lys Ser Leu Asp
    850                 855                 860

Gly Asn Lys Pro Thr His Pro Ala Asn Glu Ala Ile Lys Cys Arg Asn
865                 870                 875                 880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
            900                 905                 910

Gln Asn Tyr Lys Ala Ala Asn Asp Ser Ala Gln Leu Asn Ser Ser Ala
        915                 920                 925

Thr Glu Tyr Ile Arg Lys Ala Asp Asp Leu His Ile Ile Gly Ile Asp
    930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys
            980                 985                 990

Ala Asn Arg Gln Asn Trp Glu Ala  Val Glu Gly Ile Lys  Asp Leu Lys
        995                 1000                1005

Lys Gly  Tyr Leu Ser Gln Ala  Val His Gln Ile Ala  Gln Leu Met
    1010                1015                1020
```

```
Leu Lys  Tyr Asn Ala Ile Ile  Ala Leu Glu Asp Leu  Gly Gln Met
    1025                 1030                 1035

Phe Val  Thr Arg Gly Gln Lys  Ile Glu Lys Ala Val  Tyr Gln Gln
    1040                 1045                 1050

Phe Glu  Lys Ser Leu Val Asp  Lys Leu Ser Tyr Leu  Val Asp Lys
    1055                 1060                 1065

Lys Arg  Pro Tyr Asn Glu Leu  Gly Gly Ile Leu Lys  Ala Tyr Gln
    1070                 1075                 1080

Leu Ala  Ser Ser Ile Thr Lys  Asn Asn Ser Asp Lys  Gln Asn Gly
    1085                 1090                 1095

Phe Leu  Phe Tyr Val Pro Ala  Trp Asn Thr Ser Lys  Ile Asp Pro
    1100                 1105                 1110

Val Thr  Gly Phe Thr Asp Leu  Leu Arg Pro Lys Ala  Met Thr Ile
    1115                 1120                 1125

Lys Glu  Ala Gln Asp Phe Phe  Gly Ala Phe Asp Asn  Ile Ser Tyr
    1130                 1135                 1140

Asn Asp  Lys Gly Tyr Phe Glu  Phe Glu Thr Asn Tyr  Asp Lys Phe
    1145                 1150                 1155

Lys Ile  Arg Met Lys Ser Ala  Gln Thr Arg Trp Thr  Ile Cys Thr
    1160                 1165                 1170

Phe Gly  Asn Arg Ile Lys Arg  Lys Lys Asp Lys Asn  Tyr Trp Asn
    1175                 1180                 1185

Tyr Glu  Glu Val Glu Leu Thr  Glu Glu Phe Lys Lys  Leu Phe Lys
    1190                 1195                 1200

Asp Ser  Asn Ile Asp Tyr Glu  Asn Cys Asn Leu Lys  Glu Glu Ile
    1205                 1210                 1215

Gln Asn  Lys Asp Asn Arg Lys  Phe Phe Asp Asp Leu  Ile Lys Leu
    1220                 1225                 1230

Leu Gln  Leu Thr Leu Gln Met  Arg Asn Ser Asp Asp  Lys Gly Asn
    1235                 1240                 1245

Asp Tyr  Ile Ile Ser Pro Val  Ala Asn Ala Glu Gly  Gln Phe Phe
    1250                 1255                 1260

Asp Ser  Arg Asn Gly Asp Lys  Lys Leu Pro Leu Asp  Ala Asp Ala
    1265                 1270                 1275

Asn Gly  Ala Tyr Asn Ile Ala  Arg Lys Gly Leu Trp  Asn Ile Arg
    1280                 1285                 1290

Gln Ile  Lys Gln Thr Lys Asn  Lys Asp Asp Leu Asn  Leu Ser Ile
    1295                 1300                 1305

Ser Ser  Thr Glu Trp Leu Asp  Phe Val Arg Glu Lys  Pro Tyr Leu
    1310                 1315                 1320

Lys


<210> SEQ ID NO 228
<211> LENGTH: 1484
<212> TYPE: PRT
<213> ORGANISM: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 228

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
```

```
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
    290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
        355                 360                 365

Glu Ile Ile Asn Lys Ala Gln Glu Ala Ile Asn Lys Tyr Phe Lys Ser
    370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
            420                 425                 430

Asp Arg Leu Lys Glu Ala Lys Val Phe Gln Lys Ala Asp Lys Lys Ser
        435                 440                 445
```

```
Glu Asp Asp Ile Lys Ile Pro Glu Ala Ile Glu Leu Ser Gly Leu Phe
    450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
            500                 505                 510

Met Glu Ser Phe Leu Lys Glu Thr Asn Asp Ile Ile Thr Leu Lys Lys
        515                 520                 525

Tyr Lys Gly Asn Lys Glu Gly Thr Glu Lys Ile Lys Gln Trp Phe Asp
    530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
            580                 585                 590

Ala Leu Arg Asn Tyr Leu Thr Gln Lys Pro Gln Asp Glu Ala Lys Glu
        595                 600                 605

Asn Lys Leu Lys Leu Asn Phe Asp Asn Pro Ser Leu Ala Gly Gly Trp
    610                 615                 620

Asp Val Asn Lys Glu Cys Ser Asn Phe Cys Val Ile Leu Lys Asp Lys
625                 630                 635                 640

Asn Glu Lys Lys Tyr Leu Ala Met Ile Lys Lys Gly Glu Asn Thr Leu
                645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
        675                 680                 685

Glu Tyr Asp Phe Trp Ala Asp Val Ser Lys Met Ile Pro Lys Cys Ser
    690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
        755                 760                 765

Ser Thr Gln Glu Lys Gln Tyr Ile Lys Ala Phe Gln Lys Glu Tyr Trp
    770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
                805                 810                 815

Leu Leu Ser Trp Glu Arg Lys Tyr Lys Asp Ala Leu Thr Asn Trp Ile
            820                 825                 830

Asn Phe Cys Lys Tyr Phe Leu Ser Lys Tyr Pro Lys Thr Thr Leu Phe
        835                 840                 845

Asn Tyr Ser Phe Lys Glu Ser Glu Asn Tyr Asn Ser Leu Asp Glu Phe
    850                 855                 860
```

-continued

```
Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
                885                 890                 895

Leu Phe Glu Ile Lys Asn Gln Asp Ser Asn Asp Gly Lys Ser Ile Gly
            900                 905                 910

His Lys Asn Asn Leu His Thr Ile Tyr Trp Asn Ala Ile Phe Glu Asn
        915                 920                 925

Phe Asp Asn Arg Pro Lys Leu Asn Gly Glu Ala Glu Ile Phe Tyr Arg
    930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
            980                 985                 990

Tyr Val Asn Asp Ile Val Asn Thr  Lys Phe Tyr Asn Phe  Ser Asn Leu
        995                 1000                1005

His Phe  Leu Gly Ile Asp Arg  Gly Glu Lys His Leu  Ala Tyr Tyr
    1010                1015                1020

Ser Leu  Val Asn Lys Asn Gly  Glu Ile Val Asp Gln  Gly Thr Leu
    1025                1030                1035

Asn Leu  Pro Phe Thr Asp Lys  Asp Gly Asn Gln Arg  Ser Ile Lys
    1040                1045                1050

Lys Glu  Lys Tyr Phe Tyr Asn  Lys Gln Glu Asp Lys  Trp Glu Ala
    1055                1060                1065

Lys Glu  Val Asp Xaa Trp Asn  Tyr Asn Asp Leu Leu  Asp Ala Met
    1070                1075                1080

Ala Ser  Asn Arg Asp Met Ala  Arg Lys Asn Trp Gln  Arg Ile Gly
    1085                1090                1095

Thr Ile  Lys Glu Ala Lys Asn  Gly Tyr Val Ser Leu  Val Ile Arg
    1100                1105                1110

Lys Ile  Ala Asp Leu Ala Val  Asn Asn Glu Arg Pro  Ala Phe Ile
    1115                1120                1125

Val Leu  Glu Asp Leu Asn Thr  Gly Phe Lys Arg Ser  Arg Gln Lys
    1130                1135                1140

Ile Asp  Lys Ser Val Tyr Gln  Lys Phe Glu Leu Ala  Leu Ala Lys
    1145                1150                1155

Lys Leu  Asn Phe Leu Val Asp  Lys Asn Ala Lys Arg  Asp Glu Ile
    1160                1165                1170

Gly Ser  Pro Thr Lys Ala Leu  Gln Leu Thr Pro Pro  Val Asn Asn
    1175                1180                1185

Tyr Gly  Asp Ile Glu Asn Lys  Lys Gln Ala Gly Ile  Met Leu Tyr
    1190                1195                1200

Thr Arg  Ala Asn Tyr Thr Ser  Gln Thr Asp Pro Ala  Thr Gly Trp
    1205                1210                1215

Arg Lys  Thr Ile Tyr Leu Lys  Ala Gly Pro Glu Glu  Thr Thr Tyr
    1220                1225                1230

Lys Lys  Asp Gly Lys Ile Lys  Asn Lys Ser Val Lys  Asp Gln Ile
    1235                1240                1245

Ile Glu  Thr Phe Thr Asp Ile  Gly Phe Asp Gly Lys  Asp Tyr Tyr
    1250                1255                1260

Phe Glu  Tyr Asp Lys Gly Glu  Phe Val Asp Glu Lys  Thr Gly Glu
```

1265 1270 1275

Ile Lys Pro Lys Lys Trp Arg Leu Tyr Ser Gly Glu Asn Gly Lys
1280 1285 1290

Ser Leu Asp Arg Phe Arg Gly Glu Arg Glu Lys Asp Lys Tyr Glu
1295 1300 1305

Trp Lys Ile Asp Lys Ile Asp Ile Val Lys Ile Leu Asp Asp Leu
1310 1315 1320

Phe Val Asn Phe Asp Lys Asn Ile Ser Leu Leu Lys Gln Leu Lys
1325 1330 1335

Glu Gly Val Glu Leu Thr Arg Asn Asn Glu His Gly Thr Gly Glu
1340 1345 1350

Ser Leu Arg Phe Ala Ile Asn Leu Ile Gln Gln Ile Arg Asn Thr
1355 1360 1365

Gly Asn Asn Glu Arg Asp Asn Asp Phe Ile Leu Ser Pro Val Arg
1370 1375 1380

Asp Glu Asn Gly Lys His Phe Asp Ser Arg Glu Tyr Trp Asp Lys
1385 1390 1395

Glu Thr Lys Gly Glu Lys Ile Ser Met Pro Ser Ser Gly Asp Ala
1400 1405 1410

Asn Gly Ala Phe Asn Ile Ala Arg Lys Gly Ile Ile Met Asn Ala
1415 1420 1425

His Ile Leu Ala Asn Ser Asp Ser Lys Asp Leu Ser Leu Phe Val
1430 1435 1440

Ser Asp Glu Glu Trp Asp Leu His Leu Asn Asn Lys Thr Glu Trp
1445 1450 1455

Lys Lys Gln Leu Asn Ile Phe Ser Ser Arg Lys Ala Met Ala Lys
1460 1465 1470

Arg Lys Lys Lys Arg Pro Ala Ala Thr Lys Lys
1475 1480

<210> SEQ ID NO 229
<211> LENGTH: 1245
<212> TYPE: PRT
<213> ORGANISM: Porphyromonas macacae

<400> SEQUENCE: 229

Met Lys Thr Gln His Phe Phe Glu Asp Phe Thr Ser Leu Tyr Ser Leu
1 5 10 15

Ser Lys Thr Ile Arg Phe Glu Leu Lys Pro Ile Gly Lys Thr Leu Glu
20 25 30

Asn Ile Lys Lys Asn Gly Leu Ile Arg Arg Asp Glu Gln Arg Leu Asp
35 40 45

Asp Tyr Glu Lys Leu Lys Lys Val Ile Asp Glu Tyr His Glu Asp Phe
50 55 60

Ile Ala Asn Ile Leu Ser Ser Phe Ser Phe Ser Glu Glu Ile Leu Gln
65 70 75 80

Ser Tyr Ile Gln Asn Leu Ser Ile Ser Glu Ala Arg Ala Lys Ile Glu
85 90 95

Lys Thr Met Arg Asp Thr Leu Ala Lys Ala Phe Ser Glu Asp Glu Arg
100 105 110

Tyr Lys Ser Ile Phe Lys Lys Glu Leu Val Lys Lys Asp Ile Pro Val
115 120 125

Trp Cys Pro Ala Tyr Lys Ser Leu Cys Lys Lys Phe Asp Asn Phe Thr
130 135 140

```
Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
            420                 425                 430

Tyr Leu Val Ser Asp Gly Glu Val Ile Leu Tyr Glu Glu Gly Ser Asn
        435                 440                 445

Ile Trp Asp Glu Val Leu Ile Ala Phe Arg Asp Leu Gln Val Ile Leu
    450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
            500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
    530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
```

```
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
    770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln His Gly Ile Asp Arg Gly Glu Arg Asn
    850                 855                 860

Leu Leu Tyr Ile Ser Arg Ile Asp Thr Arg Gly Asn Leu Leu Glu Gln
865                 870                 875                 880

Phe Ser Leu Asn Val Ile Glu Ser Asp Lys Gly Asp Leu Arg Thr Asp
                885                 890                 895

Tyr Gln Lys Ile Leu Gly Asp Arg Glu Gln Glu Arg Leu Arg Arg Arg
            900                 905                 910

Gln Glu Trp Lys Ser Ile Glu Ser Ile Lys Asp Leu Lys Asp Gly Tyr
        915                 920                 925

Met Ser Gln Val Val His Lys Ile Cys Asn Met Val Val Glu His Lys
    930                 935                 940

Ala Ile Val Val Leu Glu Asn Leu Asn Leu Ser Phe Met Lys Gly Arg
945                 950                 955                 960

Lys Lys Val Glu Lys Ser Val Tyr Glu Lys Phe Glu Arg Met Leu Val
                965                 970                 975

Asp Lys Leu Asn Tyr Leu Val Val Asp Lys Lys Asn Leu Ser Asn Glu
            980                 985                 990
```

Pro Gly Gly Leu Tyr Ala Ala Tyr Gln Leu Thr Asn Pro Leu Phe Ser
995 1000 1005

Phe Glu Glu Leu His Arg Tyr Pro Gln Ser Gly Ile Leu Phe Phe
1010 1015 1020

Val Asp Pro Trp Asn Thr Ser Leu Thr Asp Pro Ser Thr Gly Phe
1025 1030 1035

Val Asn Leu Leu Gly Arg Ile Asn Tyr Thr Asn Val Gly Asp Ala
1040 1045 1050

Arg Lys Phe Phe Asp Arg Phe Asn Ala Ile Arg Tyr Asp Gly Lys
1055 1060 1065

Gly Asn Ile Leu Phe Asp Leu Asp Leu Ser Arg Phe Asp Val Arg
1070 1075 1080

Val Glu Thr Gln Arg Lys Leu Trp Thr Leu Thr Thr Phe Gly Ser
1085 1090 1095

Arg Ile Ala Lys Ser Lys Lys Ser Gly Lys Trp Met Val Glu Arg
1100 1105 1110

Ile Glu Asn Leu Ser Leu Cys Phe Leu Glu Leu Phe Glu Gln Phe
1115 1120 1125

Asn Ile Gly Tyr Arg Val Glu Lys Asp Leu Lys Lys Ala Ile Leu
1130 1135 1140

Ser Gln Asp Arg Lys Glu Phe Tyr Val Arg Leu Ile Tyr Leu Phe
1145 1150 1155

Asn Leu Met Met Gln Ile Arg Asn Ser Asp Gly Glu Glu Asp Tyr
1160 1165 1170

Ile Leu Ser Pro Ala Leu Asn Glu Lys Asn Leu Gln Phe Asp Ser
1175 1180 1185

Arg Leu Ile Glu Ala Lys Asp Leu Pro Val Asp Ala Asp Ala Asn
1190 1195 1200

Gly Ala Tyr Asn Val Ala Arg Lys Gly Leu Met Val Val Gln Arg
1205 1210 1215

Ile Lys Arg Gly Asp His Glu Ser Ile His Arg Ile Gly Arg Ala
1220 1225 1230

Gln Trp Leu Arg Tyr Val Gln Glu Gly Ile Val Glu
1235 1240 1245

<210> SEQ ID NO 230
<211> LENGTH: 1250
<212> TYPE: PRT
<213> ORGANISM: Smithella sp.

<400> SEQUENCE: 230

Met Gln Thr Leu Phe Glu Asn Phe Thr Asn Gln Tyr Pro Val Ser Lys
1 5 10 15

Thr Leu Arg Phe Glu Leu Ile Pro Gln Gly Lys Thr Lys Asp Phe Ile
20 25 30

Glu Gln Lys Gly Leu Leu Lys Lys Asp Glu Asp Arg Ala Glu Lys Tyr
35 40 45

Lys Lys Val Lys Asn Ile Ile Asp Glu Tyr His Lys Asp Phe Ile Glu
50 55 60

Lys Ser Leu Asn Gly Leu Lys Leu Asp Gly Leu Glu Lys Tyr Lys Thr
65 70 75 80

Leu Tyr Leu Lys Gln Glu Lys Asp Asp Lys Asp Lys Lys Ala Phe Asp
85 90 95

Lys Glu Lys Glu Asn Leu Arg Lys Gln Ile Ala Asn Ala Phe Arg Asn

```
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285

Ile Leu Ser Asp Arg Gln Ser Leu Ser Phe Ile Ala Glu Ala Phe Lys
    290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
            340                 345                 350

Tyr Phe Arg Ser Gly Ala Ser Leu Thr Asp Val Ser Arg Lys Val Phe
        355                 360                 365

Gly Glu Trp Ser Ile Ile Asn Arg Ala Leu Asp Asn Tyr Tyr Ala Thr
    370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
            420                 425                 430

Lys Val Ile Ala Asp Tyr Phe Ala Lys Phe Cys Asp Asp Lys Glu Thr
        435                 440                 445

Asp Leu Ile Gln Lys Val Asn Glu Gly Tyr Ile Ala Val Lys Asp Leu
    450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
            500                 505                 510

Glu Thr Phe Tyr Ser Leu Phe Thr Pro Leu Tyr Asp His Leu Thr Gln
        515                 520                 525
```

```
Thr Ile Ala Leu Tyr Asn Lys Val Arg Asn Tyr Leu Thr Gln Lys Pro
    530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
            580                 585                 590

Arg Ile Phe Arg Asn Val Pro Lys Ala Asp Lys Lys Asp Phe Cys Tyr
        595                 600                 605

Glu Lys Met Val Tyr Lys Leu Leu Pro Gly Ala Asn Lys Met Leu Pro
    610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
            660                 665                 670

Ile Asn Lys His Glu Asp Trp Lys Asn Phe Asp Phe Arg Phe Ser Ala
        675                 680                 685

Thr Ser Thr Tyr Ala Asp Leu Ser Gly Phe Tyr His Glu Val Glu His
    690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
        755                 760                 765

Leu Asn Gly Glu Ala Glu Val Phe Tyr Arg Lys Lys Ser Ile Ala Glu
    770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
        835                 840                 845

Gln Phe Leu Lys Ala Asn Pro Asp Ile Asn Ile Ile Gly Ile Asp Arg
    850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
            900                 905                 910

Ala Arg Gln Glu Trp Gly Val Ile Glu Thr Ile Lys Glu Leu Lys Glu
        915                 920                 925

Gly Tyr Leu Ser Gln Val Ile His Lys Leu Thr Asp Leu Met Ile Glu
    930                 935                 940
```

Asn Asn Ala Ile Ile Val Met Glu Asp Leu Asn Phe Gly Phe Lys Arg
945 950 955 960

Gly Arg Gln Lys Val Glu Lys Gln Val Tyr Gln Lys Phe Glu Lys Met
965 970 975

Leu Ile Asp Lys Leu Asn Tyr Leu Val Asp Lys Asn Lys Lys Ala Asn
980 985 990

Glu Leu Gly Gly Leu Leu Asn Ala Phe Gln Leu Ala Asn Lys Phe Glu
995 1000 1005

Ser Phe Gln Lys Met Gly Lys Gln Asn Gly Phe Ile Phe Tyr Val
1010 1015 1020

Pro Ala Trp Asn Thr Ser Lys Thr Asp Pro Ala Thr Gly Phe Ile
1025 1030 1035

Asp Phe Leu Lys Pro Arg Tyr Glu Asn Leu Asn Gln Ala Lys Asp
1040 1045 1050

Phe Phe Glu Lys Phe Asp Ser Ile Arg Leu Asn Ser Lys Ala Asp
1055 1060 1065

Tyr Phe Glu Phe Ala Phe Asp Phe Lys Asn Phe Thr Glu Lys Ala
1070 1075 1080

Asp Gly Gly Arg Thr Lys Trp Thr Val Cys Thr Thr Asn Glu Asp
1085 1090 1095

Arg Tyr Gln Trp Asn Arg Ala Leu Asn Asn Asn Arg Gly Ser Gln
1100 1105 1110

Glu Lys Tyr Asp Ile Thr Ala Glu Leu Lys Ser Leu Phe Asp Gly
1115 1120 1125

Lys Val Asp Tyr Lys Ser Gly Lys Asp Leu Lys Gln Gln Ile Ala
1130 1135 1140

Ser Gln Glu Ser Ala Asp Phe Phe Lys Ala Leu Met Lys Asn Leu
1145 1150 1155

Ser Ile Thr Leu Ser Leu Arg His Asn Asn Gly Glu Lys Gly Asp
1160 1165 1170

Asn Glu Gln Asp Tyr Ile Leu Ser Pro Val Ala Asp Ser Lys Gly
1175 1180 1185

Arg Phe Phe Asp Ser Arg Lys Ala Asp Asp Asp Met Pro Lys Asn
1190 1195 1200

Ala Asp Ala Asn Gly Ala Tyr His Ile Ala Leu Lys Gly Leu Trp
1205 1210 1215

Cys Leu Glu Gln Ile Ser Lys Thr Asp Asp Leu Lys Lys Val Lys
1220 1225 1230

Leu Ala Ile Ser Asn Lys Glu Trp Leu Glu Phe Val Gln Thr Leu
1235 1240 1245

Lys Gly
1250

<210> SEQ ID NO 231
<211> LENGTH: 3987
<212> TYPE: PRT
<213> ORGANISM: Artificial sequence
<220> FEATURE:
<223> OTHER INFORMATION: Synthetic Cas12a

<400> SEQUENCE: 231

Ala Thr Gly Gly Cys Cys Gly Gly Gly Ala Gly Cys Ala Ala Gly Ala
1 5 10 15

Ala Gly Cys Gly Cys Cys Gly Gly Ala Thr Ala Ala Ala Gly Cys Ala
20 25 30

```
Gly Gly Ala Cys Ala Cys Gly Cys Ala Gly Thr Thr Cys Gly Ala Gly
        35                  40                  45

Gly Gly Cys Thr Thr Cys Ala Cys Cys Ala Ala Cys Cys Thr Gly Thr
    50                  55                  60

Ala Cys Cys Ala Ala Gly Thr Cys Thr Cys Cys Ala Ala Gly Ala Cys
65                  70                  75                  80

Gly Cys Thr Cys Cys Gly Gly Thr Thr Cys Gly Ala Gly Cys Thr Thr
                85                  90                  95

Ala Thr Cys Cys Cys Gly Cys Ala Ala Gly Gly Gly Ala Ala Gly Ala
            100                 105                 110

Cys Cys Cys Thr Gly Ala Ala Ala Cys Ala Cys Ala Thr Cys Cys Ala
        115                 120                 125

Gly Gly Ala Ala Cys Ala Ala Gly Gly Thr Thr Thr Cys Ala Thr Cys
    130                 135                 140

Gly Ala Gly Gly Ala Gly Gly Ala Cys Ala Ala Gly Gly Cys Cys Cys
145                 150                 155                 160

Gly Cys Ala Ala Cys Gly Ala Cys Cys Ala Cys Thr Ala Cys Ala Ala
                165                 170                 175

Gly Gly Ala Gly Cys Thr Cys Ala Ala Gly Cys Cys Cys Ala Thr Ala
            180                 185                 190

Ala Thr Cys Gly Ala Thr Cys Gly Gly Ala Thr Cys Thr Ala Cys Ala
        195                 200                 205

Ala Gly Ala Cys Gly Thr Ala Cys Gly Cys Cys Gly Ala Cys Cys Ala
    210                 215                 220

Gly Thr Gly Cys Cys Thr Cys Cys Ala Ala Cys Thr Gly Gly Thr Gly
225                 230                 235                 240

Cys Ala Gly Cys Thr Cys Gly Ala Cys Thr Gly Gly Gly Ala Gly Ala
                245                 250                 255

Ala Cys Cys Thr Gly Ala Gly Cys Gly Cys Cys Gly Cys Cys Ala Thr
            260                 265                 270

Thr Gly Ala Cys Ala Gly Cys Thr Ala Cys Cys Gly Cys Ala Ala Gly
        275                 280                 285

Gly Ala Ala Ala Ala Gly Ala Cys Gly Gly Ala Gly Gly Ala Gly Ala
    290                 295                 300

Cys Gly Cys Gly Cys Ala Ala Cys Gly Cys Cys Cys Thr Thr Ala Thr
305                 310                 315                 320

Thr Gly Ala Gly Gly Ala Gly Cys Ala Ala Gly Cys Cys Ala Cys Cys
                325                 330                 335

Thr Ala Cys Cys Gly Cys Ala Ala Cys Gly Cys Cys Ala Thr Cys Cys
            340                 345                 350

Ala Cys Gly Ala Cys Thr Ala Cys Thr Thr Cys Ala Thr Cys Gly Gly
        355                 360                 365

Gly Cys Gly Cys Ala Cys Cys Gly Ala Cys Ala Ala Cys Cys Thr Gly
    370                 375                 380

Ala Cys Gly Gly Ala Cys Gly Cys Gly Ala Thr Cys Ala Ala Cys Ala
385                 390                 395                 400

Ala Gly Cys Gly Cys Cys Ala Cys Gly Cys Gly Gly Ala Ala Ala Thr
                405                 410                 415

Cys Thr Ala Cys Ala Ala Gly Gly Gly Cys Cys Thr Thr Thr Thr Cys
            420                 425                 430

Ala Ala Gly Gly Cys Cys Gly Ala Gly Cys Thr Cys Thr Thr Cys Ala
        435                 440                 445

Ala Cys Gly Gly Gly Ala Ala Gly Gly Thr Cys Cys Thr Ala Ala Ala
```

```
    450                 455                 460

Ala Cys Ala Gly Cys Thr Cys Gly Gly Gly Ala Cys Thr Gly Thr Cys
465                 470                 475                 480

Ala Cys Gly Ala Cys Ala Ala Cys Cys Gly Ala Gly Cys Ala Thr Gly
                485                 490                 495

Ala Gly Ala Ala Cys Gly Cys Cys Cys Thr Cys Cys Thr Thr Cys Gly
            500                 505                 510

Cys Ala Gly Cys Thr Thr Cys Gly Ala Cys Ala Ala Gly Thr Thr Cys
        515                 520                 525

Ala Cys Cys Ala Cys Ala Thr Ala Cys Thr Thr Cys Thr Cys Gly Gly
    530                 535                 540

Gly Cys Thr Thr Cys Thr Ala Cys Cys Gly Gly Ala Ala Cys Cys Gly
545                 550                 555                 560

Cys Ala Ala Gly Ala Ala Cys Gly Thr Thr Thr Thr Cys Ala Gly Cys
                565                 570                 575

Gly Cys Cys Gly Ala Gly Gly Ala Cys Ala Thr Cys Thr Cys Cys Ala
            580                 585                 590

Cys Cys Gly Cys Cys Ala Thr Cys Cys Cys Gly Cys Ala Cys Ala Gly
        595                 600                 605

Gly Ala Thr Cys Gly Thr Cys Cys Ala Gly Gly Ala Cys Ala Ala Cys
    610                 615                 620

Thr Thr Cys Cys Cys Cys Ala Ala Gly Thr Thr Cys Ala Ala Gly Gly
625                 630                 635                 640

Ala Gly Ala Ala Cys Thr Gly Cys Cys Ala Cys Ala Thr Cys Thr Thr
                645                 650                 655

Cys Ala Cys Gly Cys Gly Cys Cys Thr Gly Ala Thr Thr Ala Cys Ala
            660                 665                 670

Gly Cys Cys Gly Thr Ala Cys Cys Thr Thr Cys Ala Cys Thr Thr Cys
        675                 680                 685

Gly Thr Gly Ala Gly Cys Ala Cys Thr Thr Cys Gly Ala Gly Ala Ala
    690                 695                 700

Cys Gly Thr Cys Ala Ala Ala Ala Ala Gly Gly Cys Cys Ala Thr Cys
705                 710                 715                 720

Gly Gly Gly Ala Thr Cys Thr Thr Cys Gly Thr Cys Thr Cys Cys Ala
                725                 730                 735

Cys Gly Thr Cys Cys Ala Thr Cys Gly Ala Gly Gly Ala Gly Gly Thr
            740                 745                 750

Ala Thr Thr Cys Thr Cys Thr Thr Thr Cys Cys Cys Gly Thr Thr Cys
        755                 760                 765

Thr Ala Thr Ala Ala Cys Cys Ala Gly Cys Thr Cys Cys Thr Gly Ala
    770                 775                 780

Cys Cys Cys Ala Gly Ala Cys Gly Cys Ala Gly Ala Thr Cys Gly Ala
785                 790                 795                 800

Cys Cys Thr Cys Thr Ala Cys Ala Ala Cys Cys Ala Gly Cys Thr Ala
                805                 810                 815

Cys Thr Gly Gly Gly Cys Gly Gly Cys Ala Thr Cys Ala Gly Cys Cys
            820                 825                 830

Gly Gly Gly Ala Gly Gly Cys Cys Gly Gly Gly Ala Cys Cys Gly Ala
        835                 840                 845

Gly Ala Ala Ala Ala Thr Ala Ala Ala Gly Gly Gly Cys Cys Thr Cys
    850                 855                 860

Ala Ala Cys Gly Ala Ala Gly Thr Thr Cys Thr Cys Ala Ala Cys Cys
865                 870                 875                 880
```

Thr Gly Gly Cys Cys Ala Thr Cys Cys Ala Gly Ala Ala Gly Ala Ala
885 890 895

Cys Gly Ala Cys Gly Ala Gly Ala Cys Cys Gly Cys Gly Cys Ala Thr
900 905 910

Ala Thr Cys Ala Thr Cys Gly Cys Ala Thr Cys Cys Cys Thr Gly Cys
915 920 925

Cys Gly Cys Ala Thr Cys Gly Cys Thr Thr Cys Ala Thr Thr Cys Cys
930 935 940

Thr Thr Thr Gly Thr Thr Cys Ala Ala Gly Cys Ala Gly Ala Thr Ala
945 950 955 960

Thr Thr Gly Ala Gly Cys Gly Ala Cys Cys Gly Gly Ala Ala Cys Ala
965 970 975

Cys Cys Cys Thr Cys Thr Cys Gly Thr Thr Cys Ala Thr Cys Cys Thr
980 985 990

Cys Gly Ala Ala Gly Ala Ala Thr Thr Cys Ala Ala Gly Ala Gly Cys
995 1000 1005

Gly Ala Cys Gly Ala Gly Gly Ala Gly Gly Thr Cys Ala Thr Thr
1010 1015 1020

Cys Ala Gly Thr Cys Thr Thr Thr Cys Thr Gly Cys Ala Ala Gly
1025 1030 1035

Thr Ala Cys Ala Ala Gly Ala Cys Gly Cys Thr Cys Cys Thr Ala
1040 1045 1050

Cys Gly Gly Ala Ala Thr Gly Ala Gly Ala Ala Thr Gly Thr Gly
1055 1060 1065

Cys Thr Gly Gly Ala Gly Ala Cys Cys Gly Cys Gly Gly Ala Gly
1070 1075 1080

Gly Cys Ala Cys Thr Cys Thr Thr Cys Ala Ala Thr Gly Ala Gly
1085 1090 1095

Cys Thr Gly Ala Ala Cys Thr Cys Cys Ala Thr Thr Gly Ala Cys
1100 1105 1110

Cys Thr Gly Ala Cys Cys Cys Ala Cys Ala Thr Cys Thr Thr Cys
1115 1120 1125

Ala Thr Thr Ala Gly Cys Cys Ala Cys Ala Ala Gly Ala Ala Ala
1130 1135 1140

Cys Thr Gly Gly Ala Gly Ala Cys Gly Ala Thr Cys Thr Cys Cys
1145 1150 1155

Ala Gly Cys Gly Cys Cys Cys Thr Gly Thr Gly Cys Gly Ala Cys
1160 1165 1170

Cys Ala Cys Thr Gly Gly Gly Ala Cys Ala Cys Thr Cys Thr Cys
1175 1180 1185

Cys Gly Cys Ala Ala Cys Gly Cys Cys Cys Thr Cys Thr Ala Cys
1190 1195 1200

Gly Ala Ala Cys Gly Cys Cys Gly Gly Ala Thr Cys Thr Cys Cys
1205 1210 1215

Gly Ala Ala Cys Thr Thr Ala Cys Cys Gly Gly Cys Ala Ala Gly
1220 1225 1230

Ala Thr Ala Ala Cys Thr Ala Ala Gly Thr Cys Gly Gly Cys Thr
1235 1240 1245

Ala Ala Gly Gly Ala Gly Ala Ala Gly Gly Thr Gly Cys Ala Ala
1250 1255 1260

Cys Gly Gly Ala Gly Cys Cys Thr Cys Ala Ala Gly Cys Ala Cys
1265 1270 1275

Gly Ala Gly Gly Ala Cys Ala Thr Cys Ala Ala Cys Cys Thr Thr
1280 1285 1290

Cys Ala Gly Gly Ala Ala Ala Thr Cys Ala Thr Cys Thr Cys Ala
1295 1300 1305

Gly Cys Cys Gly Cys Gly Gly Gly Cys Ala Ala Gly Gly Ala Gly
1310 1315 1320

Cys Thr Gly Ala Gly Cys Gly Ala Gly Gly Cys Gly Thr Thr Thr
1325 1330 1335

Ala Ala Gly Cys Ala Gly Ala Ala Ala Ala Cys Ala Thr Cys Gly
1340 1345 1350

Gly Ala Gly Ala Thr Ala Cys Thr Gly Ala Gly Cys Cys Ala Cys
1355 1360 1365

Gly Cys Gly Cys Ala Cys Gly Cys Gly Gly Cys Cys Cys Thr Gly
1370 1375 1380

Gly Ala Thr Cys Ala Ala Cys Cys Gly Cys Thr Gly Cys Cys Gly
1385 1390 1395

Ala Cys Gly Ala Cys Thr Cys Thr Cys Ala Ala Gly Ala Ala Gly
1400 1405 1410

Cys Ala Ala Gly Ala Gly Gly Ala Gly Ala Ala Gly Gly Ala Ala
1415 1420 1425

Ala Thr Cys Cys Thr Thr Ala Ala Gly Thr Cys Cys Cys Ala Gly
1430 1435 1440

Cys Thr Cys Gly Ala Cys Thr Cys Gly Cys Thr Gly Cys Thr Cys
1445 1450 1455

Gly Gly Cys Cys Thr Cys Thr Ala Thr Cys Ala Cys Thr Thr Gly
1460 1465 1470

Cys Thr Cys Gly Ala Cys Thr Gly Gly Thr Thr Cys Gly Cys Gly
1475 1480 1485

Gly Thr Thr Gly Ala Thr Gly Ala Gly Thr Cys Cys Ala Ala Cys
1490 1495 1500

Gly Ala Gly Gly Thr Gly Gly Ala Cys Cys Cys Gly Gly Ala Gly
1505 1510 1515

Thr Thr Cys Thr Cys Cys Gly Cys Gly Cys Gly Cys Cys Thr Cys
1520 1525 1530

Ala Cys Gly Gly Gly Thr Ala Thr Thr Ala Ala Gly Cys Thr Gly
1535 1540 1545

Gly Ala Gly Ala Thr Gly Gly Ala Gly Cys Cys Ala Ala Gly Cys
1550 1555 1560

Thr Thr Ala Ala Gly Cys Thr Thr Cys Thr Ala Cys Ala Ala Cys
1565 1570 1575

Ala Ala Gly Gly Cys Cys Cys Gly Cys Ala Ala Cys Thr Ala Cys
1580 1585 1590

Gly Cys Gly Ala Cys Cys Ala Ala Ala Ala Ala Ala Cys Cys Gly
1595 1600 1605

Thr Ala Cys Thr Cys Ala Gly Thr Cys Gly Ala Gly Ala Ala Ala
1610 1615 1620

Thr Thr Cys Ala Ala Gly Cys Thr Gly Ala Ala Thr Thr Thr Cys
1625 1630 1635

Cys Ala Gly Ala Thr Gly Cys Cys Thr Ala Cys Ala Thr Thr Gly
1640 1645 1650

Gly Cys Gly Ala Gly Gly Gly Gly Gly Thr Gly Gly Gly Ala Cys
1655 1660 1665

Gly Thr Gly Ala Ala Cys Cys Gly Cys Gly Ala Gly Ala Ala Gly

```
    1670                1675                1680

Ala Ala  Cys Ala Ala Thr Gly  Gly Ala Gly Cys Cys  Ala Thr Cys
    1685                1690                1695

Cys Thr  Gly Thr Thr Cys Gly  Thr Cys Ala Ala Ala  Ala Ala Thr
    1700                1705                1710

Gly Gly  Gly Thr Thr Gly Thr  Ala Cys Thr Ala Cys  Cys Thr Gly
    1715                1720                1725

Gly Gly  Cys Ala Thr Cys Ala  Thr Gly Cys Cys Cys  Ala Ala Gly
    1730                1735                1740

Cys Ala  Gly Ala Ala Gly Gly  Gly Cys Cys Gly Thr  Thr Ala Cys
    1745                1750                1755

Ala Ala  Gly Gly Cys Cys Cys  Thr Gly Thr Cys Ala  Thr Thr Cys
    1760                1765                1770

Gly Ala  Gly Cys Cys Thr Ala  Cys Cys Gly Ala Gly  Ala Ala Gly
    1775                1780                1785

Ala Cys  Cys Thr Cys Gly Gly  Ala Gly Gly Gly Cys  Thr Thr Cys
    1790                1795                1800

Gly Ala  Cys Ala Ala Gly Ala  Thr Gly Thr Ala Cys  Thr Ala Cys
    1805                1810                1815

Gly Ala  Cys Thr Ala Thr Thr  Thr Cys Cys Cys Gly  Gly Ala Cys
    1820                1825                1830

Gly Cys  Cys Gly Cys Cys Ala  Ala Gly Ala Thr Gly  Ala Thr Cys
    1835                1840                1845

Cys Cys  Gly Ala Ala Gly Thr  Gly Cys Thr Cys Cys  Ala Cys Gly
    1850                1855                1860

Cys Ala  Gly Cys Thr Cys Ala  Ala Ala Gly Cys Cys  Gly Thr Cys
    1865                1870                1875

Ala Cys  Gly Gly Cys Cys Cys  Ala Cys Thr Thr Cys  Cys Ala Gly
    1880                1885                1890

Ala Cys  Gly Cys Ala Thr Ala  Cys Cys Ala Cys Gly  Cys Cys Gly
    1895                1900                1905

Ala Thr  Ala Cys Thr Thr Cys  Thr Gly Ala Gly Cys  Ala Ala Cys
    1910                1915                1920

Ala Ala  Cys Thr Thr Cys Ala  Thr Thr Gly Ala Gly  Cys Cys Gly
    1925                1930                1935

Cys Thr  Ala Gly Ala Gly Ala  Thr Cys Ala Cys Gly  Ala Ala Gly
    1940                1945                1950

Gly Ala  Gly Ala Thr Ala Thr  Ala Cys Gly Ala Cys  Cys Thr Ala
    1955                1960                1965

Ala Ala  Cys Ala Ala Cys Cys  Cys Cys Gly Ala Ala  Ala Ala Gly
    1970                1975                1980

Gly Ala  Gly Cys Cys Cys Ala  Ala Gly Ala Ala Gly  Thr Thr Cys
    1985                1990                1995

Cys Ala  Gly Ala Cys Ala Gly  Cys Cys Thr Ala Cys  Gly Cys Thr
    2000                2005                2010

Ala Ala  Gly Ala Ala Gly Ala  Cys Ala Gly Gly Thr  Gly Ala Thr
    2015                2020                2025

Cys Ala  Gly Ala Ala Gly Gly  Gly Ala Thr Ala Thr  Ala Gly Gly
    2030                2035                2040

Gly Ala  Gly Gly Cys Ala Cys  Thr Cys Thr Gly Cys  Ala Ala Gly
    2045                2050                2055

Thr Gly  Gly Ala Thr Cys Gly  Ala Cys Thr Thr Cys  Ala Cys Gly
    2060                2065                2070
```

Cys Gly Cys Gly Ala Cys Thr Thr Cys Cys Thr Gly Thr Cys Gly
2075 2080 2085

Ala Ala Ala Thr Ala Thr Ala Cys Ala Ala Ala Gly Ala Cys Gly
2090 2095 2100

Ala Cys Cys Ala Gly Cys Ala Thr Thr Gly Ala Cys Cys Thr Ala
2105 2110 2115

Ala Gly Thr Thr Cys Thr Cys Thr Cys Cys Gly Cys Cys Cys Ala
2120 2125 2130

Thr Cys Cys Thr Cys Cys Cys Ala Gly Thr Ala Cys Ala Ala Gly
2135 2140 2145

Gly Ala Thr Cys Thr Gly Gly Gly Cys Gly Ala Gly Thr Ala Thr
2150 2155 2160

Thr Ala Thr Gly Cys Gly Gly Ala Gly Cys Thr Gly Ala Ala Cys
2165 2170 2175

Cys Cys Ala Thr Thr Gly Cys Thr Gly Thr Ala Cys Cys Ala Cys
2180 2185 2190

Ala Thr Cys Ala Gly Cys Thr Thr Cys Cys Ala Gly Ala Gly Gly
2195 2200 2205

Ala Thr Cys Gly Cys Cys Gly Ala Gly Ala Ala Gly Gly Ala Gly
2210 2215 2220

Ala Thr Thr Ala Thr Gly Gly Ala Cys Gly Cys Gly Gly Thr Gly
2225 2230 2235

Gly Ala Gly Ala Cys Gly Gly Gly Gly Ala Ala Ala Cys Thr Ala
2240 2245 2250

Thr Ala Cys Cys Thr Gly Thr Thr Cys Cys Ala Ala Ala Thr Ala
2255 2260 2265

Thr Ala Thr Ala Ala Cys Ala Ala Gly Gly Ala Cys Thr Thr Cys
2270 2275 2280

Gly Cys Thr Ala Ala Ala Gly Gly Gly Cys Ala Cys Cys Ala Cys
2285 2290 2295

Gly Gly Gly Ala Ala Gly Cys Cys Cys Ala Ala Cys Cys Thr Gly
2300 2305 2310

Cys Ala Cys Ala Cys Ala Cys Thr Cys Thr Ala Cys Thr Gly Gly
2315 2320 2325

Ala Cys Gly Gly Gly Cys Thr Thr Gly Thr Thr Thr Thr Cys Gly
2330 2335 2340

Cys Cys Ala Gly Ala Ala Ala Ala Thr Thr Thr Gly Gly Cys Cys
2345 2350 2355

Ala Ala Gly Ala Cys Thr Thr Cys Gly Ala Thr Cys Ala Ala Gly
2360 2365 2370

Cys Thr Cys Ala Ala Cys Gly Gly Cys Cys Ala Gly Gly Cys Gly
2375 2380 2385

Gly Ala Gly Thr Thr Gly Thr Thr Thr Thr Ala Cys Cys Gly Thr
2390 2395 2400

Cys Cys Cys Ala Ala Gly Thr Cys Thr Cys Gly Cys Ala Thr Gly
2405 2410 2415

Ala Ala Gly Cys Gly Cys Ala Thr Gly Gly Cys Gly Cys Ala Thr
2420 2425 2430

Cys Gly Cys Cys Thr Cys Gly Gly Ala Gly Ala Gly Ala Ala Ala
2435 2440 2445

Ala Thr Gly Cys Thr Thr Ala Ala Cys Ala Ala Gly Ala Ala Gly
2450 2455 2460

```
Cys Thr  Cys Ala Ala Gly Gly  Ala Thr Cys Ala Gly  Ala Ala Gly
    2465                 2470                 2475

Ala Cys  Gly Cys Cys Cys Ala  Thr Ala Cys Cys Thr  Gly Ala Thr
    2480                 2485                 2490

Ala Cys  Gly Thr Thr Gly Thr  Ala Cys Cys Ala Gly  Gly Ala Ala
    2495                 2500                 2505

Thr Thr  Gly Thr Ala Cys Gly  Ala Cys Thr Ala Cys  Gly Thr Gly
    2510                 2515                 2520

Ala Ala  Cys Cys Ala Cys Cys  Gly Cys Cys Thr Ala  Thr Cys Gly
    2525                 2530                 2535

Cys Ala  Cys Gly Ala Cys Cys  Thr Cys Thr Cys Ala  Gly Ala Cys
    2540                 2545                 2550

Gly Ala  Gly Gly Cys Cys Cys  Gly Cys Gly Cys Cys  Cys Thr Cys
    2555                 2560                 2565

Cys Thr  Cys Cys Cys Ala Ala  Ala Cys Gly Thr Gly  Ala Thr Thr
    2570                 2575                 2580

Ala Cys  Thr Ala Ala Gly Gly  Ala Gly Gly Thr Thr  Thr Cys Cys
    2585                 2590                 2595

Cys Ala  Thr Gly Ala Ala Ala  Thr Ala Ala Thr Cys  Ala Ala Gly
    2600                 2605                 2610

Gly Ala  Cys Cys Gly Ala Cys  Gly Gly Thr Thr Cys  Ala Cys Cys
    2615                 2620                 2625

Ala Gly  Cys Gly Ala Cys Ala  Ala Ala Thr Thr Thr  Thr Thr Thr
    2630                 2635                 2640

Thr Thr  Cys Cys Ala Cys Gly  Thr Gly Cys Cys Thr  Ala Thr Cys
    2645                 2650                 2655

Ala Cys  Gly Cys Thr Cys Ala  Ala Thr Thr Ala Cys  Cys Ala Gly
    2660                 2665                 2670

Gly Cys  Gly Gly Cys Cys Ala  Ala Cys Thr Cys Cys  Cys Cys Ala
    2675                 2680                 2685

Thr Cys  Gly Ala Ala Gly Thr  Thr Cys Ala Ala Cys  Cys Ala Gly
    2690                 2695                 2700

Cys Gly  Cys Gly Thr Gly Ala  Ala Cys Gly Cys Cys  Thr Ala Cys
    2705                 2710                 2715

Cys Thr  Thr Ala Ala Gly Gly  Ala Gly Cys Ala Cys  Cys Cys Gly
    2720                 2725                 2730

Gly Ala  Gly Ala Cys Cys Cys  Cys Ala Ala Thr Cys  Ala Thr Cys
    2735                 2740                 2745

Gly Gly  Gly Ala Thr Cys Gly  Ala Cys Cys Gly Thr  Gly Gly Cys
    2750                 2755                 2760

Gly Ala  Gly Cys Gly Gly Ala  Ala Cys Cys Thr Gly  Ala Thr Cys
    2765                 2770                 2775

Thr Ala  Thr Ala Thr Thr Ala  Cys Gly Gly Thr Gly  Ala Thr Cys
    2780                 2785                 2790

Gly Ala  Thr Ala Gly Cys Ala  Cys Cys Gly Gly Gly  Ala Ala Gly
    2795                 2800                 2805

Ala Thr  Cys Cys Thr Gly Gly  Ala Gly Cys Ala Gly  Cys Gly Cys
    2810                 2815                 2820

Thr Cys  Cys Cys Thr Gly Ala  Ala Cys Ala Cys Ala  Ala Thr Cys
    2825                 2830                 2835

Cys Ala  Gly Cys Ala Gly Thr  Thr Thr Gly Ala Cys  Thr Ala Cys
    2840                 2845                 2850

Cys Ala  Gly Ala Ala Gly Ala  Ala Ala Cys Thr Cys  Gly Ala Cys
```

```
    2855                2860                2865

Ala Ala  Cys Cys Gly Gly Gly  Ala Gly Ala Ala Gly  Gly Ala Gly
    2870                2875                2880

Cys Gly  Cys Gly Thr Cys Gly  Cys Ala Gly Cys Cys  Cys Gly Gly
    2885                2890                2895

Cys Ala  Ala Gly Cys Ala Thr  Gly Gly Ala Gly Thr  Gly Thr Gly
    2900                2905                2910

Gly Thr  Cys Gly Gly Cys Ala  Cys Cys Ala Thr Ala  Ala Ala Gly
    2915                2920                2925

Gly Ala  Cys Cys Thr Gly Ala  Ala Ala Cys Ala Gly  Gly Gly Thr
    2930                2935                2940

Thr Ala  Cys Cys Thr Ala Ala  Gly Thr Cys Ala Ala  Gly Thr Thr
    2945                2950                2955

Ala Thr  Cys Cys Ala Cys Gly  Ala Gly Ala Thr Cys  Gly Thr Thr
    2960                2965                2970

Gly Ala  Cys Cys Thr Gly Ala  Thr Gly Ala Thr Ala  Cys Ala Cys
    2975                2980                2985

Thr Ala  Thr Cys Ala Ala Gly  Cys Cys Gly Thr Ala  Gly Thr Cys
    2990                2995                3000

Gly Thr  Gly Cys Thr Gly Gly  Ala Gly Ala Ala Cys  Cys Thr Cys
    3005                3010                3015

Ala Ala  Cys Thr Thr Cys Gly  Gly Gly Thr Thr Thr  Ala Ala Gly
    3020                3025                3030

Thr Cys  Cys Ala Ala Gly Cys  Gly Cys Ala Cys Cys  Gly Gly Cys
    3035                3040                3045

Ala Thr  Cys Gly Cys Gly Gly  Ala Gly Ala Ala Gly  Gly Cys Gly
    3050                3055                3060

Gly Thr  Gly Thr Ala Cys Cys  Ala Gly Cys Ala Gly  Thr Thr Cys
    3065                3070                3075

Gly Ala  Gly Ala Ala Gly Ala  Thr Gly Cys Thr Gly  Ala Thr Cys
    3080                3085                3090

Gly Ala  Cys Ala Ala Gly Cys  Thr Gly Ala Ala Cys  Thr Gly Cys
    3095                3100                3105

Cys Thr  Gly Gly Thr Gly Cys  Thr Cys Ala Ala Gly  Gly Ala Cys
    3110                3115                3120

Thr Ala  Cys Cys Cys Thr Gly  Cys Gly Gly Ala Gly  Ala Ala Gly
    3125                3130                3135

Gly Thr  Cys Gly Gly Cys Gly  Gly Gly Gly Thr Cys  Thr Thr Gly
    3140                3145                3150

Ala Ala  Cys Cys Cys Gly Thr  Ala Cys Cys Ala Gly  Cys Thr Ala
    3155                3160                3165

Ala Cys  Cys Gly Ala Cys Cys  Ala Gly Thr Thr Cys  Ala Cys Gly
    3170                3175                3180

Ala Gly  Cys Thr Thr Cys Gly  Cys Cys Ala Ala Ala  Ala Thr Gly
    3185                3190                3195

Gly Gly  Cys Ala Cys Gly Cys  Ala Gly Thr Cys Cys  Gly Gly Ala
    3200                3205                3210

Thr Thr  Cys Thr Thr Gly Thr  Thr Thr Thr Ala Thr  Gly Thr Cys
    3215                3220                3225

Cys Cys  Gly Gly Cys Thr Cys  Cys Ala Thr Ala Thr  Ala Cys Ala
    3230                3235                3240

Ala Gly  Thr Ala Ala Gly Ala  Thr Cys Gly Ala Cys  Cys Cys Gly
    3245                3250                3255
```

-continued

Cys Thr Gly Ala Cys Ala Gly Gly Gly Thr Thr Thr Gly Thr Thr
3260 3265 3270

Gly Ala Cys Cys Cys Ala Thr Thr Cys Gly Thr Gly Thr Gly Gly
3275 3280 3285

Ala Ala Gly Ala Cys Cys Ala Thr Cys Ala Ala Gly Ala Ala Cys
3290 3295 3300

Cys Ala Cys Gly Ala Gly Ala Gly Cys Ala Gly Gly Ala Ala Ala
3305 3310 3315

Cys Ala Cys Thr Thr Cys Thr Thr Ala Gly Ala Gly Gly Gly Cys
3320 3325 3330

Thr Thr Cys Gly Ala Cys Thr Thr Cys Cys Thr Gly Cys Ala Thr
3335 3340 3345

Thr Ala Cys Gly Ala Cys Gly Thr Thr Ala Ala Gly Ala Cys Ala
3350 3355 3360

Gly Gly Cys Gly Ala Cys Thr Thr Cys Ala Thr Cys Cys Thr Gly
3365 3370 3375

Cys Ala Cys Thr Thr Cys Ala Ala Gly Ala Thr Gly Ala Ala Cys
3380 3385 3390

Cys Gly Cys Ala Ala Cys Cys Thr Gly Thr Cys Gly Thr Thr Cys
3395 3400 3405

Cys Ala Gly Ala Gly Gly Gly Gly Cys Cys Thr Gly Cys Cys Cys
3410 3415 3420

Gly Gly Cys Thr Thr Cys Ala Thr Gly Cys Cys Cys Gly Cys Cys
3425 3430 3435

Thr Gly Gly Gly Ala Thr Ala Thr Cys Gly Thr Cys Thr Thr Thr
3440 3445 3450

Gly Ala Gly Ala Ala Gly Ala Ala Thr Gly Ala Gly Ala Cys Gly
3455 3460 3465

Cys Ala Gly Thr Thr Cys Gly Ala Cys Gly Cys Gly Ala Ala Gly
3470 3475 3480

Gly Gly Gly Ala Cys Gly Cys Cys Gly Thr Thr Cys Ala Thr Cys
3485 3490 3495

Gly Cys Thr Gly Gly Ala Ala Ala Gly Cys Gly Gly Ala Thr Cys
3500 3505 3510

Gly Thr Gly Cys Cys Gly Gly Thr Cys Ala Thr Cys Gly Ala Gly
3515 3520 3525

Ala Ala Cys Cys Ala Cys Cys Gly Cys Thr Thr Cys Ala Cys Gly
3530 3535 3540

Gly Gly Thr Cys Gly Cys Thr Ala Cys Cys Gly Ala Gly Ala Thr
3545 3550 3555

Thr Thr Ala Thr Ala Cys Cys Cys Cys Gly Cys Cys Ala Ala Cys
3560 3565 3570

Gly Ala Ala Cys Thr Ala Ala Thr Thr Gly Cys Gly Cys Thr Gly
3575 3580 3585

Cys Thr Gly Gly Ala Gly Gly Ala Gly Ala Ala Gly Gly Gly Gly
3590 3595 3600

Ala Thr Cys Gly Thr Gly Thr Thr Cys Cys Gly Ala Gly Ala Thr
3605 3610 3615

Gly Gly Cys Ala Gly Cys Ala Ala Cys Ala Thr Thr Cys Thr Cys
3620 3625 3630

Cys Cys Gly Ala Ala Gly Cys Thr Gly Cys Thr Gly Gly Ala Gly
3635 3640 3645

```
Ala Ala  Cys Gly Ala Cys Gly  Ala Cys Thr Cys Gly  Cys Ala Cys
    3650                 3655                 3660

Gly Cys  Thr Ala Thr Thr Gly  Ala Cys Ala Cys Gly  Ala Thr Gly
    3665                 3670                 3675

Gly Thr  Cys Gly Cys Cys Cys  Thr Cys Ala Thr Ala  Cys Gly Gly
    3680                 3685                 3690

Ala Gly  Cys Gly Thr Gly Cys  Thr Thr Cys Ala Gly  Ala Thr Gly
    3695                 3700                 3705

Cys Gly  Gly Ala Ala Cys Ala  Gly Thr Ala Ala Cys  Gly Cys Thr
    3710                 3715                 3720

Gly Cys  Cys Ala Cys Gly Gly  Gly Cys Gly Ala Gly  Gly Ala Cys
    3725                 3730                 3735

Thr Ala  Cys Ala Thr Thr Ala  Ala Cys Thr Cys Cys  Cys Cys Cys
    3740                 3745                 3750

Gly Thr  Cys Cys Gly Cys Gly  Ala Cys Cys Thr Cys  Ala Ala Cys
    3755                 3760                 3765

Gly Gly  Gly Gly Thr Cys Thr  Gly Cys Thr Thr Cys  Gly Ala Thr
    3770                 3775                 3780

Ala Gly  Cys Cys Gly Cys Thr  Thr Cys Cys Ala Gly  Ala Ala Cys
    3785                 3790                 3795

Cys Cys  Gly Gly Ala Gly Thr  Gly Gly Cys Cys Thr  Ala Thr Gly
    3800                 3805                 3810

Gly Ala  Thr Gly Cys Gly Gly  Ala Cys Gly Cys Gly  Ala Ala Cys
    3815                 3820                 3825

Gly Gly  Gly Gly Cys Cys Thr  Ala Cys Cys Ala Cys  Ala Thr Cys
    3830                 3835                 3840

Gly Cys  Cys Cys Thr Cys Ala  Ala Gly Gly Gly Cys  Cys Ala Ala
    3845                 3850                 3855

Cys Thr  Cys Cys Thr Gly Cys  Thr Cys Ala Ala Cys  Cys Ala Cys
    3860                 3865                 3870

Thr Thr  Gly Ala Ala Gly Gly  Ala Ala Ala Gly Cys  Ala Ala Ala
    3875                 3880                 3885

Gly Ala  Cys Cys Thr Cys Ala  Ala Ala Thr Thr Gly  Cys Ala Gly
    3890                 3895                 3900

Ala Ala  Thr Gly Gly Cys Ala  Thr Cys Ala Gly Thr  Ala Ala Cys
    3905                 3910                 3915

Cys Ala  Gly Gly Ala Cys Thr  Gly Gly Cys Thr Cys  Gly Cys Gly
    3920                 3925                 3930

Thr Ala  Cys Ala Thr Cys Cys  Ala Gly Gly Ala Ala  Cys Thr Gly
    3935                 3940                 3945

Ala Gly  Ala Ala Ala Cys Gly  Gly Gly Thr Cys Cys  Ala Ala Gly
    3950                 3955                 3960

Ala Ala  Gly Cys Gly Gly Cys  Gly Thr Ala Thr Cys  Ala Ala Gly
    3965                 3970                 3975

Cys Ala  Ala Gly Ala Thr Thr  Gly Ala
    3980                 3985
```

<210> SEQ ID NO 232
<211> LENGTH: 3987
<212> TYPE: DNA
<213> ORGANISM: Artificial sequence
<220> FEATURE:
<223> OTHER INFORMATION: Synthetic Cas12a

<400> SEQUENCE: 232

-continued

```
atggcgggaa gcaaaaagcg ccggattaag caagacacgc agttcgaggg cttcacgaac      60
ctctaccaag tcagcaagac cctccggttc gagctgatac cacagggaaa gacgctcaag     120
cacatccagg aacagggctt catcgaggag gacaaggcgc gcaacgacca ctacaaggag     180
ttgaaaccga tcatcgaccg catctacaag acgtacgccg accagtgcct ccagctcgtg     240
cagctcgact gggagaacct ctccgccgcc attgactcgt accggaagga gaagactgag     300
gagacccgca acgccctgat cgaggagcaa gcaacctacc ggaacgccat ccacgactac     360
ttcatcggcc gcaccgacaa cctcaccgac gcgatcaaca agcggcacgc ggagatatac     420
aaagggctgt tcaaggcgga gctgttcaac ggcaaggtgc tcaagcagct agggacggtg     480
accacgaccg agcacgagaa cgcgctcctc cgcagcttcg acaagttcac cacctacttc     540
agcggcttct accggaaccg caagaatgtg ttcagcgcgg aggacatcag cacggccatc     600
ccgcaccgca tcgtccagga caacttcccg aagttcaagg agaactgcca catcttcacc     660
cgcctgataa ccgccgtccc ctccctgcgg gagcacttcg agaacgtcaa aaaggcaatt     720
gggatcttcg tctcgaccag cattgaggag gtgttcagct tccccttcta caaccagctc     780
ctcacccaga cgcagatcga cctgtacaat cagttgctcg gcgggataag ccgcgaggcg     840
ggaaccgaaa aaatcaaggg gctgaacgaa gtgttgaacc tcgccatcca gaagaacgac     900
gagaccgcgc acatcatcgc ctccctgccc caccggttca tcccgctgtt caagcagatc     960
ctctctgacc ggaacaccct gtccttcatt cttgaggagt tcaagtcgga cgaggaggtc    1020
atccagagct tctgcaagta caagacgctg ctacggaacg agaacgtgct ggagacggcg    1080
gaggcactgt tcaacgagct aaacagcatc gacctcacgc acatcttcat cagtcacaag    1140
aaactggaga ccatctcctc cgcgctgtgc gaccactggg acacgctcag gaacgcgctc    1200
tacgagcgcc gaatcagtga gctgacgggc aagatcacga agtccgcgaa ggagaaggtg    1260
cagcggtccc tcaagcacga ggacatcaac ctccaggaga tcatctcagc ggctgggaaa    1320
gagctgtccg aggcgttcaa gcagaaaacg agcgaaatcc tgtcccacgc gcacgcggcc    1380
ctggatcagc ctctgccgac gaccctcaag aaacaagaag aaaaggaaat cctcaagtcg    1440
cagctcgact cgctgctggg cctgtaccat ctcctcgact ggttcgccgt ggacgagagc    1500
aacgaggtgg accccgagtt ctccgcgcgg cttacgggga tcaagctgga gatggagccc    1560
agcctgtcct tctacaacaa ggcgcgcaac tacgccacca agaagcccta cagcgtggag    1620
aagttcaagc tcaacttcca gatgcccact ctcgcacgtg ggtgggacgt caaccgcgaa    1680
aaaaataatg gggcgatcct gttcgtcaag aacggcctgt actacttggg catcatgccg    1740
aaacagaagg gccgctacaa ggccctgagc ttcgaaccga ccgagaaaac gagcgagggg    1800
ttcgacaaga tgtactacga ctacttcccc gacgccgcga agatgattcc aaagtgctcc    1860
acgcagctta aggccgtgac ggcccacttc cagacgcaca cgaccccgat cctcctcagc    1920
aacaacttca tcgagcccct ggagatcacg aaggagatat acgacctgaa caacccggag    1980
aaggagccca agaaattcca gaccgcctac gccaagaaga caggcgacca aaagggttac    2040
agggaggccc tctgcaagtg gatcgacttc actagggact tcctgtccaa gtacaccaag    2100
actacctcta tcgacctgtc cagcctccgc ccgtcgtccc agtacaaaga tttgggcgag    2160
tattacgcgg agctgaaccc actgctctac cacatcagct tccagcgcat cgcggagaag    2220
gagatcatgg acgcagtgga gacgggcaag ctatacctat ttcagatata caacaaagac    2280
ttcgctaagg gacaccacgg caagcctaac ctgcacaccc tctactggac ggggctcttc    2340
agcccggaga acctcgccaa gacctcgatc aagctcaacg gccaggccga gctgttctac    2400
```

cggcccaagt cccgcatgaa gcggatggcc caccggctcg gggagaaaat gctcaacaag 2460
aaattgaagg accaaaaaac gccgataccc gacaccctat accaggagct gtacgactat 2520
gtgaaccacc gcctgagcca cgacctcagc gacgaggcgc gggccctcct gccgaacgtc 2580
atcacaaagg aggtcagcca cgagatcatc aaggaccggc gcttcacctc cgacaagttt 2640
ttctttcacg tgcccatcac gctcaactac caggccgcca actcgccgtc caagttcaac 2700
cagcgcgtga acgcctacct caaggagcac cccgagaccc cgatcatcgg gattgaccga 2760
ggggagcgga acctcatcta catcaccgtc atcgacagca ccgggaagat ccttgaacag 2820
cggtcgctca acaccatcca gcagttcgac taccagaaga aactcgacaa ccgggagaag 2880
gagagagtgg cggcccgcca ggcttggtcc gtcgtcggga cgattaagga cttgaaacaa 2940
ggttacctgt cgcaagtgat ccacgagatc gttgacctga tgatccacta ccaagccgtc 3000
gtggtcctgg agaacctcaa cttcggcttc aagagcaaac gaaccggcat cgcggagaag 3060
gccgtgtacc agcagttcga aaaaatgctg atcgacaagc tgaactgcct cgtgctcaag 3120
gactaccccg ctgagaaggt cggcggggtg ctgaacccgt accagctcac tgaccagttc 3180
accagcttcg caaagatggg cacccagtcc ggcttcctgt tctacgtgcc tgcgccatac 3240
acctcgaaga tcgacccgct caccgggttc gtggacccct tcgtctggaa gaccatcaag 3300
aaccacgaga gccgcaagca cttcctggag ggcttcgact tcctccacta cgacgtcaag 3360
accggggact tcatcctgca cttcaagatg aaccgcaacc tcagtttcca gcgcggcctg 3420
ccggggttca tgcccgcttg ggatatagtc ttcgagaaga atgagacgca gttcgacgcg 3480
aagggcaccc cgttcatcgc cgggaagcgc atcgtgccgg tcatcgagaa ccaccggttc 3540
accgggcgct accgcgacct atacccggcg aacgagttga tcgccctcct ggaggagaag 3600
ggcatcgtgt tccgcgacgg ctccaacatc ctcccgaagc tgctcgaaaa cgacgactcc 3660
cacgccatcg acacgatggt cgcgctgatc cggtcggtgc tccagatgcg gaactccaac 3720
gccgcgacgg gcgaggacta catcaacagt ccggtccgcg atctgaacgg cgtctgcttc 3780
gactcccggt tccagaaccc cgagtggccg atggacgcgg acgcgaacgg cgcataccac 3840
atcgccctaa aagggcaatt gctgctcaac cacctcaagg aatccaaaga cctaaagctc 3900
cagaacggca tctccaacca ggactggctg gcgtacatcc aggaactgcg gaacgggagc 3960
aaaaaacgtc ggatcaagca agattga 3987

<210> SEQ ID NO 233
<211> LENGTH: 3987
<212> TYPE: DNA
<213> ORGANISM: Artificial sequence
<220> FEATURE:
<223> OTHER INFORMATION: Synthetic Cas12a

<400> SEQUENCE: 233
atggcgggct ccaagaaacg ccggattaag caagataccc agttcgaggg gttcacgaac 60
ctctaccaag tgagcaagac cctccgattc gaactgattc ctcaggggaa gaccctcaag 120
cacatccagg agcaagggtt catcgaggag gacaaggcgc ggaacgacca ctacaaggaa 180
ctcaaaccca tcatcgaccg catctacaag acctacgccg atcagtgcct ccagctcgtg 240
cagttggact gggagaacct cagcgcggcc attgactcct accggaagga gaaaacggag 300
gagacgcgca acgcgctcat cgaggaacag gcaacctatc gcaacgccat ccacgactac 360
ttcatcggga ggactgacaa cctcactgac gcgattaaca agcgccacgc ggagatatac 420

-continued

```
aagggactct tcaaagcgga gctgtttaac ggcaaggttc tcaagcaact cggcactgtg    480
accacgaccg agcatgagaa cgccctgctc cgctccttcg acaagttcac cacctacttc    540
tccgggttct accgcaaccg caagaatgtc ttcagcgcgg aggacatcag cacggccatt    600
ccacatcgaa tcgtccaaga taacttcccg aagttcaagg agaactgcca catcttcacc    660
cgactcatta ctgctgtacc gtcgttacgc gaacacttcg agaacgtcaa gaaggcaatt    720
ggaatcttcg tctctacgtc aatagaggag gtgttcagct tccctttcta caaccagctc    780
cttacgcaga cccagataga cctgtacaat cagctcctcg gtgggatcag ccgggaggcg    840
gggactgaga agattaaagg gctcaacgag gtcttgaacc tggccatcca aaaaaacgat    900
gagacggcgc acatcatcgc ctcgctgccc caccggttca tcccgctgtt caagcagatc    960
ctcagtgaca ggaacacctt gagctttatc ctagaggagt tcaagagcga cgaggaggtg   1020
atccagagct tctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactggg acaccctccg caacgcgctc   1200
tacgagcgcc gcatctcgga gctgaccggg aagatcacca aatccgcgaa ggaaaaggtc   1260
cagcgttccc tcaaacacga ggatattaac ttacaggaga ttatctcagc ggctgggaag   1320
gagttgtcag aggcgttcaa gcagaaaact tccgagatcc tgagccacgc gcacgcagcg   1380
ctcgaccagc ctctgcccac caccctcaaa aagcaggaag aaaaagagat cctcaagagc   1440
cagttggact ccctgctggg gctctatcac cttctcgact ggttcgccgt cgatgagtcg   1500
aacgaggtgg accccgagtt ctccgcccgg ctgaccggca tcaagctaga gatggagccg   1560
tccctcagct tctacaataa ggcccgcaac tacgcgacca aaaaaccccta cagcgtggag   1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggccctttcc ttcgagccga cggagaaaac ctccgagggg   1800
ttcgacaaga tgtactacga ctacttcccc gacgccgcca agatgatccc gaagtgctca   1860
acgcagctaa aagccgtgac cgcccacttc cagacccaca cgacgccgat cctgctgagc   1920
aacaacttca tcgagcccct tgagatcact aaggagatat acgacctgaa caaccccgag   1980
aaggagccca agaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgcgg agcttaatcc actactctac cacatctcat tccagcgcat cgctgagaag   2220
gaaatcatgg acgcggtgga gacaggcaaa ctgtacctct tccagatata caacaaagac   2280
ttcgctaagg ggcaccacgg gaagcccaac cttcatacgc tctactggac gggcctattc   2340
agccccgaaa atctggccaa gacctccatc aagctgaacg gccaagcgga gctgttctac   2400
agacccaaga gccggatgaa gcggatggcc cacaggctcg gcgagaaaat gcttaacaaa   2460
aagttgaagg accagaaaac ccctatcccc gacaccctct accaggaact gtacgactac   2520
gtgaaccaca ggctctcgca cgacctttcc gacgaggccc gtgccctact cccgaacgtc   2580
attaccaaag aggtttcgca cgagatcatc aaggaccggc ggttcacgag cgacaagttt   2640
ttctttcacg tccccatcac ccttaactac caggcggcca actccccatc caagttcaac   2700
cagcgtgtga atgcctacct caaggagcac ccagagaccc cgatcattgg gatcgaccgg   2760
ggcgagcgga acctgatcta catcaccgtc atcgactcga cgggcaagat tcttgagcag   2820
```

agatcgttga ataccataca gcagttcgac taccagaaga aactcgacaa ccgcgagaag 2880
gagcgcgtgg cggcccgcca ggcgtggtcc gtcgttggga cgattaagga cttgaaacaa 2940
ggttatctgt cccaagtcat ccacgagatc gttgatctga tgatccacta tcaggcagtg 3000
gtggtgctgg agaatctcaa cttcggcttc aagagtaagc ggacgggaat cgccgagaag 3060
gccgtgtacc agcagttcga gaagatgctg atcgacaagc tcaactgcct tgtgctgaaa 3120
gactacccgg ccgagaaggt cggcggcgtc ctcaacccgt accaacttac cgaccagttc 3180
acctccttcg ccaagatggg cactcagtcc gggttcttgt tctacgtccc cgcaccttac 3240
acctctaaga tcgaccctct gactggcttc gtagatccat tcgtgtggaa gaccattaag 3300
aaccacgaga gccgcaagca cttcctggag ggcttcgact tcctgcacta cgacgtgaag 3360
accggggact tcatccttca cttcaagatg aaccggaacc tcagcttcca gcggggcctg 3420
ccggggttca tgcccgcctg ggacatcgtg ttcgagaaga acgagaccca gttcgacgcg 3480
aagggcacgc ccttcatcgc cgggaagcgt atcgtgccgg tgatcgagaa ccatcgtttc 3540
acgggtcgct accgtgacct ctacccggcg aacgagctta tcgcactcct ggaggagaag 3600
ggcatcgtct tccgggacgg ctccaacatc ctcccgaaac tgctggaaaa cgacgactct 3660
cacgccatcg acacgatggt ggccctcatc cggtccgtgc tccaaatgcg gaacagcaac 3720
gccgccaccg gtgaggacta catcaacagc ccggtccggg atctgaacgg ggtgtgcttc 3780
gattcgcggt tccagaatcc tgagtggccg atggacgcgg atgcaaacgg ggcgtaccac 3840
atcgcgctca agggccagtt acttctgaac caccttaagg agtctaaaga tttgaaactc 3900
cagaacggga tctcgaacca ggactggctg gcctacatcc aagagttgcg gaacggcagc 3960
aagaagcggc ggattaagca agattag 3987

<210> SEQ ID NO 234
<211> LENGTH: 1367
<212> TYPE: PRT
<213> ORGANISM: Artificial sequence
<220> FEATURE:
<223> OTHER INFORMATION: Synthetic nCas9

<400> SEQUENCE: 234

Asp Lys Lys Tyr Ser Ile Gly Leu Ala Ile Gly Thr Asn Ser Val Gly
1 5 10 15

Trp Ala Val Ile Thr Asp Glu Tyr Lys Val Pro Ser Lys Lys Phe Lys
20 25 30

Val Leu Gly Asn Thr Asp Arg His Ser Ile Lys Lys Asn Leu Ile Gly
35 40 45

Ala Leu Leu Phe Asp Ser Gly Glu Thr Ala Glu Ala Thr Arg Leu Lys
50 55 60

Arg Thr Ala Arg Arg Arg Tyr Thr Arg Arg Lys Asn Arg Ile Cys Tyr
65 70 75 80

Leu Gln Glu Ile Phe Ser Asn Glu Met Ala Lys Val Asp Asp Ser Phe
85 90 95

Phe His Arg Leu Glu Glu Ser Phe Leu Val Glu Glu Asp Lys Lys His
100 105 110

Glu Arg His Pro Ile Phe Gly Asn Ile Val Asp Glu Val Ala Tyr His
115 120 125

Glu Lys Tyr Pro Thr Ile Tyr His Leu Arg Lys Lys Leu Val Asp Ser
130 135 140

Thr Asp Lys Ala Asp Leu Arg Leu Ile Tyr Leu Ala Leu Ala His Met

```
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575
```

```
Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990
```

```
Gly Thr Ala Leu Ile Lys Lys Tyr  Pro Lys Leu Glu Ser  Glu Phe Val
        995                 1000                 1005

Tyr Gly  Asp Tyr Lys Val Tyr  Asp Val Arg Lys Met  Ile Ala Lys
    1010                 1015                 1020

Ser Glu  Gln Glu Ile Gly Lys  Ala Thr Ala Lys Tyr  Phe Phe Tyr
    1025                 1030                 1035

Ser Asn  Ile Met Asn Phe Phe  Lys Thr Glu Ile Thr  Leu Ala Asn
    1040                 1045                 1050

Gly Glu  Ile Arg Lys Arg Pro  Leu Ile Glu Thr Asn  Gly Glu Thr
    1055                 1060                 1065

Gly Glu  Ile Val Trp Asp Lys  Gly Arg Asp Phe Ala  Thr Val Arg
    1070                 1075                 1080

Lys Val  Leu Ser Met Pro Gln  Val Asn Ile Val Lys  Lys Thr Glu
    1085                 1090                 1095

Val Gln  Thr Gly Gly Phe Ser  Lys Glu Ser Ile Leu  Pro Lys Arg
    1100                 1105                 1110

Asn Ser  Asp Lys Leu Ile Ala  Arg Lys Lys Asp Trp  Asp Pro Lys
    1115                 1120                 1125

Lys Tyr  Gly Gly Phe Asp Ser  Pro Thr Val Ala Tyr  Ser Val Leu
    1130                 1135                 1140

Val Val  Ala Lys Val Glu Lys  Gly Lys Ser Lys Lys  Leu Lys Ser
    1145                 1150                 1155

Val Lys  Glu Leu Leu Gly Ile  Thr Ile Met Glu Arg  Ser Ser Phe
    1160                 1165                 1170

Glu Lys  Asn Pro Ile Asp Phe  Leu Glu Ala Lys Gly  Tyr Lys Glu
    1175                 1180                 1185

Val Lys  Lys Asp Leu Ile Ile  Lys Leu Pro Lys Tyr  Ser Leu Phe
    1190                 1195                 1200

Glu Leu  Glu Asn Gly Arg Lys  Arg Met Leu Ala Ser  Ala Gly Glu
    1205                 1210                 1215

Leu Gln  Lys Gly Asn Glu Leu  Ala Leu Pro Ser Lys  Tyr Val Asn
    1220                 1225                 1230

Phe Leu  Tyr Leu Ala Ser His  Tyr Glu Lys Leu Lys  Gly Ser Pro
    1235                 1240                 1245

Glu Asp  Asn Glu Gln Lys Gln  Leu Phe Val Glu Gln  His Lys His
    1250                 1255                 1260

Tyr Leu  Asp Glu Ile Ile Glu  Gln Ile Ser Glu Phe  Ser Lys Arg
    1265                 1270                 1275

Val Ile  Leu Ala Asp Ala Asn  Leu Asp Lys Val Leu  Ser Ala Tyr
    1280                 1285                 1290

Asn Lys  His Arg Asp Lys Pro  Ile Arg Glu Gln Ala  Glu Asn Ile
    1295                 1300                 1305

Ile His  Leu Phe Thr Leu Thr  Asn Leu Gly Ala Pro  Ala Ala Phe
    1310                 1315                 1320

Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365
```

<210> SEQ ID NO 235
<211> LENGTH: 1367
<212> TYPE: PRT

<213> ORGANISM: Artificial sequence
<220> FEATURE:
<223> OTHER INFORMATION: Synthetic enCas9

<400> SEQUENCE: 235

```
Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
```

385 390 395 400

Gln Arg Thr Phe Asp Asn Gly Ser Ile Pro His Gln Ile His Leu Gly
405 410 415

Glu Leu His Ala Ile Leu Arg Arg Gln Glu Asp Phe Tyr Pro Phe Leu
420 425 430

Lys Asp Asn Arg Glu Lys Ile Glu Lys Ile Leu Thr Phe Arg Ile Pro
435 440 445

Tyr Tyr Val Gly Pro Leu Ala Arg Gly Asn Ser Arg Phe Ala Trp Met
450 455 460

Thr Arg Lys Ser Glu Glu Thr Ile Thr Pro Trp Asn Phe Glu Glu Val
465 470 475 480

Val Asp Lys Gly Ala Ser Ala Gln Ser Phe Ile Glu Arg Met Thr Asn
485 490 495

Phe Asp Lys Asn Leu Pro Asn Glu Lys Val Leu Pro Lys His Ser Leu
500 505 510

Leu Tyr Glu Tyr Phe Thr Val Tyr Asn Glu Leu Thr Lys Val Lys Tyr
515 520 525

Val Thr Glu Gly Met Arg Lys Pro Ala Phe Leu Ser Gly Glu Gln Lys
530 535 540

Lys Ala Ile Val Asp Leu Leu Phe Lys Thr Asn Arg Lys Val Thr Val
545 550 555 560

Lys Gln Leu Lys Glu Asp Tyr Phe Lys Lys Ile Glu Cys Phe Asp Ser
565 570 575

Val Glu Ile Ser Gly Val Glu Asp Arg Phe Asn Ala Ser Leu Gly Thr
580 585 590

Tyr His Asp Leu Leu Lys Ile Ile Lys Asp Lys Asp Phe Leu Asp Asn
595 600 605

Glu Glu Asn Glu Asp Ile Leu Glu Asp Ile Val Leu Thr Leu Thr Leu
610 615 620

Phe Glu Asp Arg Glu Met Ile Glu Glu Arg Leu Lys Thr Tyr Ala His
625 630 635 640

Leu Phe Asp Asp Lys Val Met Lys Gln Leu Lys Arg Arg Arg Tyr Thr
645 650 655

Gly Trp Gly Arg Leu Ser Arg Lys Leu Ile Asn Gly Ile Arg Asp Lys
660 665 670

Gln Ser Gly Lys Thr Ile Leu Asp Phe Leu Lys Ser Asp Gly Phe Ala
675 680 685

Asn Arg Asn Phe Met Gln Leu Ile His Asp Asp Ser Leu Thr Phe Lys
690 695 700

Glu Asp Ile Gln Lys Ala Gln Val Ser Gly Gln Gly Asp Ser Leu His
705 710 715 720

Glu His Ile Ala Asn Leu Ala Gly Ser Pro Ala Ile Lys Lys Gly Ile
725 730 735

Leu Gln Thr Val Lys Val Val Asp Glu Leu Val Lys Val Met Gly Arg
740 745 750

His Lys Pro Glu Asn Ile Val Ile Glu Met Ala Arg Glu Asn Gln Thr
755 760 765

Thr Gln Lys Gly Gln Lys Asn Ser Arg Glu Arg Met Lys Arg Ile Glu
770 775 780

Glu Gly Ile Lys Glu Leu Gly Ser Gln Ile Leu Lys Glu His Pro Val
785 790 795 800

Glu Asn Thr Gln Leu Gln Asn Glu Lys Leu Tyr Leu Tyr Tyr Leu Gln
805 810 815

```
Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Ala Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Ala Leu Glu Ser  Glu Phe Val
        995                 1000                 1005

Tyr Gly  Asp Tyr Lys Val Tyr  Asp Val Arg Lys Met  Ile Ala Lys
    1010                 1015                 1020

Ser Glu  Gln Glu Ile Gly Lys  Ala Thr Ala Lys Tyr  Phe Phe Tyr
    1025                 1030                 1035

Ser Asn  Ile Met Asn Phe Phe  Lys Thr Glu Ile Thr  Leu Ala Asn
    1040                 1045                 1050

Gly Glu  Ile Arg Lys Ala Pro  Leu Ile Glu Thr Asn  Gly Glu Thr
    1055                 1060                 1065

Gly Glu  Ile Val Trp Asp Lys  Gly Arg Asp Phe Ala  Thr Val Arg
    1070                 1075                 1080

Lys Val  Leu Ser Met Pro Gln  Val Asn Ile Val Lys  Lys Thr Glu
    1085                 1090                 1095

Val Gln  Thr Gly Gly Phe Ser  Lys Glu Ser Ile Leu  Pro Lys Arg
    1100                 1105                 1110

Asn Ser  Asp Lys Leu Ile Ala  Arg Lys Lys Asp Trp  Asp Pro Lys
    1115                 1120                 1125

Lys Tyr  Gly Gly Phe Asp Ser  Pro Thr Val Ala Tyr  Ser Val Leu
    1130                 1135                 1140

Val Val  Ala Lys Val Glu Lys  Gly Lys Ser Lys Lys  Leu Lys Ser
    1145                 1150                 1155

Val Lys  Glu Leu Leu Gly Ile  Thr Ile Met Glu Arg  Ser Ser Phe
    1160                 1165                 1170

Glu Lys  Asn Pro Ile Asp Phe  Leu Glu Ala Lys Gly  Tyr Lys Glu
    1175                 1180                 1185

Val Lys  Lys Asp Leu Ile Ile  Lys Leu Pro Lys Tyr  Ser Leu Phe
    1190                 1195                 1200

Glu Leu  Glu Asn Gly Arg Lys  Arg Met Leu Ala Ser  Ala Gly Glu
    1205                 1210                 1215
```

```
Leu Gln  Lys Gly Asn Glu Leu  Ala Leu Pro Ser Lys  Tyr Val Asn
    1220                 1225                 1230

Phe Leu  Tyr Leu Ala Ser His  Tyr Glu Lys Leu Lys  Gly Ser Pro
    1235                 1240                 1245

Glu Asp  Asn Glu Gln Lys Gln  Leu Phe Val Glu Gln  His Lys His
    1250                 1255                 1260

Tyr Leu  Asp Glu Ile Ile Glu  Gln Ile Ser Glu Phe  Ser Lys Arg
    1265                 1270                 1275

Val Ile  Leu Ala Asp Ala Asn  Leu Asp Lys Val Leu  Ser Ala Tyr
    1280                 1285                 1290

Asn Lys  His Arg Asp Lys Pro  Ile Arg Glu Gln Ala  Glu Asn Ile
    1295                 1300                 1305

Ile His  Leu Phe Thr Leu Thr  Asn Leu Gly Ala Pro  Ala Ala Phe
    1310                 1315                 1320

Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365
```

<210> SEQ ID NO 236
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 236

```
gacaagaagt acagcatcgg gctggcgatc gggaccaact ccgtcggctg ggctgtgatt     60

accgacgagt acaaggtgcc atccaagaag ttcaaggtcc tcggcaacac tgaccggcac    120

agcattaaga agaacctgat tggggcgctg ctgttcgatt cgggggagac tgcggaggcg    180

accaggctga agcggactgc gcgccggagg tacaccagga ggaagaatcg gatctgctac    240

ctccaggaga ttttctcgaa tgagatggcc aaggtggacg attccttctt ccatcgcctg    300

gaggagtcgt tcctcgttga ggaggacaag aagcatgaga ggcatcccat tttcgggaat    360

atcgttgacg aggtggctta ccatgagaag tacccgacca tctaccatct gcggaagaag    420

ctcgtcgatt cgaccgataa ggccgacctg cggctgatct acctggccct cgcgcacatg    480

attaagttcc ggggccattt cctcatcgag ggcgacctca acccggacaa ctcggacgtg    540

gataagctct tcattcagct cgtgcagaca tacaaccagc tcttcgagga gaatcccatt    600

aacgcctcgg gggtcgacgc taaggctatt ctctcggctc ggctgtcgaa gtcgcgccgg    660

ctggagaatc tcattgccca gctcccaggc gagaagaaga acggcctctt cggcaacctg    720

attgccctgt cgctggggct cacaccgaat ttcaagtcga acttcgacct cgccgaggac    780

gctaagctcc agctcagcaa ggatacttac gatgatgacc tcgataacct gctcgcccag    840

attggggatc agtacgcgga tctgttcctc gcggccaaga atctcagcga tgctattctc    900

ctgtcggaca ttctccgcgt caacacagag attactaagg ccccactgtc ggcgagcatg    960

attaagaggt acgatgagca tcatcaggac ctgacactgc tcaaggcgct ggtccggcag   1020

cagctccccg agaagtacaa ggagattttc ttcgatcagt caaagaatgg gtacgcgggc   1080

tacattgatg gcggcgcgtc ccaggaggag ttctacaagt tcattaagcc catcctggag   1140

aagatggacg ggaccgagga gctgctggtg aagctcaatc gggaggacct gctccggaag   1200
```

```
cagcgcacat tcgacaatgg ctcgattcct caccagattc acctgggcga gctgcacgcc   1260
attctccgca ggcaggagga cttctacccg ttcctcaagg acaaccgcga gaagatcgag   1320
aagatcctga ccttccggat tccatactac gtggggccgc tcgcgcgggg gaactcccgg   1380
ttcgcgtgga tgactcgcaa gtccgaagaa acgattacac cgtggaattt cgaggaggtc   1440
gtcgacaagg gcgctagtgc gcagtcattc attgagagga tgaccaattt cgataagaac   1500
ctgcctaacg agaaggtgct gccgaagcat tcgctgctct acgagtactt caccgtttac   1560
aatgagctga ccaaggtgaa gtatgtgact gagggcatga ggaagccagc gttcctgagc   1620
ggcgagcaga agaaggctat cgtggacctg ctcttcaaga ctaaccggaa ggtgactgtg   1680
aagcagctca aggaggacta cttcaagaag attgagtgct tcgattccgt tgagattagc   1740
ggggtggagg atcggttcaa tgcttcgctc gggacatacc acgatctcct gaagatcatt   1800
aaggataagg acttcctcga caacgaggag aacgaggaca ttctcgaaga tattgtcctg   1860
accctcaccc tcttcgagga tcgggagatg atcgaggaga ggctcaagac atacgctcat   1920
ctgttcgatg ataaggtcat gaagcagctg aagcgcaggc ggtacacagg gtgggggcgg   1980
ctgagccgga agctgatcaa cggattcgg gataagcagt ccgggaagac aattctcgac   2040
ttcctcaagt ccgacgggtt cgctaaccgg aacttcatgc agctcattca tgatgactcg   2100
ctgacattca aggaggatat tcagaaggcg caggtttcgg ggcagggcga ctcgctccac   2160
gagcatattg cgaatctggc gggctccccc gcgattaaga agggcattct gcaaaccgtc   2220
aaggtggttg atgagctggt caaggtcatg ggcggcata agccagagaa tattgtcatc   2280
gagatggcgc gggagaatca gaccacacag aaggggcaga agaactcacg ggagcggatg   2340
aagcgcatcg aggagggcat caaggagctg ggtcgcaga tcctgaagga gcatcccgtg   2400
gagaacactc agctgcaaaa tgagaagctg tacctctact acctccagaa cgggagggac   2460
atgtatgtgg atcaggagct ggatattaat aggctgagcg attacgatgt cgaccacatt   2520
gtcccacagt cgttcctgaa ggacgacagc attgacaaca aggtgctgac ccgctcggat   2580
aagaacaggg gcaagagcga taatgttcca agcgaggagg ttgtgaagaa gatgaagaac   2640
tactggcggc agctcctgaa cgcgaagctc atcacacagc ggaagttcga caacctcacc   2700
aaggctgagc gcgggggcct gagcgagctg gacaaggcgg ggttcattaa gaggcagctg   2760
gtcgagacac ggcagattac aaagcatgtt gcgcagattc tcgattcccg gatgaacacc   2820
aagtacgatg agaacgataa gctgattcgg gaggtcaagg taattaccct gaagtccaag   2880
ctggtgtccg acttcaggaa ggacttccag ttctacaagg ttcgggagat caacaactac   2940
caccacgcgc atgatgccta cctcaacgcg gtcgtgggga ccgctctcat caagaagtac   3000
ccaaagctgg agtcagagtt cgtctacggg gattacaagg tttacgacgt gcggaagatg   3060
atcgctaaga gcgagcagga gattggcaag gctaccgcta agtacttctt ctactccaac   3120
atcatgaact tcttcaagac agagattacc ctcgcgaatg gcgagatccg gaagaggccc   3180
ctcatcgaga caaatgggga gacaggggag attgtctggg ataaggggcg ggatttcgcg   3240
accgtccgga aggtcctgtc gatgccccag gttaatattg tcaagaagac tgaggtccag   3300
actggcggct tctcaaagga gtcgattctc ccaaagagga actccgataa gctcattgct   3360
cggaagaagg attgggaccc caagaagtac gggggattcg actcccccac tgttgcttac   3420
tctgttctgg ttgttgctaa ggtggagaag gggaagtcga agaagctgaa gagcgtgaag   3480
gagctgctcg ggattacaat tatggagagg tcatccttcg agaagaatcc catcgacttc   3540
```

```
ctggaggcca agggctacaa ggaggtgaag aaggacctga ttattaagct gcccaagtac   3600
tcgctcttcg agctggagaa tgggcggaag cggatgctgg cgtccgcggg ggagctgcaa   3660
aaggggaacg agctggcgct cccctccaag tatgtgaact tcctctacct ggcgtcgcac   3720
tacgagaagc tgaaggggtc cccagaggat aatgagcaga agcagctctt cgtcgagcag   3780
cataagcact acctggacga gattatcgag cagattagcg agttctcgaa gcgggtcatc   3840
ctcgcggatg cgaacctgga taaggtgctc agcgcctaca ataagcaccg ggacaagccg   3900
attcgggagc aggcggagaa tattattcac ctcttcacac tcaccaacct cggggcacca   3960
gctgcgttca agtacttcga cactactatc gaccggaagc ggtacacctc gacgaaggag   4020
gtgctcgacg ccaccctcat tcaccagtcg atcacaggcc tgtacgagac acggattgac   4080
ctgtcccagc tcgggggcga c                                             4101
```

```
<210> SEQ ID NO 237
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 237
```

```
gacaagaagt actccattgg cctggcgatt gggacaaact cggtggggtg ggccgtgatt     60
acggatgagt acaaggttcc aagcaagaag ttcaaggtcc tcgggaacac agatcggcat    120
tcgattaaga agaatctcat tggggcgctc ctcttcgact cgggggagac agcggaggct    180
accaggctca agcggacagc caggcggcgg tacacaaggc ggaagaatcg catctgctac    240
ctccaggaga ttttctcgaa tgagatggcg aaggtggacg acagcttctt ccatcggctg    300
gaggagtcct tcctggtgga ggaggataag aagcacgaga ggcatccaat tttcgggaac    360
atcgtggacg aggttgcgta ccatgagaag taccctacaa tctaccatct gcggaagaag    420
ctggttgact ccacagacaa ggcggacctg aggctgatct acctcgctct ggcccacatg    480
attaagttcc gcgggcattt cctgatcgag ggggacctga atcccgacaa ttcggatgtg    540
gacaagctct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga atgggctctt cgggaatctg    720
attgcgctct ccctggggct gacaccgaac ttcaagagca atttcgatct ggctgaggac    780
gcgaagctcc agctctcgaa ggacacttac gacgatgacc tcgataacct cctcgcgcag    840
atcggggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg ggacagagga gctgctggtg aagctcaacc gggaggatct gctcaggaag   1200
cagcggacgt tcgacaacgg gtcgattccc catcagatcc acctgggggga gctgcacgcg   1260
atcctgcgcc ggcaggagga tttctaccct ttcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
```

-continued

```
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggagc gcctgaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcagcg gccagggcga ctcgctgcat   2160
gagcacatcg ctaacctggc gggcagccca gccatcaaga agggcatcct ccagacagtg   2220
aaggtcgtgg atgagctggt gaaggtcatg ggccggcata agcccgagaa tattgtgatt   2280
gagatggcgc gggagaatca gaccactcag aagggccaga agaactcgcg ggagcgcatg   2340
aagaggatcg aggaggggat taaggagctg ggcagccaga ttctcaagga gcacccccgtg   2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtcaaag   2880
ctcgttagcg atttccggaa ggacttccag ttctacaagg tgcgggagat taacaactac   2940
catcatgcgc acgatgcgta cctcaatgcg gtggtgggca cagccctgat taagaagtac   3000
cccaagctgg agagcgagtt cgtctacggg gactacaagg tgtacgatgt tcggaagatg   3060
atcgccaaga gcgagcagga gattgggaag gccaccgcta agtacttctt ctactcgaat   3120
attatgaatt tcttcaagac cgagatcaca ctcgctaatg gggagattcg gaagcggccc   3180
ctcatcgaga ctaacgggga gactggcgag attgtgtggg acaaggggcg cgacttcgct   3240
accgtgcgca aggtcctctc gatgccccag gttaatattg ttaagaagac agaggtgcag   3300
acgggcgggt tctccaagga gtctatcctg ccgaagcgga actcggacaa gctgatcgcc   3360
cgcaagaagg attgggaccc caagaagtac gggggattcg atagcccaac cgtggcttac   3420
agcgtcctgg tggtcgccaa ggttgagaag ggaagtcga agaagctcaa gagcgttaag   3480
gagctgctgg gcatcaccat catggagcgg tccagcttcg agaagaatcc tatcgacttc   3540
ctggaggcta aggggtacaa ggaggtcaag aaggacctga tcattaagct gcccaagtac   3600
tctctgttcg agctggagaa cgggaggaag cggatgctgg cgtctgctgg cgagctacag   3660
aagggcaatg agctggcgct cccctcgaag tatgtcaact tcctctacct ggcttcccat   3720
tacgagaagc tgaagggctc gcccgaggat aatgagcaga agcagctctt cgtggagcag   3780
cacaagcact acctcgacga gatcattgag cagatttcgg agttctcgaa gcgggtcatt   3840
```

ctcgcggacg cgaacctcga caaggtcctc tcggcgtaca acaagcaccg ggacaagccc 3900
atccgggagc aggccgagaa cattatccac ctcttcacac tgaccaacct cggcgctccc 3960
gccgcgttca agtacttcga caccaccatt gaccgcaaga gatacacatc caccaaggag 4020
gtgctggacg cgaccctcat ccaccagagc atcacaggcc tctacgagac acggatcgac 4080
ctctcgcagc tcgggggcga t 4101

<210> SEQ ID NO 238
<211> LENGTH: 4092
<212> TYPE: DNA
<213> ORGANISM: Unknown
<220> FEATURE:
<223> OTHER INFORMATION: Cas9 nucleotide sequence

<400> SEQUENCE: 238
gacaagaagt actcgatcgg cctggcgatt ggcacaaaca gcgtggggtg ggctgtgatc 60
actgatgagt acaaggtgcc atcgaagaag ttcaaggtgc tggggaatac agaccggcat 120
tcgatcaaga agaatctcat tggcgctctc ctcttcgatt ccggcgagac tgctgaggcg 180
acccgcctga agcgcaccgc ccggcggcgc tacactcggc ggaagaatag gatttgctac 240
ctccaggaga ttttctcgaa tgagatggcc aaggtggatg acagcttctt ccaccgcctg 300
gaggagtcgt tcctggtcga ggaggacaag aagcatgagc ggcaccctat cttcgggaat 360
atcgttgatg aggtcgccta ccacgagaag taccccacta tctaccatct ccgcaagaag 420
ctcgtggaca gcacagataa ggccgacctc cgcctgatct acctcgccct cgcgcacatg 480
attaagttcc gggggcactt cctcattgag ggggatctga atcccgataa ctccgacgtg 540
gacaagctgt tcatccagct ggtgcagaca tacaaccagc tgttcgagga gaatcccatc 600
aacgcgagcg gcgtggacgc taaggccatt ctgtcggcta ggctctcgaa gtcgaggcgg 660
ctggagaacc tgattgcgca gctccccggc gagaagaaga acgggctgtt cgggaatctc 720
atcgccctct ccctcggcct cacaccaaac ttcaagagca atttcgacct ggctgaggac 780
gctaagctgc aactctcaaa ggatacatac gatgacgacc tggacaatct cctggctcag 840
atcggcgacc agtacgctga cctgttcctc gcggccaaga atctgtcgga cgcgattctc 900
ctcagcgaca tcctgcgcgt caataccgag attacgaagg ctccactgtc tgcgtcaatg 960
attaagcggt acgatgagca tcaccaggat ctgaccctcc tgaaggcgct cgtgcggcag 1020
cagctgcccg agaagtacaa ggagattttc ttcgatcaga gcaagaatgg ctacgccggc 1080
tacatcgacg gggcgcgag ccaggaggag ttctacaagt tcatcaagcc catcctggag 1140
aagatggacg gcaccgagga gctactcgtg aagctcaatc gggaggatct cctccggaag 1200
cagcggacat tcgataacgg gtctatccca caccagatcc acctcggcga gctgcatgcg 1260
attctgcggc ggcaggagga tttctaccct ttcctgaagg acaaccggga gaagatcgag 1320
aagatcctca cattccggat tccatactac gtcggccccc tggcgagggg caatagccgg 1380
ttcgcgtgga tgacaaggaa gtccgaggag actattaccc cgtggaattt cgaggaggtg 1440
gttgacaagg gcgcttccgc gcagagcttc attgagcgga tgacaaactt cgacaagaat 1500
ctccccaacg agaaggtcct gccgaagcat agcctcctgt acgagtactt caccgtctac 1560
aatgagctaa ctaaggtcaa gtatgtgaca gagggcatga ggaagccagc cttcctctca 1620
ggcgagcaga agaaggccat tgtggacctc ctgttcaaga caaaccgcaa ggtgacagtg 1680
aagcagctga aggaggatta cttcaagaag attgagtgct tcgactcagt ggagatttca 1740
ggcgtggagg atcggttcaa cgcgagcctg ggacttacc acgacctgct gaagattatt 1800

```
aaggacaagg acttcctgga taacgaggag aatgaggaca tcctggagga tattgtgctc    1860

accctcaccc tgttcgagga cagggagatg attgaggaga ggctcaagac ctacgcgcac    1920

ctgttcgatg acaaggtcat gaagcagctg aagaggcggc gctacactgg gtggggccgc    1980

ctgtcgcgga agctgatcaa cggcattcgg gataagcagt ccgggaagac cattctggat    2040

ttcctgaagt cggacggctt cgccaacagg aatttcatgc agctgatcca cgacgactcc    2100

ctcaccttca aggaggacat tcagaaggcc caggttagcg gccaggggga ctcactccac    2160

gagcatattg ccaatctggc cggctctcca gctatcaaga agggcatcct gcaaacagtt    2220

aaggttgttg acgagctggt taaggtcatg gggcggcata gcccgagaa cattgtcatc     2280

gagatggctc gggagaacca gacaactcag aagggccaga agaactccag ggagcgcatg    2340

aagcggattg aggagggcat taaggagctg gggtcccaga tcctcaagga gcaccctgtc    2400

gagaacactc agctgcaaaa cgagaagctc tacctgtact acctccagaa cgggcgggat    2460

atgtatgtgg atcaggagct ggacatcaac aggctctccg actacgacgt ggatcacatt    2520

gtcccacagt ctttcctcaa ggatgattcc atcgacaaca aggtgctgac gcgcagcgac    2580

aagaataggg ggaagtcgga caacgttccg agcgaggagg tcgtgaagaa gatgaagaat    2640

tactggaggc agctcctgaa tgcgaagctg atcactcaga ggaagttcga caatctgaca    2700

aaggcggaga ggggcgggct ctcggagctg gataaggcgg gcttcatcaa gcggcagctc    2760

gttgaaaccc ggcagatcac caagcatgtc gcccagatcc tcgatagccg catgaacacc    2820

aagtacgatg agaacgacaa gctcattcgg gaggttaagg tcattacgct gaagtccaag    2880

ctcgtcagcg acttcaggaa ggatttccag ttctacaagg ttcgggagat taacaactac    2940

caccacgcgc atgatgcgta cctgaacgct gttgtcggca ctgctctcat caagaagtac    3000

ccaaagctgg agtccgagtt cgtctacggg gactacaagg tctacgatgt ccggaagatg    3060

atcgccaagt cggagcagga gatcgggaag gctactgcga agtacttctt ctacagcaac    3120

attatgaatt tcttcaagac ggagattacg ctggcgaacg gggagattag gaagaggccc    3180

ctcattgaga ctaatgggga gacaggcgag attgtttggg acaagggccg cgacttcgcg    3240

actgtgcgga aggtcctgtc catgccacag gtgaatattg ttaagaagac agaggtgcag    3300

actgggggct tctcgaagga gagcattctc ccaaagcgga acagcgataa gctcatcgcg    3360

cgcaagaagg attgggaccc taagaagtac ggcggcttcg attctcccac tgtggcctac    3420

tccgttctcg tggttgccaa ggttgagaag gggaagtcga agaagctgaa gtcggtcaag    3480

gagctgctcg ggattacaat catggagcgg agcagcttcg agaagaaccc tattgatttc    3540

ctggaggcca agggctacaa ggaggttaag aaggatctca ttatcaagct ccctaagtac    3600

tctctgttcg agctggagaa tggccggaag aggatgctgg cctcggctgg cgagctacag    3660

aaggggaatg agctggccct cccgtcgaag tatgtgaatt tcctgtacct cgcgtcgcac    3720

tacgagaagc tcaagggcag cccggaggat aatgagcaga agcagctctt cgtggagcag    3780

cataagcact acctggacga gatcattgag cagatcagcg agttctcgaa gcgggttatt    3840

ctggctgatg ctaacctgga caaggttctg agcgcctaca ataagcatcg cgacaagccg    3900

attcgcgagc aggcggagaa tattatccac ctgttcaccc tcactaacct cggggctccc    3960

gcggccttca gtacttcga taccacaata gataggaagc ggtacacctc gacgaaggag    4020

gtcctcgacg ccacactcat ccatcagtcg attacaggcc tgtacgagac acggattgac    4080

ctctcgcagc tg                                                         4092
```

<210> SEQ ID NO 239
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 239

```
gacaagaagt attccatagg cctggctatc ggcaccaaca gcgtgggctg ggccgtcatc     60
accgacgagt acaaagtgcc gagtaaaaag ttcaaagtgc tcggcaacac cgaccgccac    120
tccataaaga aaaacctgat cggggcgctc ctgttcgaca gcggcgagac ggcggaggcc    180
acccgcttga aacgcacggc ccgacggcgc tacacgcggc gcaagaaccg gatctgttac    240
ctacaggaga ttttctctaa cgagatggcg aaggtggacg actcgttctt tcaccgcctc    300
gaagagtcct tcctcgtgga ggaggacaag aaacacgagc gccacccgat cttcggcaac    360
atcgtggacg aggtggccta ccacgagaag tacccgacca tctaccacct ccggaagaaa    420
ctcgtggaca gcacggacaa ggccgacctg aggctcatct acctcgccct ggcgcacatg    480
attaagttcc ggggccactt cctgatcgag ggcgacctga acccggacaa cagcgacgtg    540
gacaagctgt tcatccagct agtccagacc tacaaccagc ttttcgagga aaaccccatc    600
aacgccagcg gggtggacgc gaaggcgatc ctgtccgccc ggctgagcaa gtcccggcgg    660
ctggagaacc tcatcgcgca gttgcccggc gagaagaaga acgggctgtt cgggaacctg    720
atcgccctct ccctggggct caccccgaac ttcaagtcca acttcgacct cgccgaggac    780
gccaaactac agctgagcaa ggacacctac gacgacgacc tcgacaacct gctggcccag    840
atcggggacc agtacgcaga cctgttcctc gccgccaaga acctctccga cgccatcctg    900
ctgtcggaca tcctgcgggt gaacacggag atcacgaagg ccccgctctc ggcctcgatg    960
attaaacgct acgacgagca ccaccaggac ttgaccctcc tcaaggcgct ggtccgccag   1020
cagcttcccg agaagtacaa ggaaatcttt ttcgatcaga gcaagaacgg gtacgccggg   1080
tacatcgacg gcggggcgtc ccaggaggag ttctacaagt tcatcaagcc catcctggag   1140
aaaatggacg ggaccgagga gctgctcgtg aagctcaacc gcgaagattt gctccgcaag   1200
cagcgcacgt tcgacaacgg gtcgatcccg caccagatcc acctgggcga gctgcacgcg   1260
atcctcaggc gtcaggaaga cttctacccc ttcctcaagg acaaccgcga gaagatagag   1320
aagattctga ccttcagaat tccttattac gtgggcccgc tggctcgggg caactcgcgc   1380
ttcgcctgga tgacgcgcaa gtccgaggag accatcaccc cgtggaactt cgaggaggtg   1440
gtggataagg gtgcctcggc ccagtccttc atcgagcgga tgaccaactt cgacaagaac   1500
ctgccgaacg agaaggtgct ccccaagcac agcctgctct acgaatattt cacggtgtac   1560
aacgagctga cgaaggtcaa gtacgtgacc gagggaatga ggaaacctgc attcctctcc   1620
ggggagcaga agaaagccat agtcgacctc ctgttcaaga ccaaccggaa ggtcaccgtc   1680
aagcagctca aggaggacta cttcaagaag atcgagtgct tcgattcagt ggagatcagc   1740
ggcgtcgagg accggttcaa cgccagcctg ggcacctacc acgacctgct caagatcatc   1800
aaggacaagg acttcctcga caacgaggag aacgaggaca tcctggagga catcgtgctg   1860
accctgacgc tcttcgagga ccgcgagatg atcgaggagc gcctcaagac ctacgcccac   1920
ctgttcgacg acaaggtgat gaagcagctc aagcggcgga gatatactgg gtggggccgc   1980
ctctcccgga agctcattaa cggtatcagg gataagcagt ccgggaagac gatcctcgac   2040
ttcctcaagt cggacgggtt cgccaaccgc aacttcatgc agctcatcca cgacgactcc   2100
```

ctgacgttca aggaggacat ccagaaggcc caagtgtctg gtcaaggtga ctcgctccac 2160
gagcacatcg ccaacctcgc gggcagcccg gccatcaaga agggaatact ccagaccgtc 2220
aaggtggtgg acgagctggt gaaggtcatg ggccgccaca agccggagaa catcgtcatc 2280
gagatggcgc gggagaacca gaccacgcag aaggggcaga aaaatagccg tgagcgcatg 2340
aagcgcatcg aggaggggat taaggagttg ggcagccaga tcctcaagga gcaccctgtg 2400
gagaacacgc agttgcaaaa cgagaagctc tacctgtact acctccagaa cgggagggat 2460
atgtacgtgg accaagaact ggacatcaac cgcctgtccg actacgacgt ggaccacatc 2520
gtgccgcaga gcttcctcaa ggacgacagc atcgacaaca aggtgctcac ccggtccgac 2580
aagaatcggg gcaagtccga caacgtgccc agcgaggagg tcgtcaaaaa gatgaaaaac 2640
tactggcgac aactactgaa cgccaagctc atcacccagc gcaagttcga caacctcaca 2700
aaagccgagc gcggcgggtt gagcgagctg gacaaggccg ggttcatcaa gcgccagctc 2760
gtcgagacgc gccagatcac gaagcacgtc gcgcagatac tcgacagccg gatgaacacc 2820
aagtacgacg agaacgacaa gctcatccgg gaggtgaagg tcatcaccct caagtcgaag 2880
ctcgtgagcg acttccgcaa ggacttccag ttctacaagg tccgggagat caacaactac 2940
caccacgccc acgatgctta tcttaacgcc gtggtgggga cggccctcat taagaaatac 3000
ccgaagctgg agtcggagtt cgtgtacggc gactacaagg tgtacgacgt caggaagatg 3060
atcgccaagt ccgaacagga gatcgggaag gccacggcga aatacttctt ctacagcaac 3120
atcatgaact tcttcaagac cgagatcacc ctcgccaacg gcgagatccg caagcgcccg 3180
ctcatcgaga cgaacgggga gaccggcgag atcgtctggg acaaggggcg cgacttcgcc 3240
actgtgcgga aggtgctgtc gatgccccag gtcaacatcg tcaagaagac ggaggtccag 3300
acgggcgggt tcagcaagga gagcatcctg ccgaagcgca acagcgacaa gctgatcgcc 3360
cgcaaaaagg actgggatcc aaaaaagtac ggcggcttcg acagccccac cgtcgcctac 3420
agcgtcctcg tcgtcgctaa agtcgagaag ggcaagtcca aaaagctcaa gagcgtcaag 3480
gagctgctcg ggatcaccat catggagcgg tccagcttcg agaagaaccc aattgatttc 3540
ctggaggcga agggctacaa ggaggtcaag aaagacctca tcataaagct gccgaagtac 3600
tcactcttcg agctggagaa cgggcgcaag cggatgctgg cgtcggccgg agagctccaa 3660
aagggcaacg agctggcgct gccgagcaag tacgtgaact tcctctacct ggcgtcccac 3720
tacgagaagc tcaagggcag tccagaggat aacgagcaga agcagctatt cgtggagcag 3780
cacaagcact acctggacga gatcatcgag cagatcagcg agttctccaa gcgcgtcatc 3840
ctggcggacg ccaacctgga caaggtgctg tccgcgtaca acaagcaccg cgacaagccg 3900
atccgcgagc aagccgagaa catcatccac ctgttcaccc tcacgaacct cggggcaccc 3960
gccgccttca aatatttcga cacgaccatc gaccgcaagc gctacaccag cacgaaggag 4020
gtgctcgacg ccaccctgat ccaccagagc atcaccgggc tgtacgagac ccgcatcgac 4080
ctctcgcagc tcggcgggga c 4101

<210> SEQ ID NO 240
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 240

-continued

```
gacaagaagt acagtattgg attggccatc gggacgaaca gcgtgggctg ggccgtcatc     60
accgacgagt acaaggtgcc atccaagaag tttaaggttc tggggaatac cgaccgccac    120
tcgatcaaga aaaatctcat cggggcgctg cttttcgaca gcggcgagac ggcggaagcg    180
acgcggctca agcggacggc tcgtcgccgt tacacccggc gtaagaaccg catctgttac    240
ctccaggaga tattcagcaa cgagatggcg aaggtggacg actccttttt ccaccgtctt    300
gaggagtcct tcctggtcga ggaggacaag aagcacgagc gccaccccgat cttcgggaac    360
atcgtggacg aggtggccta ccacgagaag taccccacga tctaccacct ccgcaaaaaa    420
ctcgtggact caactgacaa ggccgatttg aggcttatct acctcgccct cgcccacatg    480
attaagttcc gtgggcactt cctaatcgag ggtgacctca accccgacaa ctctgacgtg    540
gacaagctgt tcatccagct tgtgcagacc tacaatcagc tctttgagga gaatccgatc    600
aacgcatctg gtgtggacgc aaaggccatc ctcagcgcgc ggctgagcaa gtctaggcgg    660
ttggagaacc tgatcgccca actgcccggc gagaagaaaa atggcctctt cggcaacctg    720
atcgccctgt cgctggggct cacgccgaac ttcaagagta actttgacct ggcggaggac    780
gctaagctcc agctatctaa ggacacatac gacgacgacc tggacaacct gctggcccag    840
atcggcgacc agtacgccga cctcttccta gccgccaaga acctgtccga cgccatcctc    900
ctcagcgaca tcctgcgcgt gaacacggag atcacgaagg ctccgctcag cgcctccatg    960
attaagcggt acgacgagca ccaccaagac ctaactttac tcaaagccct cgtgcggcag   1020
cagcttcccg agaagtacaa agagatattt tttgatcagt ccaagaacgg ttatgcgggc   1080
tacatcgacg gcggcgcgag ccaggaggag ttctacaagt tcatcaagcc catcctggag   1140
aagatggacg gcacggagga gctgctcgtg aagctcaacc gtgaagacct cctgcgaaag   1200
cagcgaacct tcgacaacgg ttcgatcccg caccagatcc acctcgggga gctgcacgcc   1260
atcctgaggc gacaggagga cttctaccct ttcctaaagg acaaccgcga gaagattgaa   1320
aaaatcctga cgtttcgcat accctactac gtcggcccgc tggcgcgcgg caactcccgg   1380
ttcgcctgga tgacccgtaa gagcgaggag acgatcaccc cgtggaactt cgaggaggtc   1440
gtggacaagg gcgcgagcgc gcagagcttc atcgagcgca tgaccaactt cgacaagaac   1500
ctcccgaacg agaaggtgct cccaaagcac tccctcctgt acgagtattt caccgtgtac   1560
aacgagttga caaaggtgaa gtacgtgacg gagggaatgc ggaagcctgc gttcctctcg   1620
ggcgagcaga agaaggcaat cgtggacctg ctcttcaaga ccaaccggaa ggtgacggtg   1680
aagcagctca aggaggacta cttcaaaaaa atcgagtgct tcgactccgt ggagataagc   1740
ggcgtggagg accgattcaa cgcctccctc ggcacctacc acgacctcct taagatcatc   1800
aaggacaagg acttcctgga caacgaggag aacgaggaca tcctggagga catcgtgctc   1860
accctgaccc tcttcgagga ccgggagatg atcgaggagc gcctcaagac gtacgcccac   1920
ttgttcgacg acaaggtgat gaagcagctc aagcggcggc gatacaccgg gtggggccgc   1980
ctatcccgca aacttatcaa cggcatccgc gacaagcagt ccggcaagac gatcctggat   2040
ttcctcaagt cggacgggtt cgccaaccgg aacttcatgc agctcatcca cgacgacagc   2100
ctcacgttca aggaggacat ccagaaggcc caagtgagcg gtcaagggga cagcctccac   2160
gagcacattg cgaaccttgc tgggagccct gcgatcaaga aggggatatt gcaaaccgtg   2220
aaggtcgtgg acgagttggt gaaggtcatg ggcgacacaa agcccgagaa catcgtgatc   2280
gagatggcca gggaaaatca gaccacgcag aagggccaaa aaaacagccg cgagcggatg   2340
aagcggatcg aggagggcat caaggagctg ggtcgcaga tcctcaagga gcacccggtg   2400
```

```
gagaacacgc agctccagaa cgagaagctg tacctctatt acctacagaa cgggcgggat   2460

atgtacgtgg accaggagct agacatcaac cgcctgtccg actacgacgt ggaccatatc   2520

gtcccgcagt cgttcttgaa ggacgacagc atcgacaaca aggtgctcac aagatcggat   2580

aagaatcgag gcaagtccga caacgtgccc tcggaggagg tggtcaagaa aatgaaaaac   2640

tactggcggc agttgctgaa cgccaagctc attacgcagc ggaagttcga caacctgacg   2700

aaggctgaac gtggtgggct cagcgagcta gacaaggcgg ggttcatcaa gcggcagctc   2760

gtcgagaccc ggcagatcac caagcacgtg gcgcagatcc tggactcgcg catgaacacc   2820

aagtacgacg agaacgacaa gctcatccgt gaggtgaagg tcatcaccct taagtctaag   2880

ctggtcagtg acttccgcaa ggacttccag ttctacaagg tccgggagat caacaactac   2940

caccacgcgc acgacgccta cctcaacgcg gtggtgggga cggcgcttat taagaaatat   3000

cccaagctgg aaagcgagtt cgtttacggc gactacaagg tgtacgacgt ccgcaagatg   3060

atcgcaaagt cggaacagga aatcggaaag gcgacggcca aatatttctt ttactccaac   3120

atcatgaatt tttttaagac ggagatcacc ctggcgaacg gggagatccg caagcggccc   3180

ctcatcgaga ccaacgggga gacgggcgag atcgtctggg acaagggccg ggacttcgcc   3240

accgtgcgga aggtgctttc tatgcctcaa gtcaatatcg tcaaaaagac agaggtgcag   3300

accggcgggt tcagcaagga gtctatcctg ccgaagcgca actcggacaa gctcatcgcg   3360

cgcaagaaag actgggaccc caaaaaatat ggcgggttcg actcgccgac cgtcgcctac   3420

agcgtcctcg tggtggctaa ggtcgagaag ggcaagagca aaaagctaaa gtcggtgaag   3480

gagctgctgg gcatcaccat catggagcgc tcgtctttcg agaagaatcc aatcgacttc   3540

ctagaggcga aggggtacaa ggaggtcaaa aaggatctta tcatcaaact gccgaagtac   3600

agtctgttcg agctggagaa cgggcggaag cggatgctgg ctagtgcggg cgagttgcag   3660

aagggcaacg agttggcact gccctccaag tacgtgaact tcctgtacct ggcctcccac   3720

tacgagaagc tcaaggggag ccccgaggac aacgagcaga agcagctatt cgtcgagcag   3780

cacaagcact acctggacga gatcatcgag cagatcagtg agttctccaa gcgggtcatc   3840

ctcgcggacg ccaacctgga caaggtgctg agcgcgtaca acaagcacag ggacaagcca   3900

atcagggaac aggccgagaa catcatccac ctgttcaccc tgaccaacct gggtgcaccg   3960

gctgccttca agtactttga cacgaccatc gaccggaagc gctacacctc cacgaaggag   4020

gtgctggacg ccacgctgat ccaccagagc atcaccgggc tctacgagac acggatcgac   4080

ctgagccagc ttggcgggga c                                             4101
```

<210> SEQ ID NO 241
<211> LENGTH: 4092
<212> TYPE: DNA
<213> ORGANISM: Unknown
<220> FEATURE:
<223> OTHER INFORMATION: Cas9 nucleotide sequence

<400> SEQUENCE: 241

```
gacaaaaagt attccattgg actcgctatc ggcacgaaca gcgtcgggtg ggcggtcatc     60

actgacgagt acaaggtgcc gagcaagaag tttaaggtgc tgggaaacac cgacaggcac    120

tcgatcaaga aaaatcttat cggggcccta ctcttcgact ccggagaaac cgccgaggcc    180

acccggttga agcgcacggc ccgccgtcgc tacaccaggc gcaagaaccg gatctgctac    240

ctccaggaga tattcagcaa tgagatggcg aaggtggacg actcgttttt tcacaggcta    300
```

-continued

```
gaggagtctt tcctcgtgga ggaggacaag aaacacgagc gccaccccat cttcggcaac    360
atcgtggatg aggtggcata tcacgagaag tacccaacca tctaccacct ccgcaaaaag    420
ctcgtggact ctaccgacaa ggccgacctc cgtctgatct acctcgcgct ggcccacatg    480
attaagttcc gaggacactt tctgatcgag ggcgacctga acccagacaa cagcgacgtg    540
gacaagctgt tcatccaact tgtccagacc tacaatcagc tcttcgagga gaaccctatc    600
aacgcctcgg gcgtggacgc gaaggccatc ctgtccgccc gcctgagcaa gtcgcggcgg    660
ctggagaacc tgatcgccca gctccccggc gaaaaaaaga acggcctctt cggcaacctc    720
atcgcgttgt cgctggggct caccccgaac ttcaagtcca acttcgacct ggccgaggac    780
gctaaactcc agctctcgaa ggatacctac gacgacgacc tcgacaacct gctggcccag    840
atcggcgacc agtacgcgga ccttttcctg gcggccaaga acctgagcga cgcgatcctc    900
cttagcgaca tactccgtgt gaacaccgag atcacgaagg ccccgctctc cgcgtccatg    960
attaagcgct acgacgagca ccaccaagac cttaccctgc ttaaggcgct ggtcaggcag   1020
cagttaccgg agaagtacaa ggagatcttt tttgatcaat ctaagaacgg ttacgccggg   1080
tacatcgacg gcggcgcgtc ccaggaggag ttctacaagt tcatcaagcc gatcttggag   1140
aaaatggacg ggaccgagga gctgctcgtg aagctcaacc gcgaagacct cctccgcaag   1200
cagcgcacct tcgacaacgg gagcatcccg caccagatcc acctgggaga gctgcacgcg   1260
atcctgcgga gacaagagga cttctacccc ttcctcaagg acaaccggga gaagattgaa   1320
aaaatactta cttttcgtat cccgtactac gtcgggcccc ttgcgagggg caactccaga   1380
ttcgcgtgga tgacccgcaa gtccgaggag accatcaccc cgtggaactt cgaggaggtg   1440
gtggacaagg gcgcgtcggc ccagtcgttc atcgagcgca tgaccaactt cgacaagaac   1500
cttccgaacg agaaggtgct cccgaagcac agcctgctct acgaatattt tactgtgtac   1560
aacgagctga cgaaggtcaa gtacgttacg gaggggatga ggaagcccgc cttcctctcc   1620
ggcgagcaga agaaagccat tgtggatctc ctgttcaaga ccaaccgcaa ggtgacggtg   1680
aaacagctca aagaggacta cttcaagaag atcgagtgct tcgactccgt agagatcagc   1740
ggggtcgagg accgcttcaa cgcctcgctg ggcacgtacc acgacctgct aaagattatc   1800
aaggacaaag acttcctaga caatgaggag aacgaggaca ttctggagga catcgtgctg   1860
actctgacgc tgttcgaaga ccgcgagatg atcgaggagc ggcttaagac gtacgcccac   1920
ctgttcgacg acaaggtgat gaagcagttg aaacggcggc gctacaccgg gtggggccgc   1980
ctctcccgca agctcatcaa cggcatccgc gacaagcagt cggggaagac gatcctggac   2040
ttcctcaaga gcgacggctt cgccaaccga aacttcatgc agctaatcca cgacgacagc   2100
ctgacgttca aggaggacat ccagaaggcc caagtgagcg gccagggaga ctcgctacac   2160
gagcatatcg ccaacctggc tggcagcccg gcgattaaga aaggaatcct ccaaaccgtc   2220
aaagtggtgg acgagctggt gaaggtgatg ggccgccaca agcccgagaa cattgtgatc   2280
gagatggcgc gggagaacca gacgacgcag aagggccaaa aaaatagcag ggaaaggatg   2340
aagcgaatag aggaggggat caaggagctg gggagccaga ttctcaaaga gcacccggtc   2400
gagaacacac agctccagaa cgagaagctg tacctctact acctccaaaa cggccgcgat   2460
atgtacgtgg accaggaact agacatcaac cggctgagcg actatgacgt ggaccacatc   2520
gtgccgcagt ccttcctcaa ggacgactcg attgacaaca aagtgctcac tagatccgac   2580
aagaacagag gcaagagcga taacgtcccg tcggaggagg tcgtcaagaa aatgaaaaac   2640
tactggcggc agctcctaaa cgccaagctc atcacgcagc gtaagttcga caacctgacg   2700
```

aaggcggagc ggggcgggct gagcgagctg gacaaagcgg ggttcatcaa gcggcagctc 2760
gttgagacgc ggcagatcac aaagcacgtc gcgcaaatcc tcgactcccg catgaacacc 2820
aagtacgacg agaacgacaa gctcatccgg gaggtgaagg tcattaccct taaatcgaag 2880
ctcgtcagcg actttcgtaa ggacttccag ttctacaagg tcagagagat caacaactac 2940
caccacgccc acgacgccta tctgaacgcc gtggtgggca ccgcgcttat taagaagtac 3000
cccaagctgg agtccgagtt cgtgtacggc gactacaagg tttatgacgt caggaagatg 3060
atcgccaagt cggaacagga gatcggaaaa gctaccgcca aatatttctt ctatagcaac 3120
atcatgaact tcttcaaaac cgagatcacc ctcgccaacg gcgagatccg gaagcgcccg 3180
ctcatcgaga ccaacgggga gaccggggag atcgtctggg acaaggggcg ggacttcgct 3240
actgtccgaa aggtgctctc catgccacaa gtgaatatcg tcaagaaaac agaggtgcag 3300
accggagggt tcagtaagga gtccatcctg cccaagcgga actccgacaa gctaattgct 3360
cgcaaaaagg attgggatcc taaaaaatat ggcggcttcg actcgcccac ggtcgcctac 3420
tctgtgctgg tcgtggcgaa ggtggagaag ggcaagtcca agaagctcaa gagcgtcaag 3480
gagctgctgg ggatcacgat catggagcgt agttcgtttg agaagaatcc catcgacttc 3540
ctggaggcta agggctacaa ggaggtcaaa aaggacctca tcattaagct gccgaagtac 3600
agcctcttcg agctggagaa cgggcggaag cgtatgctcg cctccgctgg ggagttacaa 3660
aaggggaacg agctggcgct gccgtctaag tacgtcaact tcctgtacct ggcctcccac 3720
tacgagaagc tcaaggggtc gccggaggac aacgagcaga agcagctctt cgtagagcag 3780
cacaagcact acctggacga gatcatcgag cagatttcag agttctcaaa gcgggtcatc 3840
ctcgccgacg ccaacctgga caaggtgctc tcggcctaca acaagcaccg ggacaagccg 3900
atccgcgaac aggccgaaaa catcatccac ctgttcacgc tcaccaacct cggtgccccg 3960
gcggccttca agtactttga cacgaccatc gaccggaagc gctatacctc gacgaaggag 4020
gtgctggacg ccaccctgat ccaccagtcc atcaccgggc tttacgagac ccggatcgac 4080
ctctcgcagc ta 4092

<210> SEQ ID NO 242
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 242
gacaagaagt atagtattgg actcgccatc ggaaccaact ctgtggggtg ggctgttatt 60
acagatgaat ataaggtgcc atccaaaaag tttaaagttc tgggcaatac tgatagacac 120
tcaatcaaga agaatctgat aggtgcactt ctgtttgata gtggagagac tgccgaggca 180
accagactta aaaggactgc aagaagaaga tataccagaa gaaagaatag gatttgctat 240
ttgcaggaaa tcttcagcaa cgaaatggcc aaggttgatg actcattttt ccataggttg 300
gaggagagtt ttcttgtgga ggaagataag aagcacgaaa gacacccaat tttcgggaat 360
atagtggacg aggtggctta tcatgagaag tatcccacta tctaccacct gagaaagaaa 420
cttgtggact caaccgataa ggctgatctt aggcttatat acttggccct tgcacatatg 480
atcaaattca ggggccattt tcttatcgaa ggcgatctta atcccgataa ctcagatgtg 540
gacaagctgt ttatacaact tgtgcaaacc tacaatcaac tcttcgagga gaatcccatt 600

-continued

```
aacgcctccg gcgtggatgc aaaagccata ctgtcagcca gactgagcaa aagtaggaga    660
ctggagaatc ttatagccca actgcccggt gaaaagaaga atgggctctt cggaaatctg    720
atcgctcttt cattggggtt gacacccaac tttaagagta actttgactt ggcagaagat    780
gcaaagttgc agctcagtaa agacacatat gacgatgacc ttgacaatct cttggcacaa    840
ataggggatc aatacgctga ccttttcctc gctgccaaga acctcagcga cgctatactg    900
ttgtccgaca ttcttagggt taataccgaa attacaaagg cccctcttag tgcaagtatg    960
atcaaaaggt atgatgagca tcaccaagac cttacactgc tgaaggctct ggttagacag   1020
caactccctg aaaagtataa ggaaatattc ttcgaccaaa gtaagaacgg gtacgccggt   1080
tatattgatg gggcgcaag tcaagaagaa ttttacaaat tcatcaagcc aattcttgaa   1140
aagatggacg ggactgagga attgctggtg aaactgaata gagaggacct tcttagaaaa   1200
cagaggacat ttgacaatgg gtccatccca caccagattc atctggggga actccacgca   1260
atattgagga gacaagaaga cttttaccca ttccttaagg ataatagaga gaaaatcgaa   1320
aaaatcctga ctttcaggat tccttactat gttgggccac tggccagggg gaactcaaga   1380
ttcgcttgga tgacaaggaa gtcagaagaa accataaccc cttggaattt tgaagaggtg   1440
gttgataagg gggcatcagc ccagtctttc atagagagga tgaccaactt tgataaaaat   1500
cttccaaatg agaaggtttt gccaaaacat agtcttttgt acgagtactt tactgtttat   1560
aacgaattga ccaaggtgaa gtatgtgacc gagggaatga ggaagccagc atttttgtcc   1620
ggggagcaaa agaaagcaat cgttgatctt ctcttcaaga ccaacagaaa agtgaccgtg   1680
aaacaactga aggaagacta cttcaaaaag atagaatgtt tcgattcagt ggaaattagc   1740
ggtgttgaag acaggttcaa tgcttcattg ggtacttacc acgacctgtt gaagataatc   1800
aaagacaagg actttctcga taatgaggag aacgaagaca tcttggaaga cattgtgctt   1860
acactcactt tgtttgagga cagggaaatg attgaggaaa gactcaaaac ttacgctcat   1920
ttgtttgatg ataaggttat gaaacaacta aaaagaagaa ggtacaccgg ctggggaaga   1980
ttgagtagga aactgatcaa cggtattaga gataaacaat ccggaaagac tatcctcgat   2040
ttccttaaga gtgatggctt tgcaaatagg aattttatgc agctgattca tgacgactca   2100
cttaccttca aagaagacat ccaaaaagct caggtgtctg ggcaaggcga cagtctgcat   2160
gaacatatag ctaacttggc tgggagtccc gccatcaaga aggggatact tcaaacagtt   2220
aaagttgtgg acgaattggt gaaggtaatg ggaaggcaca agcctgaaaa tatagtgata   2280
gaaatggcaa gggaaaatca aacaacccag aagggacaga agaacagtag ggaaaggatg   2340
aaaaggatag aagaggggat caaagagctt ggtagccaga tcctcaagga acatccagtg   2400
gagaataccc aacttcaaaa cgagaaactc tatttgtact acttgcagaa cggaagagat   2460
atgtatgtgg accaagagct tgatattaac aggctgagcg attatgacgt tgaccacata   2520
gtgccccaat cattcctcaa ggatgactct attgataata aggtgctgac aaggagtgac   2580
aagaatagag ggaaatccga caacgttcca tccgaggaag ttgtgaagaa gatgaagaac   2640
tactggaggc agttgctgaa cgctaagctc attacccaga ggaaattcga taacctgacc   2700
aaagcagaga gaggcgggct gagcgaactc gataaagcag gtttcatcaa gagacaactc   2760
gtggagacta ggcaaattac taagcacgtg gctcaaatac tcgacagcag gatgaacaca   2820
aagtacgacg agaacgacaa gctcattaga gaggttaagg ttattactct gaaaagtaaa   2880
ttggttagcg atttcagaaa ggatttccaa ttctataagg ttagagagat caacaattat   2940
catcatgcac atgatgccta tctgaatgct gtggttggta cagcccttat caagaagtac   3000
```

```
cctaagctag agagcgagtt tgtgtacgga gattataagg tgtatgatgt gaggaaaatg   3060
atcgctaaaa gtgagcaaga gattggaaag gctaccgcca aatacttctt ttattccaat   3120
attatgaatt tcttcaagac agaaatcacc ctggctaacg gcgagataag gaagaggccg   3180
cttatcgaaa ctaatgggga gacaggcgaa atagtgtggg acaaagggag ggatttcgca   3240
actgtgagga aggttttgag catgcctcag gtgaatatcg ttaagaaaac cgaagttcaa   3300
actggagggt tctctaagga aagcattctc cccaagagga actccgacaa gctgattgct   3360
agaaagaaag actgggaccc caagaagtat ggcggattcg actcacccac tgtggcatat   3420
agcgttctcg tggtggcaaa ggttgaaaag ggtaaatcca aaaaactcaa atccgtgaag   3480
gaactccttg gcataactat tatggaaagg agtagctttg aaaagaatcc catcgacttt   3540
ctcgaagcta agggctataa ggaagttaag aaggacctta taatcaaact tccaaaatac   3600
tcccttttg agttggaaaa cggcagaaag agaatgttgg ccagtgccgg ggagcttcaa   3660
aagggcaacg aactggctct gcctagcaaa tatgtgaact ttttgtatct ggcatcacac   3720
tacgagaaac ttaaaggctc tcctgaggac aacgagcaaa aacagctctt tgttgaacag   3780
cataagcact acctcgacga gattattgag cagatcagcg agttctcaaa gagagttatt   3840
ctggctgacg ctaatcttga caaggttttg tccgcttaca acaaacacag ggataagcca   3900
atcagggagc aggcagaaaa cataatccat ctctttaccc tgacaaacct cggtgccccc   3960
gctgctttca agtattttga tactaccatt gacaggaaga gatatacttc cactaaggaa   4020
gtgctcgacg caaccctcat acaccaaagt atcacaggcc tctatgaaac taggatagat   4080
ttgtctcaac ttgggggcga t                                             4101
```

<210> SEQ ID NO 243
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 243

```
gacaaaaagt attccatcgg gcttgctatc ggaaccaact ctgtggggtg ggcagttatt     60
accgacgaat acaaggtgcc cagcaagaag tttaaggttc tggggaacac agatagacat    120
agcataaaga aaaacctgat aggcgcactg ttgttcgact ccggggaaac agccgaagct    180
accaggctga agagaactgc aagaagaagg tacaccagaa gaaaaaacag aatatgttat    240
ctccaagaga ttttctctaa cgagatggcc aaggtggacg actcattctt tcacagactg    300
gaagaatctt tccttgtgga agaagataag aaacacgaga ggcaccctat ttttggcaat    360
atcgtggatg aggtggctta ccacgaaaaa taccctacaa tataccacct caggaaaaaa    420
ttggttgata gtacagacaa ggccgacctc aggctcatct atttggccct ggcccatatg    480
attaaattca gggggcactt tctcatcgag ggagatttga accccgacaa cagtgatgtt    540
gataagctct ttattcagct cgtgcagact tacaatcagt tgtttgagga aaaccccatt    600
aatgcttccg gggtggacgc caaggcaatc ctttctgcaa gactctcaaa gtcaaggaga    660
ctcgaaaatc tgatagcaca gcttccagga gagaagaaga acgggctctt tggaaacctg    720
atcgctctgt cactcggact cacacccaat ttcaaaagca attttgattt ggcagaggac    780
gctaagctgc aactcagtaa ggatacctac gacgatgact tggataatct gctcgcacaa    840
attggggacc agtatgcaga cctgtttctc gcagctaaga acttgagtga cgccatattg    900
```

-continued

```
ctcagtgaca tcctcagggt taataccgag attacaaaag ctccactctc tgcaagcatg    960
atcaagaggt atgacgagca ccatcaagac ctgacactcc ttaaggcgtt ggttaggcag   1020
caacttcctg aaaagtataa ggaaatcttc ttcgatcaaa gcaaaaacgg ctacgccggc   1080
tatatagacg gggagcatc ccaagaagaa ttttataagt tcataaaacc tatattggag    1140
aagatggacg ggacagagga attgctcgtg aaactgaaca gggaggatct cctcaggaag   1200
caaaggacct tcgacaatgg ctccatccca catcagattc acctcggcga actgcacgca   1260
atactgagaa gacaagagga cttttatcct ttcctgaagg acaacaggga gaaaatcgag   1320
aaaatcttga cattcagaat cccatactac gttgggcctc tggccagagg taacagtagg   1380
ttcgcctgga tgactaggaa atcagaggag actattacac cctggaactt tgaagaagtt   1440
gttgataagg gagcttcagc acaatcattc atcgaaagaa tgacaaactt tgacaaaaat   1500
ctgcctaatg agaaagtgct cccaaaacat tccctgctgt atgagtattt taccgtttat   1560
aacgagctta ccaaggtgaa atacgttact gaaggtatga gaaagccagc ttttctttca   1620
ggggagcaaa agaaggctat cgtggatctt ctctttaaga ccaacagaaa ggttaccgtg   1680
aagcagctta aggaagacta ctttaaaaag atcgagtgtt ttgactcagt ggaaataagc   1740
ggtgttgaag atagattcaa cgcatccttg ggaacttatc atgatcttct taagataatc   1800
aaggataaag actttctcga caacgaggaa aacgaagata tactggagga catagttctg   1860
acacttactt tgttcgagga tagggagatg atcgaggaaa gactgaaaac atatgctcac   1920
cttttcgacg acaaagttat gaaacaactc aagagaagga gatatacagg gtgggggaga   1980
ttgagcagga aactgattaa tggtatcaga gacaaacagt caggaaaaac aatactcgac   2040
tttttgaaat cagacgggtt cgcaaatagg aatttcatgc agcttataca cgacgattca   2100
cttactttta aagaggacat tcaaaaggct caagttagtg gacaaggtga ctccctccac   2160
gaacacatcg caaatctcgc tggcagccct gcaattaaga agggtatact ccagacagtt   2220
aaggttgttg acgagctggt taaagtgatg ggaagacaca aacccgagaa catagtgata   2280
gagatggcca gggaaaacca aaccactcaa aaagggcaga aaaattccag agagaggatg   2340
aaaaggattg aagaaggtat caaggagctg ggtagccaaa ttctgaaaga acatcctgtg   2400
gaaaacactc aactccagaa tgagaaactc tatctgtact atctgcaaaa tgggagagat   2460
atgtatgtgg accaggaact ggacataaac aggctctcag attacgatgt ggatcatatc   2520
gtgccacagt cctttcttaa ggatgatagc atcgacaata aggtgcttac caggtccgac   2580
aagaacaggg gaaagtcaga taacgtgcct tctgaagaag ttgttaaaaa gatgaagaac   2640
tactggagac agctgcttaa cgctaagctc ataacacaga ggaagtttga caacttgacc   2700
aaggccgaga gaggcggact ctcagaattg gataaggcag ggttcataaa aaggcagctg   2760
gtggaaacaa ggcagataac taaacatgtg gctcagatcc tcgatagtag gatgaataca   2820
aaatacgatg agaacgacaa gctcataagg gaggttaaag tgataactct gaaatccaaa   2880
ctggttagcg attttaggaa ggatttccag ttttacaaag ttagggagat caacaattat   2940
catcacgccc acgatgccta cttgaacgca gttgtgggta ctgcacttat caaaaagtac   3000
cctaagctgg aatccgagtt tgtttatgga gactataagg tgtacgacgt tagaaaaatg   3060
attgcaaagt cagagcagga gatagggaaa gccactgcaa aatatttctt ttatagcaat   3120
atcatgaatt tctttaagac agaaatcaca ctggccaatg gggaaataag gaagaggccc   3180
ctgatcgaaa ctaatggcga gacaggggag attgtgtggg ataaaggtag ggactttgca   3240
acagtgagga aagtgctgag catgccccaa gttaatatcg ttaaaaagac cgaggttcaa   3300
```

acagggggct ttagtaagga aagcattttg cccaagagga atagtgacaa attgattgct 3360
aggaaaaaag attgggaccc caaaaagtat ggcggatttg atagccccac tgttgcttac 3420
tccgtgctcg tggttgcaaa ggtggagaag ggaaagagca agaaactgaa gtcagttaag 3480
gaactccttg gtatcactat catggaaaga agctcctttg agaagaaccc tattgacttc 3540
ctggaggcta aagggtacaa agaggttaag aaagacctta tcattaaatt gcccaaatat 3600
agtcttttcg agcttgaaaa cggaagaaag aggatgcttg catccgctgg cgaattgcaa 3660
aagggcaatg agcttgctct cccttccaag tatgtgaact tcctttatct tgcctcacac 3720
tatgaaaaac tcaaaggttc acccgaagac aacgaacaaa agcaactatt tgtggaacaa 3780
cacaagcact acctggacga aatcattgag caaatttctg agttttcaaa aagggtaatc 3840
ttggctgacg caaatctcga caaagttttg tcagcttaca acaaacatag agataagcca 3900
attagagagc aagctgagaa tatcatccat ctgtttaccc tgactaacct tggagcgcct 3960
gctgctttta aatatttcga caccacaatc gacaggaaga ggtacactag cactaaggaa 4020
gttctcgacg ccaccctcat ccaccagagt attacaggcc tgtacgagac aagaattgat 4080
ctttctcaac ttggtggtga c 4101

<210> SEQ ID NO 244
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 244
gataagaagt actcaatcgg tctggcaatc ggaaccaact ctgtgggttg ggcagtgatt 60
acagatgagt ataaggtgcc aagcaaaaaa ttcaaggtgc tgggtaatac cgacagacac 120
agcattaaga agaatttgat tggagcactc ctctttgact caggggaaac agcagaggca 180
acaaggctga agaggacagc aaggcggagg tacacaaggc ggaaaaacag gatatgctac 240
ctccaggaaa tctttagcaa cgagatggct aaagtggatg atagcttttt ccatagactc 300
gaagaatcct ttcttgttga agaggacaaa aagcatgaaa ggcatcccat cttcggcaat 360
atagttgatg aggttgcata ccatgagaag taccccacaa tctaccacct cagaaagaaa 420
cttgtggact ccacagataa agcagacctg aggctcatat acctcgcact cgcacacatg 480
atcaagttca gagggcactt tctcatcgaa ggtgacctga atccagataa ttcagatgtg 540
gataaactgt ttatacagct ggtgcaaaca tacaaccaac ttttcgagga aaacccaatc 600
aatgcctccg gtgttgatgc aaaggccatc ctgtcagcaa gactcagcaa aagcaggcgg 660
ctcgaaaacc tcatcgccca gcttcccggt gaaaagaaga acgggctctt tggtaatctc 720
atcgcattga gccttggtct tactccaaac ttcaagagca attttgatct ggcagaggat 780
gctaaactgc aactctcaaa ggacacatat gacgatgacc ttgacaatct gttggcccag 840
atcggggacc aatatgcaga cctcttcctg gccgcaaaga atctgtcaga tgcaatcctc 900
ttgtccgaca tactgagagt taacactgag atcacaaagg cacctctgtc cgcctccatg 960
attaagagat acgatgagca tcaccaggat ctgactttgc tcaaagccct cgttagacag 1020
cagttgccag aaaagtacaa agaaatattc tttgatcaat caaaaaacgg atatgcaggg 1080
tacatcgacg gtggggcaag ccaggaagag ttctacaaat tcatcaaacc tatcctggaa 1140
aagatggatg ggacagaaga gctgctggtt aagctgaata gggaagacct cctcagaaag 1200
cagaggacat ttgataacgg gagcatccct catcaaatcc acctcggtga actccatgct 1260
atcctgagaa ggcaggaaga cttttatcca tttttgaagg acaataggga gaaaatcgaa 1320
aaaatcctga cattcagaat cccatactac gttggtcctc tggcaagagg taacagtagg 1380
ttcgcatgga tgacaaggaa aagcgaggag acaatcacac cctggaattt tgaggaagtt 1440
gttgacaagg gtgccagcgc acaatccttt atcgaaagaa tgacaaattt cgacaagaat 1500
ctgcctaacg aaaaggttct cccaaagcat tcactcctgt acgaatattt tacagtttat 1560
aacgaactga ctaaagttaa atacgttacc gagggtatga ggaagccagc attcctttcc 1620
ggggaacaga agaaagctat tgtggacctc ctgttcaaga caaatagaaa agtgacagtt 1680
aagcaactca aagaggatta cttcaaaaag atcgaatgtt ttgactctgt ggagatcagc 1740
ggggtggagg atagattcaa cgccagcctg ggtacatatc atgatctcct gaaaatcatt 1800
aaagacaagg acttccttga caacgaggag aacgaggaca ttctggaaga cattgttctg 1860
accctcacac tctttgagga tagggagatg attgaggaaa gactgaagac ctacgcccac 1920
ctctttgacg ataaagtgat gaaacagctc aagagaagaa ggtatacagg ttgggggaga 1980
ctgagcagga agttgatcaa tgggattagg gacaaacagt ccgggaaaac aatcctcgat 2040
tttctgaagt cagacggttt cgcaaacaga aattttatgc agctcattca cgatgacagc 2100
ttgacattca aggaagacat ccaaaaggct caagtgagcg gccaagggga tagcctccac 2160
gagcatattg caaatctggc aggttcacca gccatcaaaa agggcatact tcagacagtt 2220
aaggttgtgg acgaattggt taaagttatg ggcaggcata agccagagaa tatcgttatc 2280
gaaatggcaa gggagaacca aacaactcaa aaagggcaga aaaatagcag agagaggatg 2340
aaaagaatcg aggaagggat caaggaactt gggtcccaaa tcctcaagga gcacccagtt 2400
gaaaatactc aactgcaaaa cgagaagctc tatctctact atctccaaaa cgggagggat 2460
atgtatgttg accaggagct ggatattaac agactgtcag attatgatgt tgatcatatc 2520
gtgccccagt cattcctgaa ggacgattcc atcgacaaca aagttctcac aaggtccgat 2580
aaaaacaggg gcaagtccga taacgttcca agcgaagaag tggtgaaaaa gatgaaaaac 2640
tattggagac aacttctgaa tgcaaagttg attactcaga gaaagtttga caacctcaca 2700
aaagcagaaa gaggcgggct tagcgaactc gataaggcag ggtttatcaa aagacagctg 2760
gttgagacaa ggcagatcac aaaacatgtg gcacagatcc ttgactcaag gatgaatacc 2820
aagtatgatg agaatgataa gttgatcagg gaggttaaag ttatcacact caaatccaaa 2880
ctggtgtcag acttcaggaa agactttcaa ttttataagg tgagggagat caataactac 2940
caccatgcac atgacgccta cctgaacgca gtggtgggta cagcattgat taaaaaatac 3000
cctaagctgg agtctgagtt tgtgtacggg gactacaagg tgtacgacgt gaggaaaatg 3060
atagccaagt ccgagcagga gatcgggaaa gcaacagcta agtatttctt ttacagtaat 3120
atcatgaatt tctttaaaac tgagattact ctggcaaacg gggagatcag gaaaagaccc 3180
ctcatcgaga ctaatggtga aacaggtgag atcgtttggg acaaggggag ggattttgct 3240
actgttagaa aagttctgag tatgccacaa gtgaatattg tgaaaaagac agaagttcag 3300
acaggtgggt tctccaaaga atccatcctg cccaagagaa attcagacaa gctcatcgca 3360
agaaagaagg actgggaccc taagaagtac ggaggatttg acagccccac cgtggcctat 3420
tccgtgcttg ttgtggcaaa ggtggagaaa gggaagagca aaaaactgaa atccgtgaaa 3480
gaactgctgg gaattaccat catggaaaga agctcctttg agaagaaccc aatcgacttc 3540
ctggaagcaa aaggatataa ggaagtgaaa aaggacctca ttatcaagct cccaaaatac 3600

```
tcacttttcg agttggagaa cggtagaaag aggatgctgg caagcgcagg ggaacttcag   3660
aaaggcaatg agctggcatt gccatcaaag tatgtgaact tcctctactt ggccagccat   3720
tacgagaaac ttaaaggtag cccagaagat aacgagcaaa aacagctctt tgtggaacag   3780
cataagcatt atctggatga gatcatagaa caaatctcag agttttccaa gagagttatc   3840
ctcgcagatg caaacctgga taaggttctc tcagcctata ataagcatag agacaagcca   3900
attagagagc aagcagagaa cattatccac ttgttcactc ttacaaacct gggggcacca   3960
gccgccttca aatatttcga tacaacaata gacagaaaga ggtataccag caccaaagaa   4020
gttctcgacg ccacactgat ccatcaatca atcacaggcc tttacgaaac taggatcgac   4080
ttgtcacaac tgggtgggga t                                             4101
```

<210> SEQ ID NO 245
<211> LENGTH: 3307
<212> TYPE: DNA
<213> ORGANISM: Unknown
<220> FEATURE:
<223> OTHER INFORMATION: Cas9 nucleotide sequence

<400> SEQUENCE: 245

```
gagcaaggac acctacgacg acgacttgga caacctattg gcccagatag gtgaccagta     60
tgcagacctc ttccttgcgg ccaagaactt gagtgacgct atactgctca gtgacatcct    120
gagggtgaac actgagatca ctaaggcccc tctctctgcc tcaatgatta agcgttacga    180
cgagcatcac caggatctca ccctgcttaa ggcccttgtt cggcagcagc tccctgagaa    240
gtacaaggag atatttttg accagtctaa gaacggctac gccggttaca ttgacggtgg    300
ggcaagccag gaggagttct acaagttcat caagccgatc cttgagaaga tggacggcac    360
cgaggagcta cttgtcaagt tgaaccggga agacctgctc cggaaacagc gtacattcga    420
caacggcagc atccctcacc agatccacct gggcgaacta cacgccatcc tccgacgtca    480
ggaggacttc tatccattct tgaaagataa cagggaaaaa atcgaaaaaa tacttacgtt    540
tcgaatacct tactacgtgg ggccccttgc tcggggaaac tccagattcg catggatgac    600
caggaagtca gaggagacca tcacaccctg gaactttgag gaggtggttg acaaaggtgc    660
ttctgcccag tccttcattg agcggatgac taacttcgac aagaacctgc ccaacgagaa    720
ggtgctgcca aagcacagcc tgctctacga atactttact gtgtacaatg agctgacgaa    780
ggtgaagtac gtgacagagg ggatgcggaa gcccgctttc ctgagcggcg agcaaaaaaa    840
agcaatcgtg gacctactgt tcaagaccaa ccgaaaggtg acagtgaagc agctcaagga    900
ggactacttc aaaaaaatcg agtgcttcga ctctgttgag ataagcggcg tggaggaccg    960
attcaacgcc tcattgggaa cctatcacga cctgctcaag atcattaagg acaaggactt   1020
cctggataat gaggagaatg aggacatcct ggaggatatt gtgctgaccc ttactctatt   1080
cgaggacagg gagatgatcg aggagcgact caagacctac gctcacctgt tcgacgacaa   1140
ggttatgaag caattgaagc gtaggcgata cacggggtgg ggaagactct cccgaaaact   1200
gataaacggc atcagggaca agcagtcagg gaagacgatc ttggacttcc tgaaatccga   1260
cgggttcgcc aaccgcaact tcatgcagct cattcacgac gactcactaa cgttcaaaga   1320
ggacattcag aaggctcaag tcagtggaca aggcgactcc ctgcacgagc acattgcaaa   1380
ccttgcgggc tccccggcga ttaaaaaggg cattctccaa acggttaagg tggtggacga   1440
gctggtgaag gtgatgggcc gacacaagcc tgagaacatc gtgatcgaga tggccaggga   1500
```

-continued gaaccagact acccagaagg gtcagaagaa ctctcgggaa cgtatgaagc gtattgagga 1560
ggggattaag gagttgggct ctcaaatcct caaggagcac cctgtggaga acactcagct 1620
ccaaaacgag aagctgtacc tgtactacct gcaaaacggg cgcgatatgt acgtggatca 1680
ggagttggac atcaacaggc ttagcgatta cgacgtggac cacatcgtgc cacagtcatt 1740
cttaaaggac gacagcatcg acaacaaggt tctgacgagg agcgacaaga atcgagggaa 1800
aagtgacaat gttccatccg aggaggtggt caagaaaatg aagaactatt ggcgtcagct 1860
tctgaacgcc aagctcatca cccagcggaa attcgacaac ctgactaagg ctgagcgagg 1920
cggactctcc gagcttgaca aggctggctt catcaagcgg cagttggtcg aaacccgaca 1980
gataacgaag cacgttgccc agatacttga ctcccgtatg aacaccaagt acgacgagaa 2040
cgacaagctc atcagggagg tgaaggtcat taccettaag tccaaactcg tcagcgactt 2100
tcgtaaggac ttccagttct acaaggtgcg cgagatcaat aactaccacc acgcacacga 2160
cgcctacctg aacgcagtgg ttggaaccgc gttgattaaa aagtacccca agttggagtc 2220
ggagttcgtt tacggggact acaaggtgta cgacgttcgg aagatgatcg ccaagtctga 2280
acaggagatc gggaaagcaa ccgccaagta tttcttctat agcaacatca tgaacttctt 2340
taaaaccgag atcacacttg ccaatggcga gatccgtaag aggccgctga tcgagacaaa 2400
tggggagact ggcgagatcg tgtgggacaa gggccgcgac ttcgcaaccg ttcggaaagt 2460
cttgtccatg cctcaagtca acatcgtcaa gaagactgag gtgcaaacag gcgggttctc 2520
gaaggagtcc atactgccca agaggaactc agacaagctc atagcacgca aaaaagactg 2580
ggatccaaag aaatacggcg ggttcgactc gccgacagtc gcatactccg tgttagtggt 2640
ggctaaagtg gaaaagggga agtccaagaa gctcaagtcc gtcaaggagt tgctcgggat 2700
caccattatg gaacggtcct cattcgagaa gaatcccatt gacttcctag aggcgaaggg 2760
ctacaaagag gtcaaaaagg acctaattat taagctcccc aagtattcac tcttcgaact 2820
tgaaaatggt cgtaagcgga tgttggcaag cgctggagag cttcagaagg ggaacgagct 2880
tgcactgcct tccaagtacg tgaacttcct gtacctcgcc tctcattacg agaagttgaa 2940
gggctcaccg gaggacaacg agcagaagca gttgttcgtg gagcagcaca agcactacct 3000
cgacgagatc attgagcaga taagtgagtt cagcaaacgg gtgatccttg ccgacgctaa 3060
cctggacaag gtgctgagcg cctacaacaa gcacagagac aagccgatcc gagagcaagc 3120
ggagaacatc atacacctgt tcaccctcac gaacctcggg gctcccgcag ccttcaaata 3180
ttttgacacg accatcgacc gtaaacgcta cactagcacg aaggaggtgc tggacgctac 3240
ccttatccac cagtccatca ccggcctgta cgagacgaga atcgacttgt cgcagctcgg 3300
tggtgac 3307

<210> SEQ ID NO 246
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 246
gacaaaaaat actcaattgg tctggcaatt gggaccaaca gtgtcggatg ggccgtgatt 60
accgacgagt acaaggtgcc gtccaaaaaa ttcaaggtgc ttgggaacac cgaccgccac 120
tcgatcaaga aaaacctaat cggtgcgttg cttttcgaca gtggggagac cgccgaggca 180
acacgcttaa aacgcacagc taggaggaga tatacacggc gcaagaaccg aatatgctac 240

-continued

```
ttacaggaga tattctccaa tgagatggcg aaggtggacg actctttctt ccatcggctt    300
gaggaatcct tcctggtcga ggaggacaag aagcacgagc gacacccgat attcgggaac    360
atcgttgatg aggtggcgta ccacgagaag tacccaacga tataccactt acgcaagaag    420
ctcgtggact ctacggacaa ggccgacttg cgccttatct acttggcact ggcccacatg    480
attaagttcc gaggccactt ccttatcgag ggtgacctga accccgataa ctccgacgtg    540
gacaagctct tcatccaact cgtccagaca tacaaccagc tattcgagga gaatcctatc    600
aacgcctctg gggtggacgc taaagctatc ctctcagccc gcctgtcaaa gtcgaggagg    660
ttggagaacc taatcgccca gcttccaggc gagaagaaaa atgggctgtt cggaaacctt    720
atcgcactct cactgggcct aaccccgaac ttcaagtcca acttcgacct ggcagaggac    780
gcgaaattgc agttgtcgaa agacacctat gacgatgacc tggacaacct gttggcccag    840
atagggggacc agtacgccga cctgttccta gcggccaaga acctgtccga cgccatcttg    900
ctgtcggata tactgcgggt gaacaccgag atcactaaag cacctctctc cgccagcatg    960
attaagcgtt acgacgagca ccaccaagat ttgaccctgc taaaggcact tgtacggcag   1020
cagcttcccg agaagtacaa ggagatcttt ttcgaccaaa gcaagaacgg ctacgccggg   1080
tacatcgacg gaggtgccag ccaggaggag ttctacaagt tcattaagcc catcctggag   1140
aagatggacg ggactgagga actacttgtg aagctgaacc gggaagactt actacggaag   1200
cagcgtacct tcgacaacgg ttctatccca catcagatcc atcttgggga gttgcacgcg   1260
atcctgcgac gccaggagga cttttacccc ttcctgaaag acaaccgcga gaaaatcgag   1320
aagatactga ccttcagaat accttactac gtcggacccc ttgcgcgagg caactcaaga   1380
ttcgcgtgga tgaccaggaa atcagaggag accatcacac cctggaattt cgaggaggtg   1440
gttgacaagg gtgcctccgc ccagtccttt atcgaacgaa tgaccaactt cgacaagaac   1500
ttgcccaacg agaaggtgct ccccaaacac agcctcctct acgaatattt cacagtgtac   1560
aacgagctta ctaaagttaa gtatgttact gagggcatga ggaaacccgc cttcctgtca   1620
ggcgagcaga agaaagctat tgtggacctc cttttcaaga ccaaccggaa ggtgacagtg   1680
aagcagctca aggaggacta cttcaagaag atagagtgct tcgacagcgt ggagatcagc   1740
ggggtggagg acagattcaa tgcctctctc ggaacatacc acgacttgct taagatcatc   1800
aaggacaagg acttcctcga caacgaggaa aacgaggata ttctggagga tattgttctg   1860
actcttaccc tgttcgagga ccgggagatg atcgaggagc gtctcaagac ctacgcccac   1920
ctgttcgacg acaaagttat gaagcagctc aagcgtcgga gatataccgg atggggccgt   1980
ctgtctcgga agctcatcaa cgggatcagg gacaagcagt cagggaagac gatcttagac   2040
ttccttaagt ctgacggctt cgccaacagg aacttcatgc agttgatcca cgacgacagc   2100
cttaccttca aggaggacat ccagaaggcc caagtgagtg gccagggtga cagcctccac   2160
gagcatattg ctaatcttgc gggttcccca gcgattaaaa agggcatact tcaaaccgtt   2220
aaggtggtgg acgagcttgt caaggtgatg gggcgacaca agcccgagaa catcgtgatc   2280
gagatggcca gggagaacca gaccacccag aaggggcaga agaatagccg agaacgcatg   2340
aagcgcatcg aggaggggat taaggagcta gggagccaga tcctcaagga acatcccgtc   2400
gagaacaccc agctccagaa cgagaagcta tacctctact acttgcaaaa cgggagggat   2460
atgtacgtgg atcaggagtt ggacattaac cgcctaagcg actacgacgt agatcacatc   2520
gtgcctcagt cattcctcaa agacgacagc attgacaaca aagtcttgac ccgatccgac   2580
```

```
aagaaccgag gaaaatccga caatgtgccc tcagaggagg tcgtcaagaa aatgaagaac   2640
tattggaggc agctacttaa cgccaaactc ataacccagc ggaagttcga caacctgaca   2700
aaggctgagc ggggtgggct cagcgagctt gacaaggctg gcttcatcaa gcggcagttg   2760
gtggagacaa gacagataac gaagcacgtg gctcagatcc tggactctcg catgaacacg   2820
aagtacgacg agaacgacaa attgatccgc gaggtcaagg ttattacgct caagagcaaa   2880
cttgtcagcg atttccgcaa ggacttccag ttctacaagg tgagggagat taacaactac   2940
caccatgcac atgatgccta cttgaacgca gtggtgggga ccgcgcttat taaaaagtac   3000
cctaagttgg agtcagagtt cgtttatggg gactacaagg tgtacgacgt ccggaagatg   3060
attgcaaagt ctgaacagga aatcgggaag gccaccgcca aatatttctt ctacagtaac   3120
attatgaatt tttttaagac tgaaattact ctcgcaaacg gcgagatcag gaagcgtccc   3180
ctcatcgaga caaacgggga gaccggggag atagtctggg acaaggggcg ggacttcgct   3240
acggtgagga aggtgctctc gatgccacaa gtgaacatcg tcaaaaagac agaggtgcag   3300
accggtggct tctcaaagga gtcaatcctg ccaaaacgta acagcgacaa gctcatcgcc   3360
cgcaagaaag actgggaccc taagaagtat ggtgggttcg actcaccgac ggtcgcatac   3420
tccgttctgg tcgtggcaaa ggtggaaaag ggcaagtcca aaaaactgaa atccgtgaag   3480
gagttgcttg gcattaccat catggaacgc agcagcttcg agaagaaccc cattgacttc   3540
ctggaggcta aagggtacaa ggaggtcaag aaagatttaa ttattaagct acctaagtac   3600
agcttgttcg agctggagaa cggccgaaaa cgaatgctcg catccgccgg ggaacttcaa   3660
aagggcaacg agcttgcgct gccctccaag tacgtgaact tcctgtactt ggcatcccac   3720
tacgagaaac tcaagggtag cccagaggac aacgagcaga agcagctatt cgtggagcag   3780
cacaagcact acctcgacga gataatcgag cagatcagtg agttcagtaa gcgggtgata   3840
ctcgcggacg ccaacttgga caaggtgctt agtgcctaca acaagcaccg tgacaagccc   3900
atccgagaac aggctgagaa catcatccac cttttcactc tgacaaacct cggtgctccc   3960
gccgccttca aatacttcga cactaccatc gacaggaagc gctacacatc tacgaaggaa   4020
gttcttgacg ctacgcttat tcatcagtct atcacagggc tgtacgagac aaggatcgac   4080
cttagccaac tcggcgggga t                                             4101
```

<210> SEQ ID NO 247
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 247

```
gacaagaagt acagcatcgg cctggacatc ggcaccaact ctgtgggctg ggccgtgatc     60
accgacgagt acaaggtgcc cagcaagaaa ttcaaggtgc tgggcaacac cgaccggcac    120
agcatcaaga agaacctgat cggagccctg ctgttcgaca gcggcgaaac agccgaggcc    180
acccggctga agagaaccgc cagaagaaga tacaccagac ggaagaaccg gatctgctat    240
ctgcaagaga tcttcagcaa cgagatggcc aaggtggacg acagcttctt ccacagactg    300
gaagagtcct tcctggtgga agaggataag aagcacgagc ggcaccccat cttcggcaac    360
atcgtggacg aggtggccta ccacgagaag taccccacca tctaccacct gagaaagaaa    420
ctggtggaca gcaccgacaa ggccgacctg cggctgatct atctggccct ggcccacatg    480
atcaagttcc ggggccactt cctgatcgag ggcgacctga accccgacaa cagcgacgtg    540
```

-continued

```
gacaagctgt tcatccagct ggtgcagacc tacaaccagc tgttcgagga aaaccccatc    600
aacgccagcg gcgtggacgc caaggccatc ctgtctgcca gactgagcaa gagcagacgg    660
ctggaaaatc tgatcgccca gctgcccggc gagaagaaga atggcctgtt cggaaacctg    720
attgccctga gcctgggcct gacccccaac ttcaagagca acttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccccctgag cgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca agcccgagaa catcgtgatc   2280
gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
```

ctggtgtccg atttccggaa ggatttccag ttttacaaag tgcgcgagat caacaactac 2940
caccacgccc acgacgccta cctgaacgcc gtcgtgggaa ccgccctgat caaaaagtac 3000
cctaagctgg aaagcgagtt cgtgtacggc gactacaagg tgtacgacgt gcggaagatg 3060
atcgccaaga gcgagcagga aatcggcaag gctaccgcca agtacttctt ctacagcaac 3120
atcatgaact tttcaagac cgagattacc ctggccaacg gcgagatccg gaagcggcct 3180
ctgatcgaga caaacggcga aaccggggag atcgtgtggg ataagggccg ggattttgcc 3240
accgtgcgga aagtgctgag catgccccaa gtgaatatcg tgaaaaagac cgaggtgcag 3300
acaggcggct tcagcaaaga gtctatcctg cccaagagga acagcgataa gctgatcgcc 3360
agaaagaagg actgggaccc taagaagtac ggcggcttcg acagccccac cgtggcctat 3420
tctgtgctgg tggtggccaa agtggaaaag ggcaagtcca agaaactgaa gagtgtgaaa 3480
gagctgctgg ggatcaccat catggaaaga agcagcttcg agaagaatcc catcgacttt 3540
ctggaagcca agggctacaa agaagtgaaa aaggacctga tcatcaagct gcctaagtac 3600
tccctgttcg agctggaaaa cggccggaag agaatgctgg cctctgccgg cgaactgcag 3660
aagggaaacg aactggccct gccctccaaa tatgtgaact tcctgtacct ggccagccac 3720
tatgagaagc tgaagggctc ccccgaggat aatgagcaga aacagctgtt tgtggaacag 3780
cacaagcact acctggacga gatcatcgag cagatcagcg agttctccaa gagagtgatc 3840
ctggccgacg ctaatctgga caaagtgctg tccgcctaca acaagcaccg ggataagccc 3900
atcagagagc aggccgagaa tatcatccac ctgtttaccc tgaccaatct gggagcccct 3960
gccgccttca agtactttga caccaccatc gaccggaaga ggtacaccag caccaaagag 4020
gtgctggacg ccaccctgat ccaccagagc atcaccggcc tgtacgagac acggatcgac 4080
ctgtctcagc tgggaggtga c 4101

<210> SEQ ID NO 248
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 248
gacaagaagt acagcatcgg cctggacatc ggcaccaact ctgtgggctg ggccgtgatc 60
accgacgagt acaaggtgcc cagcaagaaa ttcaaggtgc tgggcaacac cgaccggcac 120
agcatcaaga agaacctgat cggagccctg ctgttcgaca gcggcgaaac agccgaggcc 180
acccggctga agagaaccgc cagaagaaga tacaccagac ggaagaaccg gatctgctat 240
ctgcaagaga tcttcagcaa cgagatggcc aaggtggacg acagcttctt ccacagactg 300
gaagagtcct tcctggtgga agaggataag aagcacgagc ggcaccccat cttcggcaac 360
atcgtggacg aggtggccta ccacgagaag taccccacca tctaccacct gagaaagaaa 420
ctggtggaca gcaccgacaa ggccgacctg cggctgatct atctggccct ggcccacatg 480
atcaagttcc ggggccactt cctgatcgag ggcgacctga accccgacaa cagcgacgtg 540
gacaagctgt tcatccagct ggtgcagacc tacaaccagc tgttcgagga aaaccccatc 600
aacgccagcg gcgtggacgc caaggccatc ctgtctgcca gactgagcaa gagcagacgg 660
ctggaaaatc tgatcgccca gctgcccggc gagaagaaga atggcctgtt cggaaacctg 720
attgccctga gcctgggcct gacccccaac ttcaagagca acttcgacct ggccgaggat 780
gccaaactgc agctgagcaa ggacacctac gacgacgacc tggacaacct gctggcccag 840

-continued

```
atcggcgacc agtacgccga cctgtttctg gccgccaaga acctgtccga cgccatcctg    900
ctgagcgaca tcctgagagt gaacaccgag atcaccaagg ccccctgag cgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca agcccgagaa catcgtgatc   2280
gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctggc cgacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctgccctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact ttttcaagac cgagattacc ctggccaacg gcgagatccg gaaggcccct   3180
```

-continued ctgatcgaga caaacggcga aaccggggag atcgtgtggg ataagggccg ggattttgcc 3240
accgtgcgga aagtgctgag catgccccaa gtgaatatcg tgaaaaagac cgaggtgcag 3300
acaggcggct tcagcaaaga gtctatcctg cccaagagga acagcgataa gctgatcgcc 3360
agaaagaagg actgggaccc taagaagtac ggcggcttcg acagccccac cgtggcctat 3420
tctgtgctgg tggtggccaa agtggaaaag ggcaagtcca agaaactgaa gagtgtgaaa 3480
gagctgctgg ggatcaccat catggaaaga agcagcttcg agaagaatcc catcgacttt 3540
ctggaagcca agggctacaa agaagtgaaa aaggacctga tcatcaagct gcctaagtac 3600
tccctgttcg agctggaaaa cggccggaag agaatgctgg cctctgccgg cgaactgcag 3660
aagggaaacg aactggccct gccctccaaa tatgtgaact tcctgtacct ggccagccac 3720
tatgagaagc tgaagggctc ccccgaggat aatgagcaga aacagctgtt tgtggaacag 3780
cacaagcact acctggacga gatcatcgag cagatcagcg agttctccaa gagagtgatc 3840
ctggccgacg ctaatctgga caaagtgctg tccgcctaca acaagcaccg ggataagccc 3900
atcagagagc aggccgagaa tatcatccac ctgtttaccc tgaccaatct gggagcccct 3960
gccgccttca agtactttga caccaccatc gaccggaaga ggtacaccag caccaaagag 4020
gtgctggacg ccaccctgat ccaccagagc atcaccggcc tgtacgagac acggatcgac 4080
ctgtctcagc tgggaggtga c 4101

<210> SEQ ID NO 249
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 249
gacaagaagt acagcatcgg cctggccatc ggcaccaact ctgtgggctg ggccgtgatc 60
accgacgagt acaaggtgcc cagcaagaaa ttcaaggtgc tgggcaacac cgaccggcac 120
agcatcaaga agaacctgat cggagccctg ctgttcgaca gcggcgaaac agccgaggcc 180
acccggctga agagaaccgc cagaagaaga tacaccagac ggaagaaccg gatctgctat 240
ctgcaagaga tcttcagcaa cgagatggcc aaggtggacg acagcttctt ccacagactg 300
gaagagtcct tcctggtgga agaggataag aagcacgagc ggcaccccat cttcggcaac 360
atcgtggacg aggtggccta ccacgagaag taccccacca tctaccacct gagaaagaaa 420
ctggtggaca gcaccgacaa ggccgacctg cggctgatct atctggccct ggcccacatg 480
atcaagttcc ggggccactt cctgatcgag ggcgacctga accccgacaa cagcgacgtg 540
gacaagctgt tcatccagct ggtgcagacc tacaaccagc tgttcgagga aaaccccatc 600
aacgccagcg gcgtggacgc caaggccatc ctgtctgcca gactgagcaa gagcagacgg 660
ctggaaaatc tgatcgccca gctgcccggc gagaagaaga atggcctgtt cggaaacctg 720
attgccctga gcctgggcct gacccccaac ttcaagagca acttcgacct ggccgaggat 780
gccaaactgc agctgagcaa ggacacctac gacgacgacc tggacaacct gctggcccag 840
atcggcgacc agtacgccga cctgtttctg gccgccaaga acctgtccga cgccatcctg 900
ctgagcgaca tcctgagagt gaacaccgag atcaccaagg ccccccctgag cgcctctatg 960 atcaagagat acgacgagca ccaccaggac ctgaccctgc tgaaagctct cgtgcggcag 1020
cagctgcctg agaagtacaa agagattttc ttcgaccaga gcaagaacgg ctacgccggc 1080
tacattgacg gcggagccag ccaggaagag ttctacaagt tcatcaagcc catcctggaa 1140

```
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga tttttaccca ttcctgaagg acaaccggga aaagatcgag   1320
aagatcctga ccttccgcat cccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca agcccgagaa catcgtgatc   2280
gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact tttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga acagcgataa gctgatcgcc   3360
agaaagaagg actgggaccc taagaagtac ggcggcttcg acagccccac cgtggcctat   3420
tctgtgctgg tggtggccaa agtggaaaag ggcaagtcca agaaactgaa gagtgtgaaa   3480
```

gagctgctgg ggatcaccat catggaaaga agcagcttcg agaagaatcc catcgacttt 3540
ctggaagcca agggctacaa agaagtgaaa aaggacctga tcatcaagct gcctaagtac 3600
tccctgttcg agctggaaaa cggccggaag agaatgctgg cctctgccgg cgaactgcag 3660
aagggaaacg aactggccct gccctccaaa tatgtgaact tcctgtacct ggccagccac 3720
tatgagaagc tgaagggctc ccccgaggat aatgagcaga aacagctgtt tgtggaacag 3780
cacaagcact acctggacga gatcatcgag cagatcagcg agttctccaa gagagtgatc 3840
ctggccgacg ctaatctgga caaagtgctg tccgcctaca acaagcaccg ggataagccc 3900
atcagagagc aggccgagaa tatcatccac ctgtttaccc tgaccaatct gggagcccct 3960
gccgccttca agtactttga caccaccatc gaccggaaga ggtacaccag caccaaagag 4020
gtgctggacg ccaccctgat ccaccagagc atcaccggcc tgtacgagac acggatcgac 4080
ctgtctcagc tgggaggtga c 4101

<210> SEQ ID NO 250
<211> LENGTH: 4101
<212> TYPE: DNA
<213> ORGANISM: Unknown
<220> FEATURE:
<223> OTHER INFORMATION: Cas9 nucleotide sequence

<400> SEQUENCE: 250
gacaagaagt acagcatcgg cctggacatc ggcaccaact ctgtgggctg ggccgtgatc 60
accgacgagt acaaggtgcc cagcaagaaa ttcaaggtgc tgggcaacac cgaccggcac 120
agcatcaaga agaacctgat cggagccctg ctgttcgaca gcggcgaaac agccgaggcc 180
acccggctga agagaaccgc cagaagaaga tacaccagac ggaagaaccg gatctgctat 240
ctgcaagaga tcttcagcaa cgagatggcc aaggtggacg acagcttctt ccacagactg 300
gaagagtcct tcctggtgga agaggataag aagcacgagc ggcaccccat cttcggcaac 360
atcgtggacg aggtggccta ccacgagaag taccccacca tctaccacct gagaaagaaa 420
ctggtggaca gcaccgacaa ggccgacctg cggctgatct atctggccct ggcccacatg 480
atcaagttcc ggggccactt cctgatcgag ggcgacctga accccgacaa cagcgacgtg 540
gacaagctgt tcatccagct ggtgcagacc tacaaccagc tgttcgagga aaaccccatc 600
aacgccagcg gcgtggacgc caaggccatc ctgtctgcca gactgagcaa gagcagacgg 660
ctggaaaatc tgatcgccca gctgcccggc gagaagaaga atggcctgtt cggaaacctg 720
attgccctga gcctgggcct gacccccaac ttcaagagca acttcgacct ggccgaggat 780
gccaaactgc agctgagcaa ggacacctac gacgacgacc tggacaacct gctggcccag 840
atcggcgacc agtacgccga cctgtttctg gccgccaaga acctgtccga cgccatcctg 900
ctgagcgaca tcctgagagt gaacaccgag atcaccaagg ccccccctgag cgcctctatg 960 atcaagagat acgacgagca ccaccaggac ctgaccctgc tgaaagctct cgtgcggcag 1020
cagctgcctg agaagtacaa agagattttc ttcgaccaga gcaagaacgg ctacgccggc 1080
tacattgacg gcggagccag ccaggaagag ttctacaagt tcatcaagcc catcctggaa 1140
aagatggacg gcaccgagga actgctcgtg aagctgaaca gagaggacct gctgcggaag 1200
cagcggacct tcgacaacgg cagcatcccc caccagatcc acctgggaga gctgcacgcc 1260
attctgcggc ggcaggaaga tttttaccca ttcctgaagg acaaccggga aaagatcgag 1320
aagatcctga ccttccgcat cccctactac gtgggccctc tggccagggg aaacagcaga 1380
ttcgcctgga tgaccagaaa gagcgaggaa accatcaccc cctggaactt cgaggaagtg 1440

-continued

```
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100
ctgaccttta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca agcccgagaa catcgtgatc   2280
gaaatggcca gagagaacca gaccacccag aagggacaga agaacagccg cgagagaatg   2340
aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggacgccatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
atcatgaact tttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga acagcgataa gctgatcgcc   3360
agaaagaagg actgggaccc taagaagtac ggcggcttcg acagccccac cgtggcctat   3420
tctgtgctgg tggtggccaa agtggaaaag ggcaagtcca agaaactgaa gagtgtgaaa   3480
gagctgctgg ggatcaccat catggaaaga agcagcttcg agaagaatcc catcgacttt   3540
ctggaagcca agggctacaa agaagtgaaa aaggacctga tcatcaagct gcctaagtac   3600
tccctgttcg agctggaaaa cggccggaag agaatgctgg cctctgccgg cgaactgcag   3660
aagggaaacg aactggccct gccctccaaa tatgtgaact tcctgtacct ggccagccac   3720
tatgagaagc tgaagggctc ccccgaggat aatgagcaga aacagctgtt tgtggaacag   3780
```

-continued

```
cacaagcact acctggacga gatcatcgag cagatcagcg agttctccaa gagagtgatc   3840

ctggccgacg ctaatctgga caaagtgctg tccgcctaca acaagcaccg ggataagccc   3900

atcagagagc aggccgagaa tatcatccac ctgtttaccc tgaccaatct gggagcccct   3960

gccgccttca agtactttga caccaccatc gaccggaaga ggtacaccag caccaaagag   4020

gtgctggacg ccaccctgat ccaccagagc atcaccggcc tgtacgagac acggatcgac   4080

ctgtctcagc tgggaggtga c                                             4101


<210> SEQ ID NO 251
<211> LENGTH: 23
<212> TYPE: DNA
<213> ORGANISM: Artificial sequence
<220> FEATURE:
<223> OTHER INFORMATION: Synthetic spacer

<400> SEQUENCE: 251

tgattccaca ggctttcttg aac                                             23


<210> SEQ ID NO 252
<211> LENGTH: 26
<212> TYPE: DNA
<213> ORGANISM: Artificial sequence
<220> FEATURE:
<223> OTHER INFORMATION: Synthetic binding site of GRF5

<400> SEQUENCE: 252

aaccgttcaa gaaagcctgt ggaacg                                          26


<210> SEQ ID NO 253
<211> LENGTH: 8
<212> TYPE: PRT
<213> ORGANISM: Zea mays

<400> SEQUENCE: 253

Asn Arg Ser Arg Lys Pro Val Glu
1               5


<210> SEQ ID NO 254
<211> LENGTH: 27
<212> TYPE: DNA
<213> ORGANISM: Zea mays

<400> SEQUENCE: 254

aaccgttcaa gaaagcctgt ggaaacg                                         27


<210> SEQ ID NO 255
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 255

Asn Arg Ser Arg Lys Pro Leu Lys Thr
1               5


<210> SEQ ID NO 256
<211> LENGTH: 9
<212> TYPE: PRT
<213> ORGANISM: Artificial sequence
<220> FEATURE:
<223> OTHER INFORMATION: Mutant GRF miRNA binding site

<400> SEQUENCE: 256
```

Asn Arg Ser Lys Lys Pro Val Glu Thr
1               5

<210> SEQ ID NO 257
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(27)
<223> OTHER INFORMATION: n is a, c, g, or t

<400> SEQUENCE: 257
tttvnnnnnn nnnnnnnnnn nnnnnnn 27

<210> SEQ ID NO 258
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: n is a, c, g, or t

<400> SEQUENCE: 258
nnnnnnnnnn nnnnnnnnnn ngg 23

<210> SEQ ID NO 259
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(27)
<223> OTHER INFORMATION: n is a, c, g, or t

<400> SEQUENCE: 259
tttvnnnnnn nnnnnnnnnn nnnnnnn 27

<210> SEQ ID NO 260
<211> LENGTH: 20
<212> TYPE: PRT
<213> ORGANISM: Zea mays

<400> SEQUENCE: 260

His Met His Arg Gly Arg Asn Arg Ser Arg Lys Pro Val Glu Thr Gln
1               5                   10                  15

Leu Ala Pro Gln
            20

<210> SEQ ID NO 261
<211> LENGTH: 20
<212> TYPE: DNA
<213> ORGANISM: Artificial sequence
<220> FEATURE:
<223> OTHER INFORMATION: Synthetic spacer

<400> SEQUENCE: 261
cttccacagg ctttcttgaa 20

<210> SEQ ID NO 262
<211> LENGTH: 20
<212> TYPE: DNA
<213> ORGANISM: Artificial sequence
<220> FEATURE:
<223> OTHER INFORMATION: Synthetic spacer

<400> SEQUENCE: 262
attccacagg ctttcttgaa 20

<210> SEQ ID NO 263
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 263
aaccgttcaa gaaagcctgt ggaaacc 27

<210> SEQ ID NO 264
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 264
aaccgttcaa gaaaacctgt ggaaacc 27

<210> SEQ ID NO 265
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 265
aaccgttcaa gaaagcctgt caaaacc 27

<210> SEQ ID NO 266
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 266
aaccgttcaa gaaaacctgt caaaacc 27

<210> SEQ ID NO 267
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 267
aaccgttcaa aaaagcctgt ggaaacc 27

<210> SEQ ID NO 268
<211> LENGTH: 27
<212> TYPE: DNA
<213> ORGANISM: Artificial sequence
<220> FEATURE:
<223> OTHER INFORMATION: Synthetic binding site of GRF6

-continued

<400> SEQUENCE: 268
aaccgttcaa gaaagcctgt aaaaacc 27

<210> SEQ ID NO 269
<211> LENGTH: 27
<212> TYPE: DNA
<213> ORGANISM: Artificial sequence
<220> FEATURE:
<223> OTHER INFORMATION: Synthetic binding site of GRF6

<400> SEQUENCE: 269
aaccgttcaa gaaaacctgt aaaaacc 27

<210> SEQ ID NO 270
<211> LENGTH: 23
<212> TYPE: DNA
<213> ORGANISM: Artificial sequence
<220> FEATURE:
<223> OTHER INFORMATION: Synthetic spacer

<400> SEQUENCE: 270
cacaggcttt cttgaacggt tct 23

<210> SEQ ID NO 271
<211> LENGTH: 23
<212> TYPE: DNA
<213> ORGANISM: Artificial sequence
<220> FEATURE:
<223> OTHER INFORMATION: Synthetic spacer

<400> SEQUENCE: 271
cacaggcttt cttgaacggt gac 23

<210> SEQ ID NO 272
<211> LENGTH: 23
<212> TYPE: DNA
<213> ORGANISM: Artificial sequence
<220> FEATURE:
<223> OTHER INFORMATION: Synthetic spacer

<400> SEQUENCE: 272
cacaggcttt cttgaacggt tct 23

<210> SEQ ID NO 273
<211> LENGTH: 23
<212> TYPE: DNA
<213> ORGANISM: Artificial sequence
<220> FEATURE:
<223> OTHER INFORMATION: Synthetic spacer

<400> SEQUENCE: 273
cacaggcttt cttgaacggt ggc 23

<210> SEQ ID NO 274
<211> LENGTH: 23
<212> TYPE: DNA
<213> ORGANISM: Artificial sequence
<220> FEATURE:
<223> OTHER INFORMATION: Synthetic spacer

<400> SEQUENCE: 274
cacaggcttt cttgaactgt gaa 23

<210> SEQ ID NO 275
<211> LENGTH: 68

<212> TYPE: DNA
<213> ORGANISM: Zea mays

<400> SEQUENCE: 275
agtactgcga gcgccacatg caccgcggcc gcaaccgttc aagaaagcct gtggaaacgc 60
agctcgcg 68

<210> SEQ ID NO 276
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 276
agtactgcga gcgccacatg caccgcggcc gcaagaaagc ctgtggaaac gcagctcgcg 60

<210> SEQ ID NO 277
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 277
agtactgcga gcgccacatg caccgcggcc gagaaagcct gtggaaacgc agctcgcg 58

<210> SEQ ID NO 278
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 278
agcctgtgga aacgcagctc gcg 23

<210> SEQ ID NO 279
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 279
agtactgcga gcgccacatg caccgcggcc gctcaagaaa gcctgtggaa acgcagctcg 60
cg 62

<210> SEQ ID NO 280
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 280
agtactgcga gcgccacatg caccgcggcc caagaaagcc tgtggaaacg cagctcgcg 59

<210> SEQ ID NO 281
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 281
agaaagcctg tggaaacgca gctcgcg 27

<210> SEQ ID NO 282
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 282
agtactgcga gcgccacatg caccgcggcc aagaaagcct gtggaaacgc agctcgcg 58

<210> SEQ ID NO 283
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 283
agtactgcga gcgccacatg caccgcggcc gtcaagaaag cctgtggaaa cgcagctcgc 60
g 61

<210> SEQ ID NO 284
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 284
agtactgcga gcgccacatg caccgcggcc gcaagaaagc ctgtggaaac gcagctcgcg 60

<210> SEQ ID NO 285
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 285
agtactgcga gcgccacatg caccgcggcc gaaagcctgt ggaaacgcag ctcgcg 56

<210> SEQ ID NO 286
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 286
agtactgcga gcgccacatg caccgcggcc gcaagaaagc ctgtggaaac gcagctcgcg 60

<210> SEQ ID NO 287
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 287
agtactgcga gcgccacatg caccgcggcc acggctcgcg 40

<210> SEQ ID NO 288
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 288
agtactgcga gcgccacatg caccgcggcc gcg 33

<210> SEQ ID NO 289
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 289
agtactgcga gcgccacatg caccgcggcc caagaaagcc tgtggaaacg cagctcgcg 59

<210> SEQ ID NO 290
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 290
agtactgcga gcgccacatg caccgcggcc ggttcaagaa agcctgtgga aacgcagctc 60
gcg 63

<210> SEQ ID NO 291
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 291
agtactgcga gcgccacatg caccgcggcc aagaaagcct gtggaaacgc agctcgcg 58

<210> SEQ ID NO 292
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 292
agtactgcga gcgccacatg caccgcggcc gcaaccgtca agaaagcctg tggaaacgca 60
gctcgcg 67

<210> SEQ ID NO 293
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 293
agtactgcga gcgccacatg caccgcggcc gcttcaagaa agcctgtgga aacgcagctc 60
gcg 63

<210> SEQ ID NO 294

<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 294
agtactgcga gcgccacatg caccgcggcc cagtcccaa 39

<210> SEQ ID NO 295
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 295
agtactgcga gcgccacatg caccgcggcc caagaaagcc tgtggaaacg cagctcgcg 59

<210> SEQ ID NO 296
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 296
agtactgcga gcgccacatg caccgcggcc gctcaagaaa gcctgtggaa acgcagctcg 60
cg 62

<210> SEQ ID NO 297
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 297
agtactgcga gcgccacatg caccgcggcc gcaagaagcc tgtggaaacg cagctcgcg 59

<210> SEQ ID NO 298
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 298
agtactgcga gcgccacatg caccgcggcc gcaaccgaaa gcctgtggaa acgcagctcg 60
cg 62

<210> SEQ ID NO 299
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 299
agtactgcga gcgccacatg caccgcggcc caagaaagcc tgtggaaacg cagctcgcg 59

<210> SEQ ID NO 300
<211> LENGTH: 65
<212> TYPE: DNA
<213> ORGANISM: Artificial sequence
<220> FEATURE:
<223> OTHER INFORMATION: Synthetic oligonucleotide

<400> SEQUENCE: 300
agtactgcga gcgccacatg caccgcggca accgttcaag aaagcctgtg gaaacgcagc 60
tcgcg 65

<210> SEQ ID NO 301
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 301
agtactgcga gcgccacatg caccgcggcc gcaacaagaa agcctgtgga aacgcagctc 60
gcg 63

<210> SEQ ID NO 302
<211> LENGTH: 67
<212> TYPE: DNA
<213> ORGANISM: Artificial sequence
<220> FEATURE:
<223> OTHER INFORMATION: Synthetic oligonucleotide

<400> SEQUENCE: 302
agtactgcga gcgccacatg caccgcggcc gcaaccttca agaaagcctg tggaaacgca 60
gctcgcg 67

<210> SEQ ID NO 303
<211> LENGTH: 59
<212> TYPE: DNA
<213> ORGANISM: Artificial sequence
<220> FEATURE:
<223> OTHER INFORMATION: Synthetic oligonucleotide

<400> SEQUENCE: 303
agtactgcga gcgccacatg caccgcggcc caagaaagcc tgtggaaacg cagctcgcg 59

<210> SEQ ID NO 304
<211> LENGTH: 3431
<212> TYPE: DNA
<213> ORGANISM: Zea mays

<400> SEQUENCE: 304
ggagcgaagc aaagcacatc acgagcccag cctgcgcctg cggagggagg gggctcatta 60 aagaggggc gcgagcgcga ccggccgcgg ggagcaagca gcgcgcgaga gagacaggtt 120
gagatggcga tgccgtatgc ctctctttcc ccggcaggcg ccgccgacca ccgctcctcc 180
acagccacgg cgtccctcgt ccccttctgc cgctccactc cgctctccgc gtaagtatcc 240
accaccgtcg ctcatcgctt cttggctcgt gtagtgtcgt ctcccattga tgcccgtctg 300
gttcgcggtt gtgttgtgac gacgtggtgg tatgtgtgct ggtgcagggg cggcgggctg 360
ggcgaggagg acgcccaggc gagcgcgagg tggccggccg cgaggccggt ggtgccgttc 420
acgccggcgc agtaccagga gctggagcag caggcgctca tatacaagta cctggtggcg 480
ggcgtgcccg ttccgccgga tctcgtggtt ccaatccgcc gcggcctcga ctccctcgca 540
acccgcttct acggccaacc cacacgtacg tacggcattt ccctccctct cctctcggcg 600
ccctgccaga ctccatctcc ttcctgtact gcgtccgggg tgcttggctg cttgctccct 660

-continued ccccgggatc ctgactcttt gtttattcca gccaagcgta ctttgcctcc attagttaat 720
ttgctccagt catttgttaa tccctggtgc gcgattcaag aaccgtgcgc gtgtttcata 780
caagaccccc gatttgctcc cggaaagttt ctgttttttt aatccgagct gattcatcaa 840
atgatgaggc agagctagct aggtagctcg tcatttcgtg ctgttttgat ttgataccga 900
gcttagtagt tgttggaata gaggttagaa tcagtagcac gcatcgttgt ggctcaatag 960
tacgaatact tttcttttgc catttatttc ctctccttct ggcttctgga tgatcaatac 1020
tacgtaactg tgagaggtcg ccccctcggc agcaagcaaa ttcattgaat gcaatctgca 1080
gcagctctcc gctagctgct cgccatttcg tccgactgcg cctgcatcgg tactgtcctg 1140
tactaccaaa tggcaatcca tttggacact gcagatccag atgcacgcgt agttgctgcg 1200
tacatgcaga tgcacgatga taaaagcaaa cgcacaagtg atgcttaaat acagcgtctg 1260
attttctcgg cgtgatctgt gcagtcgggt acggaccgta cctggggagg aaactggatc 1320
cggagcccgg ccggtgccgg cgaacggacg gcaagaagtg gcggtgctcc aaggaggccg 1380
ccccggactc caagtactgc gagcgccaca tgcaccgcgg ccgcaaccgt tcaagaaagc 1440
ctgtggaaac gcagctcgcg ccccagtccc aaccgcccgc cgccgcagcc gtctccgccg 1500
ctccgcccct ggcagccgcc gccgccgcca ccaccaacgg cagcggcttc cagaaccact 1560
ctctctaccc ggccatcgcc ggcagcactg gtggtggagg aggagttggc gggtccggca 1620
atatctcctc cccgttctcc tcgtcgatgg ggggatcgtc tcagctgcac atggacagtg 1680
ctgccagcta ctcctacgca gctcttggtg gtggaactgc aaaggatctc aggtgactat 1740
tctttccctt ttcttttatt tcctctccag tgaccaatgc tatcctgttt ttctaacagt 1800
gctatcgatt ttaactgatt ggcgtcagat ggccacacat gctataacat tttaccgatg 1860
atcgttcact aatctctgtc tgtttggcat cagtggcaat caaaaccagt agcgtagtgc 1920
gtgctccgta gtacttcact ggcaaaatca gcatggccta cgaggacttt actcacttca 1980
agagattacg ttagagttca ggcgctggct ggttgcctgg ccacgcttta ttaatgagtt 2040
cagttctaaa cccctgctga agcccaggca gtgtccatgt ctctacgaga tagttgtgcc 2100
cagggcaggt ggacgtgcag gtgtgcagcg cacagccttg ttggcttcgg cacagaccca 2160
gcttcgaatt cgtgctggtg ctgcgcataa agatggaact tgtttgtgtc cagcggtcgc 2220
agtgctggtg cctgctgctt gctgatgctg tccttccctg gccattactc cacgtcttta 2280
tgatctcgca ggatcaagtc gttgctcttg caactctttt agggggcagc atgtaataaa 2340
atccggtcct tgtaactact gataaacctg aaacgcatca tgctggaagt ccatcccctt 2400
ttgcccatac cagtttggtt gattttactg tacagatgtt ctttcacttt gtttacaatt 2460
tatcgaacag gataatgaag actaacacct cacaaagaag aaaacatact gcagttggca 2520
tgtgtccttt ttaacctttg caacccccct actaatttgc tgtgcccacc ccgctttctg 2580
aaatccaggt acaacgctta cggaataaga tctctggcgg acgagcacaa ccagctgatc 2640
gcagaagcca tcgactcgtc gatagagagc cagtggcgcc tccccagctc gtcgttcccg 2700
ctctcgagct acccacatct cggggcgctg ggcgacctgg gcggccagaa cagcacggtg 2760
agctcgctgc cgaagatgga gaagcagcag ccgccctcgt ccttcctagg gaacgacacc 2820
ggggccggca tggccatggg ctccgcctcc gcgaagcagg agggccagac gctgcggcac 2880
ttcttcgacg agtggcccaa ggcgcgggac tcctggccgg gcctctccga cgagaccgcc 2940
agcctcgcct cgttcccccc ggcgacccag ctgtcgatgt ccatacccat ggcgtcctcc 3000
gacttctccg tggccagctc ccagtcgccc aacggtgagt cgcgtacgtt cctgctggcc 3060

-continued

```
acggaccgaa ggtgaaaggt tgttgctggt ttactgatag gagacaacca tgtctggtct   3120

ctgcagatga ctaatggtgc gtggatcgtc gcgttctggc cctttgtctg tcttccctcc   3180

agtcctccac ccaccgcgca gtagtagctg cggaaacagc ccatgctcct gtatatttgt   3240

cggtcatttt ccgtgtcaga tctgtgtacc aaaccaagcg gcggcggccg tcgtctctcc   3300

ccgcctccgc ctcgcctcat gtgggtgggt gaacatgaga ccgttttgct taggctcaaa   3360

gctttgtgtg accccactga tcggttgtct gcgtactacc tgaaagcctg ctgcttttgt   3420

agcattactg t                                                        3431
```

MUTATION OF GROWTH REGULATING FACTOR FAMILY TRANSCRIPTION FACTORS FOR ENHANCED PLANT GROWTH

STATEMENT OF PRIORITY

This application claims the benefit, under 35 U.S.C. § 119 (e), of U.S. Provisional Application No. 62/951,593 filed on Dec. 20, 2019, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 1499-16_ST25.txt, 578,175 bytes in size, generated on Nov. 29, 2023, is provided in lieu of a paper copy. This Sequence Listing is hereby incorporated herein by reference into the specification for its disclosures.

FIELD OF THE INVENTION

This invention relates to compositions and methods for modifying growth regulating factor (GRF) family transcription factors in plants to produce plants having improved phenotypic characteristics including increased growth. The invention further relates to plants produced using the methods and compositions of the invention.

BACKGROUND OF THE INVENTION

GRFs are land-plant-specific transcription factors that function with GRF-interacting factors (GIFs), which are found in plants and metazoans but not in fungi. The number of GRF family members is about 8-20 across the land plants. Recent studies have uncovered the functions of GRFs in other aspects of plant biology such as flowering, seed and root development, the control of growth under stress conditions, and the regulation of plant longevity.

Analysis of GRF mutants and overexpressing plants have shown that these transcription factors promote cell proliferation during leaf development. It has also been established that the mRNA of some GRFs are targeted by the microRNA miR396. For example, seven out of the nine *Arabidopsis* GRFs have a binding site for micro-RNA (miRNA) miR396. While initial work on the GRF transcription factor family focused on the effect of GRF mis-expression on leaf size, later work established that larger seeds can be achieved in *Arabidopsis* by heterogeneous expression of *Brassica napus* GRF2 or overexpression of AtGRF1, AtGRF2 and AtGRF5 (van Daele et al. *Plant Biotechnology Journal* 10:488-500 2012)).

Grain size is one of the key components of grain yield and is regulated by quantitative trait loci (QTLs) in rice. A semi-dominant QM for grain size and weight (GS2) have been reported in rice, which encodes the transcription factor OsGRF4 (GROWTH-REGULATING FACTOR 4) and is regulated by OsmiR396. A 2 bp substitution mutation in GS2 perturbs OsmiR396-directed regulation of GS2, resulting in large and heavy grains and increased grain yield (FIG. 1).

SUMMARY OF THE INVENTION

One aspect of the invention provides a plant or plant part thereof comprising at least one non-natural mutation in an endogenous gene encoding a Growth Regulating Factor (GRF) transcription factor, wherein the at least one non-natural mutation in the endogenous gene encoding a GRF transcription factor results in increased levels of mRNA produced by the endogenous gene.

Another aspect of the invention provides a plant cell, comprising a base editing system comprising: (a) a CRISPR-associated effector protein; (b) a cytidine deaminase or adenosine deaminase; and (c) a guide nucleic acid (gRNA, gDNA, crRNA, crDNA) having a spacer sequence with complementarity to an endogenous target gene encoding a GRF transcription factor.

A further aspect of the invention provides a plant cell comprising at least one non-naturally occurring genomic modification within a miR396 binding site of a GRF transcription factor gene that prevents or reduces binding of the miR396 to the GRF transcription factor mRNA, wherein the genomic modification is a substitution, insertion or a deletion that is introduced using an editing system that comprises a nucleic acid binding domain that binds to a target site in the GRF transcription factor gene having the nucleotide sequence of any one of SEQ ID NOs:4-18, 121-144, or 173-198.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NOs:4, 5 and 9-18, wherein each of SEQ ID NOs:4, and 9-18 comprise a sequence having at least 90% sequence identity to SEQ ID NO:1, and the target gene is modified (e.g., mutated) within the sequence having at least 90% sequence identity to SEQ ID NO:1.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to the nucleotide sequence of SEQ ID NO:6 or SEQ ID NO:7, wherein each of SEQ ID NO:6 or SEQ ID NO:7 comprise a sequence having at least 90% sequence identity to SEQ ID NO: 2, and the target gene is modified (e.g., mutated) within the sequence having at least 90% sequence identity to SEQ ID NO: 2.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NO:8, wherein SEQ ID NO:8 comprises a sequence having at least 90% sequence identity to SEQ ID NO: 3, and the target gene is modified (e.g., mutated) within the sequence having at least 90% sequence identity to SEQ ID NO: 3.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NOs:121-144, wherein each of SEQ ID NOs: 121-144 comprise a sequence having at least 90% sequence identity to any one of SEQ ID NOs:145-146, and the target gene is modified (e.g., mutated) within the sequence having at least 90% sequence identity to any one of SEQ ID NO:145-146.

Another aspect of the invention provides a plant or part thereof comprising a mutated endogenous GRF transcription factor gene that produces a mRNA having reduced miR396 binding, wherein the mutated endogenous GRF transcription factor gene comprises a target gene (a target nucleic acid) that comprises a sequence having at least 80% identity to any one of the nucleotide sequences of SEQ ID NOs:173-198, wherein each of SEQ ID NOs:173-198 comprise a sequence having at least 90% sequence identity to any one of SEQ ID NOs:199-202, and the target gene is modified (e.g., mutated) within the sequence having at least 90% sequence identity to any one of SEQ ID NOs: 199-202.

An additional aspect of the invention provides a plant comprising a Growth Regulating Factor (GRF) transcription factor gene that comprises a mutation in any one of the nucleotide sequences of SEQ ID NOs: 1-33 and/or comprises the nucleotide sequence of any one of SEQ ID NOs:34-41.

A further aspect of the invention provides a corn plant comprising a Growth Regulating Factor (GRF) transcription factor gene that comprises a nucleotide sequence of any one of SEQ ID NOs: 34-42.

An additional aspect of the invention provides a maize plant comprising a mutation in the miR396 binding site of a Growth Regulating Factor (GRF) transcription factor gene, the GRF transcription factor gene comprising a nucleotide sequence of any one of SEQ ID NOs:1 33.

An additional aspect of the invention provides a wheat plant comprising a mutation in the miR396 binding site of a Growth Regulating Factor (GRF) transcription factor gene, the GRF transcription factor gene comprising a nucleotide sequence of any one of SEQ ID NOs: 147-202.

A further aspect of the invention provides a soybean plant comprising a mutation in the miR396 binding site of a Growth Regulating Factor (GRF) transcription factor gene comprising a nucleotide sequence of any one of SEQ ID NOs: 97-146.

The invention further provides a method of producing/breeding a transgene-free base-edited plant, comprising: (a) crossing a plant of the invention with a transgene free plant, thereby introducing the at least one mutation, the mutation, or the modification into the plant that is transgene-free; and (b) selecting a progeny plant that comprises the at least one single nucleotide substitution but is transgene-free, thereby producing a transgene free base-edited plant.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having at least 80% sequence identity to the nucleotide sequence of any one of SEQ ID NO: 4-18, 121-144, or 173-198, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having at least 65% sequence identity to the nucleotide sequence of SEQ ID NO:9 or SEQ ID NO:14 and comprising a miR396 binding site sequence at bp position 21 to 42 of SEQ ID NO:9 (GRF8 60 nt cDNA or SEQ ID NO:14 (GRF5 60 nt cDNA), the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of any one of SEQ ID NOs:4, 5, or 9-18 and comprising a miR396 binding site sequence at by position 21 to 42 of any one of SEQ ID NOs:4, 5, or 9-18, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO: 6 or SEQ ID NO:7, and comprising a miR396 binding site sequence at bp position 21 to 42 of SEQ ID NO:6 or SEQ ID NO:7, the binding site sequence having at least 90% sequence identity to SEQ ID NO:2, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO: 8, and comprising a miR396 binding site sequence at bp position 21 to 42 of SEQ ID NO:8, the binding site sequence having at least 90% sequence identity to SEQ ID NO:3, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:4, and comprising a miR396 binding site sequence at bp position 21 to 42 of SEQ ID NO:4, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:5, and comprising a miR396 binding site sequence at bp position 21 to 42 of SEQ ID NO:5, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:9, and comprising a miR396 binding site sequence at bp position 21 to 42 of SEQ ID NO:9, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:10, and comprising a miR396 binding site sequence at bp position 21 to 42 of SEQ ID NO:10, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:11, and comprising a miR396 binding site sequence at bp position 21 to 42 of SEQ ID NO:1, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:12, and comprising a miR396 binding site sequence at bp position 21 to 42 of SEQ ID NO:12, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:13, and comprising a miR396 binding site sequence at bp position 21 to 42 of SEQ ID NO:13, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:14, and comprising a miR396 binding site sequence at bp position 21 to 42 of SEQ ID NO:14, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:15, and comprising a miR396 binding site sequence at bp position 21 to 42 of SEQ ID NO:15, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:16, and comprising a miR396 binding site sequence at bp position 21 to 42 of SEQ ID NO:16, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:17, and comprising a miR396 binding site sequence at bp position 21 to 42 of SEQ ID NO:17, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of SEQ ID NO:18, and comprising a miR396 binding site sequence at bp position 21 to 42 of SEQ ID NO:18, the binding site sequence having at least 90% sequence identity to SEQ ID NO:1, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of any one of SEQ ID NOs:121-144 and comprising a miR396 binding site sequence at by position 21 to 42 of any one of SEQ ID NOs:121-144, the binding site sequence having at least 90% sequence identity to any one of SEQ ID NOs:145-146, thereby generating an edit in the endogenous GRF transcription factor gene of the plant cell.

Another aspect of the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity to the nucleotide sequence of any one of SEQ ID NOs:173-198 and comprising a miR396 binding site sequence at by position 21 to 42 of any one of SEQ ID NOs: 173-198, the binding site sequence having at least 90% sequence identity to any one of SEQ ID NOs:199-202, thereby generating an edit in the endogenous GRF transcription factor gene of the plant cell.

An additional aspect of the invention provides a method for making a plant, comprising: (a) contacting a population of plant cells comprising an endogenous gene encoding a GRF transcription factor with an editing system comprising a nucleic acid binding domain that binds to a sequence having at least 80% identity to the nucleotide sequence of SEQ ID NOs:1-3, 145, 146, or 199-202 or SEQ ID NOs:4-18, 121-144, or 173-198; (b) selecting a plant cell from said population comprising a mutation in at least one endogenous gene encoding a GRF transcription factor, wherein the mutation is a substitution of at least one nucleotide in the at least one endogenous gene, wherein the mutation reduces or eliminates the ability of miR396 to bind to a mRNA produced by the at least one endogenous gene encoding a GRF transcription factor comprising the mutation; and (c) growing the selected plant cell into a plant.

In some aspects, the invention provides a method for producing a plant or part thereof comprising at least one cell in which an endogenous GRF transcription factor gene is mutated, the method comprising contacting a target site in the GRF transcription factor gene in the plant or plant part with an editing system comprising a nucleic acid binding domain that binds to a target site in the GRF transcription factor gene having at least 80% sequence identity to the nucleotide sequence of any one of SEQ ID NOs: 1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, thereby producing a plant or part thereof comprising at least one cell having a mutation in the endogenous GRF transcription factor gene A further aspect of the invention provides a method of producing a plant or part thereof comprising a mutated endogenous GRF transcription factor gene producing a mRNA having reduced miR396 binding, the method comprising contacting a target site in an endogenous GRF transcription factor gene with an editing system comprising a nucleic acid binding domain that binds to a target site in the GRF transcription factor gene having at least 80% sequence identity to the nucleotide sequence of any one of SEQ ID NOs:1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, thereby producing a plant or part thereof comprising a mutated endogenous GRF transcription factor gene producing a mRNA having reduced miR396 binding.

Another aspect of the invention provides a method of producing a plant or part thereof having increased growth or an increased growth rate, the method comprising contacting a target site in an endogenous GRF transcription factor gene with an editing system comprising a nucleic acid binding domain that binds to a target site in the GRF transcription factor gene having at least 80% sequence identity to the nucleotide sequence of any one of SEQ ID NOs:1-3, 145, 146, or 199-202, having at least 80% sequence identity to the nucleotide sequence of any one of SEQ ID NOs: 4-18, 121-144, or 173-198, or having at least 80% sequence identity to the nucleotide sequence of any one of SEQ ID NOs: 19-33, 97-120, or 147-172, thereby producing a plant or part thereof comprising a mutated endogenous GRF transcription factor gene that produces a mRNA having reduced miR396 binding, thereby producing a plant or part thereof having increased growth or an increased growth rate.

An additional aspect of the invention provides a guide nucleic acid (e.g., gRNA) that binds to a target site in a GRF transcription factor gene, the target site comprising any one of the nucleotide sequences of SEQ ID NOs:44-71.

A further aspect of the invention provides a system comprising the guide nucleic acid of the invention and a CRISPR-Cas effector protein that associates with the guide nucleic acid.

Another aspect of the invention provides a gene editing system comprising a CRISPR-Cas effector protein in association with a guide nucleic acid, wherein the guide nucleic acid comprises a spacer sequence that binds to a GRF transcription factor gene.

An additional aspect of the invention provides a complex comprising a CRISPR-Cas effector protein comprising a cleavage domain and a guide nucleic acid (e.g., gRNA), wherein the guide nucleic acid binds to a target site in a GRF transcription factor gene having the nucleotide sequence of any one of SEQ ID NOs: 19-33, 97-120, or 147-172, wherein the nuclease cleaves the target strand.

An additional aspect of the invention provides a complex comprising a CRISPR-Cas effector protein comprising a cleavage domain and a guide nucleic acid (e.g., gRNA), wherein the guide nucleic acid binds to a target site in a GRF transcription factor gene having the nucleotide sequence of any one of SEQ ID NOs:1-3, 145, 146, or 199-202, or SEQ ID NOs:4-18, 121-144, or 173-198, wherein the nuclease cleaves the target strand.

Another aspect of the invention provides an expression cassette comprising a (a) polynucleotide encoding CRISPR-Cas effector protein comprising a cleavage domain and (b) a guide nucleic acid that binds to a target site in a GRF transcription factor gene, wherein the guide nucleic acid comprises a spacer sequence that is complementary to and binds to a sequence having at least 80% sequence identity to at least a portion of any one of the nucleotide sequences of SEQ ID NOs: 1-3, 145, 146, or 199-202, or SEQ ID NOs:4-18, 121-144, or 173-198.

A further aspect of the invention provides a nucleic acid encoding a GRF transcription factor mRNA having a mutated miR396 binding site, wherein the mutated miR396 binding site comprises a mutation that disrupts miR396 binding and results in increased levels of the GRF transcription factor mRNA.

An additional aspect of the invention provides a corn plant or plant part thereof that comprises at least one non-natural mutation in at least one endogenous Growth Regulating Factor (GRF) transcription factor that is located in a defined chromosome interval on chromosome 1, 2, 4, 5, 6, 7, 9, and/or 10 of the corn plant, wherein the mutation disrupts the binding of miR396 to the GRF transcription factor mRNA resulting in increased levels of the GRF transcription factor mRNA.

Another aspect of the invention provides a guide nucleic acid that binds to a target nucleic acid in a GRF transcription factor in a corn plant, wherein the target nucleic acid is located in a defined chromosome interval on chromosome 1, 2, 4, 5, 6, 7, 9, and/or 10 of the corn plant.

Further provided are plants produced by the methods of the invention and comprising in their genome one or more mutated GRF transcription factor genes that produce mRNAs having a reduced ability to bind the corresponding miR396, as well as polypeptides, polynucleotides, nucleic acid constructs, expression cassettes and vectors for making a plant or part thereof this invention.

These and other aspects of the invention are set forth in more detail in the description of the invention below.

BRIEF DESCRIPTION OF THE SEQUENCES

SEQ ID NOs:1-3 are miR396 binding site sequences in growth regulating factor (GRF) transcription factors from maize.

SEQ ID NOs:4-18 are partial cDNA sequences of GRF transcription factors from maize.

SEQ ID NOs:19-33 are full cDNA sequences of GRF transcription factors from maize.

SEQ ID NOs:34-41 are examples of mutated miR396 binding site sequences of growth regulating factor (GRF) transcription factor 6 (GRF6).

SEQ ID NOs:42-47 are GRF transcription factor proteins in, wild type (SEQ ID NO:42) and mutant proteins (SEQ ID NOs:43-47), respectively.

SEQ ID NOs:48-71 show example spacer sequences.

SEQ ID NOs:72-76, 209-213 are example adenosine deaminase sequences useful with this invention.

SEQ ID NOs:77-80, 206-208 are example cytosine deaminase amino acid sequences useful with this invention.

SEQ ID NO:81 is an exemplary uracil-DNA glycosylase inhibitor (UGI) useful with this invention.

SEQ ID NO:82-83 are exemplary regulatory sequences encoding a promoter and intron.

SEQ ID NOs:84-96 are the mature miR396 sequences from maize.

SEQ ID NOs:97-120 are full cDNA sequences of GRF transcription factors from soybean.

SEQ ID NOs:121-144 are partial cDNA sequences of GRF transcription factors from soybean.

SEQ ID NOs:145-146 are miR396 binding site sequence in growth regulating factor (GRF) transcription factors from soybean.

SEQ ID NOs:147-172 are full cDNA sequences of GRF transcription factors from wheat.

SEQ ID NOs:173-198 are partial cDNA sequences of GRF transcription factors from wheat.

SEQ ID NOs:199-202 are miR396 binding site sequences of growth regulating factor (GRF) transcription factors from wheat.

SEQ ID NOs:203-205 provides an example of a protospacer adjacent motif position for a Type V CRISPR-Cas12a nuclease.

SEQ ID NOs:214-230 are exemplary Cas12a amino acid sequences useful with this invention.

SEQ ID NOs:231-233 are exemplary Cas12a nucleotide sequences useful with this invention.

SEQ ID NOs:234-250 are exemplary Cas12a nucleotide sequences useful with this invention.

BRIEF DESCRIPTION OF THE DRAWINGS

FIG. 1 shows a natural QTL controlling grain size and yield in rice. A 2 bp substitution removes mir396 binding of GRF4 in rice (top sequence: SEQ ID NO:252, bottom sequence: SEQ ID NO:253).

FIG. 2 shows base pair and amino acid changes observed in the E0 plants from an experiment with a CRISPR-CBE (CRISPR-Cas cytosine base editor). From top to bottom: SEQ ID NOs:254, 42, 34, 43, 35, 44, 36, 43, 37, 45, 38, 255, 39, 46, 40, 256, 41 and 47.

FIG. 3 shows an example editing window for a miR396 binding site. From top to bottom: SEQ ID NOs:257, 258, 259, 254, 42, 257, 258, and 259.

FIGS. 4A-4B show example Cas9 base edits (FIG. 4A top sequence: SEQ ID NO:4, bottom sequence: SEQ ID NO:260; FIG. 4B top sequence: SEQ ID NO:4, bottom sequence: SEQ ID NO:260).

FIG. 5B top sequence: SEQ ID NO:4, bottom sequence: SEQ ID NO:260).

FIG. 7 shows GRF6 and four other GRF loci targeted with 100% match to the spacer sequence. The Cas9 base editor spacer sequence (TTTCCACAGGCTTTCTTGAA SEQ ID NO:58) targets several GRF transcription factors with 100% specificity. Other GRF transcription factor targets have miss-matches (underlined nucleotides) in the spacer target sequence. The target sequence, PAM, specificity score and target gene are shown. From top to bottom: SEQ ID NOs:58, 58, 261, 58, 261, 58, 261, 58, 261, 262, 261, 261, and 262.

FIG. 8 shows Cas9 base edits in E0 plants. The wildtype GRF6 sequence is on top. The miR396 sequence is highlighted red, the spacer used for base edits blue (SEQ ID NO:58). Individual NGS reads are below for plants 7469, 7480, and 7483. Edited bases are colored. Progeny from these plants were used for phenotypic analysis in subsequent plant generations. From top to bottom: SEQ ID NOs:263, 264, 265, 266, 267, 264, 264, 265, 268, 264, 268, 269 and 269.

FIG. 11 shows that Cpf1 spacer CACAGGCTTTCTTGAACGGTTGC (SEQ ID NO:55) targets only GRF6 (GRMZM2G034876) with 100% specificity. Other GRF transcription factor targets have miss-matches (red nucleotides) in the spacer target sequence. The target sequence, PAM, specificity score and target gene are shown. From top to bottom: SEQ ID NOs:270, 55, 271, 272, 273, and 274.

DETAILED DESCRIPTION

Figure 5A:
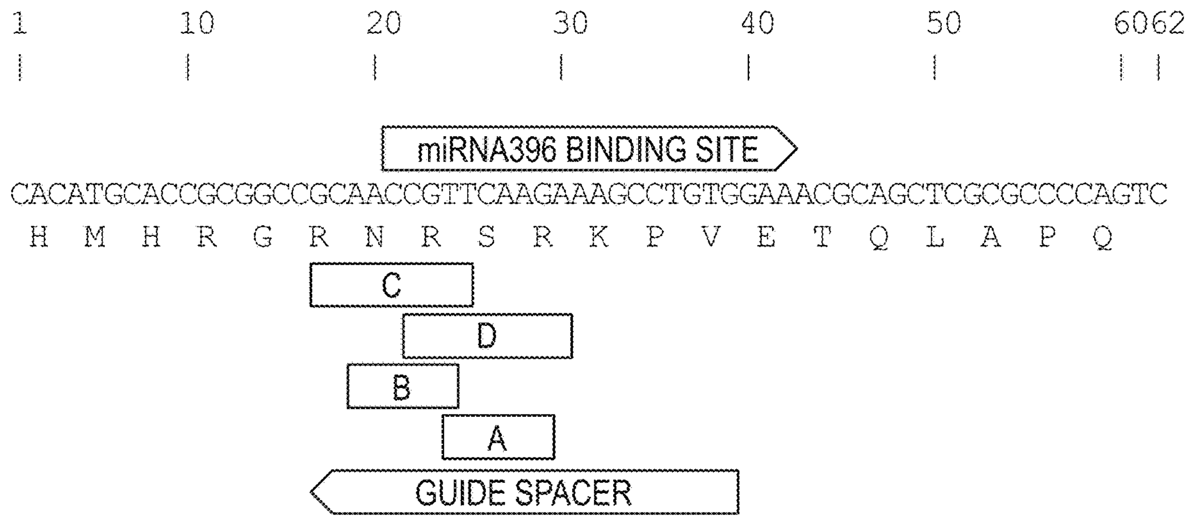
FIG. 5A-5B show example Cas12a (Cpf1) base edits (FIG. 5A top sequence: SEQ ID NO:4, bottom sequence: SEQ ID NO:260.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the reference organism.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is non-functional.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypo orphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker. For example, "a marker associated with with increased yield under non-water stress conditions" refers to a marker whose presence or absence can be used to predict whether a plant will display with increased yield under non-water stress conditions.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

As used herein, "increased growth" and/or "an increased growth rate" refers to any plant trait associated with growth, for example, biomass, yield, nitrogen use efficiency (NUE), inflorescence size/weight, fruit yield, fruit quality, fruit size, seed size, seed number, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, length of roots, number of roots, size and/or weight of root mass, or any combination thereof. Thus, in some aspects, "increased growth" and/or "an increased growth rate" may include, but is not limited to, increased inflorescence production, increased fruit production (e.g., increased number, weight and/or size of fruit; e.g., increase number, weight, and/or size of ears for, e.g., maize), increased fruit quality, increased number, size and/or weight of roots, increased meristem size, increased seed size, increased biomass, increased leaf size, increased nitrogen use efficiency, increased disease resistance, increased height and/or increased internode length as compared to a control plant or part thereof (e.g., a plant that does not comprise a modified endogenous nucleic acid encoding a GFR transcription factor as described herein).

"Seed weight" is jointly determined by grain morphology traits such as seed length, seed width and seed thickness as well as grain filling and these traits are all governed by quantitative genetics.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like). In some embodiments, a nucleic acid fragment may comprise, consist essentially of or consist of about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, 660, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 or more consecutive nucleotides of a nucleotide sequence encoding a GRF transcription factor.

In some embodiments, a fragment or portion may be a fragment or portion of a GRF transcription factor gene. In some embodiments, a fragment or portion may be a fragment or portion of any one of the nucleotide sequences of SEQ ID NOs:4-18, 121-144, or 173-198, wherein the fragment or portion comprises about 5, 6, 7, 8, 9, 10, 11, 12, 13, 14, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 consecutive nucleotides, or any range or value therein of any one of the nucleotide sequences of SEQ ID NOs:4-18, 121-144, or 173-198. In some embodiments, a fragment or portion may be a fragment or portion of the nucleotide sequence of any one of SEQ ID NOs:4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of SEQ ID NOs:4-18, 121-144, or 173-198. In some embodiments, an example fragment or portion of any one of the nucleotide sequences of SEQ ID NOs:4-18, 121-144, or 173-198 may be a fragment or portion comprising consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of SEQ ID NOs:4-18, 121-144, or 173-198 (counted from the 5' end). In some embodiments, a fragment or portion of any one of the nucleotide sequences of SEQ ID NOs:4-18, 121-144, or 173-198 may be a fragment or portion comprising consecutive nucleotides from base pair position 20 to base pair position 42 of any one of the nucleotide sequences of SEQ ID NOs:4-18, 121-144, or 173-198 (counted from the 5' end). In some embodiments, the at least a portion may comprise at least one nucleotide or at least two (e.g., 2, 3, 4, 5, 6, 7, 8, 9, 10, 11, 12, 13, 14, 15, 16, 17, 18, 19, 20, 21, or 22) consecutive nucleotides of any one of the nucleotide sequences of SEQ ID NOs:4-18, 121-144, or 173-198).

In some embodiments, a sequence-specific DNA binding domain may bind to one or more fragments or portions of nucleotide sequences as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400 or more consecutive amino acids of a reference polypeptide. In some embodiments, a polypeptide fragment may comprise, consist essentially of or consist of about 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 300, 350, 400, 450, 500, 550, 600, 660, 700 or more consecutive amino acid residues of a GRF transcription factor.

As used herein with respect to nucleic acids, the term "functional fragment" refers to nucleic acid that encodes a functional fragment of a polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinj e, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments, such as Southern and Northern hybridizations, are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific DNA binding domain (e.g., a sequence-specific DNA binding domain from a a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604, 121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), $PLA_2$-δ promoter from *arabidopsis* (U.S. Pat. No. 7,141, 424), and/or the ZmC5 promoter from maize (International PCT Publication No. WO1999/042587.

Additional examples of plant tissue-specific/tissue preferred promoters include, but are not limited to, the root hair—specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g, SEQ ID NO:83 and SEQ ID NO:84).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific DNA binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific DNA binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter or they may be different promoters. Thus, a polynucleotide encoding a sequence specific DNA binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

The plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further and particularly emphasized examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CrylA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CryIF protein or hybrids derived from a CryIF protein (e.g. hybrid CrylA-CryIF proteins or toxic fragments thereof), the CrylA-type proteins or toxic fragments thereof, preferably the CryIAc protein or hybrids derived from the CryIAc protein (e.g. hybrid CryIAb-CryIAc proteins) or the CryIAb or Bt2 protein or toxic fragments thereof, the Cry2Ae, Cry2Af or Cry2Ag proteins or toxic fragments thereof, the CrylA.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28;93(11):5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase)

inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties include but are not limited to increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLRI (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insectcontrol-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); EventEE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/

111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSl 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N° PTA-11041) optionally stacked with event EE-GM1/LL27 or event EE-GM2/LL55 (WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession N°. PTA-10296, WO2012/051199A2), event DAS-44406-6 (soybean, stacked herbicide tolerance, ATCC Accession N°. PTA-11336, WO2012/075426A1), event DAS-14536-7 (soybean, stacked herbicide tolerance, ATCC Accession N°. PTA-11335, WO2012/075429A1), event SYN-000H2-5 (soybean, herbicide tolerance, ATCC Accession N°. PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N°. PTA-11335, WO2012075429A2), event SYHT0H2 (soybean, ATCC Accession N°. PTA-11226, WO2012/082548A2), event MON88701 (cotton, ATCC Accession N° PTA-11754, WO2012/134808A1), event KK179-2 (alfalfa, ATCC Accession N° PTA-11833, WO2013/003558A1), event pDAB8264.42.32.1 (soybean, stacked herbicide tolerance, ATCC Accession N° PTA-11993, WO2013/010094A1), event MZDT09Y (corn, ATCC Accession N° PTA-13025, WO2013/012775A1).

The genes/events (e.g., polynucleotides of interest), which impart a desired trait may also be present in combinations with one another in a transgenic plant. Examples of transgenic plants include, but are not limited to, crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEN$^{D}$™, INTACTA RR2 PRO®, VISTIVE GOLD®, and/or XTENDFLEX™ trade names.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific DNA binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific DNA binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g. expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific DNA binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby sequence-specific DNA binding protein, the reverse transcriptase and the deaminase are expressed and the sequence-specific DNA binding protein binds to the target nucleic acid, and the reverse transcriptase and/or deaminase may be either fused to the sequence-specific DNA binding protein or recruited to the sequence-specific DNA binding protein (via, for example, a peptide tag fused to the sequence-specific DNA binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol.* Lett. 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

GRF transcription factors are involved in growth promotion in plants. The expression of GRF transcription factors can increase growth when they are ectopically or over expressed. One common mechanism to repress expression of the GRF transcription factors is through the microRNA, miR396. MicroRNAs are small non-coding RNA molecule found in plants, animals and some viruses, which function in RNA silencing and post-transcriptional regulation of gene expression. miRNAs function via base-pairing with complementary sequences within mRNA molecules. The present inventors have discovered that by changing the binding site of miRNA binding in a target mRNA it is possible to remove the ability of the miRNA to post-transcriptionally regulate the target genes expression.

Figure 6:
FIG. 6 shows the phenotype of an E1 corn plant having a mutation in a GRF transcription factor obtained using the methods and base editing compositions as described herein.

In some embodiments, a plant or plant part thereof is provided, the plant or part there of comprising at least one non-natural mutation in at least one gene encoding an endogenous Growth Regulating Factor (GRF) transcription factor, wherein the mutation disrupts the binding of miR396 to the mRNA that is produced by the at least one gene encoding the endogenous GRF transcription factor resulting in increased levels of the mRNA. In some embodiments, a mutation that disrupts the binding of miR396 to the GRF transcription factor mRNA and results in increased levels of the mRNA as described herein is a stable mutation, optionally wherein the mutation is in the miR396 binding site of the mRNA encoded by the GRF transcription factor gene (see, e.g., FIG. 3). In some embodiments, at least one non-natural mutation in at least one gene encoding an GRF transcription factor is a semi-dominant mutation and/or a hypomorphic mutation. In some embodiments, the endogenous GRF transcription factor that is mutated may include, but is not limited to, a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. The plant may be any plant as described herein. In some embodiments, the plant may be a wheat plant or a corn plant (see, e.g., Table 1). In some embodiments, GRF transcription factor may be from corn and may comprise a GRF6, GRF2, GRF1, GRF14, GRF15, GRF8, GRF4, GRF12, GRF10, GRF11, GRF5, GRF3, GRF9, GRF13, or a GRF7. In some embodiments, the corn plant may comprise a short stature/semi-dwarf phenotype (see, e.g., FIG. 6). In some embodiments, the at least one non-natural mutation in at least one gene encoding an endogenous GRF transcription factor in a wheat plant may be in the A genome, B genome, or D genome, or any combination thereof.

In some embodiments, a GRF transcription factor gene produces an mRNA that binds a corresponding miR396. In some embodiments, the corresponding miR396 may be a mir396a, a miR396b, a mir396c, a miR396d, a mir396e, a miR396f, a mir396g, and/or a miR396h (see, e.g., SEQ ID NOs:84-96). In some embodiments, a GRF transcription factor mRNA binds a miR396a. In some embodiments, a GRF transcription factor mRNA binds a miR396b. In some embodiments, reduced miR396 binding to a GRF transcription factor mRNA may be measured by measuring the levels of the GRF transcription factor mRNA.

In some embodiments, the at least one non-natural mutation in at least one endogenous GRF transcription factor gene may be a base substitution, a deletion and/or an insertion. In some embodiments, the at least one mutation may be a synonymous mutation in the portion of the GRF transcription factor gene that produces the miRNA binding site of the GRF transcription factor mRNA. In some embodiments, at least one non-natural mutation in at least one gene encoding an GRF transcription factor is a semi-dominant mutation and/or a hypomorphic mutation. In some embodiments, the portion of the GRF transcription factor gene that produces the miR396 binding site in the GRF transcription factor mRNA encodes a portion of the endogenous GRF transcription factor polypeptide, wherein the portion of the endogenous GRF transcription factor polypeptide comprises the amino acid sequence of NRSRKPVET (SEQ ID NO: 42). In some embodiments, the at least one mutation may be a non-synonymous mutation in the nucleotide sequence that encodes a portion of the endogenous GRF transcription factor amino acid sequence, said portion having the amino acid sequence of NRSRKPVET (SEQ ID NO:42). In some embodiments, the at least one mutation may be an in-frame deletion in the nucleotide sequence that encodes a portion of the endogenous GRF transcription factor amino acid sequence, said portion having the amino acid sequence of NRSRKPVET (SEQ ID NO:42). Thus, in some embodiments the invention provides a plant cell comprising a stable and targeted (e.g., non-natural) single nucleotide substitution in an endogenous gene encoding a GRF transcription factor. In some embodiments, a mutation in an endogenous gene encoding a GRF transcription factor does not result in a mutation in the polypeptide sequence of the GRF transcription factor. In some embodiments, a mutation in an endogenous gene encoding a GRF transcription factor produces a polypeptide comprising a mutation in the polypeptide sequence of the GRF transcription factor. In some embodiments, a mutated GRF transcription factor polypeptide may comprise the amino acid sequence of NRSRKPVKT (SEQ ID NO:43), NRSRKPIKT (SEQ ID NO:44), NRSKKPIKT (SEQ ID NO:45), NRSRKPVQT (SEQ ID NO:46), and/or NRSKKPVKT (SEQ ID NO:47).

In some embodiments, an endogenous GRF transcription factor gene that produces an mRNA having a miR396 binding site comprises: (a) a nucleotide sequence having at least 90% sequence identity to any one of the nucleotide sequences of SEQ ID NOs:1-3, 145, 146, or 199-202; (b) a nucleotide sequence having at least 95% identity (e.g., about 95, 96, 70, 98, 99, or 100%) to any one of the nucleotide sequences of SEQ ID NOs:1-3, 145, 146, or 199-202; or (c) the nucleotide sequence set forth in any one of the nucleotide sequences of SEQ ID NOs:1-3, 145, 146, or 199-202. In some embodiments, a base substitution can be a substitution of any base to any different base, e.g., to an A, T, C, or G. In some embodiments, the endogenous GRF transcription factor gene may comprise a mutation in at least one of positions 11, 19, 21 and/or 22 of any one of the nucleotide sequences of SEQ ID NOs:1-3, 145, 146, or 199-202. In some embodiments, a mutation at position 11 of any one of the nucleotide sequences of SEQ ID NOs:1-3, 145, 146, or 199-202 may be from G to A, T, or C (e.g., G>A, G>T, G>C), a mutation at position 19 of any one of the nucleotide sequences of SEQ ID NOs:1-3, 145, 146, or 199-202 may be from G to A, T, or C, a mutation at position 21 of any one of the nucleotide sequences of SEQ ID NOs:1-3, 145, 146, or 199-202 may be from G to A, T, or C and/or a mutation at position 22 of any one of the nucleotide sequences of SEQ ID NOs:1-3, 145, 146, or 199-202 is from G to A, T, or C. In some embodiments, a mutation at position 11 of any one of the nucleotide sequences of SEQ ID NOs:1-3, 145, 146, or 199-202 may be G>A. In some embodiments, a mutation at position 19 of any one of the nucleotide sequences of SEQ ID NOs:1-3, 145, 146, or 199-202 may be G>A or G>C. In some embodiments, a mutation at position 21 of any one of the nucleotide sequences of SEQ ID NOs:1-3, 145, 146, or 199-202 may be G>A or G>C. In some embodiments, a mutation at position 22 of any one of the nucleotide sequences of SEQ ID NOs:1-3, 145, 146, or 199-202 may be G>A or G>C.

A mutation in an endogenous GRF transcription factor gene that comprises the nucleotide sequence of any one of SEQ ID NOs:1-3, 145, 146, or 199-202 may or may not produce a change in the amino acid sequence. Thus, a mutation to an endogenous GRF transcription factor gene comprising the nucleotide sequence of any one of SEQ ID NOs:1-3 may result in the same amino acid sequence of NRSRKPVET (SEQ ID NO:42). In some embodiments, a mutation to endogenous GRF transcription factor gene comprising the nucleotide sequence of any one of SEQ ID NOs:1-3 may result in an amino acid sequence that can include, but is not limited to, the amino acid sequence of any one of NRSRKPVKT (SEQ ID NO:43), NRSRKPIKT (SEQ ID NO:44), NRSKKPIKT (SEQ ID NO:45), NRSRKPVQT (SEQ ID NO:46), and/or NRSKKPVKT (SEQ ID NO:47).

In some embodiments, the invention provides a plant cell, the plant cell comprising a base editing system comprising: (a) a sequence-specific binding domain (e.g., a CRISPR-associated effector protein); (b) a cytidine deaminase or adenosine deaminase; and (c) a guide nucleic acid (gRNA) having a spacer sequence with complementarity to an endogenous target gene encoding a GRF transcription factor. In some embodiments, an endogenous target gene encoding a GRF transcription factor may comprise at least about 90% sequence identity (e.g., about 90, 91, 92, 93, 94, 95, 96, 70, 98, 99, or 100%) to any one of the nucleotide sequences of SEQ ID NOs:1-3, 145, 146, or 199-202. In some embodiments, a guide nucleic acid may comprise a spacer sequence having the nucleotide sequence of, for example, any one of SEQ ID NOs:48-71.

In some embodiments, a guide nucleic acid useful with this invention may comprise spacer that is complementary to a fragment or portion of the nucleotide sequence of any one of SEQ ID NOs:4-18, 121-144, or 173-198, wherein the fragment or portion of any one of SEQ ID NOs:4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of SEQ ID NOs:4-18, 121-144, or 173-198. In some embodiments, a fragment or portion of any one of SEQ ID NOs:4-18, 121-144, or 173-198 to which a spacer for a guide nucleic acid may be complementary may comprise consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of SEQ ID NOs:4-18, 121-144, or 173-198 (counted from the 5' end). In some embodiments, a spacer sequence for a guide nucleic acid may be complementary to consecutive nucleotides from base pair position 20 to base pair position 42 of any one of the nucleotide sequences of SEQ ID NOs:4-18, 121-144, or 173-198 (counted from the 5' end). In some embodiments, a spacer sequence for a guide nucleic acid may comprise a spacer sequence having the nucleotide sequence of any one of SEQ ID NOs:48-71.

In some embodiments, a plant part or plant cell produced by the methods of this invention may be regenerated to produce a plant comprising a stable mutation in at least one gene encoding an endogenous GRF transcription factor, wherein the mutation results in reduced binding of a corresponding miR396 to the mRNA that is produced by the endogenous GRF transcription factor gene, optionally wherein the mutation is a semi-dominant mutation and/or a hypomorphic mutation.

In some embodiments, the invention further provides a plant cell comprising at least one non-naturally occurring genomic modification within a miR396 binding site of a GRF transcription factor gene that prevents or reduces binding of the miR396 to the GRF transcription factor mRNA transcribed from the GRF transcription factor gene comprising the at least one non-natural genomic modification, wherein the genomic modification is a substitution, insertion or a deletion that is introduced using an editing system that comprises a nucleic acid binding domain that binds to a target site in the GRF transcription factor gene having the nucleotide sequence of any one of SEQ ID NOs:4-18, 121-144, or 173-198.

In some embodiments, the invention provides a plant or part thereof comprising a mutated endogenous GRF transcription factor gene that produces an mRNA having reduced miR396 binding, wherein the mutated endogenous GRF transcription factor gene comprises a target gene (a target nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to any one of the nucleotide sequences of SEQ ID NOs:4, 5 or 9-18, wherein each of SEQ ID NOs:4, 5 or 9-18 comprise a sequence having at least 90% sequence identity (e.g., about 90, 91, 92, 93, 94, 95, 96, 70, 98, 99, or 100%) to SEQ ID NO:1, and the target gene is modified (e.g., mutated) within the sequence having at least 90% sequence identity to SEQ ID NO:1. In some embodiments, the modification (e.g., mutation) within the sequence having at least 90% sequence identity to the nucleotide sequence of SEQ ID NO:1 may be introduced using an editing system that comprises a sequence-specific DNA binding domain that binds to a target site within a nucleotide sequence having at least 80% identity to any one of the nucleotide sequences of SEQ ID NOs:4, 5 or 9-18. In some embodiments, the modification within the sequence having at least 90% sequence identity to the nucleotide sequence of SEQ ID NO:1 may be introduced using an editing system that comprises a sequence-specific DNA binding domain that binds to a target site within the nucleotide sequence of any one of SEQ ID NOs:19-33.

In some embodiments, a plant or part thereof is provided, the plant or plant part thereof comprising a mutated endogenous GRF transcription factor gene that produces a mRNA having reduced miR396 binding and resulting in increased levels of mRNA produced by the endogenous GRF transcription factor gene, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:6 or SEQ ID NO:7, wherein each of the nucleotide sequence of SEQ ID NO:6 or SEQ ID NO:7 comprise a sequence having at least 90% sequence identity to the nucleotide sequence of SEQ ID NO: 2, and the target gene is modified (e.g., mutated) within the sequence having at least 90% sequence identity (e.g., about 90, 91, 92, 93, 94, 95, 96, 70, 98, 99, or 100%) to the nucleotide sequence of SEQ ID NO: 2. In some embodiments, the modification (e.g., mutation) within the sequence having at least 90% sequence identity to SEQ ID NO: 2 may be introduced using an editing system that comprises a nucleic acid binding domain that binds to a target site within the sequence having at least 80% identity SEQ ID NO:6 or SEQ ID NO:7. In some embodiments, the modification/mutation within the sequence having at least 90% sequence identity to SEQ ID NO: 2 may be introduced using an editing system that comprises a sequence-specific DNA binding domain that binds to a target site within the nucleotide sequence of any one of SEQ ID NO:21 or SEQ ID NO:22. In some embodiments, the mutation that is introduced by the editing system may be in at least one gene encoding an GRF transcription factor is a semi-dominant mutation and/or a hypomorphic mutation.

In some embodiments, a plant or part thereof is provided comprising at least one non-natural mutation in an endogenous gene encoding a Growth Regulating Factor (GRF) transcription factor, wherein the at least one non-natural mutation in the endogenous gene encoding a GRF transcription factor results in increased levels of mRNA produced by the endogenous gene. In some embodiments, the at least one non-natural mutation in the endogenous gene encoding a GRF transcription factor results in increased levels of mRNA produced by the endogenous gene and disrupts binding of miR396 to the mRNA produced by the GRF transcription factor gene.

In some embodiments, a plant or part thereof is provided, the plant or plant part thereof comprising a mutated endogenous GRF transcription factor gene that produces a mRNA having reduced miR396 binding and resulting in increased levels of GRF transcription factor mRNA, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:8, wherein the nucleotide sequence of SEQ ID NO:8 comprises a sequence having at least 90% sequence identity (e.g., about 90, 91, 92, 93, 94, 95, 96, 70, 98, 99, or 100%) to the nucleotide sequence of SEQ ID NO: 3, and the target gene is modified (e.g., mutated) within the sequence having at least 90% sequence identity to the nucleotide sequence of SEQ ID NO: 3. In some embodiments, the modification (e.g., mutation) within the sequence having at least 90% sequence identity to SEQ ID NO:3 may be introduced using an editing system that comprises a nucleic acid binding domain that binds to a target site within the sequence having at least 80% identity to SEQ ID NO:8. In some embodiments, the modification within the sequence having at least 90% sequence identity to SEQ ID NO:3 may be introduced using an editing system that comprises a sequence-specific DNA binding domain that binds to a target site within the nucleotide sequence of any one of SEQ ID NO:23.

In some embodiments, the invention provides a plant or part thereof comprising a mutated endogenous GRF transcription factor gene that produces a mRNA having reduced miR396 binding, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to any one of the nucleotide sequences of SEQ ID NOs:121-144, wherein each of SEQ ID NOs:121-144 comprise a sequence having at least 90% sequence identity (e.g., about 90, 91, 92, 93, 94, 95, 96, 70, 98, 99, or 100%) to any one of SEQ ID NOs:145-146, and the target gene is modified (e.g., mutated) within the sequence having at least 90% sequence identity to any one of SEQ ID NOs:145-146. In some embodiments, the modification (e.g., mutation) within the sequence having at least 90% sequence identity to any one of the nucleotide sequence of SEQ ID NOs:145-146 may be introduced using an editing system that comprises a sequence-specific DNA binding domain that binds to a target site within a nucleotide sequence having at least 80% identity to any one of the nucleotide sequences of SEQ ID NOs:121-144. In some embodiments, the modification within the sequence having at least 90% sequence identity to any one of the nucleotide sequence of SEQ ID NOs:145-146 may be introduced using an editing system that comprises a sequence-specific DNA binding domain that binds to a target site within the nucleotide sequence of any one of SEQ ID NOs:121-144.

In some embodiments, the invention provides a plant or part thereof comprising a mutated endogenous GRF transcription factor gene that produces a mRNA having reduced miR396 binding, wherein the mutated endogenous GRF transcription factor gene comprises a target gene (a nucleic acid) that comprises a sequence having at least 80% sequence identity (e.g., about 80, 81, 82, 83, 84, 85, 86, 87, 88, 89, 90, 91, 92, 93, 94, 95, 96, 70, 98, 99, or 100%) to any one of the nucleotide sequences of SEQ ID NOs:173-198, wherein each of SEQ ID NOs:173-198 comprise a sequence having at least 90% sequence identity (e.g., about 90, 91, 92, 93, 94, 95, 96, 70, 98, 99, or 100%) to any one of SEQ ID NOs:199-202, and the target gene is modified (e.g., mutated) within the sequence having at least 90% sequence identity to any one of SEQ ID NOs:199-202, and the target gene is modified (e.g., mutated) within the sequence having at least 90% sequence identity to any one of SEQ ID NOs:199-202. In some embodiments, the modification (e.g., mutation) within the sequence having at least 90% sequence identity to any one of the nucleotide sequence of SEQ ID NOs:199-202 may be introduced using an editing system that comprises a sequence-specific DNA binding domain that binds to a target site within a nucleotide sequence having at least 80% identity to any one of the nucleotide sequences of SEQ ID NOs:173-198. In some embodiments, the modification within the sequence having at least 90% sequence identity to any one of the nucleotide sequence of SEQ ID NOs:199-202 may be introduced using an editing system that comprises a sequence-specific DNA binding domain that binds to a target site within the nucleotide sequence of any one of SEQ ID NOs:174-198.

An additional aspect of the invention provides a plant comprising a Growth Regulating Factor (GRF) transcription factor gene that comprises a mutation in any one of the nucleotide sequences of any one of SEQ ID NOs:1-33 or 97-202. In some embodiments, the invention provides a plant comprising a mutated Growth Regulating Factor (GRF) transcription factor gene that comprises a nucleotide sequence of any one of SEQ ID NOs:34-41. In some embodiments, the mutated GRF transcription factor comprises a semi-dominant mutation and/or a hypomorphic mutation.

In some embodiments, the invention provides a corn plant comprising a Growth Regulating Factor (GRF) transcription factor gene that comprises a nucleotide sequence of any one of SEQ ID NOs:34-41.

In some embodiments, the invention provides a wheat plant comprising a Growth Regulating Factor (GRF) transcription factor gene that produces a mRNA having a mutated miR396 binding site such that the binding of miR396 to the miR396 binding site of the GRF transcription factor mRNA is reduced. In some embodiments, the invention provides a wheat plant having a mutation in the miR396 binding site of a mRNA produced by a Growth Regulating Factor (GRF) transcription factor gene that comprises a nucleotide sequence of any one of SEQ ID NOs:147-198. In some embodiments, the Growth Regulating Factor (GRF) transcription factor gene that comprises a nucleotide sequence of any one of SEQ ID NOs: 147-198 is in the A genome, the B genome, the D genome, or any combination thereof, of a wheat plant.

In some embodiments, the invention provides a wheat plant comprising a Growth Regulating Factor (GRF) transcription factor gene that produces a mRNA having a mutated miR396 binding site such that the binding of miR396 to the miR396 binding site of the GRF transcription factor mRNA is reduced. In some embodiments, the invention provides a soybean plant having a mutation in the miR396 binding site of a mRNA produced by a Growth Regulating Factor (GRF) transcription factor that comprises a nucleotide sequence of any one of SEQ ID NOs:97-144. In some embodiments, the Growth Regulating Factor (GRF) transcription factor that comprises a nucleotide sequence of any one of SEQ ID NOs:97-144 is in the A genome, the B genome, the D genome, or any combination thereof, of a wheat plant.

In some embodiments, the invention provides a corn plant or plant part thereof comprising at least one non-natural mutation in at least one endogenous Growth Regulating Factor (GRF) transcription factor that is located in: (a) a chromosome interval defined by and including base pair (bp) position 211773221 to base pair position 211774543 on chromosome (e.g., Gene ID No. GRMZM5G893117), optionally a chromosome interval defined by and including base pair (bp) position 211773897 to base pair position 211773957; (b) a chromosome interval defined by and including base pair (bp) position 200344009 to base pair position 200348833 on chromosome 5 (e.g., Gene ID No. GRMZM2G034876), optionally a chromosome interval defined by and including base pair (bp) position 200346611 to base pair position 200346671; (c) a chromosome interval defined by and including base pair (bp) position 13817620 to base pair position 13822440 on chromosome 5 (e.g., Gene ID No. GRMZM2G033612), optionally a chromosome interval defined by and including base pair (bp) position 138197933 to base pair position 13819853; (d) a chromosome interval defined by and including base pair (bp) position 177151736 to base pair position 177154443 on chromosome 4 (e.g., Gene ID No. GRMZM2G105335), optionally a chromosome interval defined by and including base pair (bp) position 177152804 to base pair position 177152864; (e) a chromosome interval defined by and including base pair (bp) position 257245490 to base pair position 257249295 on chromosome 1 (e.g., Gene ID No. GRMZM2G018414), optionally a chromosome interval defined by and including base pair (bp) position 257247225 to base pair position 257247285; (f) a chromosome interval defined by and including base pair (bp) position 25722859 to base pair position 25725873 on chromosome 9 (e.g., Gene ID No. GRMZM2G119359), optionally a chromosome interval defined by and including base pair (bp) position 25723770 to base pair position 25723830; (g) a chromosome interval defined by and including base pair (bp) position 60351912 to base pair position 60356302 on chromosome 6 (e.g., Gene ID No. GRMZM2G098594), optionally a chromosome interval defined by and including base pair (bp) position 60354489 to base pair position 60354549; (h) a chromosome interval defined by and including base pair (bp) position 196192921 to base pair position 196194872 on chromosome 5, optionally a chromosome interval defined by and including base pair (bp) position 196194175 to base pair position 196194235; (i) a chromosome interval defined by and including base pair (bp) position 140393394 to base pair position 140398705 on chromosome 10 (e.g., Gene ID No. GRIVIZM2G129147), optionally a chromosome interval defined by and including base pair (bp) position 140396272 to base pair position 140396332; (j) a chromosome interval defined by and including base pair (bp) position 155831622 to base pair position 155833517 on chromosome 4 (e.g., Gene ID No. GRMZM2G124566), optionally a chromosome interval defined by and including base pair (bp) position 155832749 to base pair position 155832809; (k) a chromosome interval defined by and including base pair (bp) position 12201898 to base pair position 12208052 on chromosome 2 (e.g., Gene ID No. GRIVIZM2G041223), optionally a chromosome interval defined by and including base pair (bp) position 12204599 to base pair position 12204659; (1) a chromosome interval defined by and including base pair (bp) position 9818327 to base pair position 9820186 on chromosome 9 (e.g., Gene ID No. GRMZM2G067743), optionally a chromosome interval defined by and including base pair (bp) position 9819224 to base pair position 9819284; (m) a chromosome interval defined by and including base pair (bp) position 108477686 to base pair position 108480099 on chromosome 6 (e.g., Gene ID No. GRIVIZM5G850129), optionally a chromosome interval defined by and including base pair (bp) position 108478747 to base pair position 108478807; (n) a chromosome interval defined by and including base pair (bp) position 225827712 to base pair position 225832487 on chromosome 2 (e.g., Gene ID No. GRMZM2G099862), optionally a chromosome interval defined by and including base pair (bp) position 225830099 to base pair position 225830159; (o) a chromosome interval defined by and including base pair (bp) position 272414778 to base pair position 272420567 on chromosome 1 (e.g., Gene ID No. GRMZM2G178261); (p) a chromosome interval defined by and including base pair (bp) position 199377455 to base pair position 199381799 on chromosome 2; (q) a chromosome interval defined by and including base pair (bp) position 145016279 to base pair position 145019899 on chromosome 7; and/or (r) a chromosome interval defined by and including base pair (bp) position 8708791 to base pair position 8711617 on chromosome (e.g., Gene ID No. GRMZM5G853392), wherein the mutation results in increased GRF transcription factor mRNA, and optionally, disrupts the binding of miR396 to the GRF transcription factor, and the chromosomal intervals of (a) to (r) correspond to the reference maize genome of B73.

In some embodiments, a corn plant may comprise a mutation on chromosome 5 (a) bp position 211773927, (b) bp position 200346641, (c) bp position 13819823, and (d) bp position 196194205, wherein the chromosomal position of (a) to (e) correspond to the reference maize genome of B73.

In some embodiments, a corn plant may comprise a mutation on chromosome 4 (a) bp position 177152834, and/or (b) bp position 155832779, wherein the chromosomal position of (a) and (b) correspond to the reference maize genome of B73.

In some embodiments, a corn plant may comprise a mutation on chromosome 1, bp position 257247255, wherein the chromosomal position of 257247255 corresponds to the reference maize genome of B73.

In some embodiments, a corn plant may comprise a mutation on chromosome 9 (a) bp position 25723800 and/or (b) bp position 9819254, wherein the chromosomal position of (a) and (b) correspond to the reference maize genome of B73.

In some embodiments, a corn plant may comprise a mutation on chromosome 6 (a) bp position 60354519 and/or (b) bp position 108478777, wherein the chromosomal position of (a) and (b) correspond to the reference maize genome of B73.

In some embodiments, a corn plant may comprise a mutation on chromosome 10, bp position 140396302, wherein the chromosomal position of 140396302 corresponds to the reference maize genome of B73.

In some embodiments, a corn plant may comprise a mutation on chromosome 2 (a) bp position 12204629, and/or (b) bp position 225830129, wherein the chromosomal position of (a) and (b) correspond to the reference maize genome of B73.

With regard to corn (*Zea mays*), markers of the present invention are described herein with respect to the positions of marker loci in the B73 corn genome "B73 RefGen_v3" (assembly aka B73 RefGen_v3, AGPv3) at the MaizeGDB internet resource (maizegdb.org/assembly).

The present invention provides methods and compositions for modifying GRF transcription factors involved in plant growth and development, in particular those GRF transcription factors that regulate biomass, yield, inflorescence size/weight, fruit yield, fruit quality, fruit size, seed size, seed number, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, length of roots, number of roots, size and/or weight of root mass, or any combination of these characteristics. Thus, in some embodiments of the invention, a plant comprising a mutated endogenous GRF transcription factor gene having reduced miR396 binding, may exhibit at least one of the following phenotypes of increased meristem size, increased seed size, increased biomass, increased leaf size, increased root size, increased nitrogen use efficiency, increased disease resistance, increased height and/or increased internode length as compared to a control plant that does not comprise the mutated endogenous GRF transcription factor gene having reduced miR396 binding.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs:4-18, 121-144, or 173-198, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having at least 65% sequence identity (e.g., about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 70, 98, 99, or 100%) to the nucleotide sequence of SEQ ID NO:9 or SEQ ID NO:14 and comprising a miR396 binding site sequence at bp position 21 to 42 of SEQ ID NO:9 (GRF8 60 nt cDNA or SEQ ID NO:14 (GRFS 60 nt cDNA), the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs:4, 5, or 9-18 and comprising a miR396 binding site sequence at by position 21 to 42 of any one of SEQ ID NOs:4, 5, or 9-18, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:6 or SEQ ID NO:7, and comprising a miR396 binding site sequence at bp position 21 to 42 of SEQ ID NO:6 or SEQ ID NO:7, the binding site sequence having at least 90% sequence identity (e.g., about 90, 91, 92, 93, 94, 95, 96, 70, 98, 99, or 100%) to SEQ ID NO:2, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO: 8, and comprising a miR396 binding site sequence at by position 21 to 42 of SEQ ID NO:8, the binding site sequence having at least 90% sequence identity (e.g., about 90, 91, 92, 93, 94, 95, 96, 70, 98, 99, or 100%) to SEQ ID NO:3, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:4, and comprising a miR396 binding site sequence at bp position 21 to 42 of SEQ ID NO:4, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:5, and comprising a miR396 binding site sequence at bp position 21 to 42 of SEQ ID NO:5, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:9, and comprising a miR396 binding site sequence at bp position 21 to 42 of SEQ ID NO:9, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:10, and comprising a miR396 binding site sequence at bp position 21 to 42 of SEQ ID NO:10, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the present invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:11, and comprising a miR396 binding site sequence at by position 21 to 42 of SEQ ID NO:11, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:12, and comprising a miR396 binding site sequence at bp position 21 to 42 of SEQ ID NO:12, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:13, and comprising a miR396 binding site sequence at bp position 21 to 42 of SEQ ID NO:13, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:14, and comprising a miR396 binding site sequence at bp position 21 to 42 of SEQ ID NO:14, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:15, and comprising a miR396 binding site sequence at by position 21 to 42 of SEQ ID NO:15, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:16, and comprising a miR396 binding site sequence at bp position 21 to 42 of SEQ ID NO:16, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:17, and comprising a miR396 binding site sequence at bp position 21 to 42 of SEQ ID NO:17, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, the invention provides a method for editing a specific site in the genome of a plant cell, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NO:18, and comprising a miR396 binding site sequence at by position 21 to 42 of SEQ ID NO:18, the binding site sequence having at least 90% sequence identity (e.g., about 90, 91, 92, 93, 94, 95, 96, 70, 98, 99, or 100%) to SEQ ID NO:1, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs:121-144 and comprising a miR396 binding site sequence at by position 21 to 42 of any one of SEQ ID NOs:121-144, the binding site sequence having at least 90% sequence identity (e.g., about 90, 91, 92, 93, 94, 95, 96, 70, 98, 99, or 100%) to SEQ ID NO:145 or SEQ ID NO:146, thereby generating an edit in the endogenous GRF transcription factor gene of the plant cell.

In some embodiments, a method for editing a specific site in the genome of a plant cell is provided, the method comprising: cleaving, in a site specific manner, a target site within an endogenous GRF transcription factor gene in the plant cell, the endogenous GRF transcription factor gene comprising a sequence having about 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs:173-198 and comprising a miR396 binding site sequence at by position 21 to 42 of any one of SEQ ID NOs:173-198, the binding site sequence having at least 90% sequence identity (e.g., about 90, 91, 92, 93, 94, 95, 96, 70, 98, 99, or 100%) to SEQ ID NO:145 or SEQ ID NO:146, thereby generating an edit in the endogenous GRF transcription factor gene of the plant cell.

In some embodiments, the method may further comprise regenerating a plant from the plant cell comprising an edit in the endogenous GRF transcription factor gene to produce a plant comprising the edit in its endogenous GRF transcription factor gene. In some embodiments, the plant comprising the edit in its endogenous GRF transcription factor gene may have increased growth compared to a control plant that does not comprise the edit. In some embodiments, the edit results in a non-natural mutation.

In some embodiments, a method for making a plant is provided, the method comprising: (a) contacting a population of plant cells comprising an endogenous gene encoding a GRF transcription factor with an editing system comprising a nucleic acid binding domain that binds to a sequence having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of SEQ ID NOs: 1-3, 145, 146, or 199-202 or SEQ ID NOs:4-18, 121-144, or 173-198; (b) selecting a plant cell from said population comprising a mutation in at least one endogenous gene encoding a GRF transcription factor, wherein the mutation is a substitution of at least one nucleotide in the at least one endogenous gene, wherein the mutation reduces or eliminates the ability of miR396 to bind to a mRNA produced by the at least one endogenous gene encoding a GRF transcription factor comprising the mutation; and (c) growing the selected plant cell into a plant.

In some embodiments, the present invention provides a method for producing a plant or part thereof comprising at least one cell in which an endogenous GRF transcription factor gene is mutated, the method comprising contacting a target site in the GRF transcription factor gene in the plant or plant part with an editing system comprising a nucleic acid binding domain that binds to a target site in (or within) the GRF transcription factor gene having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs:1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, thereby producing a plant or part thereof comprising at least one cell having a mutation in the endogenous GRF transcription factor gene. In some embodiments, a mutated endogenous GRF transcription factor gene produces a mRNA that has reduced binding of its corresponding miR396 (e.g., the miR396 that naturally binds to the wild type GRF transcription factor mRNA).

In some embodiments, the present invention provides a method of producing a plant or part thereof that comprises a mutated endogenous GRF transcription factor gene that produces an mRNA having reduced miR396 binding, the method comprising contacting a target site in an endogenous GRF contacting a target site in an endogenous GRF transcription factor gene with an editing system comprising a nucleic acid binding domain that binds to a target site in the GRF transcription factor gene having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one of SEQ ID NOs:1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, thereby producing a plant or part thereof comprising a mutated endogenous GRF transcription factor gene producing a mRNA having reduced miR396 binding. In some embodiments, the nucleotide sequence of any one of SEQ ID NOs:4-18, 121-144, or 173-198, or SEQ ID NOs:19-33, 97-120, or 147-172 comprises a sequence having at least 90% sequence identity (e.g., about 90, 91, 92, 93, 94, 95, 96, 70, 98, 99, or 100%) to the nucleotide sequence of any one of SEQ ID NOs:1-3, 145, 146, or 199-202, the sequence having at least 90% sequence identity to the nucleotide sequence of any one of SEQ ID NOs:1-3, 145, 146, or 199-202 is modified.

In some embodiments, a plant comprising a mutated endogenous GRF transcription factor gene that produces a mRNA having reduced miR396 binding exhibits increased growth as compared to a control plant (e.g., a plant that does not comprise said modification or mutation in its endogenous GRF transcription factor gene or in which the plant's endogenous GRF transcription factor gene has not been contacted with the editing system). In some embodiments, a plant comprising a mutated endogenous GRF transcription factor gene that produces a mRNA having reduced miR396 binding exhibits at least one of the following phenotypes of increased meristem size, increased seed size, increased biomass, increased leaf size, increased root size, increased nitrogen use efficiency, increased disease resistance, increased height and/or increased internode length as compared to a control plant (e.g., a plant that does not comprise said modification or mutation in its endogenous GRF transcription factor gene or in which the plant's endogenous GRF transcription factor gene has not been contacted with the editing system).

In some embodiments, the present invention provides a method of producing a plant or part thereof having increased growth or an increased growth rate, the method comprising contacting a target site in an endogenous GRF transcription factor gene with an editing system comprising a nucleic acid binding domain that binds to a target site in the GRF transcription factor gene having at least 80% sequence identity (e.g., about 80, 81, 82, 83, 84, 85, 86, 87, 88, 89, 90, 91, 92, 93, 94, 95, 96, 70, 98, 99, or 100%) to the nucleotide sequence of any one SEQ ID NOs:1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, thereby producing a plant or part thereof comprising a mutated endogenous GRF transcription factor gene that produces a mRNA having reduced miR396 binding, thereby producing a plant or part thereof having increased growth or an increased growth rate. In some embodiments, the nucleotide sequence of any one of SEQ ID NOs:4-18, 121-144, or 173-198 or SEQ ID NOs:19-33, 97-120, or 147-172 comprises a sequence having at least 90% sequence identity (e.g., about 90, 91, 92, 93, 94, 95, 96, 70, 98, 99, or 100%) to the nucleotide sequence of any one of SEQ ID NOs:1-3, 145, 146, or 199-202, the sequence having at least 90% sequence identity to the nucleotide sequence of any one of SEQ ID NOs:1-3, 145, 146, or 199-202 is modified.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a GRF transcription factor may comprise contacting a target nucleic acid (e.g., a nucleic acid encoding a GRF transcription factor) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid (see, e.g., FIG. 2). In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific DNA binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a GRF transcription factor may comprise contacting a target nucleic acid (e.g., a nucleic acid encoding a GRF transcription factor) with a sequence-specific DNA binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific DNA binding fusion protein to the target nucleic acid and the sequence-specific DNA binding fusion protein is capable of recruiting the deaminase fusion protein to the target nucleic acid via the peptide tag-affinity polypeptide interaction, thereby editing a locus within the target nucleic acid. In some embodiments, the sequence-specific DNA binding fusion protein may be fused to the affinity polypeptide that binds the peptide tag and the deaminase may be fuse to the peptide tag, thereby recruiting the deaminase to the sequence-specific DNA binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific DNA binding fusion proteins, deaminase fusion proteins and guides may be provided as ribonucleoproteins (RNPs).

In some embodiments, methods such as prime editing may be used to generate a mutation in an endogenous GRF transcription factor gene. In prime editing, RNA-dependent DNA polymerase (reverse transcriptase, RT) and reverse transcriptase templates (RT template) are used in combination with sequence specific DNA binding domains that confer the ability to recognize and bind the target in a sequence-specific manner, and which can also cause a nick of the PAM-containing strand within the target. The DNA binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantageous of the various methods of recruiting proteins for use in the editing to the target site, such methods including both non-covalent and covalent interactions between the proteins and nucleic acids used in the selected process of genome editing.

In some embodiments, the mutation or modification may be an insertion, a deletion and/or a point mutation. In some embodiments, a plant part may be a cell. In some embodiments, the plant or plant part thereof may be any plant or part thereof as described herein. In some embodiments, a plant useful with this invention may be corn, soy, canola, wheat, rice, cotton, sugarcane, sugar beet, barley, oats, alfalfa, sunflower, safflower, oil palm. sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp. In some embodiments, a plant comprising a mutated endogenous GRF transcription factor gene that produces a mRNA having reduced miR396 binding may comprise increased growth and/or an increased growth rate, optionally an increased growth and/or increased growth rate of its roots and/or fruit. In some embodiments, the plant may be corn and the fruit may be an ear, optionally wherein the corn plant comprises a short stature/semi-dwarf phenotype.

In some embodiments, a mutation that is introduced into an endogenous GRF transcription factor gene and resulting in the production of a mRNA having reduced miR396 binding may be a non-naturally occurring mutation. In some embodiments, a mutation that is introduced into an endogenous GRF transcription factor gene and resulting in the production of a mRNA having reduced miR396 binding may be a substitution, an insertion and/or a deletion. In some embodiments, a mutation that is introduced into an endogenous GRF transcription factor gene and resulting in the production of a mRNA having reduced miR396 binding may be a point mutation.

In some embodiments, a GRF transcription factor may include, but is not limited to, a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. In some embodiments, a GRF transcription factor may include, but is not limited to, a GRF6, GRF2, GRF1, GRF14, GRF15, GRF8, GRF4, GRF12, GRF10, GRF11, GRF5, GRF3, GRF9, GRF13, or a GRF7.

In some embodiments, the present invention further provides a method of producing/breeding a transgene-free base-edited plant, the method comprising: (a) crossing a plant of this invention comprising at least one mutation/modification in at least one endogenous GRF transcription factor gene that results in a mRNA having reduced binding of the corresponding miR396 with a transgene free plant, thereby introducing the at least one mutation/modification into the plant that is transgene-free; and (b) selecting a progeny plant that comprises the at least one single nucleotide substitution but is transgene-free, thereby producing a transgene free base-edited plant.

In some embodiments, a plant comprising a mutated endogenous GRF transcription factor gene that produces a mRNA having reduced miR396 binding may exhibit increased growth as compared to a control plant (e.g., a plant that does not comprise said modification or mutation in its endogenous GRF transcription factor gene or in which the plant's endogenous GRF transcription factor gene has not been contacted with the nuclease). In some embodiments, a plant comprising a mutated endogenous GRF transcription factor gene that produces a mRNA having reduced miR396 binding may exhibit at least one of the following phenotypes of increased meristem size, increased seed size, increased biomass, increased leaf size, increased root size, increased nitrogen use efficiency, increased disease resistance, increased height and/or increased internode length as compared to a control plant (e.g., a plant that does not comprise said modification or mutation in its endogenous GRF transcription factor gene or in which the plant's endogenous GRF transcription factor gene has not been contacted with the nuclease).

The present invention further provides a guide nucleic acid (e.g., gRNA) that binds to a target site in a GRF transcription factor gene, the target site comprising any one of the nucleotide sequences of SEQ ID NOs:4-18, 121-144, or 173-198, optionally wherein the GRF transcription factor may be a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. In some embodiments, a guide nucleic acid (e.g., gRNA) that binds to a target site in a GRF transcription factor gene is provide, the target site comprising any one of the nucleotide sequences of SEQ ID NOs:4-18, 121-144, or 173-198, optionally wherein the GRF transcription factor may be a GRF6, GRF2, GRF1, GRF14, GRF15, GRF8, GRF4, GRF12, GRF10, GRF11, GRF5, GRF3, GRF9, GRF13, or a GRF7.

In some embodiments, a guide nucleic acid of a gene editing system of this invention may comprise a spacer that is complementary to a fragment or portion of the nucleotide sequence of any one of SEQ ID NOs:4-18, 121-144, or 173-198, wherein the fragment or portion of any one of SEQ ID NOs:4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of SEQ ID NOs:4-18, 121-144, or 173-198. In some embodiments, a guide nucleic acid may comprise a spacer having complementary to consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position 25 to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of SEQ ID NOs:4-18, 121-144, or 173-198 (counted from the 5' end). In some embodiments, a guide nucleic acid may comprise a spacer that is complementary to consecutive nucleotides from base pair position 20 to base pair position 42 of any one of the nucleotide sequences of SEQ ID NOs:4-18, 121-144, or 173-198 (counted from the 5' end). In some embodiments, the guide nucleic acid may comprise a spacer having the nucleotide sequence of any one of SEQ ID NOs:48-71.

The present invention further provides an editing system comprising a guide nucleic acid of the invention and a CRISPR-Cas effector protein that associates with the guide nucleic acid. In some embodiments, an editing system of the invention may further comprise tracr nucleic acid that associates with the guide nucleic acid and a CRISPR-Cas effector protein, optionally wherein the tracr nucleic acid and the guide nucleic acid are covalently linked.

The present invention further provides an editing system comprising a CRISPR-Cas effector protein in association with a guide nucleic acid, wherein the guide nucleic acid comprises a spacer sequence that binds to a GRF transcription factor gene. In some embodiments, the GRF transcription factor gene may be a GRF1 gene, GRF2 gene, GRF3 gene, GRF4 gene, GRF5 gene, GRF6 gene, GRF7 gene, GRF8 gene, GRF9 gene, GRF10 gene, GRF11 gene, GRF12 gene, GRF13 gene, GRF14 gene, GRF15 gene, GRF16 gene, GRF17 gene, GRF18 gene, GRF19 gene, or a GRF20 gene. In some embodiments, the GRF transcription factor gene may be a GRF6 gene, GRF2 gene, GRF1 gene, GRF14 gene, GRF15 gene, GRF8 gene, GRF4 gene, GRF12 gene, GRF10 gene, GRF11 gene, GRF5 gene, GRF3 gene, GRF9 gene, GRF13 gene, or a GRF7 gene. In some embodiments, the GRF transcription factor gene of the gene editing system may comprise the nucleotide sequence of any one of SEQ ID NOs:1-3, 145, 146, or 199-202.

In some embodiments, a guide nucleic acid of the gene editing system may comprise a spacer sequence having the nucleotide sequence of any one of SEQ ID NOs:48-71.

The present invention further provides a complex comprising a CRISPR-Cas effector protein comprising a cleavage domain and a guide nucleic acid (e.g., gRNA), wherein the guide nucleic acid binds to a target site in a GRF transcription factor gene having the nucleotide sequence of any one SEQ ID NOs:4-18, 121-144, or 173-198, wherein the nuclease cleaves the target strand.

Further provided herein are expression cassettes comprising a (a) polynucleotide encoding CRISPR-Cas effector protein comprising a cleavage domain and (b) a guide nucleic acid that binds to a target site in a GRF transcription factor gene, wherein the guide nucleic acid comprises a spacer sequence that is complementary to and binds to a sequence having at least 80% sequence identity to at least a portion of any one of the nucleotide sequences of SEQ ID NOs:1-3, 145, 146, or 199-202 or a sequence having at least 80% sequence identity to at least a portion of any one of the nucleotide sequences of SEQ ID NOs:4-18, 121-144, or 173-198, as described herein. In some embodiments, the at least a portion may comprise at least one nucleotide or at least two (e.g., 2, 3, 4, 5, 6, 7, 8, 9, 10, 11, 12, 13, 14, 15, 16, 17, 18, 19, 20, 21, or 22) consecutive nucleotides of any one of the nucleotide sequences of SEQ ID NOs:1-3, 145, 146, or 199-202.

In some embodiments, the at least a portion may be a portion of the nucleotide sequence of any one of SEQ ID NOs:1-3, 145, 146, or 199-202 and/or any one of SEQ ID NOs:4-18, 121-144, or 173-198, wherein the portion of any one of SEQ ID NOs:1-3, 145, 146, or 199-202 and/or any one of SEQ ID NOs:4-18, 121-144, or 173-198 may be from base pair position 5, 6, 7, 8, 9, 10, 11, 12, 13, 14, 15, 20, 21, 22, 23, 24, 25, 26, 27, 28, 29, 30, 31, 32, 33, 34, 35 to base pair position 36, 37, 38, 39, 40, 41, 42, 43, 44, 45, 46, 47, 48, 49, 50, 51, 52, 53, 54, 55, 56, 57, 58, 59, 60 of any one of any one of SEQ ID NOs:1-3, 145, 146, or 199-202 and/or any one of SEQ ID NOs:4-18, 121-144, or 173-198. In some embodiments, the at least a portion may comprise consecutive nucleotides from base pair position 1 to base pair position 21 or 22, from base pair position 5 to base pair position 21, 22, 23, 24, 25, 26 or 27, from base pair position 10 to base pair position 25, 26, 27, 28, 29, 30, 31, or 32, from base pair position 15 to base pair position 30, 31, 32, 33, 34, 35, 36, or 37, from base pair position 20 to base pair position 35, 36, 37, 38, 39, 40, 41, or 42, from base pair position 21 to base pair position 37, 38, 39, 40, 41, 42, 43, or 44, from base pair position to base pair position 40, 41, 42, 43, 44, 45, 46, 47, or 48, from base pair position 30 to base pair position 45, 46, 47, 48, 49, 50, 51, or 52, from base pair position 35 to base pair position 50, 51, 52, 53, 54, 55, 56, or 57, from base pair position 40 to base pair position 55, 56, 57, 58, 59, 60, 61, or 62, from base pair position 42 to base pair position 57, 58, 59, 60, 61, or 62, and the like, of any one of the nucleotide sequences of any one of SEQ ID NOs:1-3, 145, 146, or 199-202 and/or any one of SEQ ID NOs:4-18, 121-144, or 173-198 (counted from the 5' end). In some embodiments, the at least a portion may comprise consecutive nucleotides from base pair position 20 to base pair position 42 of any one of the nucleotide sequences of any one of SEQ ID NOs:1-3, 145, 146, or 199-202 and/or any one of SEQ ID NOs:4-18, 121-144, or 173-198 (counted from the 5' end). In some embodiments, a portion of any one of SEQ ID NOs:1-3, 145, 146, or 199-202 and/or any one of SEQ ID NOs:4-18, 121-144, or 173-198 may be at least about 1, 2, 3, 4, 5, 6, 7, 8, 9, 10, 11, 12, 13, 14, 15, 16, 17, 18, 19, 20, 21, 22, 23, 24, or 25 or more consecutive nucleotides of any one of SEQ ID NOs:1-3, 145, 146, or 199-202 and/or any one of SEQ ID NOs:4-18, 121-144, or 173-198.

Also provided herein is a nucleic acid encoding GRF transcription factor that produces a mRNA having a mutated miR396 binding site, wherein the mutated miR396 binding site comprises a mutation that results in increased levels of the mRNA, and optionally, disrupts (reduced or eliminates) miR396 binding to the mRNA. In some embodiments, the mutation may eliminate the binding of the corresponding miR396 (e.g., zero detectable binding). In some embodiments, the mutation may reduce the ability of the corresponding miR396 to bind to the GRF transcription factor mRNA by at least about 75% (e.g., about 75, 76, 77, 78, 79, 80, 81, 82, 83, 84, 85, 86, 87, 88, 89, 90, 91, 92, 93, 94, 95, 96, 97, 98, 99% or more, or any range or value therein, of a reduction in miR396 binding, or any range or value therein). In some embodiments, the GRF transcription factor may be a GRF1, GRF2, GRF3, GRF4, GRF5, GRF6, GRF7, GRF8, GRF9, GRF10, GRF11, GRF12, GRF13, GRF14, GRF15, GRF16, GRF17, GRF18, GRF19 or a GRF20. In some embodiments, the GRF transcription factor may be a GRF6, GRF2, GRF1, GRF14, GRF15, GRF8, GRF4, GRF12, GRF10, GRF11, GRF5, GRF3, GRF9, GRF13, or a GRF7. In some embodiments, a plant or part thereof is provided that comprises a nucleic acid of the invention encoding a GRF transcription factor that produces a mRNA having a mutated miR396 binding site, wherein the mutated miR396 binding site comprises a mutation that results in increased levels of the mRNA, and optionally, disrupts miR396 binding. In some embodiments the plant is a corn plant, optionally wherein the corn plant comprises a short stature/semi-dwarf phenotype. In some embodiments, the plant is a wheat plant or part thereof, optionally wherein the nucleic acid encoding a GRF transcription factor that produces a mRNA having a mutated miR396 binding site may be comprised in the A genome, the B genome, the D genome or in any combination thereof. In some embodiments, the plant or part thereof that comprises a nucleic acid of the invention encoding a GRF transcription factor that produces a mRNA having a mutated miR396 binding site may comprise increased growth or an increased rate of growth. In some embodiments, the plant or part thereof that comprises a nucleic acid of the invention encoding a GRF transcription factor that produces a mRNA having a mutated miR396 binding site may exhibit at least one of the following phenotypes of increased meristem size, increased seed size, increased biomass, increased leaf size, increased root size, increased nitrogen use efficiency, increased disease resistance, increased height and/or increased internode length.

In some embodiments, the present invention further provides a guide nucleic acid that binds to a target nucleic acid in a GRF transcription factor in a corn plant, wherein the target nucleic acid is located in: (a) a chromosome interval defined by and including base pair (bp) position 211773221 to base pair position 211774543 on chromosome 5, optionally a chromosome interval defined by and including base pair (bp) position 211773897 to base pair position 211773957; (b) a chromosome interval defined by and including base pair (bp) position 200344009 to base pair position 200348833 on chromosome 5, optionally a chromosome interval defined by and including base pair (bp) position 200346611 to base pair position 200346671; (c) a chromosome interval defined by and including base pair (bp)

position 13817620 to base pair position 13822440 on chromosome 5, optionally a chromosome interval defined by and including base pair (bp) position 138197933 to base pair position 13819853; (d) a chromosome interval defined by and including base pair (bp) position 177151736 to base pair position 177154443 on chromosome 4, optionally a chromosome interval defined by and including base pair (bp) position 177152804 to base pair position 177152864; (e) a chromosome interval defined by and including base pair (bp) position 257245490 to base pair position 257249295 on chromosome 1, optionally a chromosome interval defined by and including base pair (bp) position 257247225 to base pair position 257247285; (f) a chromosome interval defined by and including base pair (bp) position 25722859 to base pair position 25725873 on chromosome 9, optionally a chromosome interval defined by and including base pair (bp) position 25723770 to base pair position 25723830; (g) a chromosome interval defined by and including base pair (bp) position 60351912 to base pair position 60356302 on chromosome 6, optionally a chromosome interval defined by and including base pair (bp) position 60354489 to base pair position 60354549; (h) a chromosome interval defined by and including base pair (bp) position 196192921 to base pair position 196194872 on chromosome 5, optionally a chromosome interval defined by and including base pair (bp) position 196194175 to base pair position 196194235; (i) a chromosome interval defined by and including base pair (bp) position 140393394 to base pair position 140398705 on chromosome 10, optionally a chromosome interval defined by and including base pair (bp) position 140396272 to base pair position 140396332; (j) a chromosome interval defined by and including base pair (bp) position 155831622 to base pair position 155833517 on chromosome 4, optionally a chromosome interval defined by and including base pair (bp) position 155832749 to base pair position 155832809; (k) a chromosome interval defined by and including base pair (bp) position 12201898 to base pair position 12208052 on chromosome 2, optionally a chromosome interval defined by and including base pair (bp) position 12204599 to base pair position 12204659; (1) a chromosome interval defined by and including base pair (bp) position 9818327 to base pair position 9820186 on chromosome 9, optionally a chromosome interval defined by and including base pair (bp) position 9819224 to base pair position 9819284; (m) a chromosome interval defined by and including base pair (bp) position 108477686 to base pair position 108480099 on chromosome 6, optionally a chromosome interval defined by and including base pair (bp) position 108478747 to base pair position 108478807; (n) a chromosome interval defined by and including base pair (bp) position 225827712 to base pair position 225832487 on chromosome 2, optionally a chromosome interval defined by and including base pair (bp) position 225830099 to base pair position 225830159; (o) a chromosome interval defined by and including base pair (bp) position 272414778 to base pair position 272420567 on chromosome 1; (p) a chromosome interval defined by and including base pair (bp) position 199377455 to base pair position 199381799 on chromosome 2; (q) a chromosome interval defined by and including base pair (bp) position 145016279 to base pair position 145019899 on chromosome 7; and/or (r) a chromosome interval defined by and including base pair (bp) position 8708791 to base pair position 8711617 on chromosome 5, wherein the mutation results in increased levels of the mRNA, and optionally, disrupts the binding of miR396 to the GRF transcription factor, wherein the chromosomal intervals of (a) to (r) correspond to the reference corn genome of B73 (see e.g., Table 1).

In some embodiments, a sequence-specific nucleic acid binding domain (DNA binding domains) of an editing system useful with this invention can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein.

In some embodiments, a sequence-specific DNA binding domain may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Casl, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

A CRISPR Cas9 effector protein or CRISPR Cas9 effector domain useful with this invention may be any known or later identified Cas9 nuclease (see, e.g., SEQ ID NOs:234-250). In some embodiments, a CRISPR Cas9 polypeptide can be a Cas9 polypeptide from, for example, *Streptococcus* spp. (e.g., *S. pyogenes*, S. thermophiles), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. FIGS. 4A-4B show example base edits using Cas9.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from *Leptotrichia shahii*, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease (see, e.g., SEQ ID NOs:214-230, SEQ ID NOs:231-233). Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

Figure 5B:
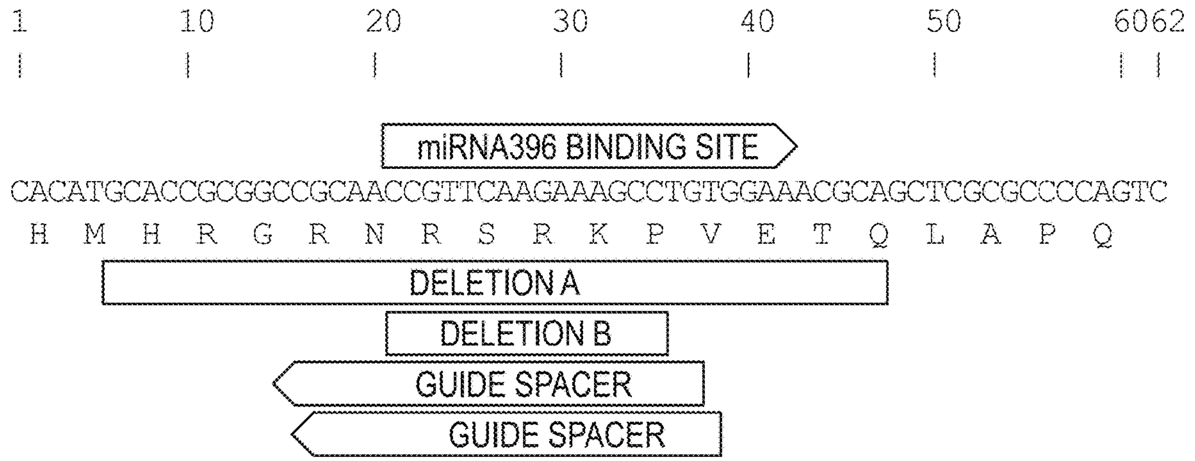

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity. FIG. 5A-5B show example base edits using Cas12a (Cpf1).

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:206, SEQ ID NO:207 or SEQ ID NO:208). In some embodiments, the cytosine deaminase may be an APOBEC1 deaminase having the amino acid sequence of SEQ ID NO:77. In some embodiments, the cytosine deaminase may be an APOBEC3A deaminase having the amino acid sequence of SEQ ID NO:78. In some embodiments, the cytosine deaminase may be an CDA1 deaminase, optionally a CDA1 having the amino acid sequence of SEQ ID NO:79. In some embodiments, the cytosine deaminase may be a FERNY deaminase, optionally a FERNY having the amino acid sequence of SEQ ID NO:80. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:77, SEQ ID NO:78, SEQ ID NO:79 or SEQ ID NO:80 (e.g., at least 80%, at least 85%, at least 90%, at least 92%, at least 95%, at least 96%, at least 97%, at least 98%, at least 99%, or at least 99.5% identical to the amino acid sequence of SEQ ID NO:77, SEQ ID NO:78, SEQ ID NO:79 or SEQ ID NO:80, SEQ ID NO:206, SEQ ID NO:207 or SEQ ID NO:208). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:81 or a polypeptide having about 70% to about 99.5% identity to the amino acid sequence of SEQ ID NO:81 (e.g., at least 80%, at least 85%, at least 90%, at least 92%, at least 95%, at least 96%, at least 97%, at least 98%, at least 99%, or at least 99.5% identical to the amino acid sequence of SEQ ID NO:81). For example, in some embodiments, a UGI domain may comprise a fragment of the amino acid sequence of SEQ ID NO:81 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:81. In some embodiments, a UGI domain may be a variant of a known UGI (e.g., SEQ ID NO:81) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally-occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:72. In some embodiments, a mutated/evolved *E. coli* TadA* comprises the amino acid sequence of SEQ ID NOs:73-76 or 209-213 (e.g., SEQ ID NOs:73, 74, 75, 76, 209, 210, 211, 212 or 213). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific DNA binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a sequence-specific DNA binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, CasI, Cas1B, Cas2, Cas3, Cas3', Cas3'', Cas4, Cas5, Cas6, Cas7, Cas8, Cas9 (also known as Csn1 and Csx12), Cas10, Csy1, Csy2, Csy3, Cse1, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, CasI, Cas1B, Cas2, Cas3, Cas3', Cas3'', Cas4, Cas5, Cas6, Cas7, Cas8, Cas9 (also known as Csn1 and Csx12), Cas10, Csy1, Csy2, Csy3, Csel, Cse2, Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csfl, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer) (e.g., consecutive nucleotides of any one of SEQ ID NOs:1-18) (e.g., SEQ ID NOs:48-71). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

```
 5'-NNNNNNNNNNNNNNNNNNNN-3'  RNA Spacer         (SEQ ID NO: 203)
     ||||||||||||||||||
3'AAANNNNNNNNNNNNNNNNNNNN-5'  Target strand      (SEQ ID NO: 204)
  ||||
5'TTTNNNNNNNNNNNNNNNNNNNN-3'  Non-target strand  (SEQ ID NO: 205)
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Fusion proteins of the invention may comprise sequence-specific DNA binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag 11, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat—spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g. dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

In some embodiments, the invention provides cells comprising one or more polynucleotides, guide nucleic acids, nucleic acid constructs, expression cassettes or vectors of the invention.

In some embodiments, a method of editing an endogenous GRF transcription factor gene in a plant or plant part is provided, the method comprising contacting a target site in the GRF transcription factor gene in the plant or plant part with a cytosine base editing system comprising a cytosine deaminase and a nucleic acid binding domain that binds to a target site in the GRF transcription factor gene having at least 80% sequence identity to the nucleotide sequence of any one of SEQ ID NOs:1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, wherein the cytosine deaminase generates at least one C to T conversion in the nucleotide sequence of any one of SEQ ID NOs:1-3, 145, 146, or 199-202, thereby producing a plant or part thereof comprising at least one cell having a mutation in the endogenous GRF transcription factor gene.

In some embodiments, a method of editing an endogenous GRF transcription factor gene in a plant or plant part is provided, the method comprising contacting a target site in the GRF transcription factor gene in the plant or plant part with an adenine base editing system comprising an adenine deaminase and a nucleic acid binding domain that binds to a target site in the GRF transcription factor gene having at least 80% sequence identity to the nucleotide sequence of any one of SEQ ID NOs:1-3, 145, 146, or 199-202, having at least 80% sequence identity to the nucleotide sequence of any one of SEQ ID NOs:4-18, 121-144, or 173-198, or having at least 80% sequence identity to the nucleotide sequence of any one of SEQ ID NOs:19-33, 97-120, or 147-172, wherein the cytosine deaminase generates at least one A to G conversion in the nucleotide sequence of any one of SEQ ID NOs:1-3, 145, 146, or 199-202, thereby producing a plant or part thereof comprising at least one cell having a mutation in the endogenous GRF transcription factor gene.

In some embodiments, a method of detecting a mutant GRF (a mutation in an endogenous GRF transcription factor gene) is provide, the method comprising detecting in the genome of a plant a base substitution in at least one of positions 11, 19, 21 and/or 22 of the nucleotide sequence of any one of SEQ ID NOs:1-3, 145, 146, or 199-202. In some embodiments, the substitution that is detected at position 11 of the nucleotide sequence of any one of SEQ ID NOs:1-3, 145, 146, or 199-202 may be from G>A. In some embodiments, the substitution that is detected at position 19 of the nucleotide sequence of any one of SEQ ID NOs:1-3, 145, 146, or 199-202 may be from G>A or G>C. In some embodiments, the substitution that is detected at position that is detected at position 21 of the nucleotide sequence of any one of SEQ ID NOs:1-3, 145, 146, or 199-202 may be from G>A or G>C. In some embodiments, the substitution that is detected at position 22 of the nucleotide sequence of any one of SEQ ID NOs:1-3, 145, 146, or 199-202 may be from G>A or G>C.

In some embodiments, the present invention provides a method of detecting a mutation in an endogenous GRF gene, comprising detecting in the genome of a plant one or more of any one of the nucleotide sequences of SEQ ID NOs:34-41.

In some embodiments, the present invention provides a method of producing a plant comprising a mutation in an endogenous GRF transcription factor gene and at least one polynucleotide of interest, the method comprising crossing a plant of the invention comprising at least one mutation in an endogenous GRF transcription factor gene (a first plant) with a second plant that comprises the at least one polynucleotide of interest to produce progeny plants; and selecting progeny plants comprising at least one mutation in the GRF transcription factor gene and the at least one polynucleotide of interest, thereby producing the plant comprising a mutation in an endogenous GRF transcription factor gene and at least one polynucleotide of interest.

The present invention further provides a method of producing a plant comprising a mutation in an endogenous GRF transcription factor gene and at least one polynucleotide of interest, the method comprising introducing at least one polynucleotide of interest into a plant of the present invention comprising at least one mutation in a GRF transcription factor gene, thereby producing a plant comprising at least one mutation in a GRF transcription factor gene and at least one polynucleotide of interest.

In some embodiments, the present invention provides a method of producing a plant comprising a mutation in an endogenous GRF transcription factor gene and at least one polynucleotide of interest, the method comprising introducing at least one polynucleotide of interest into a plant of the invention comprising at least one mutation in an endogenous GRF transcription factor gene, thereby producing a plant comprising at least one mutation in a GRF transcription factor gene and at least one polynucleotide of interest.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, disease resistance, increased yield, increased nutrient use efficiency or abiotic stress resistance.

In some embodiments, a method of producing a plant comprising a mutation in an endogenous GRF transcription factor gene and having a dwarf or short stature phenotype is provided, the method comprising crossing a plant of the invention (a first plant) having at least one mutation in an endogenous GRF transcription factor gene with a second plant that comprises the dwarf or short stature phenotype to produce progeny plants; and selecting progeny plants comprising the at least one mutation in the GRF transcription factor gene and the dwarf or short stature phenotype, thereby producing the plant having a dwarf or short stature and comprising at least one mutation in an endogenous GRF transcription factor gene.

The present invention further provides a method of controlling weeds in a container (e.g., pot, or seed tray and the like), a growth chamber, a greenhouse, a field (e.g., a cultivated field), a recreational area, a lawn, and/or a roadside, comprising applying an herbicide to one or more (a plurality) plants of the present invention growing in the container, growth chamber, field or greenhouse, thereby controlling the weeds in the container, growth chamber, greenhouse, field, recreational area, a lawn, and/or a roadside in which the one or more plants are growing.

In some embodiments, a method of reducing insect predation on a plant (or a plurality of plants) is provided, comprising applying an insecticide to one or more (a plurality) plants of the present invention, thereby reducing the insect predation on the one or more (a plurality) plants. In some embodiments the one or more plants may be growing in a container, a growth chamber, a field, a recreational area (e.g., playing field, golf course), a lawn, roadside, or a greenhouse.

In some embodiments, the present invention provides a method of reducing fungal disease on a plant, comprising applying a fungicide to one or more (a plurality) plants of the present invention, thereby reducing fungal disease on the on the one or more (a plurality) plants. In some embodiments the one or more plants may be growing in a container, a growth chamber, a field, a recreational area (e.g., playing field, golf course), a lawn, a roadside, or a greenhouse.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Non-limiting examples of plants that may be modified as described herein may include, but are not limited to, turf grasses (e.g., bluegrass, bentgrass, ryegrass, fescue), feather reed grass, tufted hair grass, *miscanthus, arundo*, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, *papaya*, and lychee, a field crop plant such as clover, alfalfa, timothy, evening primrose, meadow foam, corn/maize (field, sweet, popcorn), hops, jojoba, buckwheat, safflower, *quinoa*, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), *lauraceae* (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, *eucalyptus*, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, corn, soy, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleraceae, B. rapa, B. juncea*, and/or *B. nigra.*

In some embodiments, a plant that may be modified as described herein is corn (i.e., maize, *Zea mays*, optionally wherein the corn plant comprises a short stature/semi-dwarf phenotype.

In some embodiments, a plant that may be modified as described herein is wheat (e.g., *Triticum aestivum, T. durum*, and/or *T. compactum*). In some embodiments, a wheat plant may comprise at least one non-natural mutation in an endogenous Growth Regulating Factor (GRF) transcription factor in its A genome, in its B genome, and/or in its D genome.

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1

Modification of Endogenous Maize GRF Transcription Factor Family with Base Editing This example demonstrates the use of DNA base-editing to modify maize GRF transcription factors resulting in an increase in plant height and ear length.

Figure 9:
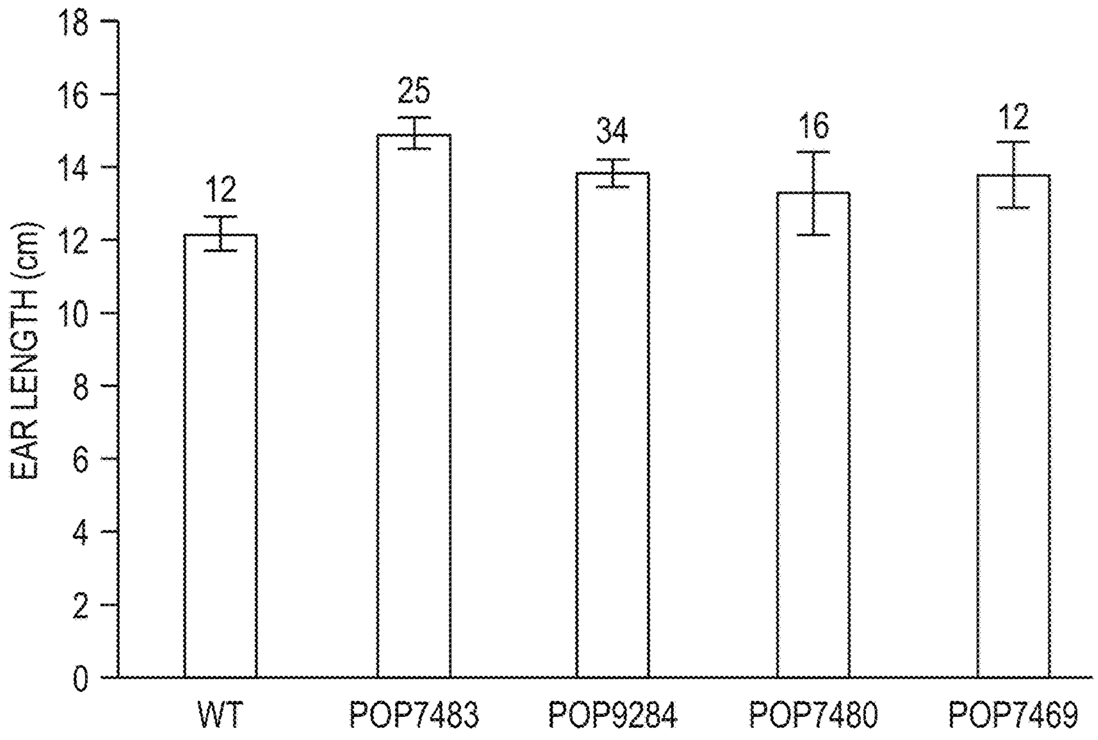
FIG. 9 provides a plot showing average ear length measurements from progeny of GRF4 family edits. X axis labels indicate the family of plants represented by the bar, WT indicating wild-type unedited lines, Population (Pop) 7483, Pop 9284, Pop 7480, Pop 7469 each indicating a family of progeny derived from an edited parent. Bars represent means, error bars represent 95% confidence interval around means, labels above error bars indicate number of measured samples for each family.
Figure 10:
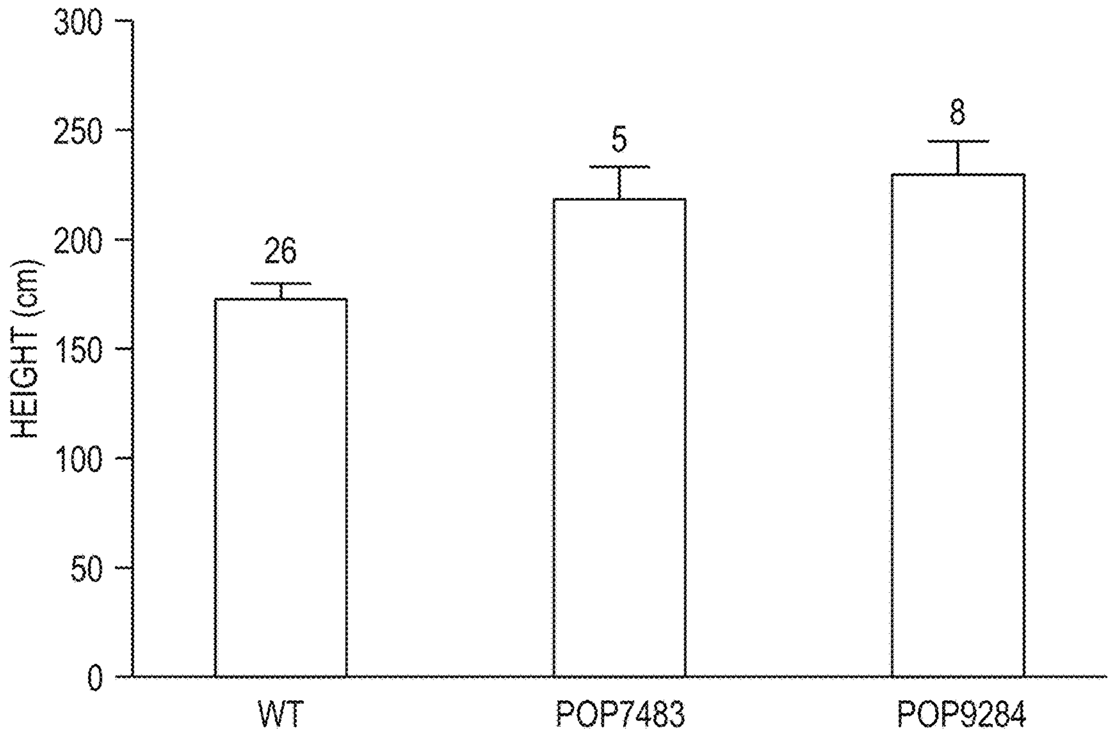
FIG. 10 provides a plot showing the average height from progeny of GRF4 family edits. X axis labels indicate the family of plants represented by the bar, WT indicating wild-type unedited lines, Pop 7483 and Pop 9284 each indicating a family of progeny derived from an edited parent. Bars represent means, error bars represent 95% confidence interval around means, labels above error bars indicate number of measured samples for each family.

The spacer sequence comprising SEQ ID NO:58 was selected for use in a Cas9 base editing approach targeting the conserved miR396 region of several maize GRF transcription factors. GRF6 and four other GRF loci were targeted with 100% match to the spacer sequence, FIG. 7. A vector encoding the spacer as well as a mutated Cas9 effector fused to a cytosine deaminase were introduced into maize dry-excised embryos (DEEs) using *Agrobacterium*. After transformation, we assayed regenerating plants (E0 generation) for edits at the GRF6 locus with standard next-gen-sequencing (NGS) methods and identified several families with base-edit mutations in the miR396 targets site, FIG. 8. We grew four different populations for trait testing in the next generation, three derived from selfed E0 plants that showed editing at GRF6 (Population 7483, 7480, 7469), and a fourth with seed derived from a backcross of plant 7469 to the transformation germplasm (Population 9284). These four populations were grown in controlled environment and transgene-free plants were selfed and subjected to trait testing. Our results show the progeny of E0 base-edited plants have increased ear length FIG. 9, and plant height FIG. 10. These results show that base editing within the miRNA396 target site of one of these GRF transcription factors results in increased maize plant growth.

Example 2

Increasing the mRNA Level of Maize GRF6 Transcription Factor with Cpf1 In-Frame Deletion Gene Editing.

This example demonstrates the modification of an endogenous maize GRF6 transcription factor, GRMZM2G034876 (GRF6) to disrupt miRNA396 action and increase GRF6 mRNA levels using a Cpf1 cutting nuclease.

Figure 12:
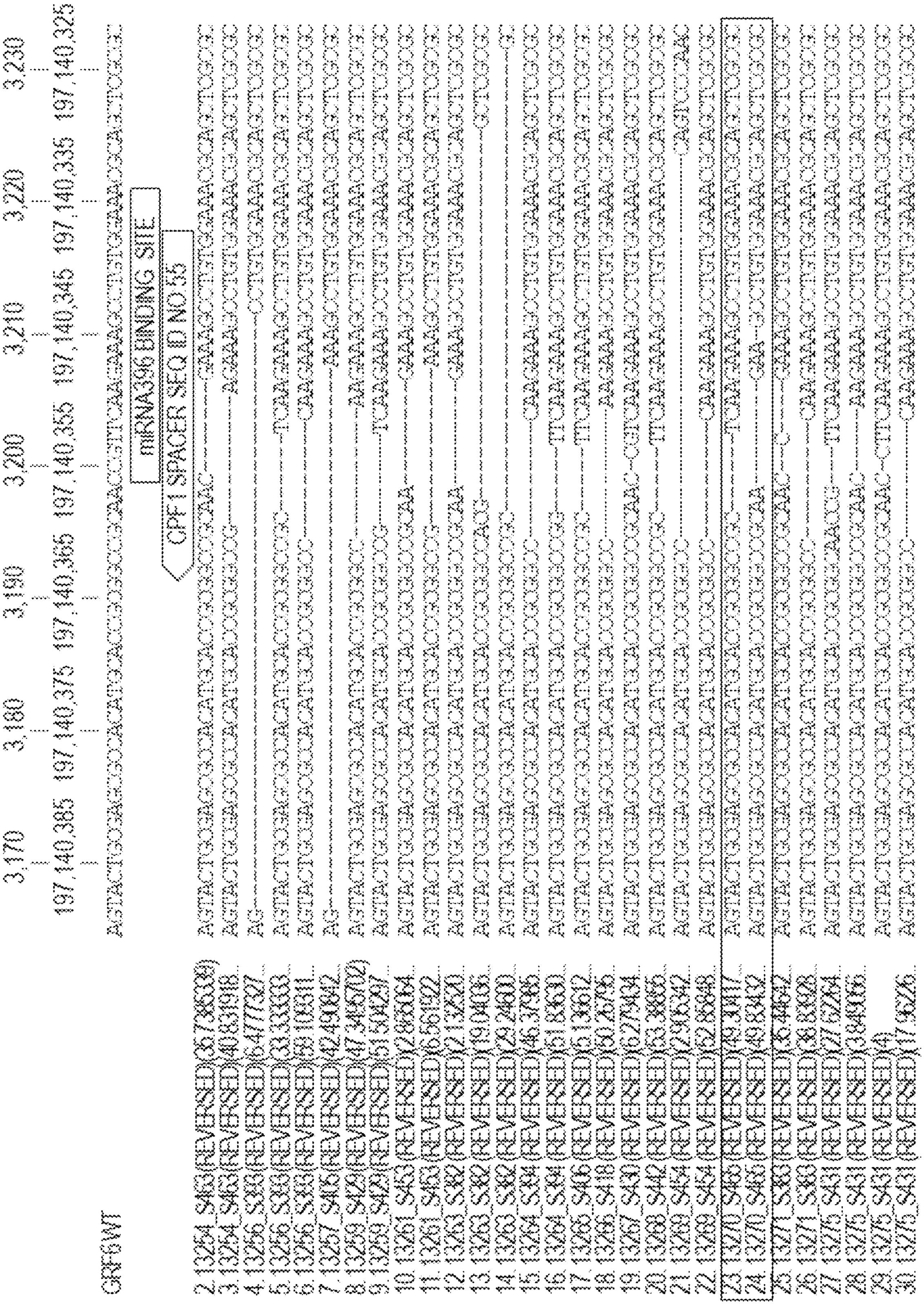
FIG. 12 shows edits achieved in maize GRF6 in E0 plants from Cpf1-based deletion construct. The top sequence is the wildtype GRF6 sequence. Also shown are the miR396 target sequence and the Cpf1 spacer (SEQ ID NO:55) positions. Individual reads from E0 plants are below. The boxed reads show the 6 bp and 9 bp deletions recovered from E0 plant 13270 which is used for subsequent analyses. Numbers next to each read name are the % NGS reads recovered. From top to bottom: SEQ ID NOs:275, 276, 277, 278, 279, 280, 281, 282, 283, 284, 285, 286, 287, 288, 289, 290, 290, 291, 292, 293, 294, 295, 296, 297, 298, 299, 300, 301, 302, and 303.
Figure 13:
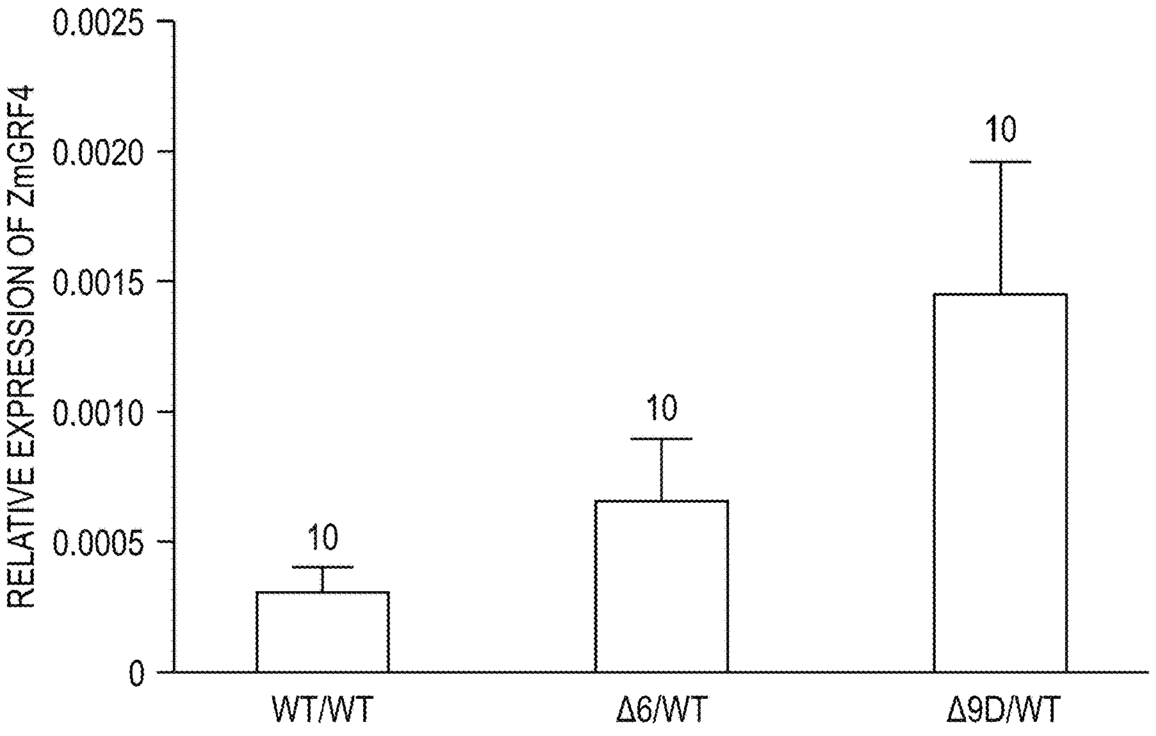
FIG. 13 provides a plot showing the average expression level of GRF4 in edited corn genotypes. X axis labels indicate the genotype of plants represented by the bar, WT/WT indicating wild-type unedited lines, Δ6/WT indicating lines heterozygous for a 6 bp deletion, and Δ9/WT indicating lines heterozygous for a 9 bp deletion. Y axis indicates expression of ZmGRF4 relative to endogenous control genes EF1α and Tubulin. Bars represent means, error bars represent 95% confidence interval around means, labels above error bars indicate number of measured samples for each family.

A spacer sequence comprising SEQ ID NO:55 with high specificity to the GRF6 target locus was designed. In this case only GRF6 was targeted with 100% specificity (FIG. 11). A vector encoding the spacer and a Cpf1-based nuclease were introduced into maize dry-excised embryos (DEEs) using *Agrobacterium*. After transformation, we assayed regenerating plants (E0 generation) for edits at the GRF6 locus with standard NGS methods and identified several families with in-frame deletions in the miR396 targets site, FIG. 12. Plant 13270 had ~50% reads for a 6 bp in-frame deletion and ~50% reads 9 bp in-frame deletion and was selected for further analysis. Plant 13270 was selfed and the progeny grown another generation (E1). In E1, a transgene-free plant containing both 6 bp and 9 bp deletions was backcrossed to the transformation germplasm (01DKD2). The progeny from this cross were grown, assayed for edits at GRF6, and subjected to trait testing. The GRF6 mRNA levels in leaf tissue of heterozygous 6 bp deletion, heterozygous 9 bp deletion, and a wildtype control plants were compared using standard quantitative PCR (qPCR) methods and we observed an increase in GRF6 mRNA levels in both heterozygous edit populations, FIG. 13. This example shows that in-frame deletion within the maize GRF6 miRNA396 target site using gene editing can increase GRF6 mRNA levels, even when the edit is in the heterozygous state. No statistical differences in plant phenotypes were observed, including, for example, plant height, ear length and 100 kernel weight. These results suggest it is one of the other GRFs and not GRF6 that explain the increased plant height and ear length resulting from the base edits in Example 1.

Example 3

Increasing the mRNA Level of Soy GRF Transcription Factor with Cpf1 in Frame Deletion Gene Editing.

Figure 14:
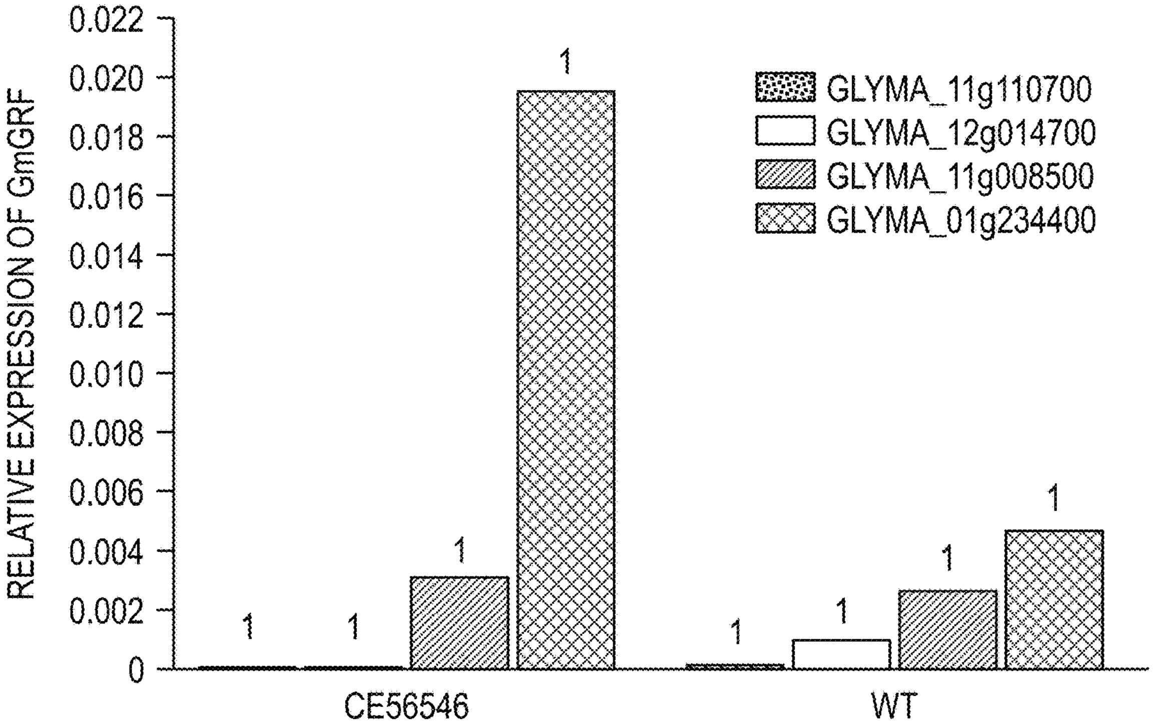
FIG. 14 provides a plot showing the expression level of a GRF in edited soybean plant compared to wild type. X axis labels indicate genotype of GRF family member (GLYMA_12g014700) allele. Y axis indicates expression of GmGRF relative to endogenous control gene ActII. Labels above bars indicate the number of samples included for each genotype.

This example demonstrates the modification of an endogenous soy GRF transcription factor (GLYMA_01g234400) to disrupt miRNA396 action and increase GRF mRNA levels. A spacer simultaneously targeting four different GRF transcription factors (GLYMA_01g234400 SEQ ID NO:97, GLYMA_11g008500 SEQ ID NO:110, GLYMA_12g014700 SEQ ID NO:108, GLYMA_11g110700 SEQ ID NO:112) was designed (TGATTCCACAGGCTTTCTTGAAC (SEQ ID NO:251)). A vector expressing the spacer and a Cpf1-based nuclease was transformed into Soy dry-excised embryos (DEEs) using *Agrobacterium*. Regenerating plants were assayed for deletions at all four target loci using standard NGS methods. A plant (CE56546) was identified with a 6 bp in-frame deletion in the miR396 target site in locus GLYMA_01g234400 at high % reads. Leaf tissue was sampled from this plant and the mRNA level of all four GRF loci were compared to wildtype controls using standard qPCR methods (FIG. 14). Only GLYMA_01g234400 showed an increase in mRNA levels consistent with the high % editing of this locus. The other GRFs assayed showed relatively low % edit and no increase in mRNA levels. These results show that in-frame deletions within the miR396 target of Soy GRFs can also increase mRNA levels in this species.

TABLE 1

Maize GRF transcription factor gene names as provided in the V1-V4 B73 corn strain gene models along with corresponding GRF name as use herein. Also provided are the chromosome positions of the GRF genes and miRNA binding sites (based on B73 RefGen v3)

| v1_gene_model | v2_gene_model | v3_gene_model | v4_gene_model | GRF Name | Chromosome | v3_Coordinates | v3_Binding Site Start Position |
|---|---|---|---|---|---|---|---|
| GRMZM2G178261 | GRMZM2G178261 | GRMZM2G178261 | Zm00001d033876 | GRF1 | 1 | 1:272414778..272420567 | |
| GRMZM2G119359 | GRMZM2G119359 | GRMZM2G119359 | Zm00001d045533 | GRF2 | 9 | 9:25722859..25725873 | 25723800 |
| GRMZM2G048993 | GRMZM5G893117 | GRMZM5G893117 | Zm00001d018260 | GRF3 | 5 | 5:211773221..211774543 | 211773927 |
| GRMZM2G018414 | GRMZM2G018414 | GRMZM2G018414 | Zm00001d033396 | GRF4 | 1 | 1:257245490..257249295 | 257247255 |
| GRMZM2G129147 | GRMZM2G129147 | GRMZM2G129147 | Zm00001d026240 | GRF5 | 10 | 10:140393394..140398705 | 140396302 |
| GRMZM2G034876 | GRMZM2G034876 | GRMZM2G034876 | Zm00001d017742 | GRF6 | 5 | 5:200344009..200348833 | 200346641 |
| GRMZM2G098594 | GRMZM2G098594 | GRMZM2G098594 | Zm00001d035965 | GRF7 | 6 | 6:60351912..60356302 | 60354519 |
| GRMZM2G041223 | GRMZM2G041223 | GRMZM2G041223 | Zm00001d002429 | GRF8 | 2 | 2:12201898..12208052 | 12204629 |
| GRMZM2G124566 | GRMZM2G124566 | GRMZM2G124566 | Zm00001d051456 | GRF9 | 4 | 4:155831622..155833517 | 155832779 |
| GRMZM2G105335 | GRMZM2G105335 | GRMZM2G105335 | Zm00001d052112 | GRF10 | 4 | 4:177151736..177154443 | 177152834 |
| | GRMZM5G850129 | GRMZM5G850129 | Zm00001d037117 | GRF11 | 6 | 6:108477686..108480099 | 108478777 |
| GRMZM2G067743 | GRMZM2G067743 | GRMZM2G067743 | Zm00001d000238 | GRF12 | 9 | 9:9818327..9820186 | 9819254 |

TABLE 1-continued

Maize GRF transcription factor gene names as provided in the V1-V4 B73 corn strain gene models along with corresponding GRF name as use herein. Also provided are the chromosome positions of the GRF genes and miRNA binding sites (based on B73 RefGen v3)

| v1_gene_model | v2_gene_model | v3_gene_model | v4_gene_model | GRF Name | Chromo-some | v3_Coordinates | v3_Binding Site Start Position |
|---|---|---|---|---|---|---|---|
| GRMZM2G033612 | GRMZM2G033612 | GRMZM2G033612 | Zm00001d013555 | GRF13 | 5 | 5:13817620..13822440 | 13819823 |
| | GRMZM5G853392 | GRMZM5G853392 | Zm00001d013346 | GRF14 | 5 | 5:8708791..8711617 | |
| GRMZM2G099862 | GRMZM2G099862 | GRMZM2G099862 | Zm00001d007465 | GRF15 | 2 | 2:225827712..225832487 | 225830129 |

The foregoing is illustrative of the present invention and is not to be construed as limiting thereof. The invention is defined by the following claims, with equivalents of the claims to be included therein.

That which is claimed is:

1. A method for editing a specific site in the genome of a corn plant cell, the method comprising:

contacting a target site in an endogenous GRF transcription factor gene in the corn plant cell with an editing system comprising a nucleic acid binding domain that binds to the target site;

cleaving, in a site specific manner, the target site within the endogenous GRF transcription factor gene, the endogenous GRF transcription factor gene comprising a sequence having at least 90% sequence identity to the nucleotide sequence of SEQ ID NO: 304, thereby generating an edit in the endogenous GRF transcription factor gene of the corn plant cell, wherein the edit is located in a region of the endogenous GRF transcription factor gene, the region comprising: (a) the sequence of SEQ ID NO:275 and the edit resulting in the nucleic acid sequence of any one of SEQ ID NOs:276-303, or (b) the sequence of SEQ ID NO:254 and the edit resulting in the nucleic acid sequence of any one of SEQ ID NOs:34-41.

2. The method of claim 1, wherein the nucleic acid binding domain of the editing system is comprised in a nuclease that cleaves the endogenous GRF transcription factor gene, thereby introducing a mutation into a miR396 binding site sequence of the endogenous GRF transcription factor gene.

3. The method of claim 1, further comprising regenerating a corn plant from the corn plant cell comprising the edit in the endogenous GRF transcription factor gene to produce a corn plant comprising the edit in its endogenous GRF transcription factor gene, optionally, wherein the corn plant comprising the edit in its endogenous GRF transcription factor gene has increased growth compared to a control corn plant that does not comprise the edit.

4. The method of claim 3, wherein the corn plant exhibits increased growth as compared to a control corn plant that does not comprise the edit and, optionally, at least one of the following phenotypes of increased meristem size, increased seed size, increased biomass, increased leaf size, increased root size, increased nitrogen use efficiency, increased disease resistance, increased height and/or increased internode length.

* * * * *

UNITED STATES PATENT AND TRADEMARK OFFICE

CERTIFICATE OF CORRECTION

PATENT NO. : 11,965,170 B2
APPLICATION NO. : 17/126469
DATED : April 23, 2024
INVENTOR(S) : Brian Charles Wilding Crawford It is certified that error appears in the above-identified patent and that said Letters Patent is hereby corrected as shown below:

In the Specification

Column 2, Line 30: Please correct “SEQ ID NOs: 4, and 9-18” to read --SEQ ID NOs:4, 5 and 9-18--

Column 13, Line 40: Please correct ““hypo orphic mutation”” to read --“hypomorphic mutation”--

Column 14, Lines 21-23: Please correct “TECHNIQUES ET UTILISATIONS DES MARQUEURS MOLECULAIRES LES COLLOQUES” to read --TECHNIQUES ET UTILISATIONS DES MARQUEURS MOLECULAIRES LES COLLOQUES--

Column 14, Lines 25-26: Please correct “PROCEEDINGS OF THE SYMPOSIUM “ANALYSIS OF MOLECULAR MARKER DATA,”” to read --PROCEEDINGS OF THE SYMPOSIUM “ANALYSIS OF MOLECULAR MARKER DATA,”--

Column 43, Line 37: Please correct “GRIVIZM2G041223” to read --GRMZM2G041223--

Column 43, Line 48: Please correct “GRIVIZM5G850129” to read --GRMZM5G850129--

Column 45, Line 22: Please correct “GRFS” to read --GRF5--

Column 55, Line 51: Please correct “position to base pair” to read --position 25 to base pair--

Column 58, Line 26: Please correct “Cash” to read --Cas6--

Signed and Sealed this
Eighth Day of April, 2025

Coke Morgan Stewart
*Acting Director of the United States Patent and Trademark Office*